US012474342B2

(12) United States Patent
Filvaroff et al.

(10) Patent No.: US 12,474,342 B2
(45) Date of Patent: Nov. 18, 2025

(54) METHODS FOR TREATING CANCER AND THE USE OF BIOMARKERS AS A PREDICTOR OF CLINICAL SENSITIVITY TO THERAPIES

(71) Applicant: CELGENE CORPORATION, Summit, NJ (US)

(72) Inventors: Ellen Filvaroff, San Francisco, CA (US); Antonia Lopez-Girona, San Diego, CA (US); Gang Lu, San Diego, CA (US)

(73) Assignee: Celgene Corporation, Summit, NJ (US)

(*) Notice: Subject to any disclaimer, the term of this patent is extended or adjusted under 35 U.S.C. 154(b) by 756 days.

(21) Appl. No.: 17/882,278

(22) Filed: Aug. 5, 2022

(65) Prior Publication Data

US 2023/0064156 A1 Mar. 2, 2023

Related U.S. Application Data

(62) Division of application No. 16/840,299, filed on Apr. 3, 2020, now Pat. No. 11,460,471, which is a division of application No. 15/400,766, filed on Jan. 6, 2017, now Pat. No. 10,648,983.

(60) Provisional application No. 62/404,638, filed on Oct. 5, 2016, provisional application No. 62/276,700, filed on Jan. 8, 2016.

(51) Int. Cl.

| | |
|---|---|
| ***G01N 33/574*** | (2006.01) |
| ***A61K 31/454*** | (2006.01) |
| ***A61K 45/06*** | (2006.01) |
| ***A61P 35/02*** | (2006.01) |
| ***C12Q 1/6886*** | (2018.01) |

(52) U.S. Cl.

CPC ......... *G01N 33/574* (2013.01); *A61K 31/454* (2013.01); *A61K 45/06* (2013.01); *C12Q 1/6886* (2013.01); *G01N 33/57426* (2013.01); *A61P 35/02* (2018.01); *C12Q 2600/106* (2013.01); *C12Q 2600/136* (2013.01); *C12Q 2600/158* (2013.01); *G01N 2800/52* (2013.01)

(58) Field of Classification Search

CPC ...... G01N 33/574; A61P 35/00; A61K 31/454

See application file for complete search history.

(56) References Cited

U.S. PATENT DOCUMENTS

| | | | |
|---|---|---|---|
| 9,365,640 | B2 | 6/2016 | Lopez-Girona et al. |
| 9,499,514 | B2 | 11/2016 | Hansen et al. |
| 9,808,451 | B2 | 11/2017 | Cathers et al. |
| 9,857,359 | B2 | 1/2018 | Schafer et al. |
| 10,047,151 | B2 | 8/2018 | Lopez-Girona et al. |
| 10,052,315 | B2 | 8/2018 | Hui et al. |
| 10,189,808 | B2 | 1/2019 | Fernandez et al. |
| 10,245,258 | B2 | 4/2019 | Carrancio et al. |
| 10,338,077 | B2 | 7/2019 | Iha et al. |
| 10,648,983 | B2 | 5/2020 | Filvaroff et al. |
| 10,689,708 | B2 | 6/2020 | Trotter et al. |
| 10,996,215 | B2 | 5/2021 | Trotter et al. |
| 11,460,471 | B2 | 10/2022 | Filvaroff et al. |
| 2011/0223157 | A1 | 9/2011 | Schafer et al. |
| 2012/0122865 | A1 | 5/2012 | Muller et al. |
| 2012/0252844 | A1 | 10/2012 | Dewitt |
| 2012/0322073 | A1 | 12/2012 | Lopez-Girona et al. |
| 2014/0162282 | A1 | 6/2014 | Schafer et al. |
| 2014/0328832 | A1 | 11/2014 | Chopra et al. |
| 2016/0009683 | A1 | 1/2016 | Hansen et al. |
| 2016/0312292 | A1 | 10/2016 | Trotter |
| 2016/0313300 | A1 | 10/2016 | Trotter et al. |
| 2016/0319005 | A1 | 11/2016 | Lopez-Girona et al. |
| 2016/0356778 | A1 | 12/2016 | Iha et al. |
| 2017/0038387 | A1 | 2/2017 | Gandhi et al. |
| 2017/0088901 | A1 | 3/2017 | Trotter et al. |

(Continued)

FOREIGN PATENT DOCUMENTS

| | | |
|---|---|---|
| JP | 2008545399 A | 12/2008 |
| JP | 2012507541 A | 3/2012 |

(Continued)

OTHER PUBLICATIONS

Angers et al., 2006, "Molecular architecture and assembly of the DDB1-CUL4A ubiquitin ligase machinery," Nature, 443(7111):590-593.

(Continued)

*Primary Examiner* — Theodore R. Howell

(74) *Attorney, Agent, or Firm* — Jones Day

(57) ABSTRACT

A method of identifying a subject having cancer who is likely to be responsive to a treatment compound, comprising administering the treatment compound to the subject having the cancer; obtaining a sample from the subject; determining the level of a biomarker in the sample from the subject; and diagnosing the subject as being likely to be responsive to the treatment compound if the level of the biomarker in the sample of the subject changes as compared to a reference level of the biomarker; wherein the treatment compound is a compound of Formula I:

I

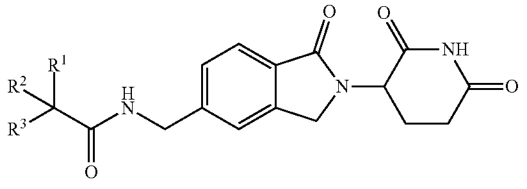

25 Claims, 62 Drawing Sheets

(56) References Cited

U.S. PATENT DOCUMENTS

| | | | |
|---|---|---|---|
| 2017/0199193 | A1 | 7/2017 | Filvaroff et al. |
| 2017/0242014 | A1 | 8/2017 | Hagner et al. |
| 2018/0209961 | A1 | 7/2018 | Schafer et al. |
| 2018/0231561 | A1 | 8/2018 | Gandhi et al. |
| 2019/0004033 | A1 | 1/2019 | Trotter et al. |
| 2020/0333340 | A1 | 10/2020 | Filvaroff et al. |
| 2021/0102257 | A1 | 4/2021 | Trotter et al. |
| 2022/0003749 | A1 | 1/2022 | Trotter et al. |

FOREIGN PATENT DOCUMENTS

| | | | |
|---|---|---|---|
| JP | 2013522236 | A | 6/2013 |
| WO | WO 2006125195 | A2 | 11/2006 |
| WO | WO 2010053732 | A1 | 5/2010 |
| WO | WO 2011112933 | A1 | 9/2011 |
| WO | WO 2016007848 | A1 | 1/2016 |
| WO | WO 2017027672 | A1 | 2/2017 |

OTHER PUBLICATIONS

Chamberlain et al., 2014, "Structure of the human Cereblon-DDB1-lenalidomide complex reveals basis for responsiveness to thalidomide analogs," Nat. Struct. Mol. Bio., 21(9):803-809.

Fischer et al., 2014, "Structure of the DDB1-CRBN E3 ubiquitin ligase in complex with thalidomide," Nature, 512(7512):49-53.

Gandhi et al., 2014, "Immunomodulatory agents lenalidomide and pomalidomide co-stimulate T cells by inducing degradation of T cell repressors Ikaros and Aiolos via modulation of the E3 ubiquitin ligase complex CRL4(CRBN)," Br. J. Haematol., 164(6):811-821.

International Search Report and Written Opinion dated Mar. 13, 2017, of corresponding PCT Application No. PCT/US2017/012496 (8 pages).

Ito et al., 2010, "Identification of a primary target of thalidomide teratogenicity," Science, 327(5871):1345-1350.

Kronke et al., 2014, "Lenalidomide causes selective degradation of IKZF1 and IKZF3 in multiple myeloma cells," Science, 343(6168):301-305.

Kronke et al., 2015, "Lenalidomide induces ubiquitination and degradation of CK1alpha in del(5q) MDS," Nature, 523(7559):183-188.

Lopez-Girona et al., 2012, "Cereblon is a direct protein target for immunomodulatory and antiproliferative activities of lenalidomide and pomalidomide," Leukemia, 26(11):2326-2335.

Lu et al., 2014, "The myeloma drug lenalidomide promotes the cereblon-dependent destruction of Ikaros proteins," Science, 343(6168):305-309.

Ozawa et al., 1992, "Mapping of the human GSPT1 gene, a human homolog of the yeast GST1 gene, to chromosomal band 16p13.1," Somat Cell Mol Genet., 18(2):189-194.

Sheard et al., 2010, "Jasmonate perception by inositol-phosphate-potentiated CoI1-JAZ co-receptor," Nature, 468(7322):400-405.

Tan et al., 2007, "Mechanism of auxin perception by the TIR1 ubiquitin ligase," Nature, 446(7136):640-645.

Winter et al., 2015, "Drug Development. Phthalimide conjugation as a strategy for in vivo target protein degradation," Science, 348(6241):1376-1381.

Zhu et al., 2011, "Cereblon expression is required for the antimyeloma activity of lenalidomide and pomalidomide," Blood, 118(18):4771-4779.

METHODS FOR TREATING CANCER AND THE USE OF BIOMARKERS AS A PREDICTOR OF CLINICAL SENSITIVITY TO THERAPIES

CROSS-REFERENCE TO RELATED APPLICATIONS

This application is a divisional of U.S. application Ser. No. 16/840,299, filed Apr. 3, 2020, which is a divisional of U.S. application Ser. No. 15/400,766, filed Jan. 6, 2017, now U.S. Pat. No. 10,648,983, issued May 12, 2020, which claims the benefit of U.S. Provisional Application No. 62/276,700, filed Jan. 8, 2016, and U.S. Provisional Application No. 62/404,638, filed Oct. 5, 2016, the disclosure of each of which is incorporated by reference herein in its entirety.

1. FIELD

Provided herein, in some embodiments, are methods of using certain biomarkers, such as GSPT1, GSPT2, IKZF1, ATF4, ATF3, DDIT3, cleaved PARP, SRSF3 NMD transcript, or SRSF6 NMD transcript, in predicting and monitoring clinical sensitivity and therapeutic response to certain compounds in patients having various diseases and disorders, such as cancer (e.g., lymphoma, multiple myeloma (MM), and leukemia, such as acute myeloid leukemia (AML)). Further provided are kits for carrying out the methods. Also provided herein, in certain embodiments, are methods of determining the efficacy of a compound in treating diseases.

2. BACKGROUND

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). In general, cancer is divided into solid cancer and blood borne cancer. Examples of solid cancer include, but are not limited to, melanoma, adrenal carcinoma, breast carcinoma, renal cell cancer, pancreatic carcinoma, and small-cell lung carcinoma (SCLC), etc.

Blood cancer generally includes three main types: lymphoma, leukemia, and myeloma. Lymphoma refers to cancers that originate in the lymphatic system. Lymphoma includes, but is not limited to, Hodgkin's lymphoma, non-Hodgkin's lymphoma (NHL), diffuse large B-cell lymphoma (DLBCL), and peripheral T-cell lymphomas (PTCL), etc. Leukemia refers to malignant neoplasms of the blood-forming tissues. Acute leukemia involves predominantly undifferentiated cell populations, whereas chronic leukemia involves more mature cell forms. Acute leukemia is divided into acute lymphoblastic leukemia (ALL) and acute myeloblastic leukemia (AML) types. *The Merck Manual,* 946-949 (17th ed. 1999). Chronic leukemia is divided into chronic lymphocytic leukemia (CLL) or chronic myelocytic leukemia (CML). *The Merck Manual,* 949-952 (17th ed. 1999). Myeloma is a cancer of plasma cells in the bone marrow. Because myeloma frequently occurs at many sites in the bone marrow, it is often referred to as multiple myeloma (MM).

Current cancer therapy may involve surgery, chemotherapy, hormonal therapy and/or radiation treatment to eradicate neoplastic cells in a patient (see, e.g., Stockdale, *Medicine*, vol. 3, Chapter 12, Section IV (Rubenstein and Federman eds., 1998). Recently, cancer therapy could also involve biological therapy or immunotherapy. All of these approaches may pose significant drawbacks for the patient.

A tremendous demand therefore exists for new methods, treatments and compositions that can be used to treat patients with cancer including but not limited to, lymphoma (e.g., NHL), MM, leukemia (e.g., AML), and solid cancer.

A number of studies have been conducted with the aim of providing compounds that can safely and effectively be used to treat cancers. Clinical efficacy of these compounds cannot easily be correctly predicted, as it can only be measured in terms of patient response, which usually requires a minimum of several months of treatment. In view of the deficiencies of the conventional methods, there is a need to develop efficient, sensitive, and accurate methods to detect, quantify, and characterize the pharmacodynamic activity of certain compounds. The present invention satisfies these and other needs.

3. SUMMARY OF THE INVENTION

In one aspect, provided herein is a method of identifying a subject having cancer who is likely to be responsive to a treatment compound, comprising:

(a) administering the treatment compound to the subject;

(b) obtaining a sample from the subject;

(c) determining the level of a biomarker in the sample; and (d) diagnosing the subject as being likely to be responsive to the treatment compound if the level of the biomarker in the sample is different from a reference level of the biomarker;

wherein the treatment compound is a compound of Formula I:

I

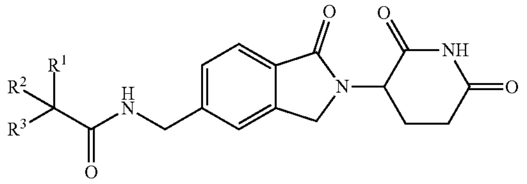

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, $—R^4OR^5$, $—R^4SR^5$, $—R^4N(R^6)(R^7)$, $—R^4OR^4N(R^6)(R^7)$, or $—R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In some embodiments, the level of the biomarker in the sample is higher than the reference level of the biomarker. In other embodiments, the level of the biomarker in the sample is lower than the reference level of the biomarker.

In another aspect, provided herein is a method of identifying a subject having cancer who is likely to be responsive to a treatment compound, comprising:

(a) obtaining a sample from the subject;

(b) administering the treatment compound to the sample;

(c) determining the level of a biomarker in the sample; and (d) diagnosing the subject as being likely to be responsive to the treatment compound if the level of the biomarker in the sample is different from a reference level of the biomarker;

wherein the treatment compound is a compound of Formula I:

I

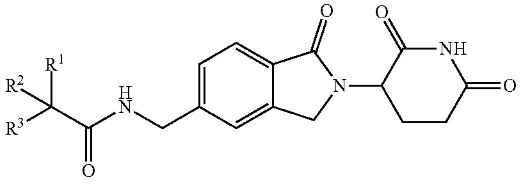

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, $—R^4OR^5$, $—R^4SR^5$, $—R^4N(R^6)(R^7)$, $—R^4OR^4N(R^6)(R^7)$, or $—R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In some embodiments, the level of the biomarker in the sample is higher than the reference level of the biomarker. In other embodiments, the level of the biomarker in the sample is lower than the reference level of the biomarker.

In another aspect, provided herein is a method of treating cancer, comprising:

(a) obtaining a sample from a subject having the cancer;

(b) determining the level of a biomarker in the sample;

(c) diagnosing the subject as being likely to be responsive to a treatment compound if the level of the biomarker in the sample is different from a reference level of the biomarker; and (d) administering a therapeutically effective amount of the treatment compound to the subject;

wherein the treatment compound is a compound of Formula I:

I

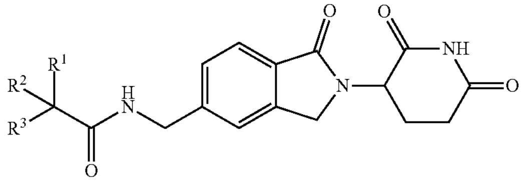

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, $—R^4OR^5$, $—R^4SR^5$, $—R^4N(R^6)(R^7)$, $—R^4OR^4N(R^6)(R^7)$, or $—R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In some embodiments, the level of the biomarker in the sample is higher than the reference level of the biomarker. In other embodiments, the level of the biomarker in the sample is lower than the reference level of the biomarker.

In yet another aspect, provided herein is a method of predicting the responsiveness of a subject having or suspected of having cancer to a treatment compound, comprising:

(a) administering the treatment compound to the subject;

(b) obtaining a sample from the subject;

(c) determining the level of a biomarker in the sample;

(d) diagnosing the subject as being likely to be responsive to a treatment of the cancer with the treatment compound if the level of the biomarker in the sample is different from the level of the biomarker obtained from a reference sample;

wherein the treatment compound is a compound of Formula I:

I

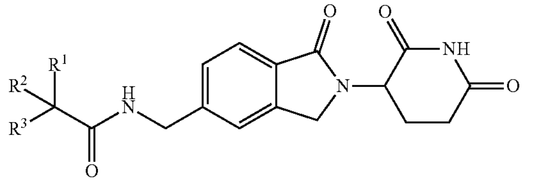

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, $—R^4OR^5$, $—R^4SR^5$, $—R^4N(R^6)(R^7)$, $—R^4OR^4N(R^6)(R^7)$, or $—R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In some embodiments, the level of the biomarker in the sample is higher than the reference level of the biomarker. In other embodiments, the level of the biomarker in the sample is lower than the reference level of the biomarker In yet another aspect, provided herein is a method of predicting the responsiveness of a subject having or suspected of having cancer to a treatment compound, comprising:

(a) obtaining a sample from the subject;
(b) administering the treatment compound to the sample;
(c) determining the level of a biomarker in the sample;
(d) diagnosing the subject as being likely to be responsive to a treatment of the cancer with the treatment compound if the level of the biomarker in the sample is different from the level of the biomarker obtained from a reference sample;

wherein the treatment compound is a compound of Formula I:

I

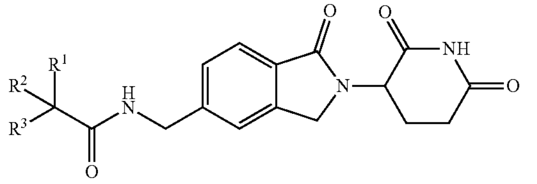

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, $—R^4OR^5$, $—R^4SR^5$, $—R^4N(R^6)(R^7)$, $—R^4OR^4N(R^6)(R^7)$, or $—R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In some embodiments, the level of the biomarker in the sample is higher than the reference level of the biomarker. In other embodiments, the level of the biomarker in the sample is lower than the reference level of the biomarker.

In yet another aspect, provided herein is a method of monitoring the efficacy of a treatment compound in treating cancer in a subject, comprising:

(a) administering the treatment compound to the subject;
(b) obtaining a sample from the subject;
(c) determining the level of a biomarker in the sample;
(d) comparing the level of the biomarker in the sample with the level of the biomarker obtained from a reference sample, wherein a change in the level as compared to the reference is indicative of the efficacy of the treatment compound in treating the cancer in the subject;

wherein the treatment compound is a compound of Formula I:

I

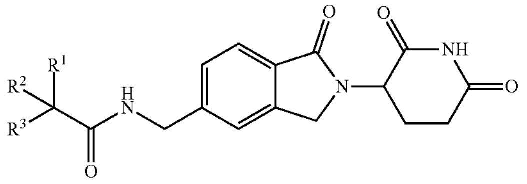

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, $-R^4OR^5$, $-R^4SR^5$, $-R^4N(R^6)(R^7)$, $-R^4OR^4N(R^6)(R^7)$, or $-R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In some embodiments, an increased level as compared to the reference is indicative of the efficacy of the treatment compound in treating the cancer in the subject. In other embodiments, a decreased level as compared to the reference is indicative of the efficacy of the treatment compound in treating the cancer in the subject.

In some embodiments of the various methods provided herein, the method further comprises administering a therapeutically effective amount of the treatment compound to the subject diagnosed as being likely to be responsive to the treatment compound.

In some embodiments of the various methods provided herein, the method further comprises administering a therapeutically effective amount of a second active agent or a supportive care therapy. In some embodiments, the second active agent is a hematopoietic growth factor, cytokine, anti-cancer agent (e.g., a checkpoint inhibitor), antibiotic, cox-2 inhibitor, immunomodulatory agent, immunosuppressive agent, corticosteroid, therapeutic antibody that specifically binds to a cancer antigen or a pharmacologically active mutant, or derivative thereof. In certain embodiments, the anti-cancer agent is a checkpoint inhibitor.

As used herein and unless otherwise indicated, the term "immunomodulatory compound" or "immunomodulatory agent" can encompass certain small organic molecules that inhibit one or more LPS induced monocyte TNF-α, IL-1β, IL-12, IL-6, MIP-1α, MCP-1, GM-CSF, G-CSF, and COX-2 production. Immunomodulatory compounds disclosed herein may enhance the degradation of TNF-α mRNA. Further, without being limited by theory, immunomodulatory compounds disclosed herein may also be potent co-stimulators of T cells and increase cell proliferation dramatically in a dose dependent manner. Immunomodulatory compounds disclosed herein may also have a greater co-stimulatory effect on the CD8+ T cell subset than on the CD4+ T cell subset. In addition, the compounds may have anti-inflammatory properties against myeloid cell responses, yet efficiently co-stimulate T cells to produce greater amounts of IL-2, IFN-γ, and to enhance T cell proliferation and CD8+ T cell cytotoxic activity. Further, without being limited by a particular theory, immunomodulatory compounds disclosed herein may be capable of acting both indirectly through cytokine activation and directly on Natural Killer ("NK") cells and Natural Killer T ("NKT") cells, and increase the NK cells' ability to produce beneficial cytokines such as, but not limited to, IFN-γ, and to enhance NK and NKT cell cytotoxic activity.

In some embodiments of the various methods provided herein, the reference is prepared by using a control sample obtained from the subject prior to administering the treatment compound to the subject, and the control sample is from the same source as the sample. In other embodiments of the various methods provided herein, the reference is prepared by using a control sample obtained from a healthy subject not having cancer, and the control sample is from the same source as the sample. In other embodiments of the various methods provided herein, the reference is prepared by using a control sample obtained from a group of healthy subjects not having cancer, and the control sample is from the same source as the sample. In other embodiments of the various methods provided herein, the reference is prepared by using a control sample obtained from a second subject having cancer, and the control sample is from the same source as the sample. In still other embodiments of the various methods provided herein, the reference is prepared by using a control sample obtained from a group of subjects having cancer, and the control sample is from the same source as the sample.

In some embodiments of the various methods provided herein, the cancer is multiple myeloma (MM), lymphoma, or leukemia. In some embodiments, the cancer is MM. In some embodiments, the cancer is lymphoma. In other embodiments, the cancer is leukemia. In some embodiments, the leukemia is chronic lymphocytic leukemia (CLL), chronic myelocytic leukemia (CML), acute lymphoblastic leukemia (ALL), or acute myeloid leukemia (AML). In a specific embodiment, the leukemia is AML. In a specific embodiment, the leukemia is relapsed, refractory or resistant to conventional therapy. In some embodiments, the cancer is a myelodysplastic syndrome (MDS).

In some embodiments of the methods provided herein, the biomarker is a protein that is directly or indirectly affected by CRBN. In certain embodiments, the biomarker is a protein that is directly affected by CRBN (such as a CRBN substrate). In other embodiments, the biomarker is a protein that is indirectly affected by CRBN (such as a downstream protein that is affected by a CRBN substrate). In some embodiments of the various methods provided herein, the biomarker is a CRBN-associated protein (CAP). In some embodiments, the CAP is a substrate of CRBN. In some embodiments, the CAP is a binding partner of CRBN under certain conditions. In some embodiments, the CAP is a downstream factor impacted by the substrate of CRBN.

In some embodiments, the biomarker has a function in unfolded protein response (UPR). In certain embodiments, the biomarker has a function in GCN2 related signaling pathway. In other embodiments, the biomarker has a function in ATF4 related signaling pathway. In yet other embodiments, the biomarker has a function in IRE1 related signaling pathway. In still other embodiments, the biomarker has a function in XBP1 related signaling pathway. In some embodiments, the biomarker has a function in ATF6 related signaling pathway. In certain embodiments, the biomarker has a function in apoptosis pathway. In other embodiments, the biomarker is an RNA substrate of nonsense-mediated mRNA decay (NMD) pathway.

In some embodiments, the biomarker is an eRF3 family member selected from the group consisting of GSPT1 and GSPT2. In some embodiments, the biomarker is an eRF3 family member selected from the group consisting of GSPT1 and GSPT2, and the level of the biomarker is lower than a reference. In one embodiment, biomarker is GSPT1. In another embodiment, the biomarker is GSPT2. In yet another embodiment, the biomarker is GSPT1, and the level of GSPT1 is lower than a reference. In still another embodiment, the biomarker is GSPT2, and the level of GSPT2 is lower than a reference.

In certain embodiments, the biomarker is IKZF1. In some embodiments, the biomarker is IKZF1, and the level of IKZF1 is lower than a reference.

In certain embodiments, the biomarker is selected from the group consisting of ATF4, ATF3, and DDIT3. In some embodiments, the biomarker is selected from the group consisting of ATF4, ATF3, and DDIT3, and the level of the biomarker is higher than a reference. In one embodiment, the biomarker is ATF4. In another embodiment, the biomarker is ATF3. In yet another embodiment, the biomarker is DDIT3. In one embodiment, the biomarker is ATF4, and the level of ATF4 is higher than a reference. In another embodiment, the biomarker is ATF3, and the level of ATF3 is higher than a reference. In still another embodiment, the biomarker is DDIT3, and the level of DDIT3 is higher than a reference.

In certain embodiments, the biomarker is selected from the group consisting of cleaved PARP, SRSF3 NMD transcript, and SRSF6 NMD transcript. In some embodiments, the biomarker is selected from the group consisting of cleaved PARP, SRSF3 NMD transcript, and SRSF6 NMD transcript, and the level of the biomarker is higher than a reference. In one embodiment, the biomarker is cleaved PARP. In another embodiment, the biomarker is SRSF3 NMD transcript. In yet another embodiment, the biomarker is SRSF6 NMD transcript. In one embodiment, the biomarker is cleaved PARP, and the level of cleaved PARP is higher than a reference. In another embodiment, the biomarker is SRSF3 NMD transcript, and the level of SRSF3 NMD transcript is higher than a reference. In still another embodiment, the biomarker is SRSF6 NMD transcript, and the level of SRSF6 NMD transcript is higher than a reference.

In some embodiments of the various methods provided herein, the level of the biomarkers is measured by determining the protein level of the biomarker.

In other embodiments of the various methods provided herein, the method provided herein further comprises contacting proteins within the sample with a first antibody that immunospecifically binds to the biomarker protein.

In one embodiment, the method provided herein further comprises:

(i) contacting the biomarker protein bound to the first antibody with a second antibody with a detectable label, wherein the second antibody immunospecifically binds to the biomarker protein, and wherein the second antibody immunospecifically binds to a different epitope on the biomarker protein than the first antibody;
(ii) detecting the presence of the second antibody bound to the biomarker protein; and
(iii) determining the amount of the biomarker protein based on the amount of detectable label in the second antibody.

In another embodiment, the method provided herein further comprises:

(i) contacting the first antibody bound to the biomarker protein with a second antibody with a detectable label, wherein the second antibody immunospecifically binds to the first antibody;
(ii) detecting the presence of the second antibody bound to the first antibody; and
(iii) determining the amount of the biomarker protein based on the amount of detectable label in the second antibody.

In some embodiments of the various methods provided herein, the level of the biomarker is measured by determining the mRNA level of the biomarker. In other embodiments of the various methods provided herein, the level of the biomarker is measured by determining the cDNA level of the biomarker.

In some embodiments of the various methods provided herein, the treatment compound is a compound of Formula I:

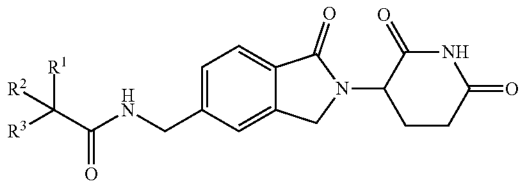

I or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is a halo-substituted aryl; and $R^2$ and $R^3$ are each halo.

In one embodiment, the treatment compound is selected from the group consisting of:

2-(3-chloro-4-methylphenyl)-N-((2-(2,6-dioxopiperidin-3-yl)-1-oxoisoindolin-5-yl)methyl)-2,2-difluoroacetamide;
2-(4-chlorophenyl)-N-((2-(2,6-dioxopiperidin-3-yl)-1-oxoisoindolin-5-yl)methyl)-2,2-difluoroacetamide;
N-((2-(2,6-dioxopiperidin-3-yl)-1-oxoisoindolin-5-yl)methyl)-2,2-difluoro-2-(4-methoxyphenyl)acetamide;
2-(3-chlorophenyl)-N-((2-(2,6-dioxopiperidin-3-yl)-1-oxoisoindolin-5-yl)methyl)-2,2-difluoroacetamide;
N-((2-(2,6-dioxopiperidin-3-yl)-1-oxoisoindolin-5-yl)methyl)-2,2-difluoro-2-(4-fluorophenyl)acetamide;
N-((2-(2,6-dioxopiperidin-3-yl)-1-oxoisoindolin-5-yl)methyl)-2,2-difluoro-2-p-tolylacetamide;
2-(3,4-dichlorophenyl)-N-((2-(2,6-dioxopiperidin-3-yl)-1-oxoisoindolin-5-yl)methyl)-2,2-difluoroacetamide;
2-(2-chlorophenyl)-N-((2-(2,6-dioxopiperidin-3-yl)-1-oxoisoindolin-5-yl)methyl)-2,2-difluoroacetamide;
N-((2-(2,6-dioxopiperidin-3-yl)-1-oxoisoindolin-5-yl)methyl)-2,2-difluoro-2-(2-(trifluoromethyl)phenyl)acetamide;
2-(4-tert-butylphenyl)-N-((2-(2,6-dioxopiperidin-3-yl)-1-oxoisoindolin-5-yl)methyl)-2,2-difluoroacetamide;
N-((2-(2,6-dioxopiperidin-3-yl)-1-oxoisoindolin-5-yl)methyl)-2,2-difluoro-2-phenylacetamide;
2-(3-chloro-4-fluorophenyl)-N-((2-(2,6-dioxopiperidin-3-yl)-1-oxoisoindolin-5-yl)methyl)-2,2-difluoroacetamide;
N-((2-(2,6-dioxopiperidin-3-yl)-1-oxoisoindolin-5-yl)methyl)-2,2-difluoro-2-(4-(trifluoromethylthio)phenyl)acetamide;
2-(2,6-difluorophenyl)-N-((2-(2,6-dioxopiperidin-3-yl)-1-oxoisoindolin-5-yl)methyl)-2,2-difluoroacetamide;
N-((2-(2,6-dioxopiperidin-3-yl)-1-oxoisoindolin-5-yl)methyl)-2,2-difluoro-2-o-tolylacetamide;
N-((2-(2,6-dioxopiperidin-3-yl)-1-oxoisoindolin-5-yl)methyl)-2,2-difluoro-2-(2-fluorophenyl)acetamide;
N-((2-(2,6-dioxopiperidin-3-yl)-1-oxoisoindolin-5-yl)methyl)-2-(2-ethoxyphenyl)-2,2-difluoroacetamide;
N-((2-(2,6-dioxopiperidin-3-yl)-1-oxoisoindolin-5-yl)methyl)-2,2-difluoro-2-(2-(trifluoromethoxy)phenyl)acetamide;
2-(3-bromo-4-(trifluoromethoxy)phenyl)-N-((2-(2,6-dioxopiperidin-3-yl)-1-oxoisoindolin-5-yl)methyl)-2,2-difluoroacetamide;
2-(3-chloro-4-methoxyphenyl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl)methyl)-2,2-difluoro-2-m-tolylacetamide;
N-((2-(2,6-dioxopiperidin-3-yl)-1-oxoisoindolin-5-yl)methyl)-2,2-difluoro-2-(4-isopropoxyphenyl)acetamide;
2-(3,4-difluorophenyl)-N-((2-(2,6-dioxopiperidin-3-yl)-1-oxoisoindolin-5-yl)methyl)-2,2-difluoroacetamide;
N-((2-(2,6-dioxopiperidin-3-yl)-1-oxoisoindolin-5-yl)methyl)-2,2-difluoro-2-(3-fluorophenyl)acetamide;
N-((2-(2,6-dioxopiperidin-3-yl)-1-oxoisoindolin-5-yl)methyl)-2,2-difluoro-2-(3-(trifluoromethyl)pyridin-2-yl)acetamide;
N-((2-(2,6-dioxopiperidin-3-yl)-1-oxoisoindolin-5-yl)methyl)-2,2-difluoro-2-(4-isopropylphenyl)acetamide;
2-(2,4-dichlorophenyl)-N-((2-(2,6-dioxopiperidin-3-yl)-1-oxoisoindolin-5-yl)methyl)-2,2-difluoroacetamide;
N-((2-(2,6-dioxopiperidin-3-yl)-1-oxoisoindolin-5-yl)methyl)-2,2-difluoro-2-(2-methoxyphenyl)acetamide;
2-(4-cyclopropylphenyl)-N-((2-(2,6-dioxopiperidin-3-yl)-1-oxoisoindolin-5-yl)methyl)-2,2-difluoroacetamide;
2-(4-chloro-2-fluorophenyl)-N-((2-(2,6-dioxopiperidin-3-yl)-1-oxoisoindolin-5-yl)methyl)-2,2-difluoroacetamide;
2-(4-chloro-3-fluorophenyl)-N-((2-(2,6-dioxopiperidin-3-yl)-1-oxoisoindolin-5-yl)methyl)-2,2-difluoroacetamide;
N-((2-(2,6-dioxopiperidin-3-yl)-1-oxoisoindolin-5-yl)methyl)-2,2-difluoro-2-(3-fluoro-2-methylphenyl)acetamide;
2-(3-chloro-2-methylphenyl)-N-((2-(2,6-dioxopiperidin-3-yl)-1-oxoisoindolin-5-yl)methyl)-2,2-difluoroacetamide;
N-((2-(2,6-dioxopiperidin-3-yl)-1-oxoisoindolin-5-yl)methyl)-2,2-difluoro-2-(4-fluoro-2-(trifluoromethyl)phenyl)acetamide;
2-(4-chloro-2-methylphenyl)-N-((2-(2,6-dioxopiperidin-3-yl)-1-oxoisoindolin-5-yl)methyl)-2,2-difluoroacetamide;
N-((2-(2,6-dioxopiperidin-3-yl)-1-oxoisoindolin-5-yl)methyl)-2,2-difluoro-2-(4-fluoro-2-methylphenyl)acetamide;
2-(4-chloro-2-(trifluoromethyl)phenyl)-N-((2-(2,6-dioxopiperidin-3-yl)-1-oxoisoindolin-5-yl)methyl)-2,2-difluoroacetamide;
2-cyclohexyl-N-((2-(2,6-dioxopiperidin-3-yl)-1-oxoisoindolin-5-yl)methyl)-2,2-difluoroacetamide;
2-(4-chloro-2-(trifluoromethoxy)phenyl)-N-((2-(2,6-dioxopiperidin-3-yl)-1-oxoisoindolin-5-yl)methyl)-2,2-difluoroacetamide;
N-((2-(2,6-dioxopiperidin-3-yl)-1-oxoisoindolin-5-yl)methyl)-2,2-difluoro-2-(3-(2-methoxyethoxy)phenyl)acetamide;
N-((2-(2,6-dioxopiperidin-3-yl)-1-oxoisoindolin-5-yl)methyl)-2,2-difluoro-2-(3-(2-hydroxyethoxy)phenyl)acetamide;
N-((2-(2,6-dioxopiperidin-3-yl)-1-oxoisoindolin-5-yl)methyl)-2,2-difluoro-2-(4-(2-methoxyethoxy)phenyl)acetamide;
N-((2-(2,6-dioxopiperidin-3-yl)-1-oxoisoindolin-5-yl)methyl)-2,2-difluoro-2-(3-(2-hydroxyethyl)phenyl)acetamide;
2-(3-(dimethylamino)phenyl)-N-((2-(2,6-dioxopiperidin-3-yl)-1-oxoisoindolin-5-yl)methyl)-2,2-difluoroacetamide;
N-((2-(2,6-dioxopiperidin-3-yl)-1-oxoisoindolin-5-yl)methyl)-2,2-difluoro-2-(3-(piperidin-1-yl)phenyl)acetamide;
N-((2-(2,6-dioxopiperidin-3-yl)-1-oxoisoindolin-5-yl)methyl)-2,2-difluoro-2-(3-morpholinophenyl)acetamide;
N-((2-(2,6-dioxopiperidin-3-yl)-1-oxoisoindolin-5-yl)methyl)-2,2-difluoro-2-(4-fluoro-2-isopropoxyphenyl)acetamide;
N-((2-(2,6-dioxopiperidin-3-yl)-1-oxoisoindolin-5-yl)methyl)-2,2-difluoro-2-(2-(2,2,2-trifluoroethoxy)phenyl)acetamide;
N-((2-(2,6-dioxopiperidin-3-yl)-1-oxoisoindolin-5-yl)methyl)-2-(2-ethoxy-4-fluorophenyl)-2,2-difluoroacetamide;
N-((2-(2,6-dioxopiperidin-3-yl)-1-oxoisoindolin-5-yl)methyl)-2,2-difluoro-2-(2-isopropoxyphenyl)acetamide;
N-((2-(2,6-dioxopiperidin-3-yl)-1-oxoisoindolin-5-yl)methyl)-2,2-difluoro-2-(2-fluoro-4-isopropoxyphenyl)acetamide;
N-((2-(2,6-dioxopiperidin-3-yl)-1-oxoisoindolin-5-yl)methyl)-2,2-difluoro-2-(3-(morpholinomethyl)phenyl)acetamide;
N-((2-(2,6-dioxopiperidin-3-yl)-1-oxoisoindolin-5-yl)methyl)-2,2-difluoro-2-(4-fluoro-2-(2,2,2-trifluoroethoxy)phenyl)acetamide;
N-((2-(2,6-dioxopiperidin-3-yl)-1-oxoisoindolin-5-yl)methyl)-2,2-difluoro-2-(4-isopropoxy-2-methylphenyl)acetamide;
N-((2-(2,6-dioxopiperidin-3-yl)-1-oxoisoindolin-5-yl)methyl)-2,2-difluoro-2-(4-isopropoxy-3-methylphenyl)acetamide;
N-((2-(2,6-dioxopiperidin-3-yl)-1-oxoisoindolin-5-yl)methyl)-2,2-difluoro-2-(3-fluoro-4-isopropoxyphenyl)acetamide;
2-(3-chloro-4-isopropoxyphenyl)-N-((2-(2,6-dioxopiperidin-3-yl)-1-oxoisoindolin-5-yl)methyl)-2,2-difluoroacetamide;
N-((2-(2,6-dioxopiperidin-3-yl)-1-oxoisoindolin-5-yl)methyl)-2,2-difluoro-2-(2-methyl-4-(trifluoromethoxy)phenyl)acetamide;
N-((2-(2,6-dioxopiperidin-3-yl)-1-oxoisoindolin-5-yl)methyl)-2,2-difluoro-2-(2-fluoro-4-(trifluoromethoxy)phenyl)acetamide;
2-(5-chloropyridin-2-yl)-N-((2-(2,6-dioxopiperidin-3-yl)-1-oxoisoindolin-5-yl)methyl)-2,2-difluoroacetamide;
N-((2-(2,6-dioxopiperidin-3-yl)-1-oxoisoindolin-5-yl)methyl)-2,2-difluoro-2-(5-fluoropyridin-2-yl)acetamide;
2-(2,4-difluorophenyl)-N-((2-(2,6-dioxopiperidin-3-yl)-1-oxoisoindolin-5-yl)methyl)-2,2-difluoroacetamide;
2-(4-bromophenyl)-N-((2-(2,6-dioxopiperidin-3-yl)-1-oxoisoindolin-5-yl)methyl)-2,2-difluoroacetamide;
N-((2-(2,6-dioxopiperidin-3-yl)-1-oxoisoindolin-5-yl)methyl)-2,2-difluoro-2-(2-(2-methoxyethoxy)phenyl)acetamide;
N-((2-(2,6-dioxopiperidin-3-yl)-1-oxoisoindolin-5-yl)methyl)-2,2-difluoro-2-(1-hydroxycyclohexyl)acetamide;
N-((2-(2,6-dioxopiperidin-3-yl)-1-oxoisoindolin-5-yl)methyl)-2,2-difluoro-2-(1-hydroxycyclopentyl)acetamide;
N-((2-(2,6-dioxopiperidin-3-yl)-1-oxoisoindolin-5-yl)methyl)-2,2-difluoro-2-(3-methyl-4-(trifluoromethoxy)phenyl)acetamide;
N-((2-(2,6-dioxopiperidin-3-yl)-1-oxoisoindolin-5-yl)methyl)-2-(3-ethoxypyridin-2-yl)-2,2-difluoroacetamide;
N-((2-(2,6-dioxopiperidin-3-yl)-1-oxoisoindolin-5-yl)methyl)-2,2-difluoro-2-(3-methylpyridin-2-yl)acetamide;
N-((2-(2,6-dioxopiperidin-3-yl)-1-oxoisoindolin-5-yl)methyl)-2,2-difluoro-2-(5-methylpyridin-2-yl)acetamide;
N-((2-(2,6-dioxopiperidin-3-yl)-1-oxoisoindolin-5-yl)methyl)-2-(2-ethoxy-6-fluorophenyl)-2,2-difluoroacetamide;
N-((2-(2,6-dioxopiperidin-3-yl)-1-oxoisoindolin-5-yl)methyl)-2,2-difluoro-2-(4'-fluorobiphenyl-4-yl)acetamide;

N-((2-(2,6-dioxopiperidin-3-yl)-1-oxoisoindolin-5-yl)methyl)-2-(2-ethoxy-5-fluorophenyl)-2,2-difluoroacetamide;

2-cyclopentyl-N-((2-(2,6-dioxopiperidin-3-yl)-1-oxoisoindolin-5-yl)methyl)-2,2-difluoroacetamide;

2-(3-chloro-4-(trifluoromethoxy)phenyl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl)methyl)-2,2-difluoro-2-(4-methoxy-2-(trifluoromethyl)phenyl)acetamide;

N-((2-(2,6-dioxopiperidin-3-yl)-1-oxoisoindolin-5-yl)methyl)-2,2-difluoro-2-(2-(2-hydroxyethoxy)phenyl)acetamide;

2-(4-chloro-2-ethoxyphenyl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl)methyl)-2,2-difluoro-2-(2-hydroxyphenyl)acetamide;

N-((2-(2,6-dioxopiperidin-3-yl)-1-oxoisoindolin-5-yl)methyl)-2,2-difluoro-2-(2-(methylamino)phenyl)acetamide;

N-((2-(2,6-dioxopiperidin-3-yl)-1-oxoisoindolin-5-yl)methyl)-2,2-difluoro-2-(4-isopropoxy-2-(trifluoromethyl)phenyl)acetamide;

N-((2-(2,6-dioxopiperidin-3-yl)-1-oxoisoindolin-5-yl)methyl)-2,2-difluoro-2-(4-methylcyclohexyl)acetamide;

N-((2-(2,6-dioxopiperidin-3-yl)-1-oxoisoindolin-5-yl)methyl)-2,2-difluoro-2-(3-(2-isopropoxyethoxy)phenyl)acetamide;

N-((2-(2,6-dioxopiperidin-3-yl)-1-oxoisoindolin-5-yl)methyl)-2,2-difluoro-2-(3-hydroxyphenyl)acetamide;

N-((2-(2,6-dioxopiperidin-3-yl)-1-oxoisoindolin-5-yl)methyl)-2,2-difluoro-2-(3-((4-methylpiperazin-1-yl)methyl)phenyl)acetamide;

N-((2-(2,6-dioxopiperidin-3-yl)-1-oxoisoindolin-5-yl)methyl)-2,2-difluoro-2-(4-methyl-2-(trifluoromethyl)phenyl)acetamide;

N-((2-(2,6-dioxopiperidin-3-yl)-1-oxoisoindolin-5-yl)methyl)-2,2-difluoro-2-(3-(2-(2-methoxyethoxy)ethoxy)phenyl)acetamide;

2-(3-(2-(dimethylamino)ethoxy)phenyl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl)methyl)-2,2-difluoro-2-(5-isopropylpyridin-2-yl)acetamide;

N-((2-(2,6-dioxopiperidin-3-yl)-1-oxoisoindolin-5-yl)methyl)-2,2-difluoro-2-(3-(2-(methylsulfonyl)ethoxy)phenyl)acetamide;

N-((2-(2,6-dioxopiperidin-3-yl)-1-oxoisoindolin-5-yl)methyl)-2,2-difluoro-2-(3-(3-(methylsulfonyl)propyl)phenyl)acetamide;

N-((2-(2,6-dioxopiperidin-3-yl)-1-oxoisoindolin-5-yl)methyl)-2,2-difluoro-2-(4-(2-fluoropropan-2-yl)phenyl)acetamide;

2-(1-benzyl-6-oxo-1,6-dihydropyridin-3-yl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl)methyl)-2,2-difluoro-2-(5-methoxypyridin-2-yl)acetamide;

N-((2-(2,6-dioxopiperidin-3-yl)-1-oxoisoindolin-5-yl)methyl)-2,2-difluoro-2-(1-methyl-6-oxo-1,6-dihydropyridin-3-yl)acetamide;

2-(5-tert-butylpyridin-2-yl)-N-((2-(2,6-dioxopiperidin-3-yl)-1-oxoisoindolin-5-yl)methyl)-2,2-difluoroacetamide;

2-(5-cyclopropylpyridin-2-yl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl)methyl)-2,2-difluoro-2-(5-isopropoxypyridin-2-yl)acetamide;

2-(5-bromopyridin-2-yl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl)methyl)-2,2-difluoro-2-(4-fluoro-2-(trifluoromethoxy)phenyl)acetamide;

N-((2-(2,6-dioxopiperidin-3-yl)-1-oxoisoindolin-5-yl)methyl)-2,2-difluoro-2-(4-fluorocyclohexyl)acetamide;

N-((2-(2,6-dioxopiperidin-3-yl)-1-oxoisoindolin-5-yl)methyl)-2,2-difluoro-2-(4-(methylsulfonyl)phenyl)acetamide;

N-((2-(2,6-dioxopiperidin-3-yl)-1-oxoisoindolin-5-yl)methyl)-2,2-difluoro-2-(3-(methylsulfonyl)phenyl)acetamide;

2-(2-aminopyrimidin-5-yl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl)methyl)-2,2-difluoro-2-(5-(trifluoromethylthio)pyridin-2-yl)acetamide;

N-((2-(2,6-dioxopiperidin-3-yl)-1-oxoisoindolin-5-yl)methyl)-2,2-difluoro-2-(3-(2-(methylamino)ethoxy)phenyl)acetamide;

N-((2-(2,6-dioxopiperidin-3-yl)-1-oxoisoindolin-5-yl)methyl)-2,2-difluoro-2-(1-methyl-6-oxo-1,6-dihydropyridazin-3-yl)acetamide;

2-(2-aminopyrimidin-4-yl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl)methyl)-2,2-difluoro-2-(pyrimidin-4-yl)acetamide;

N-((2-(2,6-dioxopiperidin-3-yl)-1-oxoisoindolin-5-yl)methyl)-2,2-difluoro-2-(3-(2-(piperidin-1-yl)ethoxy)phenyl)acetamide;

N-((2-(2,6-dioxopiperidin-3-yl)-1-oxoisoindolin-5-yl)methyl)-2,2-difluoro-2-(3-(2-morpholinoethoxy)phenyl)acetamide;

2-(3-(2-(4,4-difluoropiperidin-1-yl)ethoxy)phenyl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl)methyl)-2,2-difluoro-2-(1-methyl-6-oxo-1,6-dihydropyridazin-4-yl)acetamide; and N-((2-(2,6-dioxopiperidin-3-yl)-1-oxoisoindolin-5-yl)methyl)-2,2-difluoro-2-(3-(4-methylpiperazin-1-yl)phenyl)acetamide.

In a specific embodiment, the treatment compound is 2-(4-chlorophenyl)-N-((2-(2,6-dioxopiperidin-3-yl)-1-oxoisoindolin-5-yl)methyl)-2,2-difluoroacetamide (Compound D), or a stereoisomer or a mixture of stereoisomers, tautomer, pharmaceutically acceptable salt, solvate, isotopologue, prodrug, hydrate, co-crystal, clathrate, or a polymorph thereof.

In another specific embodiment, the treatment compound is the treatment compound is 2-(4-flurophenyl)-N-((2-(2,6-dioxopiperidin-3-yl)-1-oxoisoindolin-5-yl)methyl)-2,2-difluoroacetamide (Compound E), or a stereoisomer or a mixture of stereoisomers, tautomer, pharmaceutically acceptable salt, solvate, isotopologue, prodrug, hydrate, co-crystal, clathrate, or a polymorph thereof.

4. BRIEF DESCRIPTION OF THE FIGURES

FIGS. 1A and 1B show that Compound D induced degradation of GSPT1 in various AML cell lines. FIG. 1A shows that, in NB4 cell line, Compound D induced degradation of GSPT1 and IKZF1, which can be blocked by a proteasome inhibitor MG132. FIG. 1A also shows that pomalidomide and lenalidomide induced degradation of IKZF1 but had no significant effect on GSPT1 level. FIG. 1B shows that Compound D induced degradation of GSPT1 to various extent in four different AML cell lines, including HNT-34, KG-1, HL-60, and U937. FIG. 1B also shows that Compound D had little effect on GSPT1 in an insensitive AML cell line, OCI-AML3.

FIGS. 2A-2D show that the anti-proliferative effect of Compound D and Compound D-induced degradation of GSPT1 are CRBN-dependent in OCI-AML2 cells and MOLM-13 cells. FIGS. 2A and 2B show that the anti-proliferative effect of Compound D is CRBN-dependent in OCI-AML2 cells (FIG. 2A) and MOLM-13 cells (FIG. 2B). FIGS. 2C and 2D show that Compound D-induced degradation of GSPT1 is CRBN-dependent in OCI-AML2 cells (FIG. 2C) and MOLM-13 cells (FIG. 2D).

FIGS. 3A-3C show that stabilization of GSPT1 abrogated the anti-proliferative effect of Compound D. FIG. 3A illustrates the full-length GSPT1 and GSPT1 sequence with a deletion of amino acids 1-138. FIG. 3B shows that the G575N mutation in HA-GSPT1-G575N and HA-GSPT1-Δ(1-138)-G575N prevented the degradation of HA-GSPT1 and HA-GSPT1-Δ(1-138) induced by Compound D. FIG. 3C demonstrates that overexpression of stabilized GSPT1-G575N and GSPT1-Δ(1-138)-G575N abrogated the anti-proliferative effect of Compound D.

FIGS. 4A-4K show that GSPT1-specific shRNAs knocked down GSPT1 expression and inhibited cell proliferation in various cell lines. FIG. 4A shows that 293FT human embryonic kidney cells expressing GSPT1-specific shRNAs (such as shGSPT1-1, shGSPT1-2, shGSPT1-3, and shGSPT1-4) exhibited various degrees of inhibition on cell proliferation, and that GSPT1 depletion using shGSPT1-4 also reduced the levels of eRF1 and CRBN. FIGS. 4B-4K show knock down of GSPT1 expression (FIGS. 4E, 4I, and 4K) and inhibition of cell growth (FIGS. 4B-4D, 4F, 411, and 4J) in seven AML cell lines, including KG1 (FIGS. 4B and 4E), U937 (FIGS. 4C and 4E), NB-4 (FIGS. 4D and 4E), Kasumi-1 (FIGS. 4F and 4I), HL-60 (FIGS. 4G and 4I), MV-4-11 (FIGS. 4H and 4I), and OCI-AML3 (FIGS. 4J and 4K).

FIGS. 5A-5H show that overexpression of GSPT1 reduced the anti-proliferative effect of Compound D in various AML cell lines. FIGS. 5A-5D show that Compound D (FIGS. 5A and 5C) and Compound E (FIGS. 5B and 5D) inhibited cell proliferation, and that the anti-proliferative effect was abolished by depletion of CRBN using CRISPR genome editing tool and was dramatically reduced by overexpression of exogenous GSPT1 via the EF1a promoter, in human histiocytic lymphoma cell line U937 (FIGS. 5A and 5B) and acute myeloid leukemia cell line MOLM-13 (FIGS. 5C and 5D). FIGS. 5E-5H show that overexpression of GSPT1 (FIGS. 5F and 5H) reduced anti-proliferative effect of Compound D (FIGS. 5E and 5G) in OCI-AML2 (FIGS. 5E and 5F) and MOLM-13 (FIGS. 5G and 5H) cells.

FIGS. 6A-6E show that depletion of GSPT1 sensitized acute myelogenous leukemia cell lines AML3 and KG1 to Compound D and Compound E. FIGS. 6A-6D show that, in KG1 (FIGS. 6A and 6B) and AML (FIGS. 6C and 6D) cells, Compound D (FIGS. 6A and 6C) and Compound E (FIGS. 6B and 6D) exhibited an anti-proliferative effect, particularly at high concentration, and that the anti-proliferative effect increased when the expression of GSPT1 was down-regulated by shGSPT1-1 or shGSPT1-3. FIG. 6E shows that both shGSPT1-1 and shGSPT1-3 reduced the expression of GSPT1 and eRF1.

FIGS. 7A and 7B show that Compound D-induced Unfolded Protein Response (UPR) preceded apoptotic cell death in human acute myeloblastic leukemia cell line KG1. FIG. 7A shows that Compound D induced degradation of GSPT1 and BIP (detected by CT-RmAb). FIG. 7B shows that the levels of p-eIF2α, ATF4, ATF3, DDIT3, cleaved Caspase-3, and cleaved PARP increased in response to Compound D treatment.

FIGS. 8A and 8B show that Compound D and Compound E induced apoptosis in KG1 cells. FIG. 8A shows that both Compound D and Compound E decreased the level of GSPT1, GSPT2, and BIP (detected by CT-Ab). FIG. 8B shows that both Compound D and Compound E increased the level of ATF-3, DDIT3, cleaved Caspase-3, and cleaved PARP.

FIGS. 9A and 9B show that Compound D-induced activation of the ATF4 pathway preceded the appearance of apoptotic markers in KG1 cells. FIG. 9A shows that Compound D induced degradation of GSPT1 and increased the levels of p-eIF2a, ATF4, ATF3, and CHOP (i.e., DDIT3) as early as 2 hours after the treatment by Compound D. FIG. 9B shows that the levels of apoptotic markers, such as cleaved Caspase-8, cleaved Caspase-9, cleaved Caspase-3, cleaved Caspase-7, and cleaved PARP, increased at approximately 6 hours after the treatment by Compound D.

FIGS. 10A and 10B show that stabilization of GSPT1 abrogated the activation of ATF4 pathway by Compound D in OCI-AML2 Cells. FIG. 10A shows that the G575N mutation in HA-GSPT1-G575N and HA-GSPT1-Δ(1-138)-G575N prevented the degradation of HA-GSPT1 and HA-GSPT1-Δ(1-138) induced by Compound D. The stabilization of GSPT1 abrogated the activation of ATF4 and apoptosis pathways by Compound D, as shown by unchanged levels of p-eIF2α, ATF4, ATF3, CHOP/DDIT3 (FIG. 10A), cleaved Caspase-8, cleaved Caspase-9, cleaved Caspase-3, cleaved Caspase-7, and cleaved PARP (FIG. 10B).

FIG. 11 demonstrates that Compound D activated the ATF4 pathway in KG-1 cells.

FIG. 12 demonstrates that Compound D activated the IRE1 and ATF6 pathways in KG-1 cells.

Figure 25A:
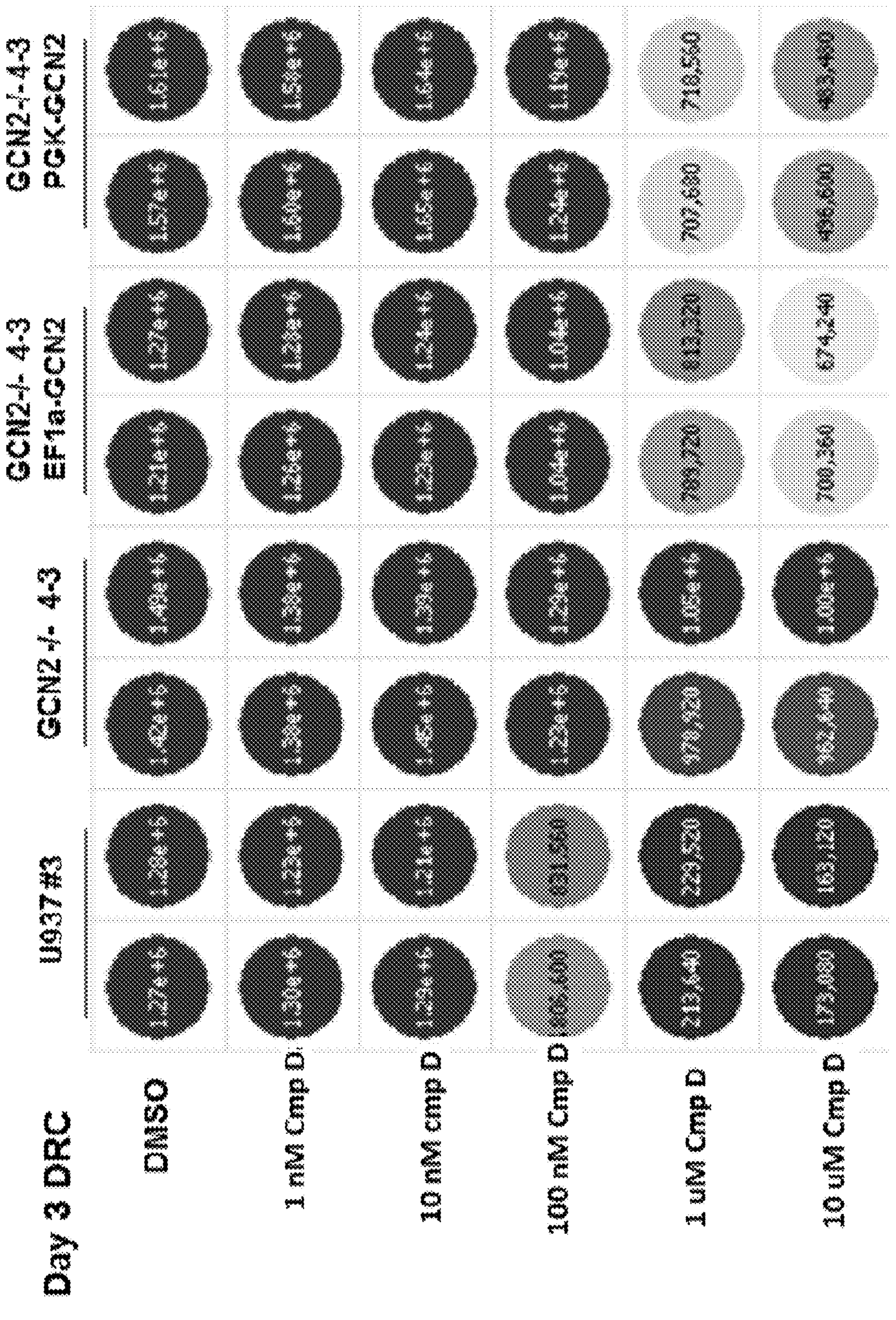
Figure 25B:
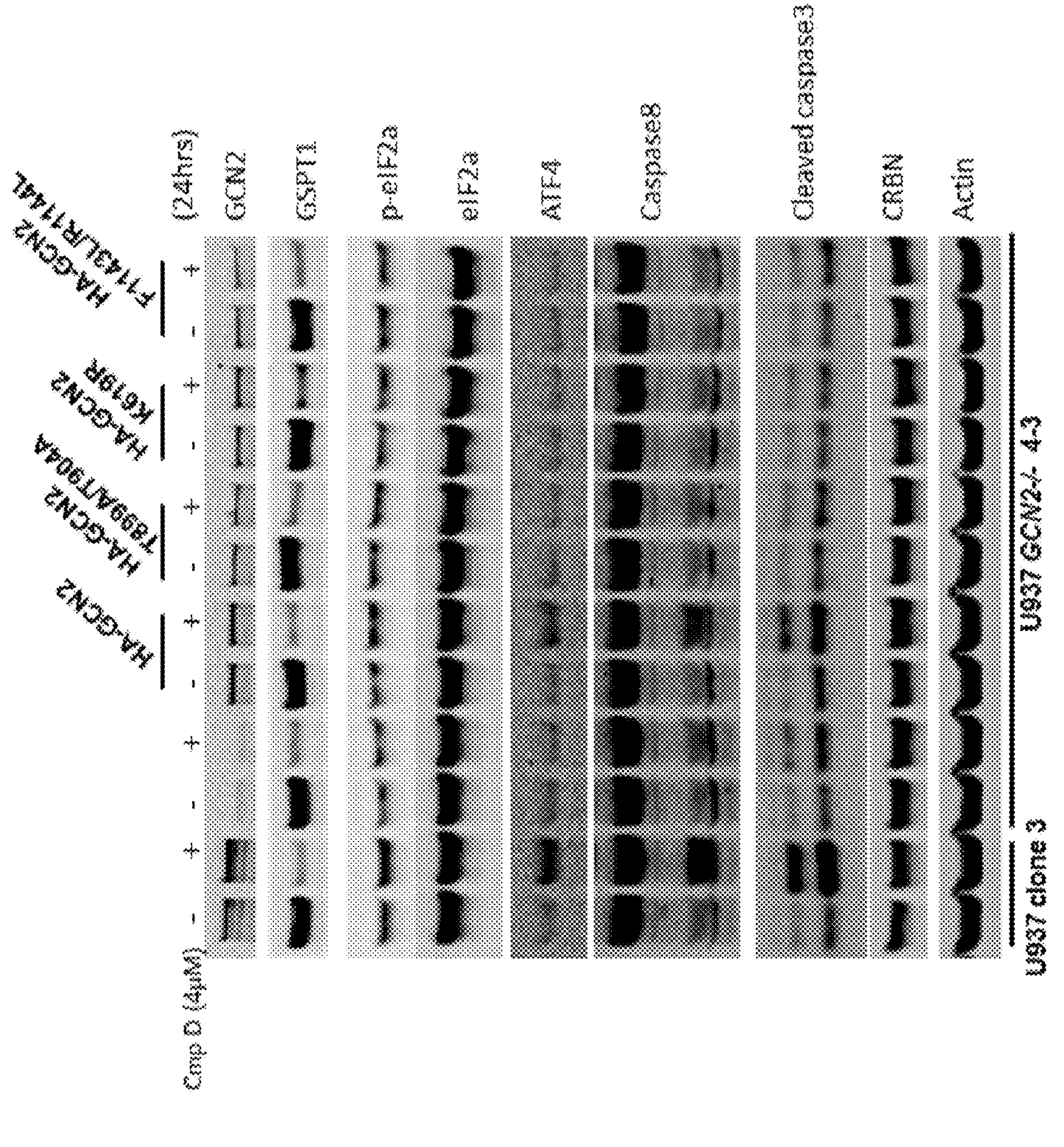
Figure 25C:
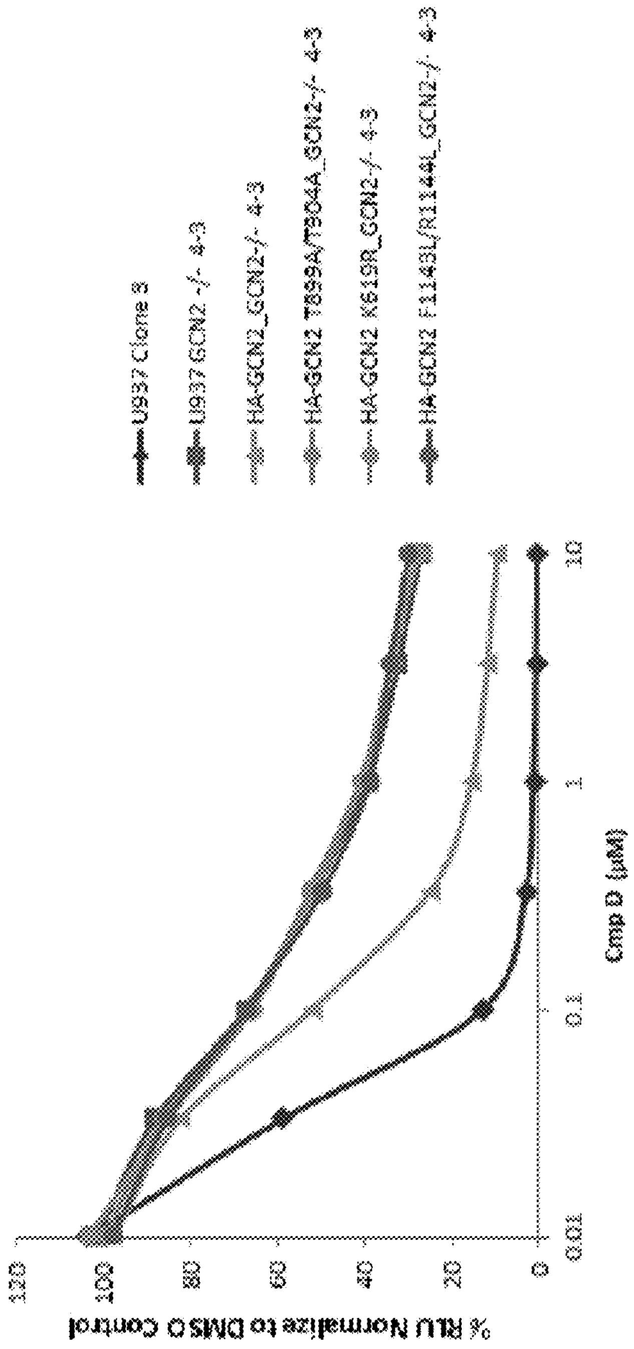

FIGS. 25A-25C show that reintroduction of wild type but not mutant GCN2 restored the Compound D-induced activation of ATF-4 pathway, apoptosis, and anti-proliferation in U937 GCN2 knockout cells. FIG. 25A shows Cell TiterGlo in a 48-well plate, seeded with U937 clone 3 cells, GCN2 knockout U937 cells by GCN2 –/– 4-3, GCN2 knockout U937 cells transfected with EF1a-GCN2, and GCN2 knockout U937 cells transfected with PGK-GCN2. FIG. 25B shows that reintroduction of wild type but not mutant GCN2 restored the activation of ATF-4 pathway and apoptosis induced by Compound D. FIG. 25C shows that reintroduction of wild type but not mutant GCN2 restored the anti-proliferative effect of Compound D.

Figure 26A:
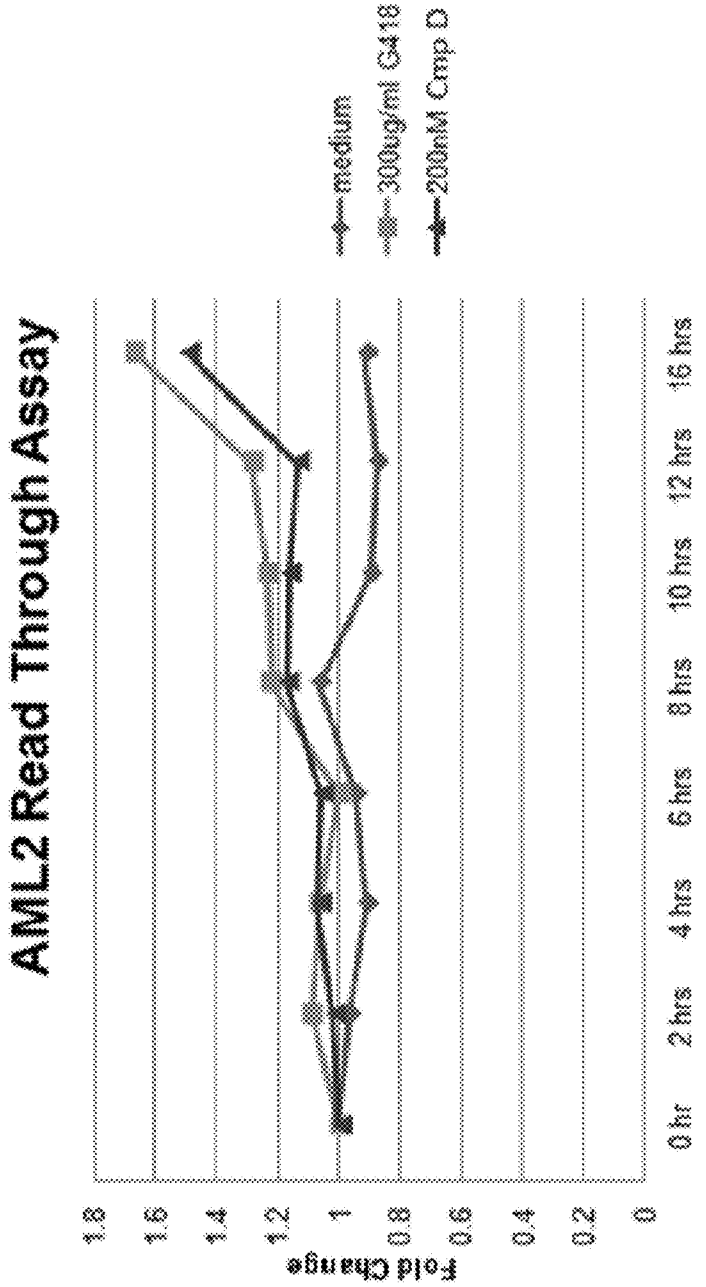
Figure 26B:
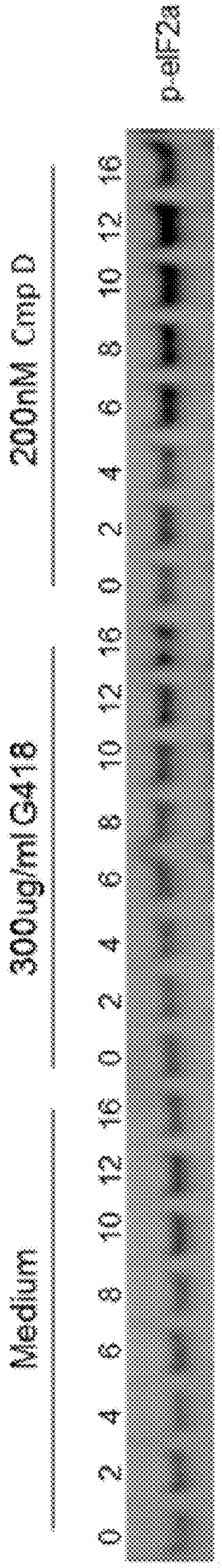

FIGS. 26A and 26B show that translational readthrough is not the cause of increased level of p-eIF2α. FIG. 26A shows that Compound D and G418 induced translational readthrough at a comparable level. FIG. 26B shows that Compound D increased the levels of p-eIF2α, whereas G418 had no effect.

Figure 27:
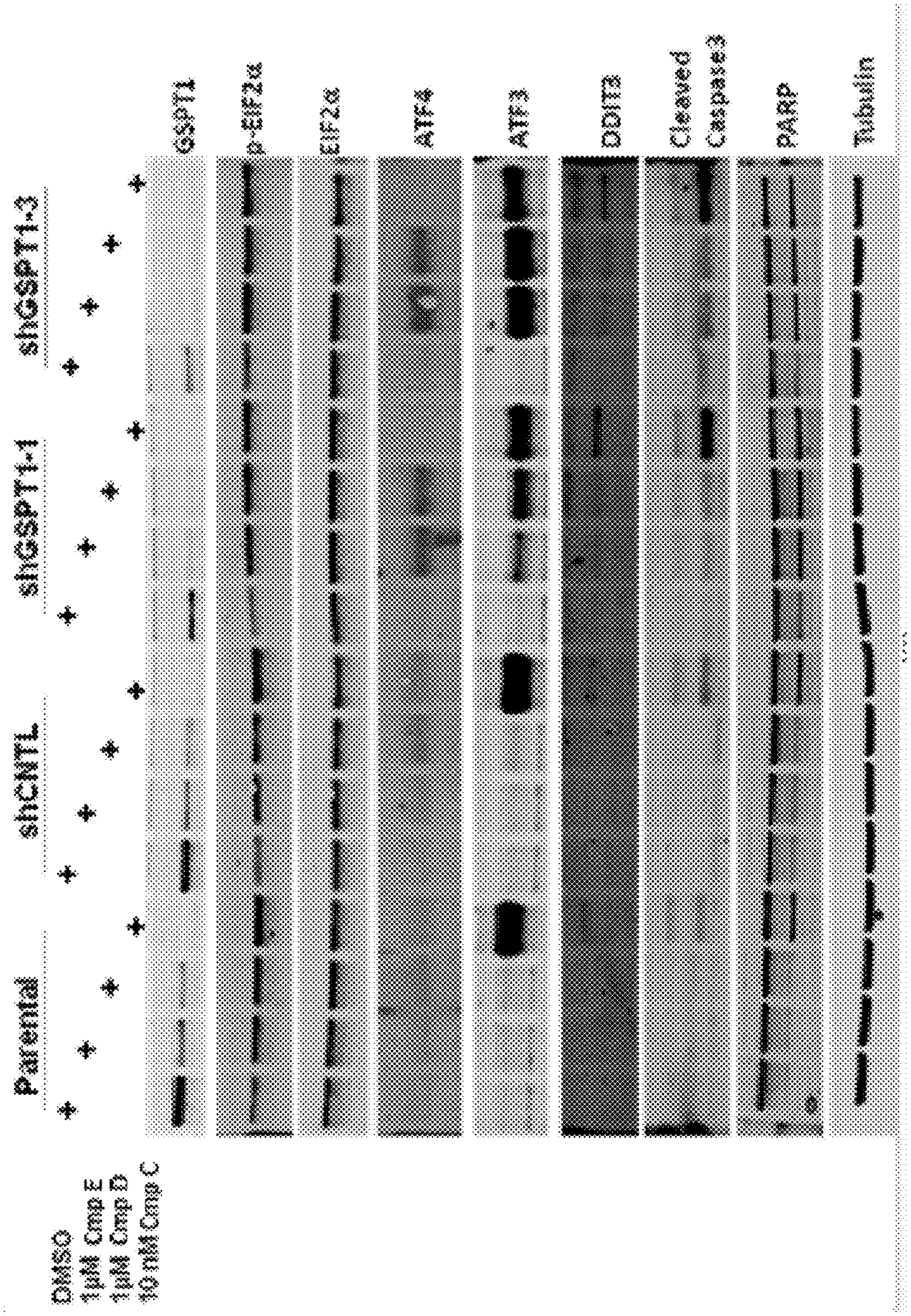

FIG. 27 shows that ATF4, ATF3, and DDIT3 serve as predictive biomarkers for Compound D- and Compound E-induced apoptosis, and that in response to treatment with Compound D or Compound E, the level of GSPT1 decreased, and the levels of p-eIF2α, ATF4, ATF3, DDIT3, cleaved Caspase-3, and cleaved PARP increased.

Figure 28A:
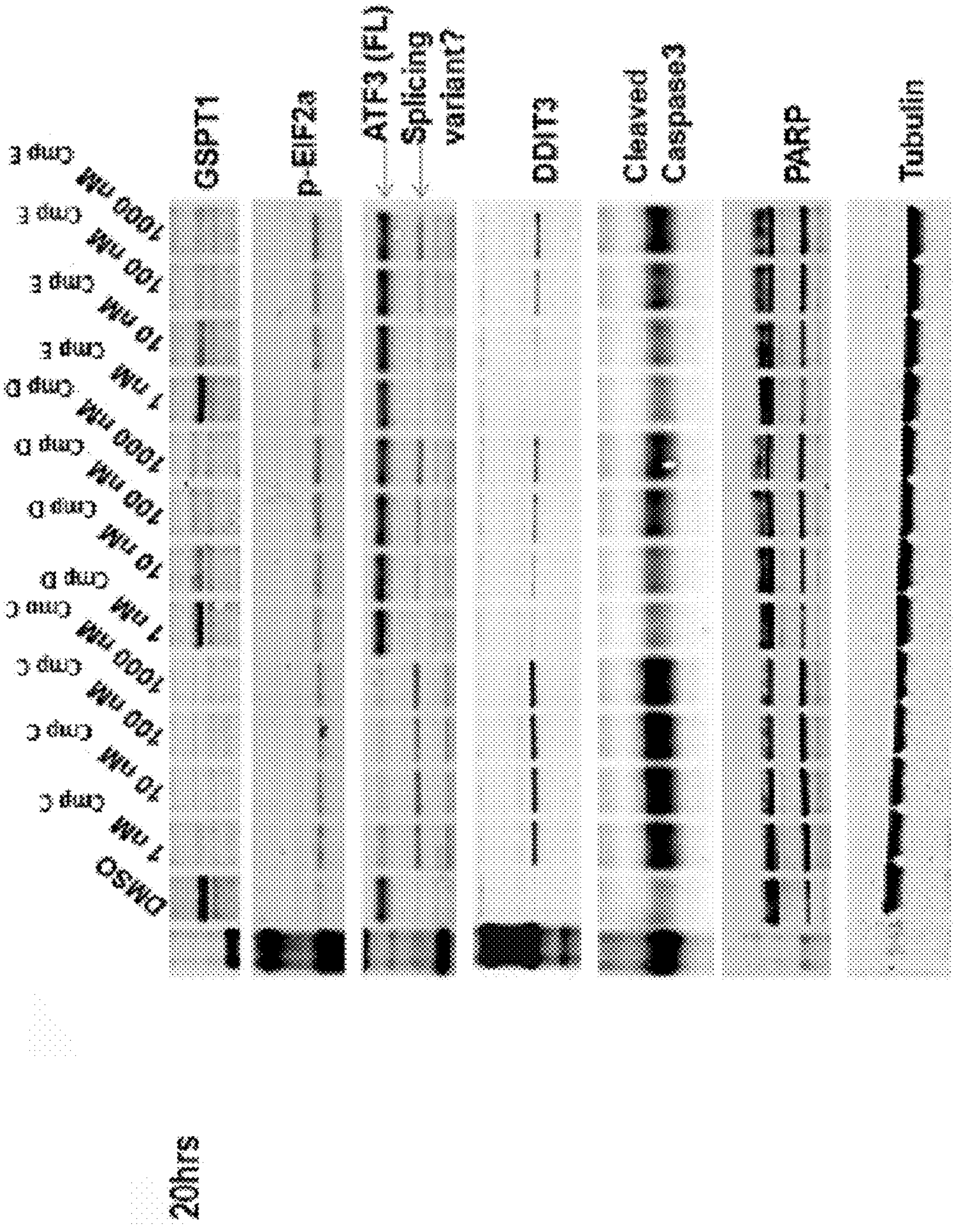
Figure 28B:
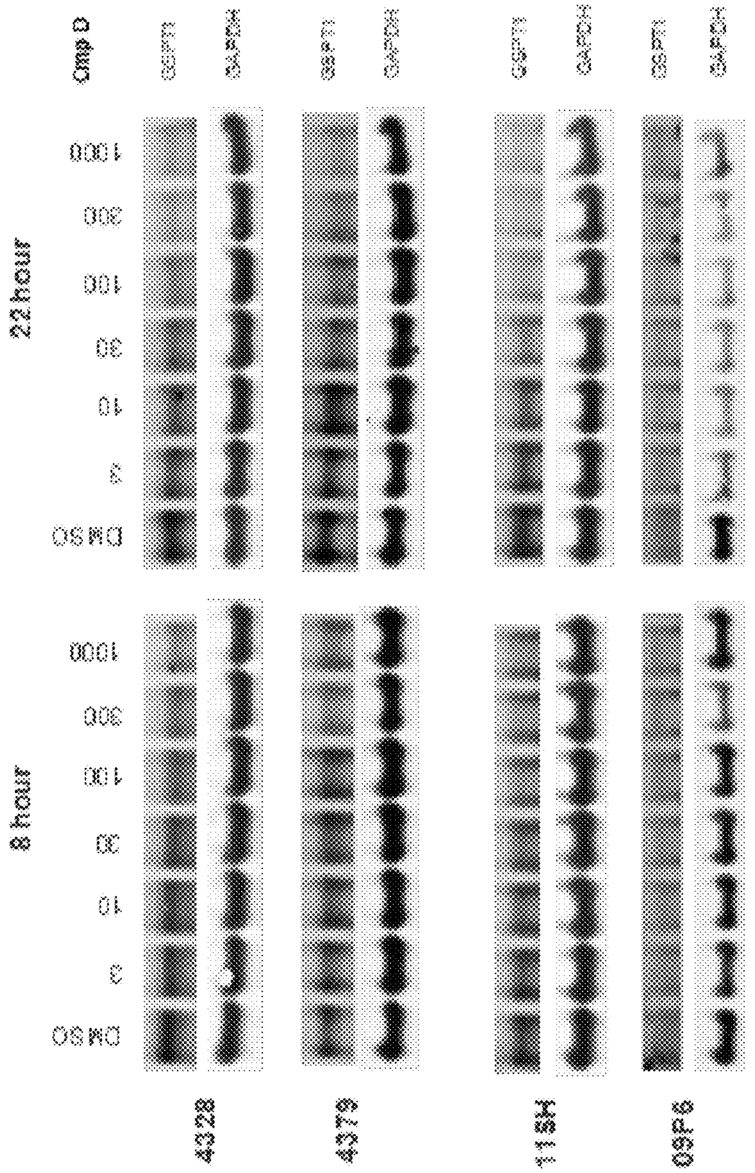

FIGS. 28A and 28B show that GSPT1 can be used as a biomarker for compound toxicity in PBMC. FIG. 28A shows the prediction of compound toxicity in Normal Peripheral Blood Mononuclear Cell (PBMC). FIG. 28A shows that Compound D and Compound E decreased the expression of GSPT1, but increased the level of p-eIF2α, ATF3 (likely in a splicing variant) and DDIT3, which consequently activated Caspase-3 by increasing cleaved Caspase-3. The cleaved Caspase-3 then inactivated PARP by cleaving PARP and induced apoptosis. FIG. 28B shows the GSPT1 level in response to treatment of Compound D in PBMC from two normal donors ((ID NOS. 4328 and 4379) and two AML patients (ID NOS. 11SH and 09P6).

Figure 29A:
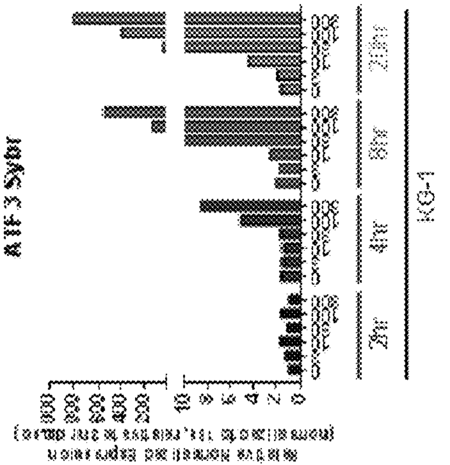
Figure 29B:
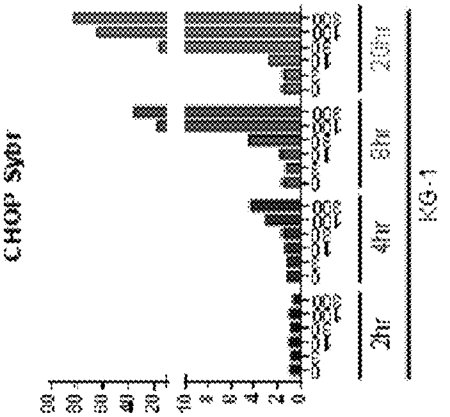
Figure 29C:
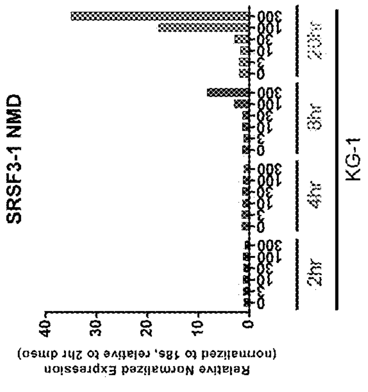
Figure 29D:
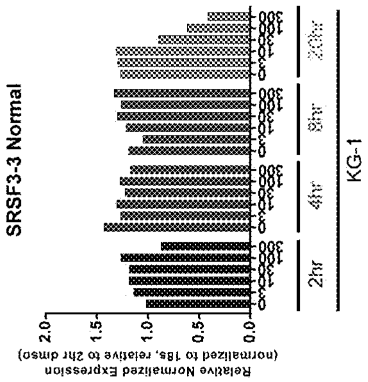
Figure 29E:
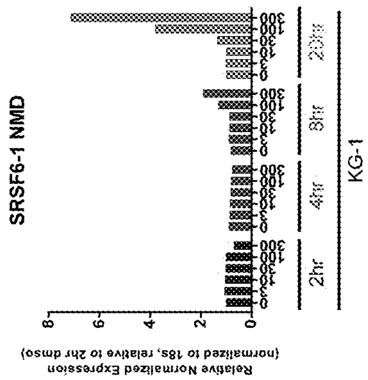
Figure 29F:
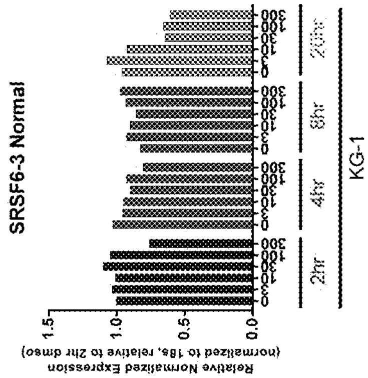
Figure 29G:
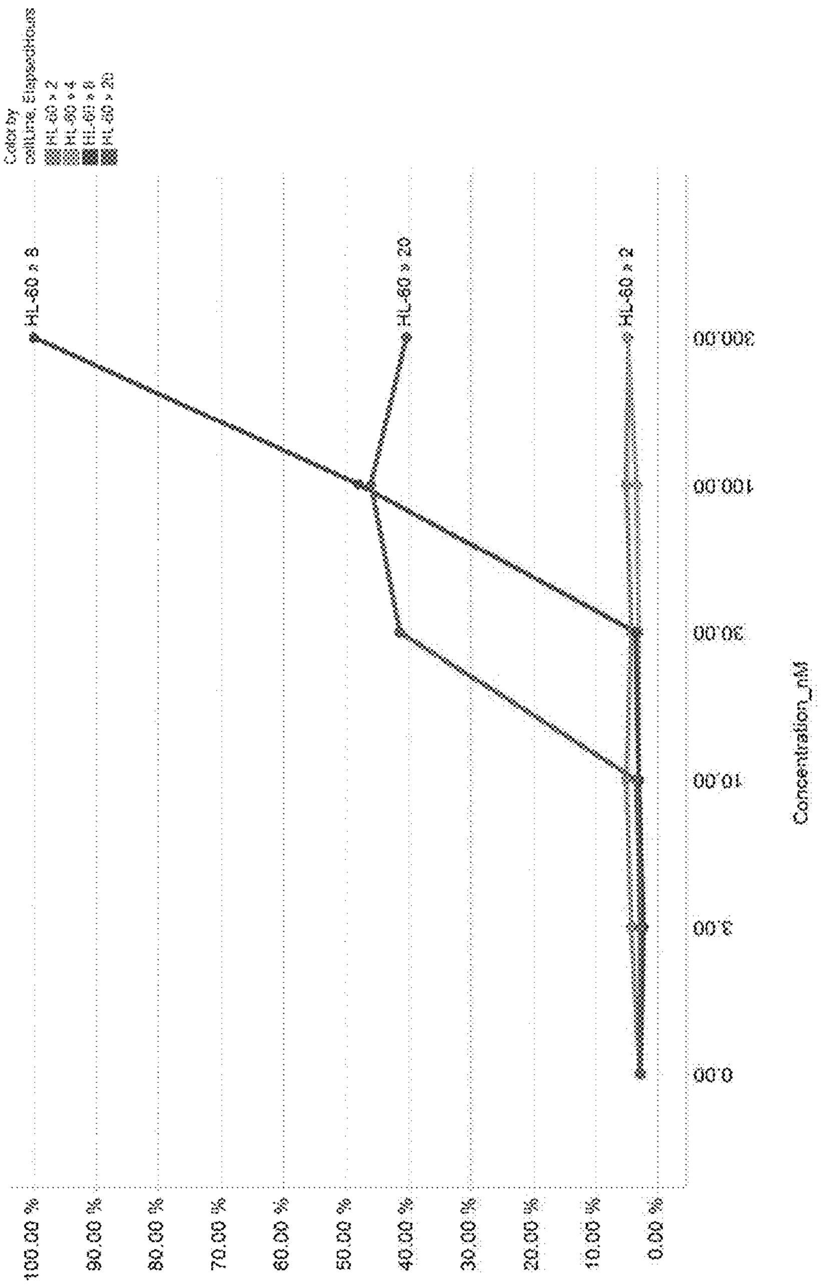
Figure 29H:
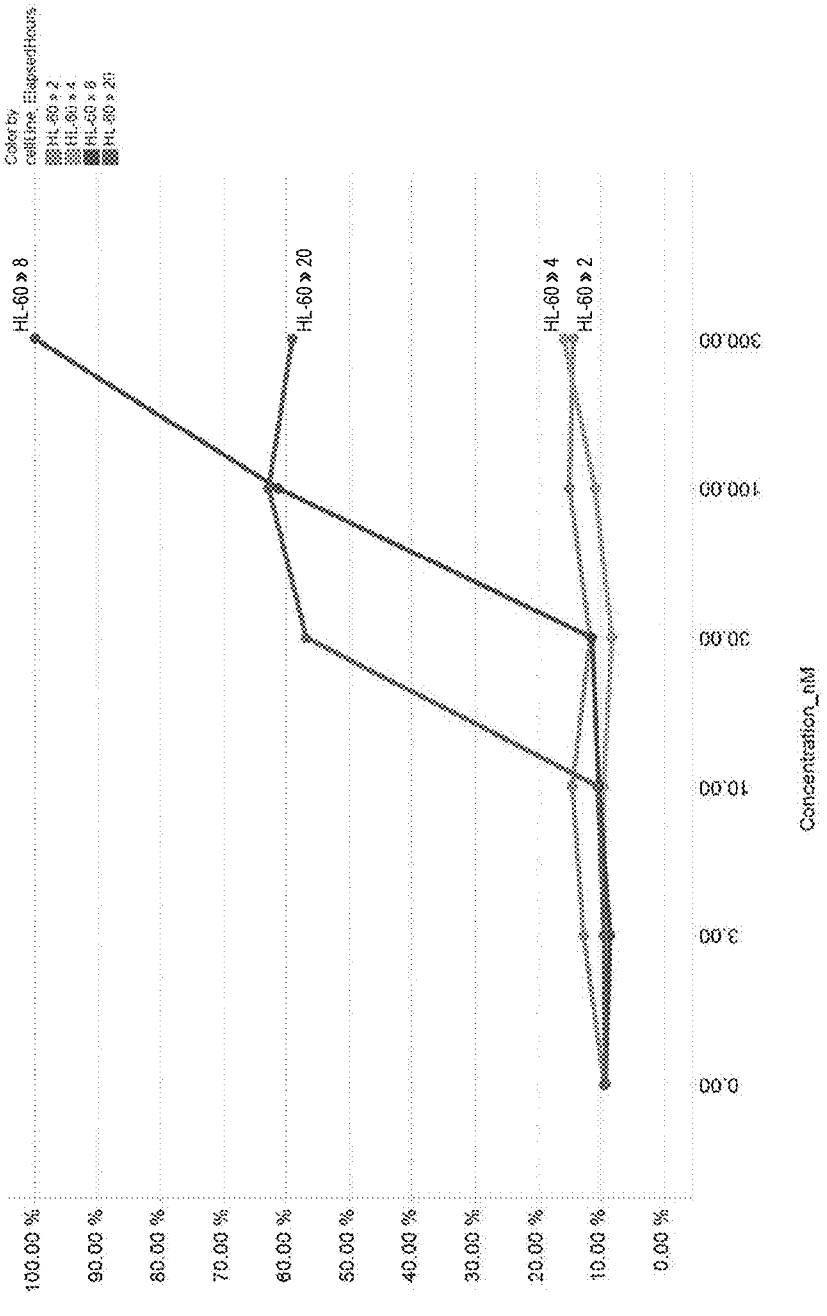
Figure 29I:
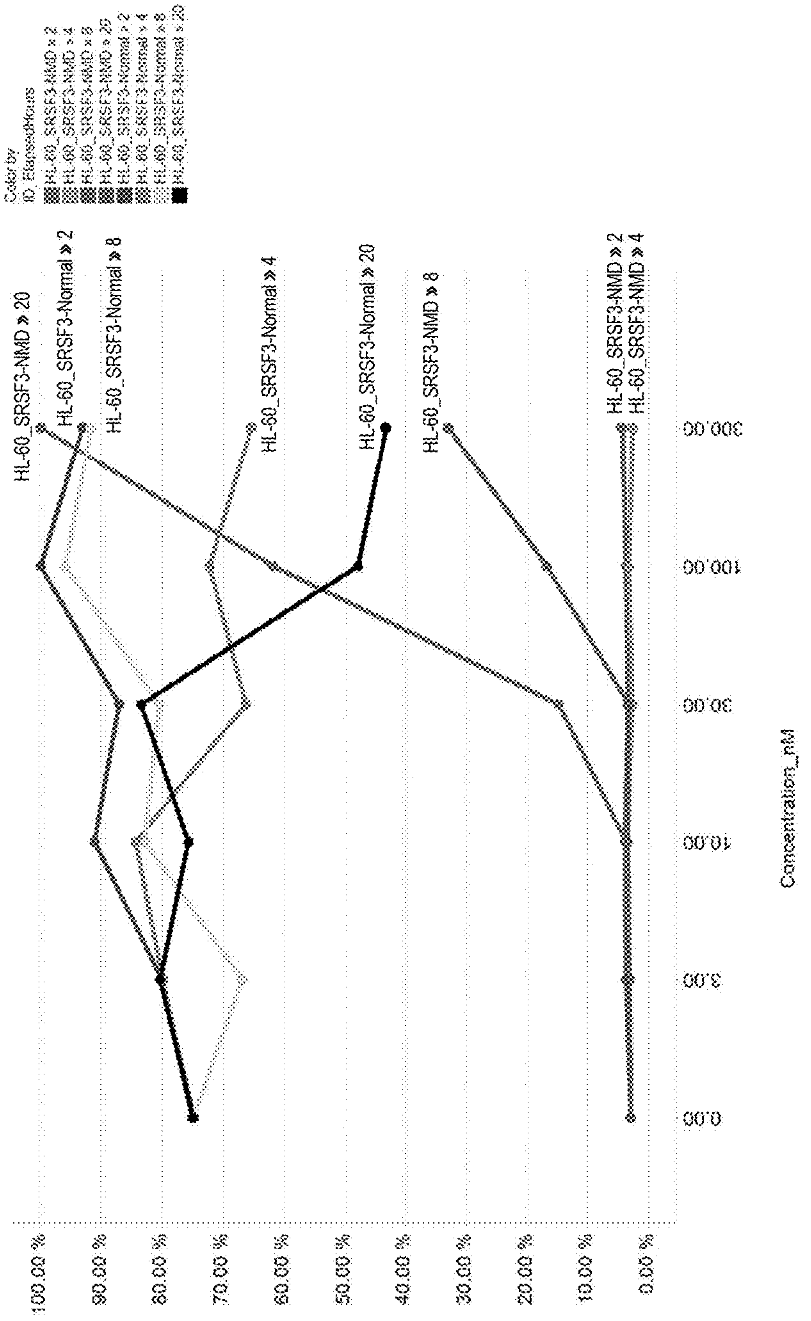
Figure 29J:
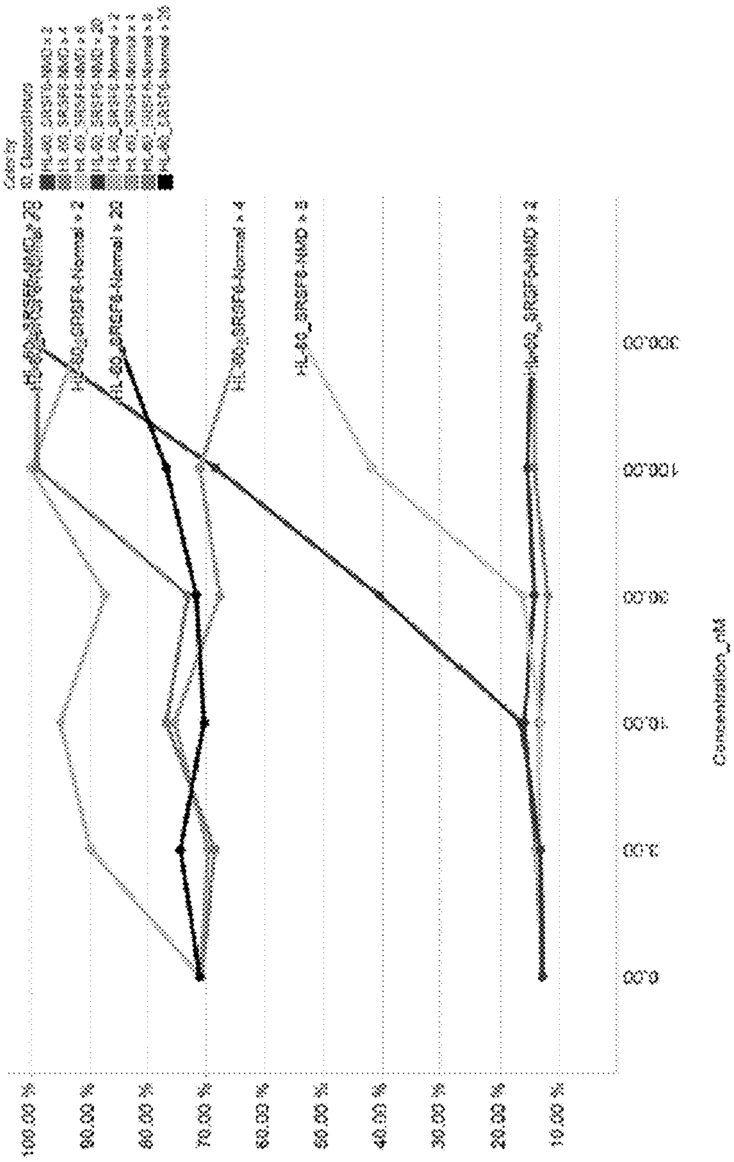

FIGS. 29A-29J show effects of Compound D on activation of UPR pathway and inhibition of NMD pathway in various AML cell lines. FIGS. 29A-29F show effects of Compound D treatment on UPR and NMD pathways in KG-1 cells. FIGS. 29A and 29B show that Compound D increased the mRNA levels of ATF3 (FIG. 29A) and DDIT3 (CHOP) (FIG. 29B). FIGS. 29C and 29D show that Compound D increased the mRNA levels of SRSF3-1 (NMD transcript) (FIG. 29C) but not those of SRSF3-3 (normal transcript) (FIG. 29D). FIGS. 29E and 29F show that Compound D increased the mRNA levels of SRSF6-1 (NMD transcript) (FIG. 29E) but not those of SRSF6-3 (normal transcript) (FIG. 29F). FIGS. 29G-29J show effects of Compound D treatment on UPR and NMD pathways in HL-60 cells. Compound D increased the level of ATF3 (FIG. 29G), DDIT3 (CHOP, FIG. 2911), SRSF3 NMD transcripts (FIG. 29I), SRSF6 NMD transcripts (FIG. 29J) but not SRSF3 non-NMD (normal) transcripts (FIG. 29I) and SRSF6 non-NMD (normal) transcripts (FIG. 29J).

Figure 30A:
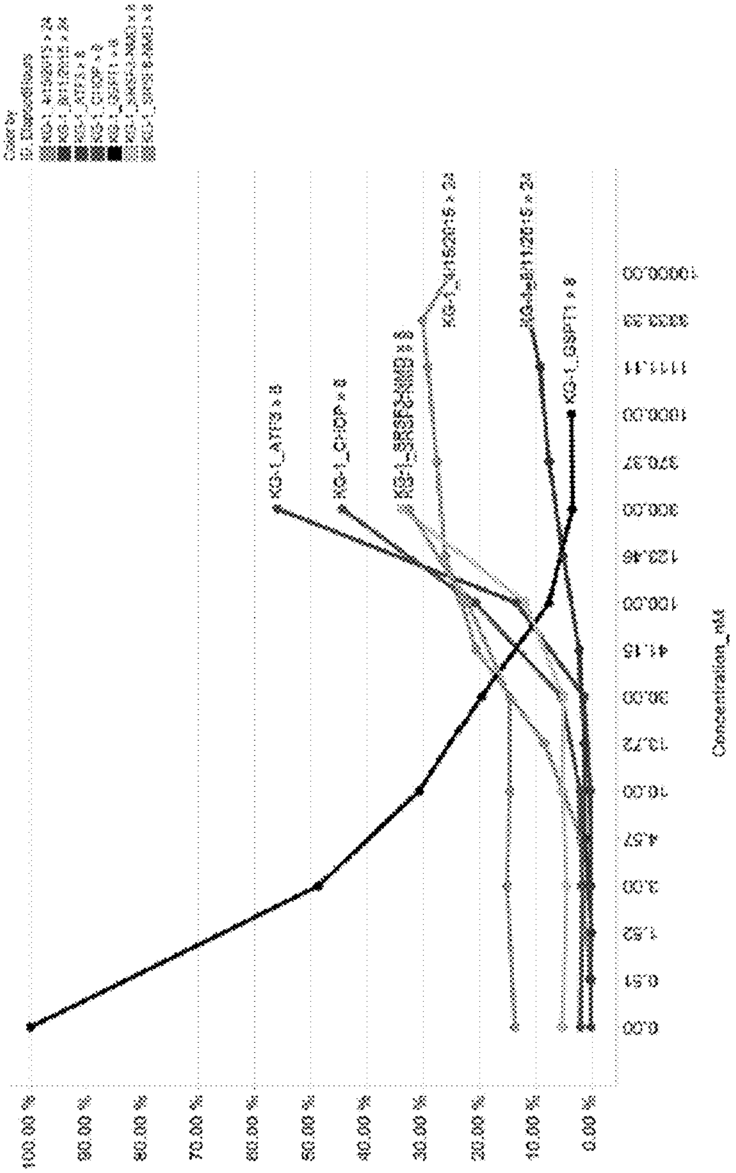
Figure 30B:
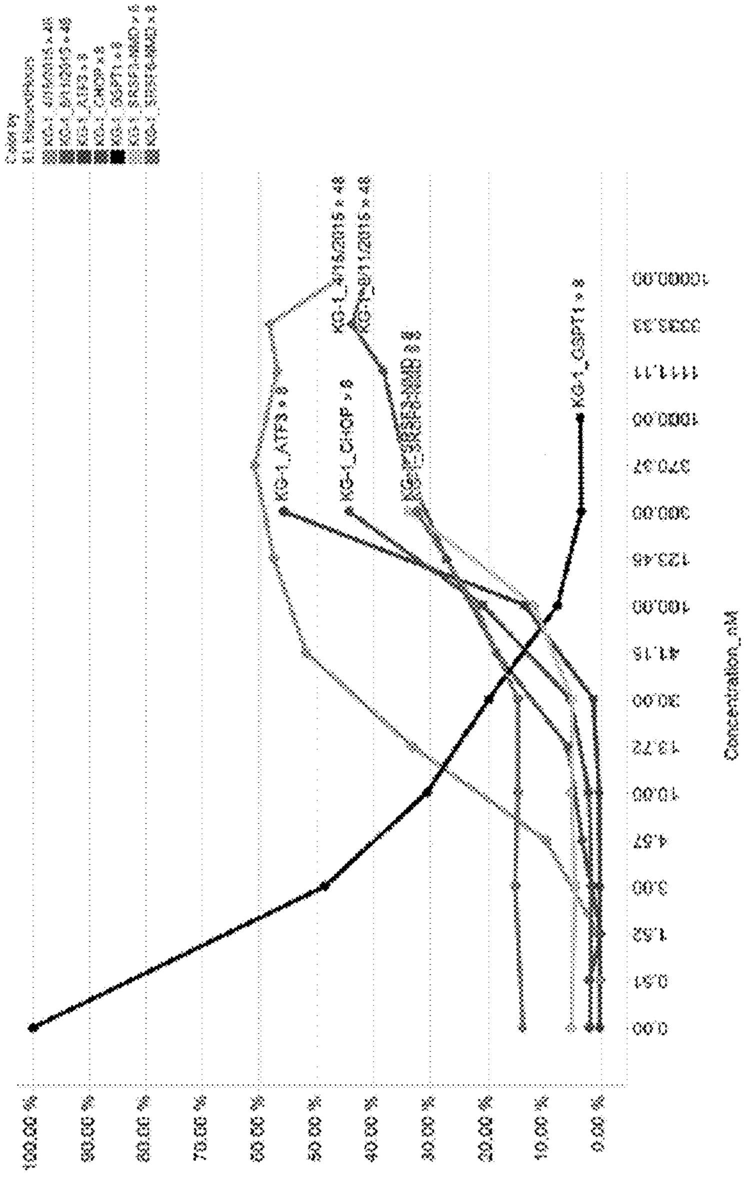
Figure 30C:
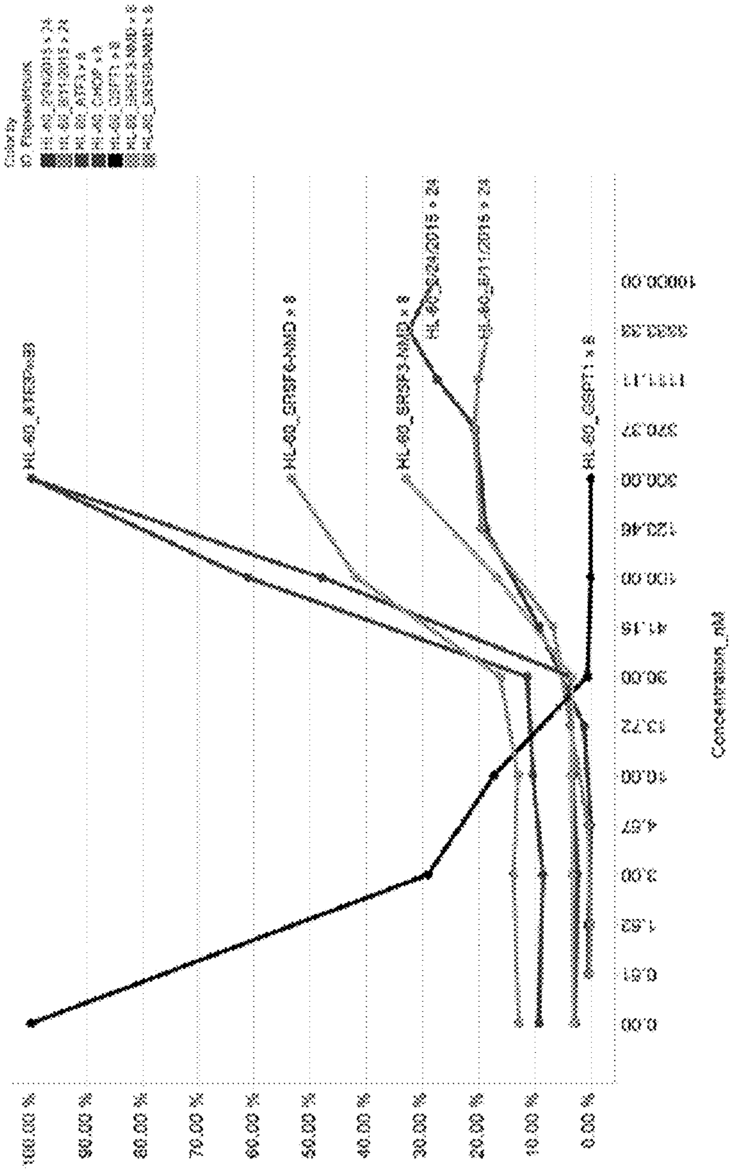
Figure 30D:
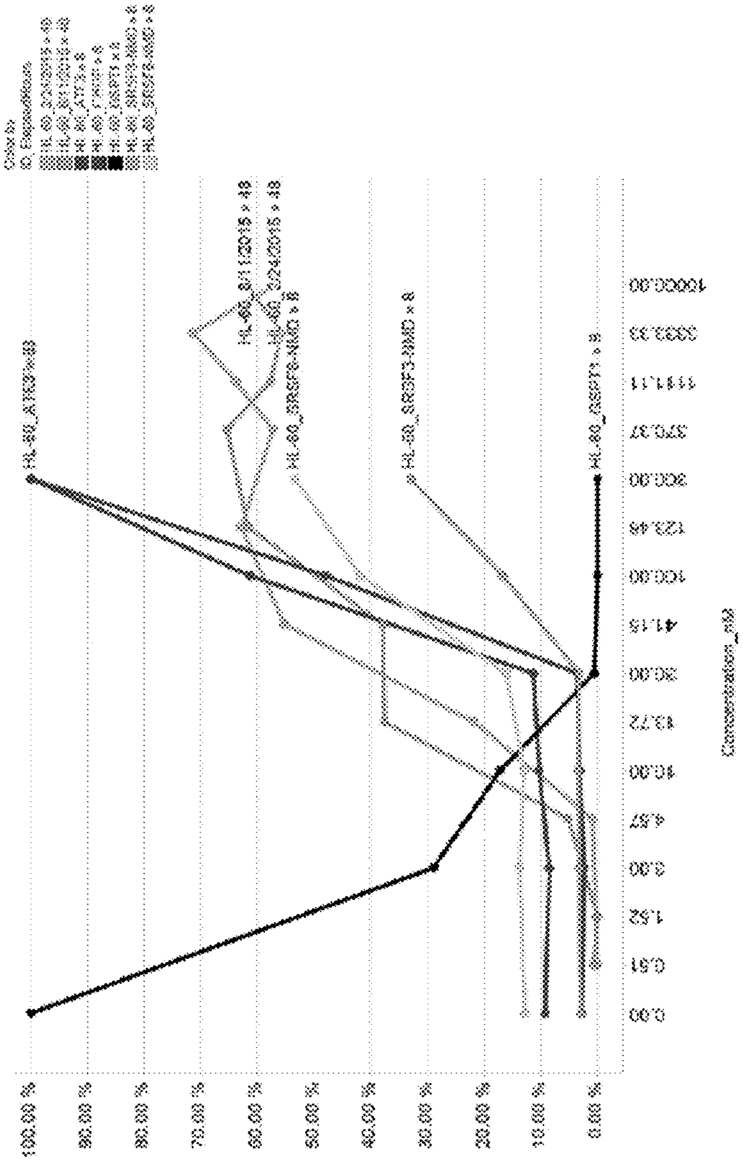

FIGS. 30A-30D show correlation of GSPT1 reduction, UPR pathway activation, and NMD pathway inhibition with apoptosis induction in KG-1 (FIGS. 30A and 30B) and HL-60 (FIGS. 30C and 30D). FIGS. 30A-30C compare caspase 3/7 activation at the 24-hour time point with decrease in GSPT1 protein and increase in ATF3, CHOP, SRSF3 and SRSF6 NMD transcripts at the 8-hour time point. FIGS. 30B-30D compare caspase 3/7 activation at the 48-hour time point with decrease in GSPT1 protein and increase in ATF3, CHOP, SRSF3 and SRSF6 NMD transcripts at the 8-hour time point.

Figure 31A:
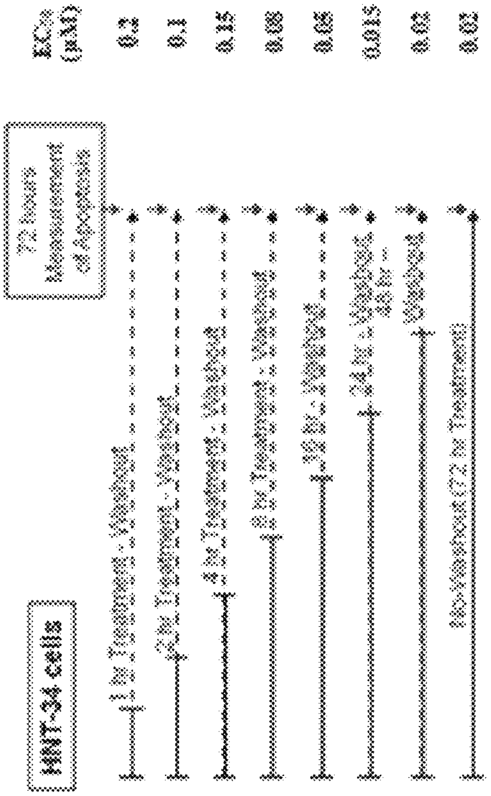
Figure 31B:
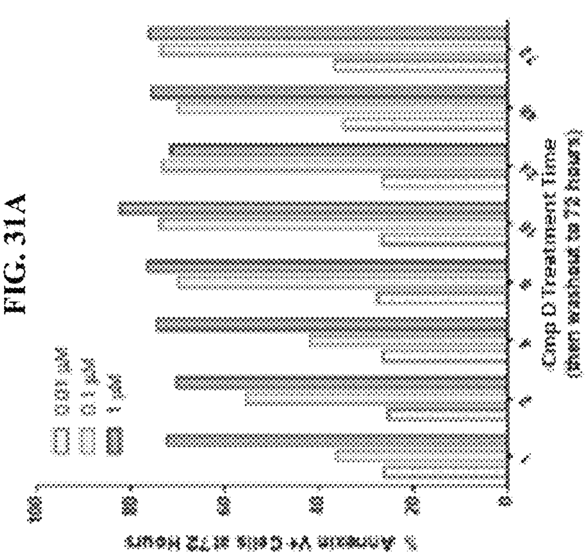

FIGS. 31A and 31B show that Compound D induced apoptosis in the most sensitive AML cell line tested, HNT-34. FIG. 31A shows $EC_{50}$ values of Compound D in inducing apoptosis at different lengths of treatment time. FIG. 31B shows apoptosis level induced by various concentrations of Compound D at different lengths of treatment time.

Figure 32A:
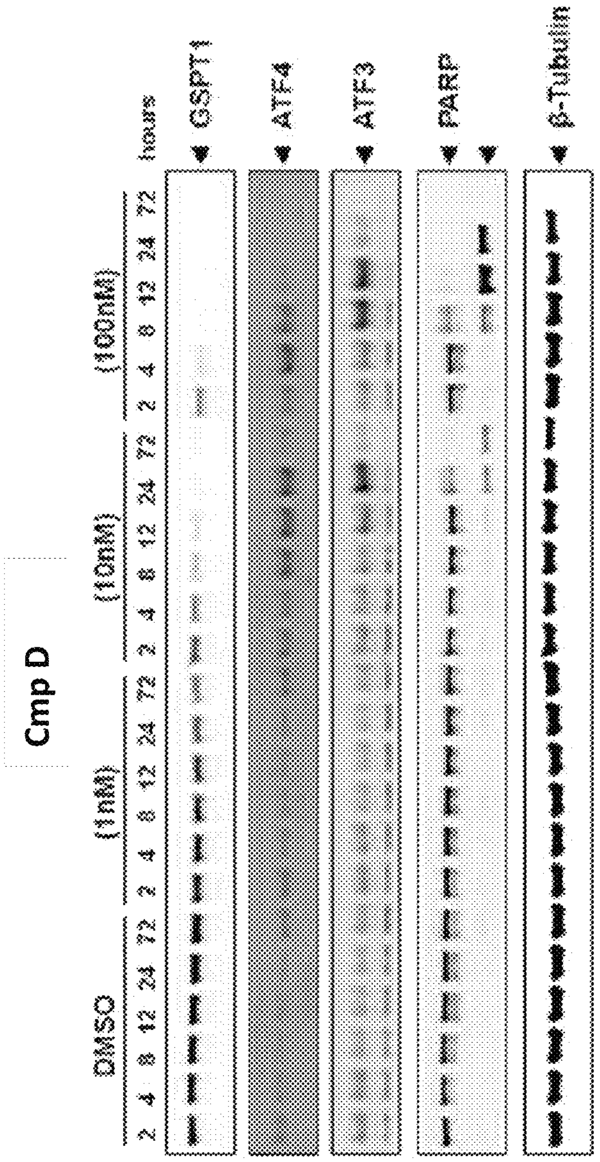
Figures 32B, 32C, 32D, 32E:
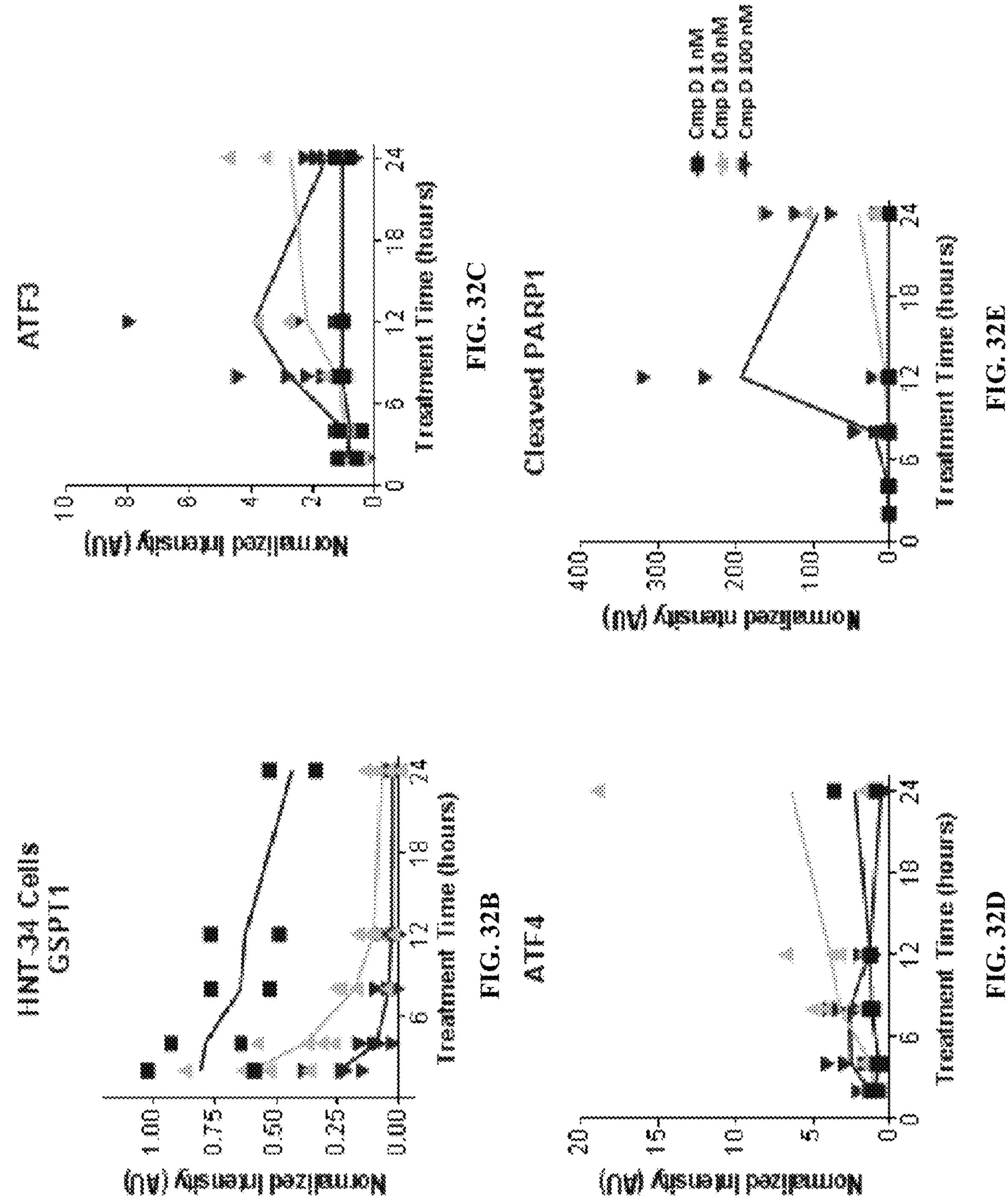
Figure 32F:
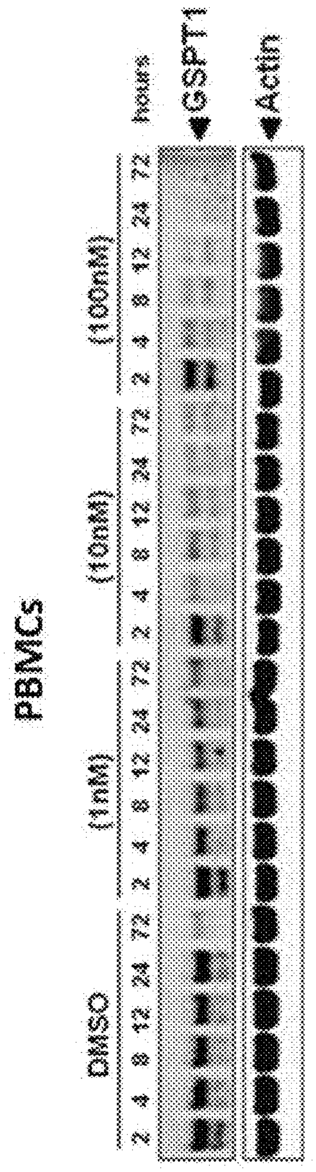
Figure 32G:
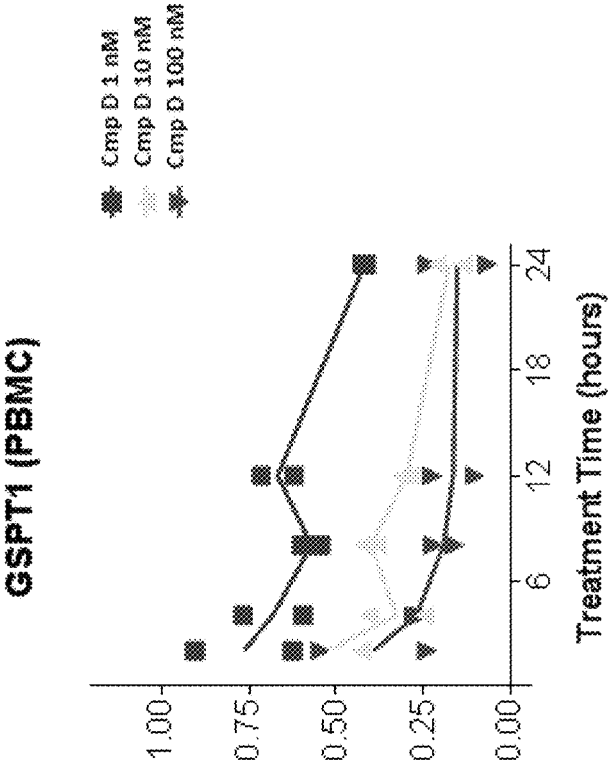

FIGS. 32A-32G show that Compound D induced UPR pathway and subsequent apoptosis in HNT-34 cells (FIGS. 32A-32E) but exhibited reduced effects in PBMCs (FIGS. 32F and 32G). FIG. 32A shows western blot analysis of GSPT1, ATF4, ATF3, and PARP in HNT-34 cells in response to treatment of various concentrations of Compound D for different lengths of time. FIGS. 32B-32E quantify the western blot intensity for GSPT1 (FIG. 32B), ATF3 (FIG. 32C), ATF4 (FIG. 32D), and cleaved PARP (FIG. 32E). FIG. 32F shows western blot analysis of GSPT1 in PBMCs in response to treatment of various concentrations of Compound D for different lengths of time. FIG. 32G quantifies the western blot intensity for GSPT1 in PBMCs.

Figure 33A:
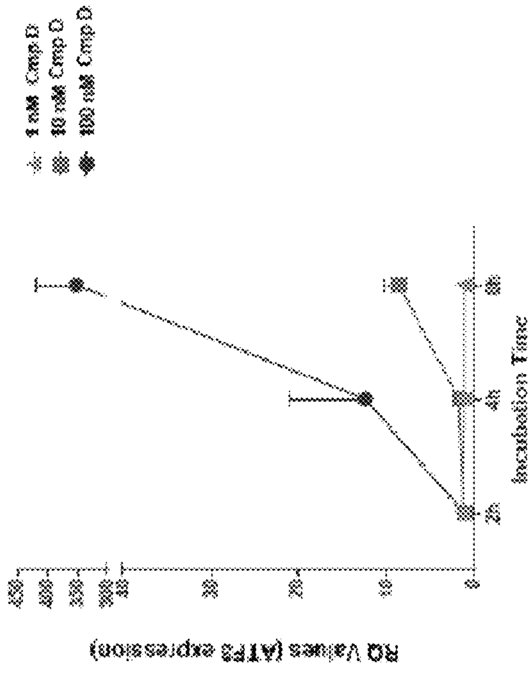
Figure 33B:
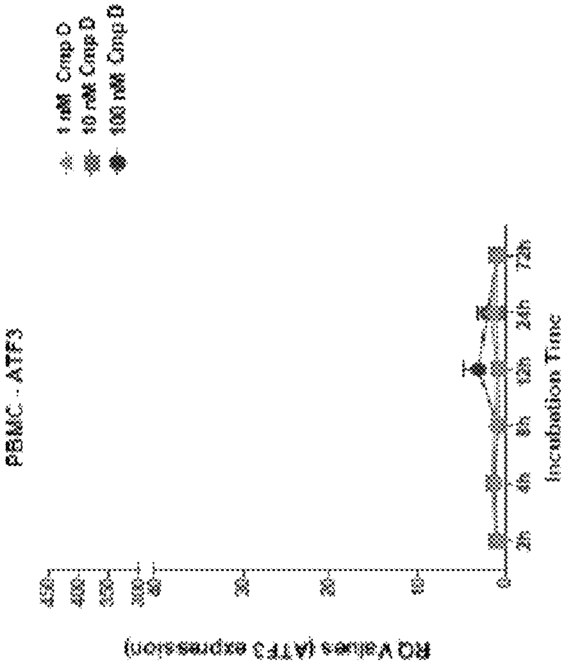
Figure 33D:
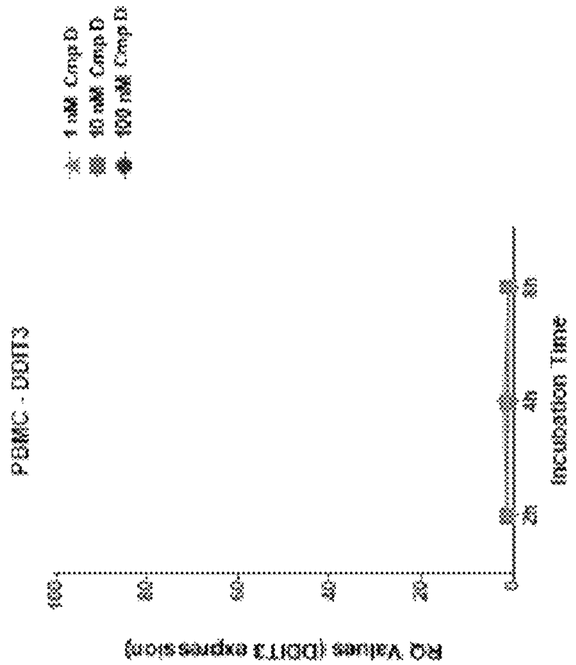

FIGS. 33A-33D show mRNA level of ATF3 (FIGS. 33A and 33B) and DDIT3 (FIGS. 33C and 33D) in response to treatment of various concentrations of Compound D for different lengths of time in HNT-34 cells (FIGS. 33A and 33C) and PBMCs (FIGS. 33B and 33D).

Figure 34:
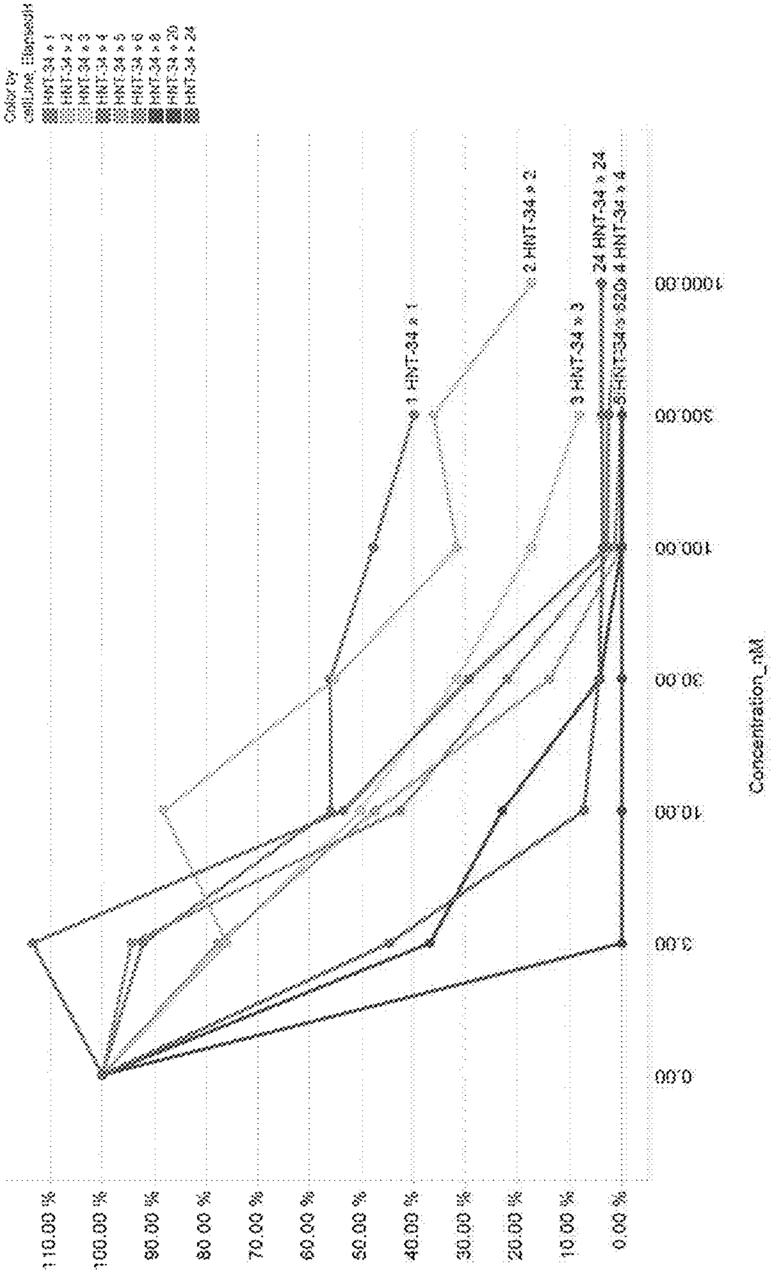

FIG. 34 shows time- and concentration-dependent effect of Compound D on GSPT1 expression in HNT-34 cells.

Figure 35A:
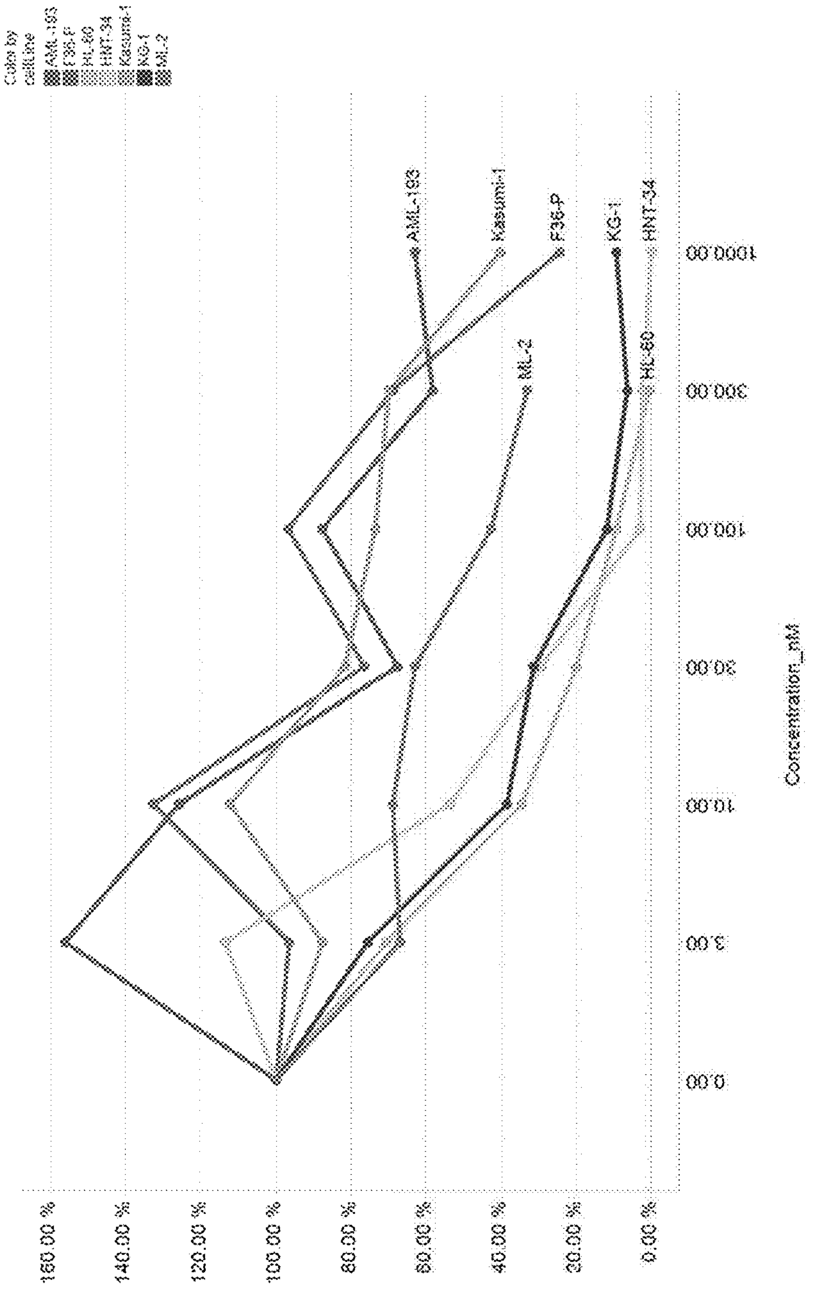
Figure 35B:
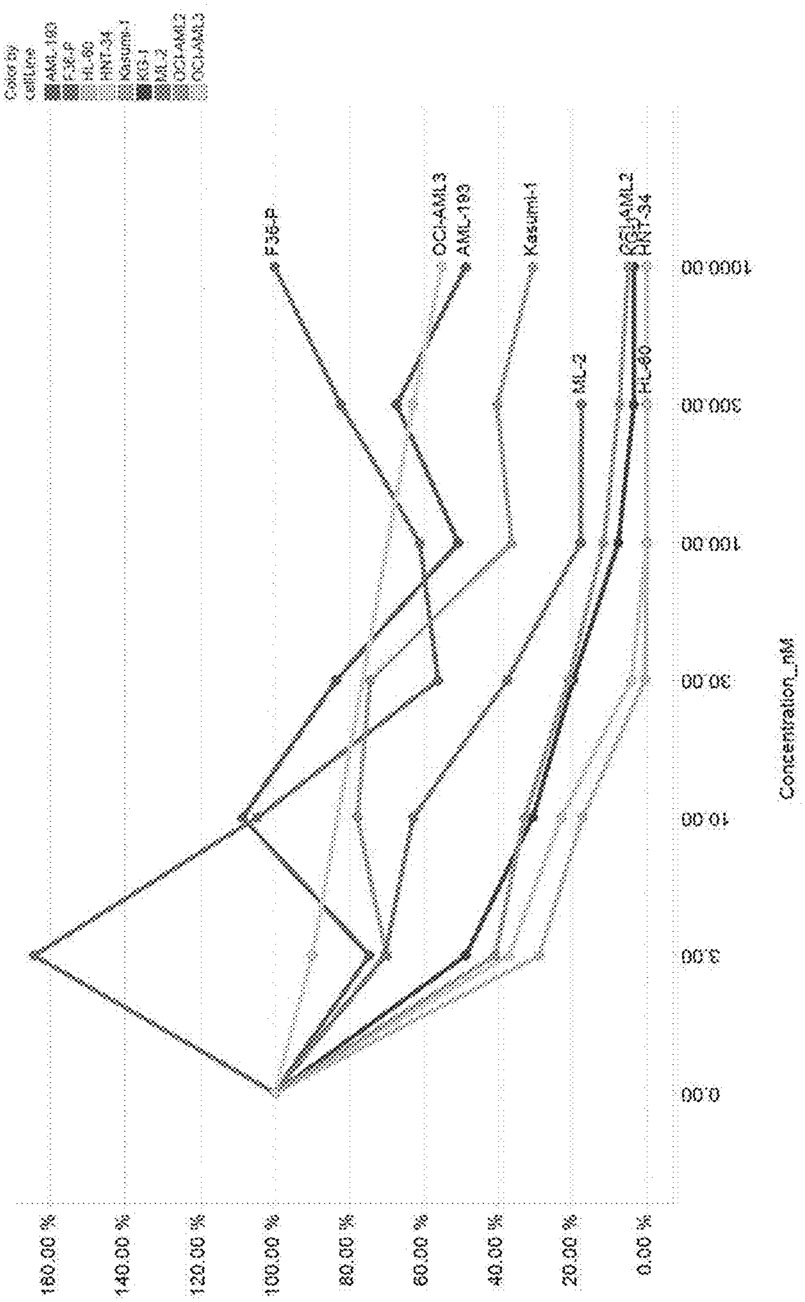
Figure 35C:
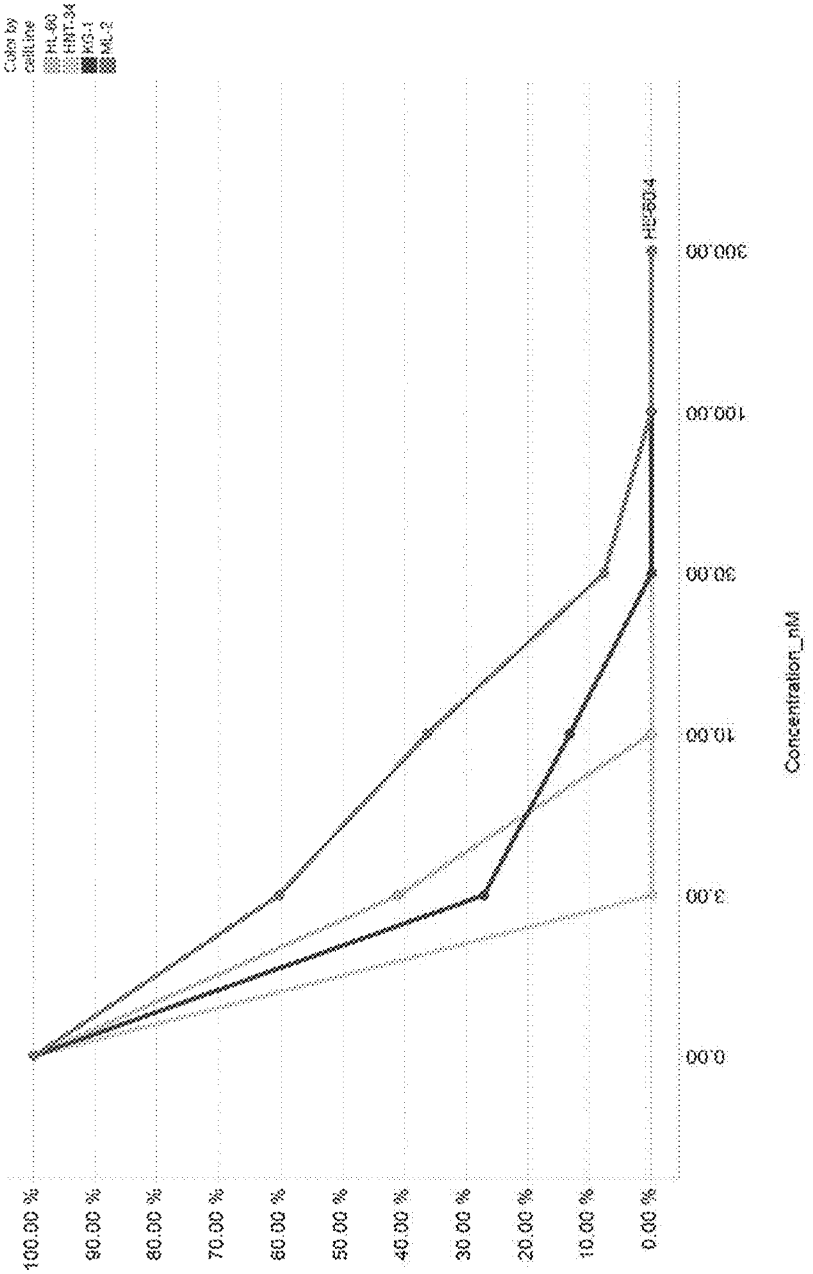
Figure 35D:
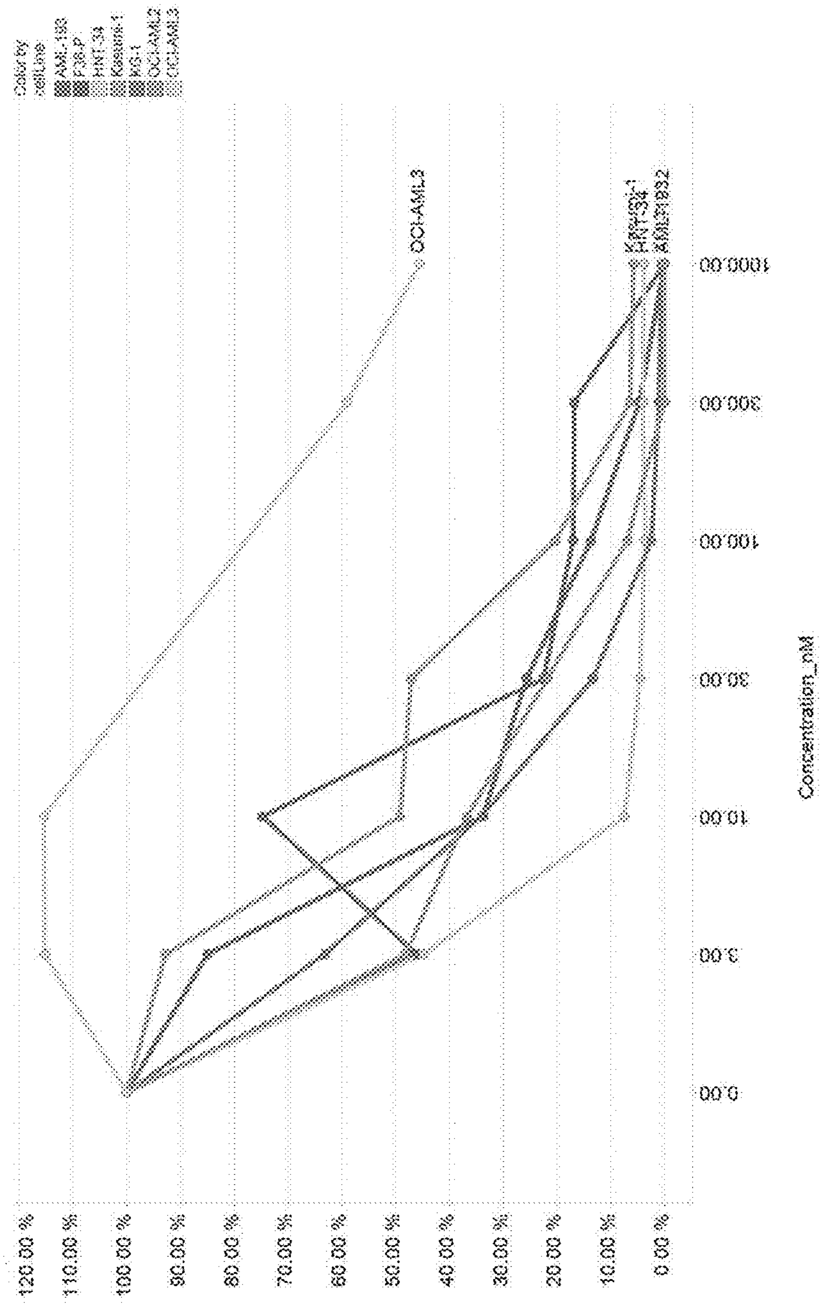

FIGS. 35A-35D show concentration-dependent effect of Compound D on GSPT1 expression in a panel of nine AML cell lines at treatment of 4 hours (FIG. 35A), 8 hours (FIG. 35B), 20 hours (FIG. 35C), and 24 hours (FIG. 35D).

Figure 36:
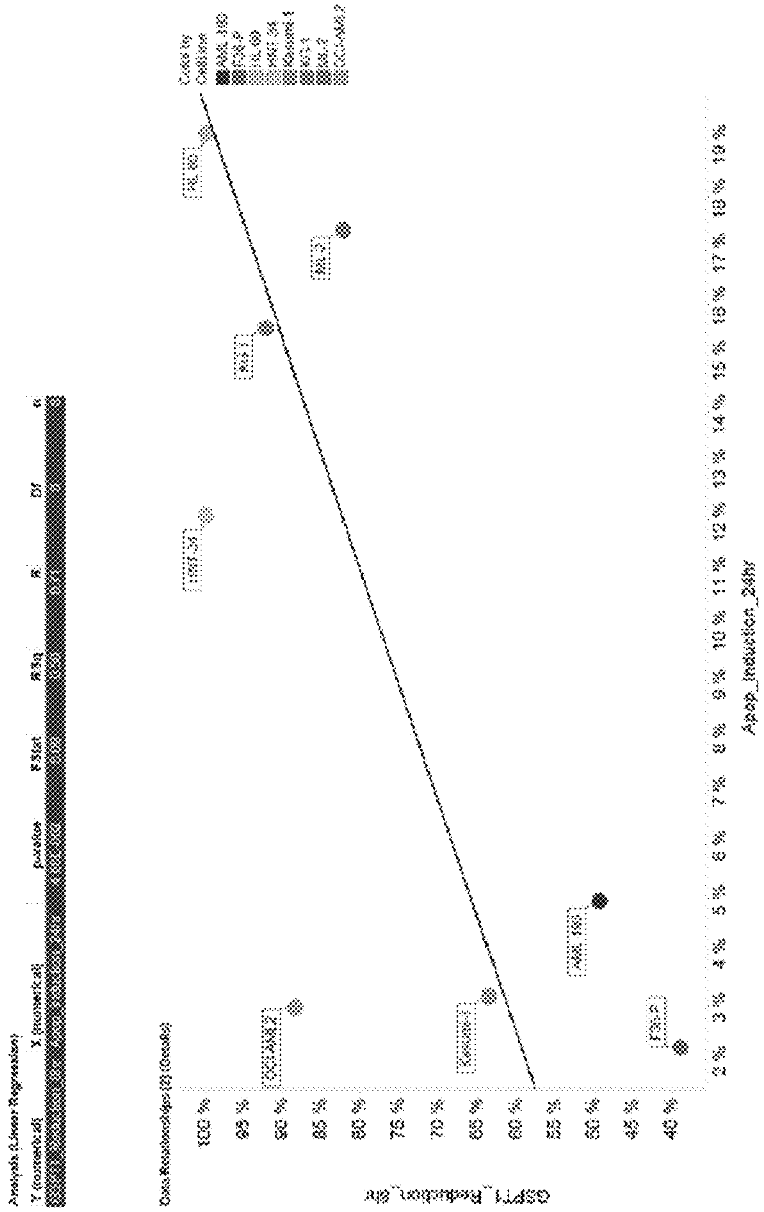

FIG. 36 shows a positive association between the level of GSPT1 reduction and apoptosis induction in the AML cell panel.

5. DETAILED DESCRIPTION OF THE INVENTION

The methods provided herein are based, in part, on the discovery that a changed level, e.g., an increased level and/or a decreased level, of certain molecules (e.g., mRNAs, cDNAs, or proteins) in a biological sample can be used to predict responsiveness of a subject having or suspected to have cancer (e.g., MDS, lymphoma, MM, or leukemia) to a treatment compound (e.g., Compound D, or Compound E, or a stereoisomer or a mixture of stereoisomers, tautomer, pharmaceutically acceptable salt, solvate, isotopologue, prodrug, hydrate, co-crystal, clathrate, or a polymorph thereof).

5.1 Definitions

As used herein, the term "cancer" includes, but is not limited to, solid cancer and blood borne cancer. The term "cancer" refers to disease of tissues or organs, including but not limited to, cancers of the bladder, bone, blood, brain, breast, cervix, chest, colon, endrometrium, esophagus, eye, head, kidney, liver, lymph nodes, lung, mouth, neck, ovaries, pancreas, prostate, rectum, skin, stomach, testis, throat, and uterus. Specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, colorectal cancer, including stage 3 and stage 4 colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma.

As used herein, the term "tumor," refers to all neoplastic cell growth and proliferation, whether malignant or benign, and all pre-cancerous and cancerous cells and tissues. "Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth.

As used herein, "blood borne cancer" or "hematologic malignancy" refers to cancer of the body's blood—forming and immune system—the bone marrow and lymphatic tissue. Such cancers include leukemias, lymphomas (Non-Hodgkin's Lymphoma), Hodgkin's disease (also called Hodgkin's Lymphoma) and myeloma. In one embodiment, the myeloma is multiple myeloma. In some embodiments, the leukemia is, for example, acute myelogenous leukemia (AML), acute lymphocytic leukemia (ALL), adult T-cell leukemia, chronic lymphocytic leukemia (CLL), hairy cell leukemia, myelodysplasia, myeloproliferative disorders, chronic myelogenous leukemia (CML), myelodysplastic syndrome (MDS), human lymphotropic virus-type 1 (HTLV-1) leukemia, mastocytosis, or B-cell acute lymphoblastic leukemia. In some embodiments, the lymphoma is, for example, diffuse large B-cell lymphoma (DLBCL), B-cell immunoblastic lymphoma, small non-cleaved cell lymphoma, human lymphotropic virus-type 1 (HTLV-1) leukemia/lymphoma, adult T-cell lymphoma, peripheral T-cell lymphoma (PTCL), cutaneous T-cell lymphoma (CTCL), mantle cell lymphoma (MCL), Hodgkin lymphoma (HL), non-Hodgkin lymphoma (NHL), AIDS-related lymphoma, follicular lymphoma, small lymphocytic lymphoma, T-cell/histiocyte rich large B-cell lymphoma, transformed lymphoma, primary mediastinal (thymic) large B-cell lymphoma, splenic marginal zone lymphoma, Richter's transformation, nodal marginal zone lymphoma, or ALK-positive large B-cell lymphoma. In one embodiment, the hematological cancer is indolent lymphoma including, for example, DLBCL, follicular lymphoma, or marginal zone lymphoma.

The term "leukemia" refers to malignant neoplasms of the blood-forming tissues. The leukemia includes, but is not limited to, chronic lymphocytic leukemia, chronic myelocytic leukemia, acute lymphoblastic leukemia, acute myeloid leukemia, and acute myeloblastic leukemia. The leukemia can be relapsed, refractory or resistant to conventional therapy.

The term "myelodysplastic syndrome" refers to hematological conditions characterized by abnormalities in the production of one or more of the cellular components of blood (red cells, white cells (other than lymphocytes) and platelets (or their progenitor cells, megakaryocytes)), and includes the following disorders: refractory anemia (RA); RA with ringed sideroblasts (RARS); RA with excess of blasts (RAEB); refractory cytopenia with multilineage dysplasia (RCMD), refractory cytopenia with unilineage dysplasia (RCUD); unclassifiable myelodysplastic syndrome (MDS-U), myelodysplastic syndrome associated with an isolated del(5q) chromosome abnormality, therapy-related myeloid neoplasms and chronic myelomonocytic leukemia (CMML).

As used herein, "promyelocytic leukemia" or "acute promyelocytic leukemia" refers to a malignancy of the bone marrow in which there is a deficiency of mature blood cells in the myeloid line of cells and an excess of immature cells called promyelocytes. It is usually marked by an exchange of regions of chromosomes 15 and 17.

As used herein, "acute lymphocytic leukemia (ALL)", also known as "acute lymphoblastic leukemia" refers to a malignant disease caused by the abnormal growth and development of early nongranular white blood cells, or lymphocytes.

As used herein, "T-cell leukemia" refers to a disease in which certain cells of the lymphoid system called T lymphocytes or T cells are malignant. T cells are white blood cells that normally can attack virus-infected cells, foreign cells, and cancer cells and produce substances that regulate the immune response.

As used herein, and unless otherwise specified, the terms "treat," "treating," and "treatment" refer to an action that occurs while a patient is suffering from the specified cancer, which reduces the severity of the cancer or retards or slows the progression of the cancer.

The term "sensitivity" or "sensitive" when made in reference to treatment with compound is a relative term which refers to the degree of effectiveness of the compound in lessening or decreasing the progress of a tumor or the disease being treated. For example, the term "increased sensitivity" when used in reference to treatment of a cell or tumor in connection with a compound refers to an increase of, at least about 5%, or more, in the effectiveness of the tumor treatment.

As used herein, the terms "compound" and "treatment compound" are used interchangeably, and include the compounds of Formula I. Non-limiting examples of compounds include those disclosed in Section 5.7 below.

As used herein, and unless otherwise specified, the term "therapeutically effective amount" of a compound is an amount sufficient to provide a therapeutic benefit in the treatment or management of a cancer, or to delay or minimize one or more symptoms associated with the presence of the cancer. A therapeutically effective amount of a compound means an amount of therapeutic agent, alone or in combination with other therapies, which provides a therapeutic benefit in the treatment or management of the cancer. The term "therapeutically effective amount" can encompass an amount that improves overall therapy, reduces or avoids symptoms or causes of cancer, or enhances the therapeutic efficacy of another therapeutic agent. The term also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The term "responsiveness" or "responsive" when used in reference to a treatment refers to the degree of effectiveness of the treatment in lessening or decreasing the symptoms of a disease, e.g., MM or AML, being treated. For example, the term "increased responsiveness" when used in reference to a treatment of a cell or a subject refers to an increase in the effectiveness in lessening or decreasing the symptoms of the disease compared to a reference treatment (e.g., of the same cell or subject, or of a different cell or subject) when measured using any methods known in the art. In certain embodiments, the increase in the effectiveness is at least about 5%, at least about 10%, at least about 20%, at least about 30%, at least about 40%, or at least about 50%.

As used herein, the terms "effective subject response," "effective patient response," and "effective patient tumor response" refer to any increase in the therapeutic benefit to the patient. An "effective patient tumor response" can be, for example, about 5%, about 10%, about 25%, about 50%, or about 100% decrease in the rate of progress of the tumor. An "effective patient tumor response" can be, for example, about 5%, about 10%, about 25%, about 50%, or about 100% decrease in the physical symptoms of a cancer. An "effective patient tumor response" can also be, for example, about 5%, about 10%, about 25%, about 50%, about 100%, about 200%, or more increase in the response of the patient, as measured by any suitable means, such as gene expression, cell counts, assay results, tumor size, etc.

An improvement in the cancer or cancer-related disease can be characterized as a complete or partial response. "Complete response" refers to an absence of clinically detectable disease with normalization of any previously abnormal radiographic studies, bone marrow, and cerebrospinal fluid (CSF) or abnormal monoclonal protein measurements. "Partial response" refers to at least about 10%, about 20%, about 30%, about 40%, about 50%, about 60%, about 70%, about 80%, or about 90% decrease in all measurable tumor burden (i.e., the number of malignant cells present in the subject, or the measured bulk of tumor masses or the quantity of abnormal monoclonal protein) in the absence of new lesions. The term "treatment" contemplates both a complete and a partial response.

The term "likelihood" generally refers to an increase in the probability of an event. The term "likelihood" when used in reference to the effectiveness of a patient tumor response generally contemplates an increased probability that the rate of tumor progress or tumor cell growth will decrease. The term "likelihood" when used in reference to the effectiveness of a patient tumor response can also generally mean the increase of indicators, such as mRNA or protein expression, that may evidence an increase in the progress in treating the tumor.

The term "predict" generally means to determine or tell in advance. When used to "predict" the effectiveness of a cancer treatment, for example, the term "predict" can mean that the likelihood of the outcome of the cancer treatment can be determined at the outset, before the treatment has begun, or before the treatment period has progressed substantially.

The term "monitor," as used herein, generally refers to the overseeing, supervision, regulation, watching, tracking, or surveillance of an activity. For example, the term "monitoring the effectiveness of a compound" refers to tracking the effectiveness in treating cancer in a patient or in a tumor cell culture. Similarly, the term "monitoring," when used in connection with patient compliance, either individually, or in a clinical trial, refers to the tracking or confirming that the patient is actually taking a drug being tested as prescribed. The monitoring can be performed, for example, by following the expression of mRNA or protein biomarkers.

"Tumor," as used herein, refers to all neoplastic cell growth and proliferation, whether malignant or benign, and all pre-cancerous and cancerous cells and tissues. "Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth.

As used herein, the term "cereblon-associated protein" or "CAP" refers to a protein that interacts with or binds to cereblon (CRBN) directly or indirectly. For example, the term refers to any protein that directly binds to cereblon, as well as any protein that is an indirect downstream effector of CRBN pathways. In certain embodiments, a "cereblon-associated protein" or "CAP" is a substrate of CRBN, for example, a protein substrate of the E3 ubiquitin ligase complex involving CRBN, or the downstream substrates thereof. In some embodiments, a "cereblon-associated protein" or "CAP" is GSPT1, GSPT2, IKZF1, ATF4, ATF3, or DDIT3.

The term "regulate" as used herein refers to controlling the activity of a molecule or biological function, such as enhancing or diminishing the activity or function.

The terms "cancer" and "cancerous" refer to or describe the physiological condition in mammals that is typically characterized by unregulated cell growth. Examples of cancer include, but are not limited to, blood-borne cancers (e.g., multiple myeloma, lymphoma and leukemia), and solid cancers.

The term "refractory" or "resistant" refers to a circumstance where patients, even after intensive treatment, have residual cancer cells (e.g., leukemia or lymphoma cells) in their lymphatic system, blood, and/or blood forming tissues (e.g., marrow).

The term "relapsed" refers to a situation where patients who have had a remission of cancer after therapy have a return of cancer cells (e.g., leukemia or lymphoma cells) in their lymphatic system, blood, and/or blood forming tissues (e.g. marrow) and a decrease in normal blood cells.

A "biological marker" or "biomarker" is a substance whose detection indicates a particular biological state, such as, for example, the presence of cancer. In some embodiments, biomarkers can be determined individually. In other embodiments, several biomarkers can be measured simultaneously.

In some embodiments, a "biomarker" indicates a change in the level of mRNA expression that may correlate with the risk or progression of a disease, or with the susceptibility of the disease to a given treatment. In some embodiments, the biomarker is a nucleic acid, such as mRNA or cDNA.

In additional embodiments, a "biomarker" indicates a change in the level of polypeptide or protein expression that may correlate with the risk or progression of a disease, or patient's susceptibility to treatment. In some embodiments, the biomarker can be a polypeptide or protein, or a fragment thereof. The relative level of specific proteins can be determined by methods known in the art. For example, antibody based methods, such as an immunoblot, enzyme-linked immunosorbent assay (ELISA), or other methods can be used.

The terms "polypeptide" and "protein," as used interchangeably herein, refer to a polymer of three or more amino acids in a serial array, linked through peptide bonds. The term "polypeptide" includes proteins, protein fragments, protein analogues, oligopeptides, and the like. The term "polypeptide" as used herein can also refer to a peptide. The amino acids making up the polypeptide may be naturally derived, or may be synthetic. The polypeptide can be purified from a biological sample. The polypeptide, protein, or peptide also encompasses modified polypeptides, proteins, and peptides, e.g., glycopolypeptides, glycoproteins, or glycopeptides; or lipopolypeptides, lipoproteins, or lipopeptides.

The term "antibody," "immunoglobulin," or "Ig" as used interchangeably herein, encompasses fully assembled antibodies and antibody fragments that retain the ability to specifically bind to the antigen. Antibodies provided herein include, but are not limited to, synthetic antibodies, monoclonal antibodies, polyclonal antibodies, recombinantly produced antibodies, multispecific antibodies (including bispecific antibodies), human antibodies, humanized antibodies, chimeric antibodies, intrabodies, single-chain Fvs (scFv) (e.g., including monospecific, bispecific, etc.), camelized antibodies, Fab fragments, F(ab') fragments, disulfide-linked Fvs (sdFv), anti-idiotypic (anti-Id) antibodies, and epitope-binding fragments of any of the above. In particular, antibodies provided herein include immunoglobulin molecules and immunologically active portions of immunoglobulin molecules, i.e., antigen binding domains or molecules that contain an antigen-binding site that immunospecifically binds to CRBN antigen (e.g., one or more complementarity determining regions (CDRs) of an anti-CRBN antibody). The antibodies provided herein can be of any class (e.g., IgG, IgE, IgM, IgD, and IgA) or any subclass (e.g., IgG1, IgG2, IgG3, IgG4, IgA1, and IgA2) of immunoglobulin molecule. In some embodiments, the anti-CRBN antibodies are fully human, such as fully human monoclonal CRBN antibodies. In certain embodiments, antibodies provided herein are IgG antibodies, or a subclass thereof (e.g., human IgG1 or IgG4).

The terms "antigen binding domain," "antigen binding region," "antigen binding fragment," and similar terms refer to the portion of an antibody that comprises the amino acid residues that interact with an antigen and confer on the binding agent its specificity and affinity for the antigen (e.g., the CDR). The antigen binding region can be derived from any animal species, such as rodents (e.g., rabbit, rat, or hamster) and humans. In some embodiments, the antigen binding region is of human origin.

The term "epitope" as used herein refers to a localized region on the surface of an antigen that is capable of binding to one or more antigen binding regions of an antibody, that has antigenic or immunogenic activity in an animal, such as a mammal (e.g., a human), and that is capable of eliciting an immune response. An epitope having immunogenic activity is a portion of a polypeptide that elicits an antibody response in an animal. An epitope having antigenic activity is a portion of a polypeptide to which an antibody immunospecifically binds as determined by any method well known in the art, for example, by the immunoassays described herein. Antigenic epitopes need not necessarily be immunogenic. Epitopes usually consist of chemically active surface groupings of molecules, such as amino acids or sugar side chains, and have specific three dimensional structural characteristics as well as specific charge characteristics. A region of a polypeptide contributing to an epitope may be contiguous amino acids of the polypeptide, or the epitope may come together from two or more non-contiguous regions of the polypeptide. The epitope may or may not be a three-dimensional surface feature of the antigen.

The terms "fully human antibody" and "human antibody" are used interchangeably herein and refer to an antibody that comprises a human variable region and, in some embodiments, a human constant region. In specific embodiments, the terms refer to an antibody that comprises a variable region and a constant region of human origin. The term "fully human antibody" includes antibodies having variable and constant regions corresponding to human germline immunoglobulin sequences as described by Kabat et al., *Sequences of Proteins of Immunological Interest*, U.S. Department of Health and Human Services, NIH Publication No. 91-3242 (5th ed. 1991).

The phrase "recombinant human antibody" includes human antibodies that are prepared, expressed, created, or isolated by recombinant means, such as antibodies expressed using a recombinant expression vector transfected into a host cell, antibodies isolated from a recombinant, combinatorial human antibody library, antibodies isolated from an animal (e.g., a mouse or a cow) that is transgenic and/or transchromosomal for human immunoglobulin genes (see, e.g., Taylor et al., *Nucl. Acids Res.* 1992, 20:6287-6295) or antibodies prepared, expressed, created, or isolated by any other means that involves splicing of human immunoglobulin gene sequences to other DNA sequences. Such recombinant human antibodies can have variable and constant regions derived from human germline immunoglobulin sequences. See Kabat et al., *Sequences of Proteins of Immunological Interest*, U.S. Department of Health and Human Services, NIH Publication No. 91-3242 (5th ed. 1991). In certain embodiments, however, such recombinant human antibodies are subjected to in vitro mutagenesis (or, when an animal transgenic for human Ig sequences is used, in vivo somatic mutagenesis) and thus the amino acid sequences of the heavy chain variable and light chain variable regions of the recombinant antibodies are sequences that, while derived from and related to human germline heavy chain variable and light chain variable sequences, may not naturally exist within the human antibody germline repertoire in vivo.

The term "monoclonal antibody" refers to an antibody obtained from a population of homogenous or substantially homogeneous antibodies, and each monoclonal antibody will typically recognize a single epitope on the antigen. In some embodiments, a "monoclonal antibody," as used herein, is an antibody produced by a single hybridoma or other cell, wherein the antibody immunospecifically binds to only an epitope as determined, e.g., by ELISA or other antigen-binding or competitive binding assay known in the art or in the Examples provided herein. The term "monoclonal" is not limited to any particular method for making the antibody. For example, monoclonal antibodies provided herein may be made by the hybridoma method as described in Kohler et al., Nature 1975, 256:495-497, or may be isolated from phage libraries using the techniques as described herein. Other methods for the preparation of clonal cell lines and of monoclonal antibodies expressed thereby are well known in the art. See, e.g., *Short Protocols in Molecular Biology*, Chapter 11 (Ausubel et al., eds., John Wiley and Sons, New York, 5th ed. 2002). Other exemplary methods of producing other monoclonal antibodies are provided in the Examples herein.

"Polyclonal antibodies" as used herein refers to an antibody population generated in an immunogenic response to a protein having many epitopes and thus includes a variety of different antibodies directed to the same or to different epitopes within the protein. Methods for producing polyclonal antibodies are known in the art. See, e.g., *Short Protocols in Molecular Biology*, Chapter 11 (Ausubel et al., eds., John Wiley and Sons, New York, 5th ed. 2002).

The terms "cereblon" or "CRBN" and similar terms refers to the polypeptides ("polypeptides," "peptides," and "proteins" are used interchangeably herein) comprising the amino acid sequence of any CRBN, such as a human CRBN protein (e.g., human CRBN isoform 1, GenBank Accession No. NP_057386; or human CRBN isoforms 2, GenBank Accession No. NP_001166953, each of which is herein incorporated by reference in its entirety), and related polypeptides, including SNP variants thereof. Related CRBN polypeptides include allelic variants (e.g., SNP variants), splice variants, fragments, derivatives, substitution variant, deletion variant, insertion variant, fusion polypeptides, and interspecies homologs, which, in certain embodiments, retain CRBN activity and/or are sufficient to generate an anti-CRBN immune response.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from the RNA molecule to give a protein, a polypeptide, or a portion thereof.

The term "level" refers to the amount, accumulation, or rate of a biomarker molecule. A level can be represented, for example, by the amount or the rate of synthesis of a messenger RNA (mRNA) encoded by a gene, the amount or the rate of synthesis of a polypeptide or protein encoded by a gene, or the amount or the rate of synthesis of a biological molecule accumulated in a cell or biological fluid. The term "level" refers to an absolute amount of a molecule in a sample or a relative amount of the molecule, determined under steady-state or non-steady-state conditions.

An mRNA that is "upregulated" is generally increased upon a given treatment or condition. An mRNA that is "downregulated" generally refers to a decrease in the level of expression of the mRNA in response to a given treatment or condition. In some situations, the mRNA level can remain unchanged upon a given treatment or condition. An mRNA from a patient sample can be "upregulated" when treated with a drug, as compared to a non-treated control. This upregulation can be, for example, an increase of about 5%, about 10%, about 20%, about 30%, about 40%, about 50%, about 60%, about 70%, about 80%, about 90%, about 100%, about 200%, about 300%, about 500%, about 1,000%, about 5,000%, or more of the comparative control mRNA level. Alternatively, an mRNA can be "downregulated", or expressed at a lower level, in response to administration of certain compounds or other agents. A downregulated mRNA can be, for example, present at a level of about 99%, about 95%, about 90%, about 80%, about 70%, about 60%, about 50%, about 40%, about 30%, about 20%, about 10%, about 1%, or less of the comparative control mRNA level.

Similarly, the level of a polypeptide or protein biomarker from a patient sample can be increased when treated with a drug, as compared to a non-treated control. This increase can be about 5%, about 10%, about 20%, about 30%, about 40%, about 50%, about 60%, about 70%, about 80%, about 90%, about 100%, about 200%, about 300%, about 500%, about 1,000%, about 5,000%, or more of the comparative control protein level. Alternatively, the level of a protein biomarker can be decreased in response to administration of certain compounds or other agents. This decrease can be, for example, present at a level of about 99%, about 95%, about 90%, about 80%, about 70%, about 60%, about 50%, about 40%, about 30%, about 20%, about 10%, about 1%, or less of the comparative control protein level.

The terms "determining," "measuring," "evaluating," "assessing," and "assaying" as used herein generally refer to any form of measurement, and include determining whether an element is present or not. These terms include quantitative and/or qualitative determinations. Assessing may be relative or absolute. "Assessing the presence of" can include determining the amount of something present, as well as determining whether it is present or absent.

The terms "nucleic acid" and "polynucleotide" are used interchangeably herein to describe a polymer of any length composed of nucleotides, e.g., deoxyribonucleotides or ribonucleotides, or compounds produced synthetically, which can hybridize with naturally occurring nucleic acids in a sequence specific manner analogous to that of two naturally occurring nucleic acids, e.g., can participate in Watson-Crick base pairing interactions. As used herein in the context of a polynucleotide sequence, the term "bases" (or "base") is synonymous with "nucleotides" (or "nucleotide"), i.e., the monomer subunit of a polynucleotide. The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. "Analogues" refer to molecules having structural features that are recognized in the literature as being mimetics, derivatives, having analogous structures, or other like terms, and include, for example, polynucleotides incorporating non-natural nucleotides, nucleotide mimetics such as 2'-modified nucleosides, peptide nucleic acids, oligomeric nucleoside phosphonates, and any polynucleotide that has added substituent groups, such as protecting groups or linking moieties.

The term "complementary" refers to specific binding between polynucleotides based on the sequences of the polynucleotides. As used herein, a first polynucleotide and a second polynucleotide are complementary if they bind to each other in a hybridization assay under stringent conditions, e.g., if they produce a given or detectable level of signal in a hybridization assay. Portions of polynucleotides are complementary to each other if they follow conventional base-pairing rules, e.g., A pairs with T (or U) and G pairs with C, although small regions (e.g., fewer than about 3 bases) of mismatch, insertion, or deleted sequence may be present.

"Sequence identity" or "identity" in the context of two nucleic acid sequences refers to the residues in the two sequences that are the same when aligned for maximum correspondence over a specified comparison window, and can take into consideration of additions, deletions, and substitutions.

The term "substantial identity" or "homologous" in their various grammatical forms in the context of polynucleotides generally means that a polynucleotide comprises a sequence that has a desired identity, for example, at least 60% identity, at least 70% identity, at least 80% identity, at least 90% identity, and at least 95% identity, compared to a reference sequence. Another indication that nucleotide sequences are substantially identical is if two molecules hybridize to each other under stringent conditions.

The terms "isolated" and "purified" refer to isolation of a substance (such as mRNA, DNA, or protein) such that the substance comprises a substantial portion of the sample in which it resides, i.e., greater than the portion of the substance that is typically found in its natural or un-isolated state. Typically, a substantial portion of the sample comprises, e.g., greater than 1%, greater than 2%, greater than 5%, greater than 10%, greater than 20%, greater than 50%, or more, usually up to about 90%-100% of the sample. For example, a sample of isolated mRNA can typically comprise at least about 1% total mRNA. Techniques for purifying polynucleotides are well known in the art and include, for example, gel electrophoresis, ion-exchange chromatography, affinity chromatography, flow sorting, and sedimentation according to density.

As used herein, the term "bound" indicates direct or indirect attachment. In the context of chemical structures, "bound" (or "bonded") may refer to the existence of a chemical bond directly joining two moieties or indirectly joining two moieties (e.g., via a linking group or any other intervening portion of the molecule). The chemical bond may be a covalent bond, an ionic bond, a coordination complex, hydrogen bonding, van der Waals interactions, or hydrophobic stacking, or may exhibit characteristics of multiple types of chemical bonds. In certain instances, "bound" includes embodiments where the attachment is direct and embodiments where the attachment is indirect.

The term "sample" as used herein relates to a material or mixture of materials, typically, although not necessarily, in fluid form, containing one or more components of interest.

"Biological sample" as used herein refers to a sample obtained from a biological subject, including a sample of biological tissue or fluid origin, obtained, reached, or collected in vivo or in situ. A biological sample also includes samples from a region of a biological subject containing precancerous or cancer cells or tissues. Such samples can be, but are not limited to, organs, tissues, and cells isolated from a mammal. Exemplary biological samples include but are not limited to cell lysate, a cell culture, a cell line, a tissue, oral tissue, gastrointestinal tissue, an organ, an organelle, a biological fluid, a blood sample, a urine sample, a skin sample, and the like. Preferred biological samples include, but are not limited to, whole blood, partially purified blood, PBMC, tissue biopsies, and the like.

The term "analyte" as used herein refers to a known or unknown component of a sample.

The term "capture agent" as used herein refers to an agent that binds an mRNA or protein through an interaction that is sufficient to permit the agent to bind and to concentrate the mRNA or protein from a heterogeneous mixture.

The term "probe" as used herein refers to a capture agent that is directed to a specific target mRNA biomarker sequence. Accordingly, each probe of a probe set has a respective target mRNA biomarker. A probe/target mRNA duplex is a structure formed by hybridizing a probe to its target mRNA biomarker.

The term "nucleic acid probe" or "oligonucleotide probe" refers to a nucleic acid capable of binding to a target nucleic acid of complementary sequence, such as the mRNA biomarkers provided herein, usually through complementary base pairing by forming hydrogen bond. As used herein, a probe may include natural (e.g., A, G, C, or T) or modified bases (7-deazaguanosine, inosine, etc.). In addition, the bases in a probe may be joined by a linkage other than a phosphodiester bond, so long as it does not interfere with hybridization. It will be understood by one of skill in the art that probes may bind target sequences lacking complete complementarity with the probe sequence depending upon the stringency of the hybridization conditions. The probes are preferably directly labeled with tags, for example, chromophores, lumiphores, chromogens, or indirectly labeled with biotin to which a streptavidin complex may later bind. By assaying for the presence or absence of the probe, one can detect the presence or absence of a target mRNA biomarker of interest.

The term "stringent assay conditions" refers to conditions that are compatible to produce binding pairs of nucleic acids, e.g., probes and target mRNAs, of sufficient complementarity to provide for the desired level of specificity in the assay while being generally incompatible to the formation of binding pairs between binding members of insufficient complementarity to provide for the desired specificity. The term "stringent assay conditions" generally refers to the combination of hybridization and wash conditions.

A "label" or "detectable moiety" in reference to a nucleic acid refers to a composition that, when linked with a nucleic acid, renders the nucleic acid detectable, for example, by spectroscopic, photochemical, biochemical, immunochemical, or chemical means. Exemplary labels include, but are not limited to, radioactive isotopes, magnetic beads, metallic beads, colloidal particles, fluorescent dyes, enzymes, biotin, digoxigenin, haptens, and the like. A "labeled nucleic acid or oligonucleotide probe" is generally one that is bound, either covalently through a linker or a chemical bond, or noncovalently through ionic bonds, van der Waals forces, electrostatic attractions, hydrophobic interactions, or hydrogen bonds, to a label such that the presence of the nucleic acid or probe can be detected by detecting the presence of the label bound to the nucleic acid or probe.

The term "polymerase chain reaction" or "PCR" as used herein generally refers to a procedure wherein small amounts of a nucleic acid, RNA and/or DNA, are amplified as described, for example, in U.S. Pat. No. 4,683,195. Generally, sequence information from the ends or beyond of the region of interest needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage, or plasmid sequences, etc. See generally Mullis et al., *Cold Spring Harbor Symp. Quant. Biol.* 1987, 51:263-273; *PCR Technology* (Stockton Press, NY, Erlich, ed., 1989).

The term "cycle number" or "$C_T$" when used herein in reference to PCR methods, refers to the PCR cycle number at which the fluorescence level passes a given set threshold level. The $C_T$ measurement can be used, for example, to approximate levels of mRNA in an original sample. The $C_T$ measurement is often used in terms of "d$C_T$" or the "difference in the $C_T$" score, when the $C_T$ of one nucleic acid is subtracted from the $C_T$ of another nucleic acid.

"Tautomer" as used herein refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

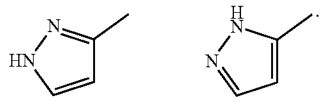

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids know in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like. Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts (calcium, magnesium, sodium, or potassium salts in particular). Suitable organic bases include, but are not limited to, N,N-dibenzylethylenediamine, chloroprocaine, choline, diethanolamine, ethylenediamine, meglumaine (N-methylglucamine), lysine, and procaine.

As used herein and unless otherwise indicated, the term "solvate" means a compound provided herein or a salt thereof that further includes a stoichiometric or non-stoichiometric amount of solvent bound by non-covalent intermolecular forces. Where the solvent is water, the solvate is a hydrate.

As used herein and unless otherwise indicated, the term "co-crystal" means a crystalline form that contains more than one compound in a crystal lattice. Co-crystals include crystalline molecular complexes of two or more non-volatile compounds bound together in a crystal lattice through non-ionic interactions. As used herein, co-crystals include pharmaceutical co-crystals wherein the crystalline molecular complexes containing a therapeutic compound and one or more additional non-volatile compound(s) (referred to herein as counter-molecule(s)). A counter-molecule in a pharmaceutical co-crystal is typically a non-toxic pharmaceutically acceptable molecule, such as, for example, food additives, preservatives, pharmaceutical excipients, or other active pharmaceutical ingredients (API). In some embodiments, pharmaceutical co-crystals enhance certain physicochemical properties of drug products (e.g., solubility, dissolution rate, bioavailability, and/or stability) without compromising the chemical structural integrity of the API. See, e.g., Jones et al., *MRS Bulletin* 2006, 31,875-879; Trask, *Mol. Pharmaceutics* 2007, 4(3):301-309; Schultheiss & Newman, *Crystal Growth & Design* 2009, 9(6):2950-2967; Shan & Zaworotko, *Drug Discovery Today* 2008, 13(9/10):440-446; and Vishweshwar et al., *J. Pharm. Sci.* 2006, 95(3):499-516.

As used herein, and unless otherwise specified, the term "stereoisomer" encompasses all enantiomerically/stereomerically pure and enantiomerically/stereomerically enriched compounds of this invention.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein and unless otherwise indicated, the term "stereomerically enriched" means a composition that comprises greater than about 60% by weight of one stereoisomer of a compound, preferably greater than about 70% by weight, more preferably greater than about 80% by weight of one stereoisomer of a compound. As used herein and unless otherwise indicated, the term "enantiomerically pure" means a stereomerically pure composition of a compound having one chiral center. Similarly, the term "stereomerically enriched" means a stereomerically enriched composition of a compound having one chiral center.

As used herein, and unless otherwise specified, the term "prodrug" means a derivative of a compound that can hydrolyze, oxidize, or otherwise react under biological conditions (in vitro or in vivo) to provide the compound. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include compounds that comprise —NO, —$NO_2$, —ONO, or —$ONO_2$ moieties. Prodrugs can typically be prepared using well-known methods, such as those described in *Burger's Medicinal Chemistry and Drug Discovery,* 172-178, 949-982 (Manfred E. Wolff, ed., 5th ed. 1995), and *Design of Prodrugs* (H. Bundgaard, ed., Elselvier, New York 1985).

It should also be noted compounds can contain unnatural proportions of atomic isotopes at one or more of the atoms. For example, the compounds may be radiolabeled with radioactive isotopes, such as for example tritium ($^3H$), iodine-125 ($^{125}I$), sulfur-35 ($^{35}S$), or carbon-14 ($^{14}C$), or may be isotopically enriched, such as with deuterium ($^2H$), carbon-13 ($^{13}C$), or nitrogen-15 ($^{15}N$). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer and inflammation therapeutic agents, research reagents, e.g., binding assay reagents, and diagnostic agents, e.g., in vivo imaging agents. All isotopic variations of the compounds as described herein, whether radioactive or not, are intended to be encompassed within the scope of the embodiments provided herein. In some embodiments, there are provided isotopologues of the compounds, for example, the isotopologues are deuterium, carbon-13, or nitrogen-15 enriched compounds. In some embodiments, isotopologues provided herein are deuterium enriched compounds. In some embodiments, isotopologues provided herein are deuterium enriched compounds, where the deuteration occurs on the chiral center. In some embodiments, provided herein are isotopologues of the compounds of Formula I, where deuteration occurs on the chiral center. In some embodiments, provided herein are isotopologues of Compound C, where deuteration occurs on the chiral center.

When the groups described herein, with the exception of alkyl group, are said to be "substituted," they may be substituted with any appropriate substituent or substituents. Illustrative examples of substituents are those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; oxygen (=O); B(OH)2, O(alkyl)aminocarbonyl; cycloalkyl, which may be monocyclic or fused or non-fused polycyclic (e.g., cyclopropyl, cyclobutyl, cyclopentyl, or cyclohexyl), or a heterocyclyl, which may be monocyclic or fused or non-fused polycyclic (e.g., pyrrolidyl, piperidyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridyl, quinolinyl, isoquinolinyl, acridinyl, pyrazinyl, pyridazinyl, pyrimidyl, benzimidazolyl, benzothiophenyl, or benzofuranyl) aryloxy; aralkyloxy; heterocyclyloxy; and heterocyclyl alkoxy.

As used herein, and unless otherwise indicated, the term "alkyl" refers to a saturated straight chain or branched hydrocarbon having number of carbon atoms as specified herein. Representative saturated straight chain alkyls include -methyl, -ethyl, -n-propyl, -n-butyl, -n-pentyl, and -n-hexyl; while saturated branched alkyls include -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. An alkyl may be unsubstituted or substituted. When the alkyl groups described herein are said to be "substituted," they may be substituted with any substituent or substituents as those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; B(OH)2, or O(alkyl)aminocarbonyl.

As used herein, and unless otherwise specified, the term "cycloalkyl" means a saturated, or partially saturated cyclic alkyl containing from 3 to 15 carbon atoms, without alternating or resonating double bonds between carbon atoms. It may contain from 1 to 4 rings. Examples of unsubstituted cycloalkyls include, but are not limited to, cyclopropyl, cyclobutyl, cyclopentyl, cyclohexyl, and adamantyl. A cycloalkyl may be substituted with one or more of the substituents as defined below. A cycloalkyl may be unsubstituted or substituted.

As used herein, and unless otherwise specified, the term "alkoxy" refers to —O-(alkyl), wherein alkyl is defined herein. Examples of alkoxy include, but are not limited to, $—OCH_3$, $—OCH_2CH_3$, $—O(CH_2)_2CH_3$, $—O(CH_2)_3CH_3$, $—O(CH_2)_4CH_3$, and $—O(CH_2)_5CH_3$.

As used herein, the term "aryl" means a carbocyclic aromatic ring containing from 5 to 14 ring atoms. The ring atoms of a carbocyclic aryl group are all carbon atoms. Aryl ring structures include compounds having one or more ring structures such as mono-, bi-, or tricyclic compounds as well as benzo-fused carbocyclic moieties such as 5,6,7,8-tetrahydronaphthyl, and the like. Representative aryl groups include phenyl, anthracenyl, fluorenyl, indenyl, azulenyl, phenanthrenyl, and naphthyl. An aryl may be unsubstituted or substituted.

As used herein, and unless otherwise specified, the term "heteroaryl" means an aromatic ring containing from 5 to 14 ring atoms, of which at least one (e.g., one, two, or three) is a heteroatom (e.g., nitrogen, oxygen, or sulfur). Heteroaryl ring structures include compounds having one or more ring structures such as mono-, bi-, or tricyclic compounds, as well as fused heterocyclic moieties. Examples of heteroaryls include, but are not limited to, triazolyl, tetrazolyl, oxadiazolyl, pyridyl, furyl, benzofuranyl, thiophenyl, thiazolyl, benzothiophenyl, benzoisoxazolyl, benzoisothiazolyl, quinolinyl, isoquinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, benzoquinazolinyl, quinoxalinyl, acridinyl, pyrimidyl, oxazolyl, benzo[1,3]dioxole, and 2,3-dihydro-benzo[1,4]dioxine. An heteroaryl may be unsubstituted or substituted.

As used herein, and unless otherwise indicated, the term "heterocycle" means a monocyclic or polycyclic ring comprising carbon and hydrogen atoms, optionally having 1 or 2 multiple bonds, and the ring atoms contain at least one heteroatom, specifically 1 to 3 heteroatoms, independently selected from nitrogen, oxygen, and sulfur. Heterocycle ring structures include, but are not limited to, mono-, bi-, and tri-cyclic compounds. Specific heterocycles are monocyclic or bicyclic. Representative heterocycles include morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, and tetrahydrothiopyranyl. A heterocyclic ring may be unsubstituted or substituted.

As used herein, and unless otherwise specified, the term "heterocycloalkyl" refers to a cycloalkyl group in which at least one of the carbon atoms in the ring is replaced by a heteroatom (e.g., nitrogen, oxygen, or sulfur). A heterocycloalkyl ring may be unsubstituted or substituted.

As used herein, and unless otherwise indicated, the term "alkylenedioxy" refers to multiples of the —$CH_2$ group with an oxygen atom at each end, the —$CH_2$ groups optionally substituted with alkyl groups. Examples include —O—$CH_2$—O-(methylenedioxy), —O—$CH_2CH_2$—O-(ethylenedioxy), —O—$CH_2CH_2CH_2$—O-(trimethylenedioxy), —O—$CH_2CH_2CH_2CH_2$—O-(tetramethylenedioxy), —O—$CH(CH_3)CH_2$—O-(α-methylethylenedioxy), —O—$CH(C_2H_5)CH_2$—O-(α-ethylethylenedioxy), etc.

As used herein, and unless otherwise indicated, the term "alkylthio" refers to groups having the formula Y—S—, wherein Y is alkyl as defined above.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

It should be noted that if there is a discrepancy between a depicted structure and a name given to that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

The practice of the embodiments provided herein will employ, unless otherwise indicated, conventional techniques of molecular biology, microbiology, and immunology, which are within the skill of those working in the art. Such techniques are explained fully in the literature. Examples of particularly suitable texts for consultation include the following: Sambrook et al., *Molecular Cloning: A Laboratory Manual* (2d ed. 1989); Glover, ed., *DNA Cloning*, Volumes I and II (1985); Gait, ed., *Oligonucleotide Synthesis* (1984); Hames & Higgins, eds., *Nucleic Acid Hybridization* (1984); Hames & Higgins, eds., *Transcription and Translation* (1984); Freshney, ed., *Animal Cell Culture: Immobilized Cells and Enzymes* (IRL Press, 1986); *Immunochemical Methods in Cell and Molecular Biology* (Academic Press, London); Scopes, *Protein Purification: Principles and Practice* (Springer Verlag, N.Y., 2d ed. 1987); and Weir & Blackwell, eds., *Handbook of Experimental Immunology*, Volumes I-IV (1986).

5.2 Biomarkers and Methods of Use Thereof

The methods provided herein are based, in part, on the finding that detectable increase or decrease in certain biomarkers upon compound treatment are observed in subjects with cancer (e.g., lymphoma, MM, MDS, or leukemia), who are responsive to a given treatment, e.g., a compound, such as a compound of Formula I, or a stereoisomer or a mixture of stereoisomers, tautomer, pharmaceutically acceptable salt, solvate, isotopologue, prodrug, hydrate, co-crystal, clathrate, or a polymorph thereof, and that the levels of these biomarkers may be used for predicting the responsiveness of the subjects to the treatment. In some embodiments, the compound is as described herein. In certain embodiments, the compound of Formula I is Compound D or Compound E. In one embodiment, the compound of Formula I is Compound D. In another embodiment, the compound of Formula I is Compound E.

A "biological marker" or "biomarker" is a substance, the change and/or the detection of which indicates a particular biological state. In some embodiments, the indication is the responsiveness of a disease, e.g., cancer (e.g., lymphoma, MM, MDS, or leukemia), to a given treatment (e.g., a compound, such as a compound of Formula I, or a stereoisomer or a mixture of stereoisomers, tautomer, pharmaceutically acceptable salt, solvate, isotopologue, prodrug, hydrate, co-crystal, clathrate, or a polymorph thereof).

As described in the Examples and shown in the figures, the levels of certain proteins and/or mRNAs change in response to Compound D or Compound E treatment. These biomarkers include GSPT1, GSPT2, IKZF1, eRF1, BIP, GCN2, eIF2a, ATF4, ATF3, DDIT3, PPP1R15A, TNFRSF10B, GADD45A, FAS, IRE1, XBP1, SEC24D, DNAJB9, EDEM1, ATF6, Caspase 3, Caspase 7, Caspase 8, BID, Caspase 9, PARP, Mcl-1, SRSF3, and SRSF6. Thus, in some embodiments, the biomarker provided herein is selected from the group consisting of GSPT1, GSPT2, IKZF1, eRF1, BIP, GCN2, eIF2a, ATF4, ATF3, DDIT3, PPP1R15A, TNFRSF10B, GADD45A, FAS, IRE1, XBP1, SEC24D, DNAJB9, EDEM1, ATF6, Caspase 3, Caspase 7, Caspase 8, BID, Caspase 9, PARP, Mcl-1, SRSF3, and SRSF6. Each of the biomarkers provided herein includes various isoforms, phosphorylated forms, cleaved forms, modified forms, and splicing variants thereof. For example, eIF2a includes the phosphorylated form of eIF2α (i.e., p-eIF2α). GCN2 includes the phosphorylated form of GCN2 (i.e., p-GCN2). BIP includes the modified form (e.g., C-terminal modified BIP). ATF3 includes the splicing variant of ATF3. Caspase 3 includes the cleaved form of Caspase 3. Caspase 7 includes the cleaved form of Caspase 7. Caspase 8 includes the cleaved form of Caspase 8. Caspase 9 includes the cleaved form of Caspase 9. PARP includes the cleaved form of PARP. Thus, in some embodiments, the levels of the isoforms, phosphorylated forms, cleaved forms, modified forms, and/or splicing variants of these biomarkers increase or decrease in response to the compound treatment, and thus these isoforms, phosphorylated forms, cleaved forms, modified forms, and/or splicing variants of the biomarkers can be used to predict a patient's response.

Eukaryotic peptide chain release factor GTP-binding subunit GSPT1 is also called GSPT1 (G1 to S phase transition protein 1 homolog). It is involved in translation termination in response to the termination codons UAA, UAG, and UGA, and is also involved in regulation of mammalian cell growth. GSPT1 stimulates the activity of eRF1 and is a component of the transient SURF complex, which recruits UPF1 to stalled ribosomes in the context of nonsense-mediated decay (NMD) of mRNAs.

Eukaryotic peptide chain release factor GTP-binding subunit GSPT2 is also called GSPT2 (G1 to S phase transition protein 2 homolog). Like GSPT1, GSPT2 is also involved in translation termination in response to the termination codons UAA, UAG, and UGA, and is a component of the transient SURF complex, which recruits UPF1 to stalled ribosomes in the context of nonsense-mediated decay (NMD) of mRNAs. It is suggested that GSPT2 plays a role as a potent stimulator of the release factor activity of ETF1, and that it may play a role in cell cycle progression. In addition, GSPT2 has been shown to exhibit GTPase activity, which is ribosome- and ETF1-dependent.

Activating Transcription Factor 4 (ATF4) is a transcription factor also known as the cAMP-response element binding protein 2 (CREB-2). It belongs to a family of DNA-binding proteins that includes the AP-1 family, CREBs, and CREB-like proteins.

Activating Transcription Factor 3 (ATF3) belongs to the mammalian activation transcription factor/cAMP responsive element-binding (CREB) protein family of transcription factors. The ATF3 gene is induced by a variety of signals, including many of those encountered by cancer cells, and is involved in the complex process of cellular stress response.

DNA-Damage-Inducible Transcript 3 (DDIT3) is a member of the CCAAT/enhancer-binding protein (C/EBP) family of transcription factors. DDIT3 is also known as C/EBP homologous protein (CHOP). The protein functions as a dominant-negative inhibitor by forming heterodimers with other C/EBP members, such as C/EBP and LAP (liver activator protein), and preventing their DNA binding activity. DDIT3 is a multifunctional transcription factor in endoplasmic reticulum (ER) stress response. It plays an essential role in the response to a wide variety of cell stresses and induces cell cycle arrest and apoptosis in response to ER stress.

IKAROS Family Zinc Finger 1 (IKZF1, also known as Ikaros) is a transcription factor that belongs to the family of zinc-finger DNA-binding proteins associated with chromatin remodeling. The expression of IKZF1 is restricted to the fetal and adult hemo-lymphopoietic system, and it functions as a regulator of lymphocyte differentiation. Most isoforms share a common C-terminal domain, which contains two zinc finger motifs that are required for hetero- or homodimerization, and for interactions with other proteins. The isoforms, however, differ in the number of N-terminal zinc finger motifs that bind DNA and in nuclear localization signal presence, resulting in members with and without DNA-binding properties. Only a few isoforms contain the requisite three or more N-terminal zinc motifs that confer high affinity binding to a specific core DNA sequence element in the promoters of target genes. The non-DNA-binding isoforms are largely found in the cytoplasm, and are thought to function as dominant-negative factors. Overexpression of some dominant-negative isoforms have been associated with B-cell malignancies, such as acute lymphoblastic leukemia (ALL).

Eukaryotic Release Factor 1 (eRF1) is a protein that recognizes all three stop codons in the mRNA sequence and terminates protein translation by releasing the nascent polypeptide. It is a component of the SURF complex that promotes degradation of prematurely terminated mRNAs via the mechanism of nonsense-mediated mRNA decay (NMD).

SEC24D is a member of the SEC24 subfamily of the SEC23/SEC24 family, which is involved in vesicle trafficking. SEC24D is implicated in the shaping of the vesicle, cargo selection and concentration.

DNAJB9 is a member of the J protein family. J proteins regulate the ATPase activity of hsp70s. DNAJB9 is induced during UPR by the ER stress and plays a role in protecting stressed cells from apoptosis.

DNAJC6 is also a member of the J protein family, which regulates molecular chaperone activity by stimulating ATPase activity. DNAJ proteins may have up to 3 distinct domains: a conserved 70-amino acid J domain, usually at the N terminus, a glycine/phenylalanine (G/F)-rich region, and a cysteine-rich domain containing 4 motifs resembling a zinc finger domain.

X-Box Binding Protein 1 (XBP1) is a transcription factor that regulates MHC class II genes by binding to a promoter element referred to as an X box. It is a bZIP protein, identified as a cellular transcription factor that binds to an enhancer in the promoter of the T cell leukemia virus type 1 promoter. It may increase expression of viral proteins by acting as the DNA binding partner of a viral transactivator. XBP1 functions as a transcription factor regulating UPR during the ER stress.

ER Degradation Enhancer Mannosidase Alpha-Like 1 (EDEM1) and ER Degradation Enhancer, Mannosidase Alpha-Like 2 (EDEM2) are directly involved in ER-associated degradation (ERAD) and targets misfolded glycoproteins for degradation in an N-glycan-independent manner.

Hypoxia Up-Regulated 1 (HYOU1) belongs to the heat shock protein 70 family. A cis-acting segment in the 5'-UTR of HYOU1 is involved in stress-dependent induction, resulting in the accumulation of HYOU1 in the ER under hypoxic conditions. HYOU1 plays an important role in protein folding and secretion in the ER. HYOU1 is also up-regulated in tumors, especially in breast tumors, and is associated with tumor invasiveness.

Heat Shock 70 kDa Protein 5 (HSPA5, also known as BIP) is a member of the heat shock protein 70 family. BIP is an ER luminal KDEL protein that requires binding with KDEL receptor in the Cis-Golgi to be retro-transported into the ER lumen for retention. BIP interacts with the ER luminal domain of UPR sensors PERK, IRE1, and ATF6 to prevent their activation. Reduction of BIP C-terminal immunoreactivity indicates a mislocalization of BIP, which presumably leads to its dissociation from PERK, IRE1, and ATF6 and induces UPR.

Eukaryotic Translation Initiation Factor 2a (eIF2a) directs methionyl-initiator tRNA binding to 40S ribosomal subunits and catalyzes the formation of puromycin-sensitive 80S preinitiation complexes. IL-6 signaling pathway and TGF-β receptor signaling are among its related pathways.

Protein Phosphatase 1 Regulatory Subunit 15A (PPP1R15A) belongs to a group of genes, whose mRNA levels are increased following treatment with DNA-damaging agents and stressful growth arrest conditions. In certain cell lines, the induction of PPP1R15A by ionizing radiation occurs regardless of p53 status, and its protein response is correlated with apoptosis following ionizing radiation. GPCR signaling is one of PPP1R15A related pathways.

Growth Arrest and DNA-Damage-Inducible 45 Alpha (GADD45A) is a member of a family of genes, whose mRNA levels are increased following treatment with DNA-damaging agents and stressful growth arrest conditions. GADD45A mediates activation of the p38/JNK pathway via MTK1/MEKK4 kinase, thereby responding to environmental stresses. The DNA damage-induced transcription of this gene is mediated by both p53-dependent and -independent mechanisms.

Tumor Necrosis Factor Receptor Superfamily Member 1A (TNFRSF1A) is a member of the TNF-receptor family. It is one of the major receptors for TNF-alpha. TNFRSF1A activates NF-κB, mediates apoptosis, and regulates inflammation. Antiapoptotic protein BCL2-associated athanogene 4 (BAG4/SODD) and adaptor proteins TRADD and TRAF2 interact with TNFRSF1A, and thus play regulatory roles in the signal transduction mediated by TNFRSF1A. The adapter molecule FADD recruits Caspase-8 to the activated TNFRSF1A. The resulting death-inducing signaling complex (DISC) performs Caspase-8 proteolytic activation, which initiates the subsequent cascade of cysteine-aspartic acid protease (caspase)-mediated apoptosis.

Tumor Necrosis Factor Receptor Superfamily Member 1B (TNFRSF1B) is also a member of the TNF-receptor family. TNFRSF1B associates with TNF-receptor 1, and the heterocomplex recruits two anti-apoptotic proteins, c-IAP1 and c-IAP2, which possess E3 ubiquitin ligase activity. c-IAP1 promotes TNF-induced apoptosis by the ubiquitination and degradation of TNF-receptor-associated factor 2, which mediates anti-apoptotic signals.

Tumor Necrosis Factor Receptor Superfamily Member 10B (TNFRSF10B) is a member of the TNF-receptor family and contains an intracellular death domain. Upon activation by TNF-related apoptosis inducing ligand (TNFSF10/TRAIL/APO-2L), TNFRSF10B transduces an apoptosis signal. FADD, a death domain containing adaptor protein, is required for the apoptosis mediated by TNFRSF10B.

BH3 Interacting Domain (BID) is a death agonist that heterodimerizes with either agonist BAX or antagonist BCL2. BID is a member of the BCL-2 family of cell death regulators. It mediates mitochondrial damage induced by Caspase 8. Caspase 8 cleaves BID, then the C-terminal part of BID translocates to mitochondria and triggers cytochrome c release.

Caspase 8 is a member of the caspase family. Sequential activation of caspases plays a central role in apoptosis. Caspases exist as inactive proenzymes composed of a large protease subunit, a small protease subunit, and a prodomain. Activation of caspases requires proteolysis to generate a heterodimeric enzyme consisting of the large and small subunits. Caspase 8 is involved in the programmed cell death induced by FAS and other apoptotic stimuli. Caspase 8 may interact with Fas-interacting protein FADD through the N-terminal FADD-like death effector domain.

Caspase 9 is a member of the caspase family. Caspase 9 activation is one of the earliest in the caspase activation cascade. Caspase 9 undergoes autoproteolysis and activation by the apoptosome, a protein complex of cytochrome c and the apoptotic peptidase activating factor 1. Caspase 9 is a tumor suppressor and plays a central role in apoptosis.

Caspase 3 is also a member of the caspase family. It cleaves and activates Caspases 6, 7, and 9. Caspase 3 itself is processed by Caspases 8, 9, and 10.

Caspase 7 also belongs to the caspase family. The precursor of Caspase 7 is cleaved by Caspase 3 and 10. It is activated upon cell death stimuli and induces apoptosis.

Poly ADP-Ribose Polymerase (PARP) is a family of proteins involved in regulating various important cellular processes such as differentiation, proliferation, and tumor transformation. PARP also regulates the molecular events involved in cell recovery from DNA damage.

Fas Cell Surface Death Receptor (FAS) is a member of the TNF-receptor family. It contains a death domain. FAS plays a central role in regulating programmed cell death and has been involved in various malignancies and diseases of the immune system. The interaction of FAS with its ligand allows the formation of a death-inducing signaling complex that includes Fas-associated death domain protein (FADD), Caspase 8, and Caspase 10. The autoproteolytic processing of the caspases in the complex triggers a downstream caspase cascade and leads to apoptosis.

Fas-Associated via Death Domain (FADD) interacts with various cell surface receptors and mediates cell apoptotic signals. FADD can be recruited by FAS, TNF receptor, TNFRSF25, and TNFSF10/TRAIL-receptor through its C-terminal death domain, and participates in the death signaling initiated by these receptors. Interaction of FADD with the receptors reveals the N-terminal effector domain of FADD, thus allows it to recruit Caspase-8 and thereby activates the caspase cascade.

Inositol-requiring enzyme 1 (IRE1, also known as ERN1) is a transmembrane ER protein that possesses kinase and endonuclease domains. IRE1 regulates the degradation of misfolded proteins, as part of the UPR pathway. IRE1 catalyzes the splicing of XBP1 mRNA so that the active form of XBP1 protein is produced. Active XBP1, as a transcription factor, upregulates genes involved in the ERAD pathway and induces XBP1 expression and the synthesis of ER chaperones.

Activating Transcription Factor 6 (ATF6) activates target genes for the UPR during ER stress. ATF is a transmembrane ER protein and functions as an ER stress sensor/transducer. Following ER stress-induced proteolysis, ATF functions as a nuclear transcription factor via an ER stress response element (ERSE) present in the promoters of genes encoding ER chaperones.

Myeloid Cell Leukemia 1 (Mcl-1) is a member of the BCL-2 family. BCL-2 family members are regulators of programmed cell death. Alternative splicing results in multiple transcript variants. The longest gene product (isoform 1) inhibits apoptosis and enhances cell survival, while the shorter gene products (isoform 2 and isoform 3) promote apoptosis and induce cell death.

General Control Nonderepressible 2 (GCN2, also called eIF2a, kinase 4) is one of the four kinases that phosphorylate and inactivate eIF2a, resulting in repression of protein synthesis. Amino acid deprivation activates GCN2 by the binding of uncharged tRNA to GCN2. The tRNA binding induces a conformational change in GCN2, which facilitates ATP binding and autophosphorylation of GCN2.

Serine/Arginine-Rich Spicing Factor 3 (SRSF3, also called SFRS3) is a member of the serine/arginine (SR)-rich family of pre-mRNA splicing factors, which form part of the spliceosome. Each SR-rich family member includes an RNA recognition motif (RRM) for binding RNA and an RS domain for binding other proteins. The RS domain, abundant in serine and arginine, facilitates interaction between these splicing factors. The SR family proteins are critical for mRNA splicing, mRNA export from the nucleus, and translation. At least two different transcript variants of SRSF3 have been found: a normal transcript encoding a full-length functional protein and an NMD transcript containing premature stop codons, which may be eliminated through NMD pathway.

Serine/Arginine-Rich Spicing Factor 6 (SRSF6, also called SFRS6) is also a member of the serine/arginine (SR)-rich family of pre-mRNA splicing factors. SRSF6 has been shown to interact with another family member, SRSF12. Alternative splicing generates different transcript variants of SRSF6, including at least a normal transcript encoding a full-length functional protein and an NMD transcript containing premature stop codons.

In certain embodiments of the various methods provided herein, the biomarker is a protein that is directly or indirectly affected by cereblon (CRBN), for example through protein-protein interactions (e.g., certain CRBN substrates or downstream effectors thereof), or through various cellular pathways (e.g., signal transduction pathways). In specific embodiments, the biomarker is a CRBN-associated protein (CAP). In some embodiments, the biomarker is mRNA of a protein that is directly or indirectly affected by CRBN. In other embodiments, the biomarker is cDNA of a protein that is directly or indirectly affected by CRBN. At least two isoforms of the protein CRBN exist, which are 442 and 441 amino acids long, respectively. CRBN has recently been identified as a key molecular target that binds to thalidomide to cause birth defects. See Ito et al., Science 2010, 327: 1345-1350. Damaged DNA-binding protein 1 (DDB1) was found to interact with CRBN and, thus, was indirectly associated with thalidomide. Moreover, thalidomide was able to inhibit auto-ubiquitination of CRBN in vitro, suggesting that thalidomide is an E3 ubiquitin-ligase inhibitor. Id. Importantly, this activity was inhibited by thalidomide in wild-type cells, but not in cells with mutated CRBN binding sites that prevent thalidomide binding. Id. The thalidomide binding site was mapped to a highly conserved C-terminal 104 amino acid region in CRBN. Id. Individual point mutants in CRBN, Y384A and W386A, were both defective for thalidomide binding, with the double mutant having the lowest thalidomide-binding activity. Id. A link between CRBN and the teratogenic effect of thalidomide was confirmed in animal models of zebra-fish and chick embryos. Id.

It is yet to be established whether binding of thalidomide or other drugs to CRBN, the CRBN E3 ubiquitin-ligase complex, or one or more substrates of CRBN, is required for the beneficial effects of these drugs. Understanding the interactions between these drugs and CRBN or CRBN-associated proteins will facilitate elucidating molecular mechanisms of drug efficacy and/or toxicity and may lead to development of new drugs with improved efficacy and toxicity profiles.

As shown in the Examples, the levels of certain CAP changes in response to Compound D or E treatment, such as GSPT1, GSPT2, IKZF1, ATF4, ATF3, and DDIT3. Thus, in some embodiments, the biomarker is a CAP selected from the group consisting of GSPT1, GSPT2, IKZF1, ATF4, ATF3, and DDIT3. In some embodiments, the biomarker is an eRF3 family member, such as GSPT1 or GSPT2. In a specific embodiment, the biomarker is GSPT1. In another specific embodiment, the biomarker is GSPT2. In yet another specific embodiment, the biomarker is IKZF1. In certain embodiments, the biomarker is a CAP selected from the group consisting of ATF4, ATF3, and DDIT3. In one specific embodiment, the biomarker is ATF4. In yet another embodiment, the biomarker is ATF3. In still another embodiment, the biomarker is DDIT3. In other embodiments, the biomarker is a binding partner of, downstream effector thereof, or a factor in a cellular pathway impacted by GSPT1, GSPT2, IKZF1, ATF4, ATF3, or DDIT3. For example, in some embodiments, the biomarker is a binding partner of, downstream effector of, or a factor in a cellular pathway impacted by an eRF3 family member. In a specific embodiment, the biomarker is a binding partner of GSPT1, such as eRF1.

As shown in the Examples, the level of GSPT1, GSPT2, or IKZF1 decreases as compared to a reference in response to Compound D or E treatment. Downregulation of the eRF3 family members result in protein misfolding and/or aggregation, protein mislocation, and direct change of protein function, among other effects. As shown in the Examples, one cellular pathway affected is unfolded protein response (UPR), which is a cellular stress response related to the endoplasmic reticulum (ER). Thus, a factor or a protein involved in UPR or a downstream pathway thereof can be used as a biomarker according to the present disclosure. The pathways related to UPR include, but not limited to, ATF4 signaling pathway way (ATF4 related signaling pathway) and related apoptosis pathway, IRE1 signaling pathway (IRE1 related signaling pathway), and ATF6 signaling pathway (ATF6 related signaling pathway). Thus, in some embodiments, the biomarker provided herein has a function in ER stress pathway. In some embodiments, the biomarker provided herein has a function in UPR pathway. In certain embodiments, the biomarker provided herein has a function in ATF4 related signaling pathway. In other embodiments, the biomarker provided herein has a function in IRE1 related signaling pathway. In yet other embodiments, the biomarker provided herein has a function in ATF6 related signaling pathway. In some embodiments, the biomarker provided herein has a function in FAS/FADD related signaling and apoptosis pathway.

ATF4 related signaling pathway is a signaling pathway activated by phosphorylated eIF2a. Activation of ATF4 leads to its downstream signaling pathway, including components such as ATF3 and DDIT3. This also produces translational attenuation of the protein machinery involved in the cell cycle, producing cell cycle arrest in the G1 phase. ATF related signaling pathway includes any downstream pathways that are directly or indirectly affected by ATF4 pathway. Thus, in some embodiments, the biomarker has a function in ATF4 related signaling pathway. Exemplary biomarkers (components) involved in ATF4 related signaling pathway include, but not limited to, ATF4, ATF3, PPP1R15A, TNFRSF10B, DDIT3, GADD45A, TNFRSF1A, TNFRSF1B, FAS, and FADD.

eIF2α can be phosphorylated by four different kinases, including PERK, GCN2, PKR, and HRI. Thus, the ATF4 related signaling pathway can be activated by PERK, GCN2, PKR, and/or HRI. As shown in the Examples, GCN2 is important for Compound D induced ATF4 signaling pathway. Thus, in certain embodiments, the biomarker provided herein has a function in GCN2 related signaling pathway. Exemplary biomarkers (components) involved in GCN2 related signaling pathway include, but not limited to, GCN2, eIF2a, ATF4, ATF3, PPP1R15A, TNFRSF10B, DDIT3, GADD45A, TNFRSF1A, TNFRSF1B, FAS, and FADD. Also as shown in the Examples, the levels of proteins in GCN2 related signaling pathway change in response to Compound D or E treatment, such as GCN2, eIF2a, ATF4, ATF3, DDIT3, PPP1R15A, TNFRSF10B, GADD45A, and FAS. Thus, in some embodiments, the biomarker provided herein is selected from the group consisting of GCN2, eIF2a, ATF4, ATF3, DDIT3, PPP1R15A, TNFRSF10B, GADD45A, and FAS. In a specific embodiment, the biomarker is GCN2. In another specific embodiment, the biomarker is eIF2a. In yet another specific embodiment, the biomarker is ATF4. In still another specific embodiment, the biomarker is ATF3. In one specific embodiment, the biomarker is DDIT3. In another specific embodiment, the biomarker is PPP1R15A. In yet another specific embodiment, the biomarker is TNFRSF10B. In still another specific embodiment, the biomarker is GADD45A. In a specific embodiment, the biomarker is FAS.

IRE1 related signaling pathway is another signaling pathway activated during UPR. Upon UPR activation, IRE1, an ER transmembrane receptor, activates itself by homodimerization and transautophosphorylation. The activated IRE1 luminal domain is able to activate the transcription factor XBP1 mRNA by splicing a 252 bp intron. The activated XBP1 upregulates expression of UPR-related genes by directly binding to the stress element promoters of these target genes. In certain embodiments, the biomarker has a function in IRE1 related signaling pathway. In some embodiments, the biomarker has a function in XBP1 related signaling pathway. Exemplary biomarkers (components) involved in IRE1 related signaling pathway include, but not limited to, IRE1, XBP1, SEC24D, DNAJB9, DNAJC6, EDEM1, EDEM2, and HYOU1. Exemplary biomarkers (components) involved in XBP1 related signaling pathway include, but not limited to, XBP1, SEC24D, DNAJB9, DNAJC6, EDEM1, EDEM2, and HYOU1. In some embodiments, the biomarker is a protein in IRE1 related pathway, such as IRE1, XBP1, SEC24D, DNAJB9, and EDEM1.

Thus, in some embodiments, the biomarker is selected from the group consisting of IRE1, XBP1, SEC24D, DNAJB9, and EDEM1. In a specific embodiment, the biomarker is IRE1. In another specific embodiment, the biomarker is XBP1. In yet another specific embodiment, the biomarker is SEC24D. In still another specific embodiment, the biomarker is DNAJB9. In a specific embodiment, the biomarker is EDEM1.

ATF6 related signaling pathway is also activated during UPR. Like PERK and IRE1, ATF6 is an ER transmembrane receptor. Upon HSPA5 dissociation from ATF6 during UPR activation, the entire 90 kDa ATF6 translocates to the Golgi, where it is cleaved by proteases to form an active 50 kDa transcription factor that translocates to the nucleus. The 50 kDa ATF6 binds to stress element promoters upstream of genes that are upregulated in the UPR. In certain embodiments, the biomarker has a function in ATF6 related signaling pathway. Exemplary biomarkers (components) involved in ATF6 related signaling pathway include, but not limited to, ATF6, XBP1, EDEM1, EDEM2, HYOU1, and HSPA5. In some embodiments, the biomarker is a protein in ATF6 related pathway, such as ATF6, XBP1, and EDEM1. Thus, in some embodiments, the biomarker is selected from the group consisting of ATF6, XBP1, and EDEM1. In a specific embodiment, the biomarker is ATF6. In another specific embodiment, the biomarker is XBP1. In yet another specific embodiment, the biomarker is EDEM1.

FAS/FADD related signaling and apoptosis pathway is a downstream pathway that may be activated upon UPR. When the primary goals of UPR (such as attenuating protein translation, degrading misfolded proteins, and activating signaling pathways that increase production of chaperone proteins) are not achieved, UPR directs towards apoptosis. Upon stimulation by ligand, FAS receptor trimerizes. FADD, an adaptor protein, bridges FAS to procaspases 8 and 10 to form the death-inducing signaling complex (DISC) during apoptosis. In certain embodiments, the biomarker has a function in FAS/FADD related signaling and apoptosis pathway. Exemplary biomarkers (components) involved in FAS/FADD related signaling and apoptosis pathway include, but not limited to, FAS, FADD, Caspase 8, BID, Caspase 9, Caspase 3, Caspase 7, and PARP. As described in the Examples, the levels of the proteins in apoptosis pathway change in response to Compound D or E treatment. Such proteins include Caspase 3, Caspase 7, Caspase 8, Caspase 9, PARP, and Mcl-1. Thus, in some embodiments, the biomarker is selected from the group consisting of Caspase 3, Caspase 7, Caspase 8, Caspase 9, PARP, and Mcl-1. In a specific embodiment, the biomarker is Caspase 3. In another specific embodiment, the biomarker is Caspase 7. In yet another specific embodiment, the biomarker is Caspase 8. In still another specific embodiment, the biomarker is Caspase 9. In one specific embodiment, the biomarker is PARP. In another specific embodiment, the biomarker is Mcl-1.

NMD related signaling pathway is a surveillance pathway of eukaryotes that decreases errors in gene expression by eliminating nonsense mRNA variants, for example, alternative splicing forms of mRNA that contain premature stop codons. Three main components in NMD pathway include UPF1, UPF2, and UPF3. UPF2 and UPF3 are part of the exon-exon junction complex (EJC) bound to mRNA. Phosphorylation of UPF1 is mediated by SMG-1, SMG-5, SMG-6, and SMG-7. Alternative splicing variants of mRNA containing premature stop codons (such as, NMD transcripts for SRSF3 and SRSF6) can be eliminated by the NMD pathway to reduce aberrant proteins. Exemplary biomarkers involved in NMD related signaling pathway include, but not limited to, components along the NMD pathway (e.g., UPF1, UPF2, UPF3, SMG-1, SMG-5, SMG-6, and SMG-7) and RNA substrates of the NMD pathway (e.g., NMD transcripts for SRSF3 and SRSF6). As described in the Examples, the levels of the RNA substrates of the NMD pathway change in response to Compound D treatment. Such RNA substrates include NMD transcripts for SRSF3 and SRSF6. Thus, in some embodiments, the biomarker is selected from the group consisting of UPF1, UPF2, UPF3, SMG-1, SMG-5, SMG-6, and SMG-7. In other embodiments, the biomarker is an NMD transcript for SRSF3 or SRSF6. In a specific embodiment, the biomarker is an NMD transcript for SRSF3. In another specific embodiment, the biomarker is an NMD transcript for SRSF6.

In some embodiments, the biomarker measured comprises one biomarker. In certain embodiments, the biomarkers measured comprise two biomarkers. In other embodiments, the biomarkers measured comprise three biomarkers. In certain embodiments, the biomarkers measured comprise four biomarkers. In some embodiments, the biomarkers measured comprise five biomarkers. In other embodiments, the biomarkers measured comprise six biomarkers. In yet other embodiments, the biomarkers measured comprise seven biomarkers. In certain embodiments, the biomarkers measured comprise eight biomarkers. In other embodiments, the biomarkers measured comprise nine biomarkers. In another embodiment, the biomarkers measured comprise ten or more biomarkers.

Also provided herein are methods for the treatment or management of cancer using a biomarker, e.g., GSPT1, GSPT2, IKZF1, ATF4, ATF3, DDIT3, cleaved PARP, SRSF3 NMD transcript, or SFSR6 NMD transcript, as a predictive or prognostic factor for the compounds provided herein. In certain embodiments, provided herein are methods for screening or identifying cancer patients, e.g., multiple myeloma, lymphoma, MDS, or leukemia patients, for treatment with a compound using the level of one or more biomarkers provided herein, e.g., GSPT1, GSPT2, IKZF1, ATF4, ATF3, DDIT3, cleaved PARP, SRSF3 NMD transcript, or SFSR6 NMD transcript, as a predictive or prognostic factor. In some embodiments, provided herein are methods for selecting patients having a higher response rate to therapy with a compound provided herein, using a biomarker (e.g., GSPT1, GSPT2, IKZF1, ATF4, ATF3, DDIT3, cleaved PARP, SRSF3 NMD transcript, or SFSR6 NMD transcript) level as a predictive or prognostic factor. In certain embodiments, the compound of Formula I is Compound D or Compound E. In one embodiment, the compound of Formula I is Compound D. In another embodiment, the compound of Formula I is Compound E.

In one aspect, provided herein is a method of identifying a subject having cancer who is likely to be responsive to a treatment compound, comprising:

(a) administering the treatment compound to the subject;

(b) obtaining a sample from the subject;

(c) determining the level of a biomarker in the sample; and (d) diagnosing the subject as being likely to be responsive to the treatment compound if the level of the biomarker in the sample is different from a reference level of the biomarker;

wherein the treatment compound is a compound of Formula I:

I

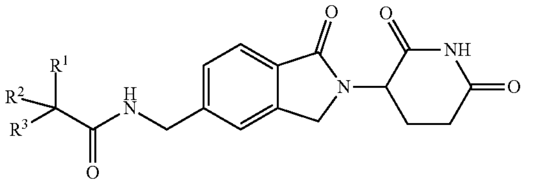

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, —$R^4OR^4N(R^6)(R^7)$, or —$R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In another aspect, provided herein is a method of identifying a subject having cancer who is likely to be responsive to a treatment compound, comprising:

(a) obtaining a sample from the subject;

(b) administering the treatment compound to the sample;

(c) determining the level of a biomarker in the sample; and (d) diagnosing the subject as being likely to be responsive to the treatment compound if the level of the biomarker in the sample is different from a reference level of the biomarker; wherein the treatment compound is a compound of Formula I:

I

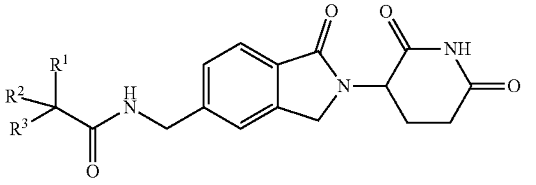

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, —$R^4OR^4N(R^6)(R^7)$, or —$R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In some embodiments of the methods provided herein, administering a treatment compound to the sample from the subject having cancer is performed in vitro. In other embodiments, administering a treatment compound to the sample from the subject having cancer is performed in vivo. In certain embodiments, the sample is cells. In one embodiment, the cells are contacted with the compound for a period of time, e.g., 5, 10, 15, 20, 25, 30, 35, 40, 45, 50, or 55 minutes, or 1, 2, 3, 4, 5, 6, 7, 8, 9, 10, 11, 12, 13, 14, 15, 16, 17, 18, 19, 20, 21, 22, 23, or 24 hours, or 2, 3, or more days. In other embodiments, the cells are obtained from a subject having (or suspected of having) cancer.

In some embodiments, the level of the biomarker in the sample of the subject is higher than the reference level of the biomarker. In other embodiments, the level of the biomarker in the sample of the subject is lower than the reference level of the biomarker.

In another aspect, when a subject is diagnosed as being likely to be responsive to a treatment compound, the methods provided herein further comprise administering a therapeutically effective amount of the treatment compound to the subject.

Thus, in some embodiments, provided herein is a method of treating cancer, comprising:

(a) obtaining a sample from a subject having the cancer;

(b) determining the level of a biomarker in the sample;

(c) diagnosing the subject as being likely to be responsive to a treatment compound if the level of the biomarker in the sample is different from a reference level of the biomarker; and (d) administering a therapeutically effective amount of the treatment compound to the subject;

wherein the treatment compound is a compound of Formula I:

I

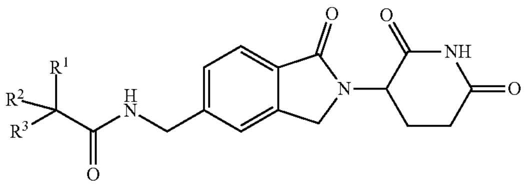

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, $—R^4OR^5$, $—R^4SR^5$, $—R^4N(R^6)(R^7)$, $—R^4OR^4N(R^6)(R^7)$, or $—R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In certain embodiments of the methods provided herein, the compound of Formula I is Compound D or Compound E. In one embodiment, the compound of Formula I is Compound D. In another embodiment, the compound of Formula I is Compound E.

In some embodiments of the methods provided herein, administering a treatment compound to a subject having cancer is performed in vitro. In other embodiments, administering a treatment compound to a subject having cancer is performed in vivo. In certain embodiments, the sample is cells. In one embodiment, the cells are contacted with the compound for a period of time, e.g., 5, 10, 15, 20, 25, 30, 35, 40, 45, 50, or 55 minutes, or 1, 2, 3, 4, 5, 6, 7, 8, 9, 10, 11, 12, 13, 14, 15, 16, 17, 18, 19, 20, 21, 22, 23, or 24 hours, or 2, 3, or more days. In other embodiments, the cells are obtained from a subject having (or suspected of having) the cancer.

In some embodiments, the level of the biomarker in the sample of the subject is higher than the reference level of the biomarker. In other embodiments, the level of the biomarker in the sample of the subject is lower than the reference level of the biomarker.

In some embodiments of the various methods provided herein, a treatment compound is administered to a patient likely to be responsive to the treatment compound. Also provided herein are methods of treating patients who have been previously treated for cancer but are non-responsive to standard therapies, as well as those who have not previously been treated. The invention also encompasses methods of treating patients regardless of patient's age, although some diseases or disorders are more common in certain age groups. The invention further encompasses methods of treating patients who have undergone surgery in an attempt to treat the disease or condition at issue, as well as those who have not. Because patients with cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer.

In certain embodiments, a therapeutically or prophylactically effective amount of the compound is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, or from about 0.05 to about 10 mg per day.

In certain embodiments, the therapeutically or prophylactically effective amount is about 0.1, about 0.2, about 0.5, about 1, about 2, about 5, about 10, about 15, about 20, about 25, about 30, about 40, about 45, about 50, about 60, about 70, about 80, about 90, about 100, or about 150 mg per day.

In one embodiment, the recommended daily dose range of the compound of Formula I, or a stereoisomer or a mixture of stereoisomers, tautomer, pharmaceutically acceptable salt, solvate, isotopologue, prodrug, hydrate, co-crystal, clathrate, or a polymorph thereof, for the conditions described herein lie within the range of from about 0.1 mg to about 50 mg per day, preferably given as a single once-a-day dose, or in divided doses throughout a day. In some embodiments, the dosage ranges from about 1 mg to about 50 mg per day. In other embodiments, the dosage ranges from about 0.5 mg to about 5 mg per day. Specific doses per day include 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mg per day. In certain embodiments, the compound of Formula I is Compound D or Compound E. In one embodiment, the compound of Formula I is Compound D. In another embodiment, the compound of Formula I is Compound E.

In a specific embodiment, the recommended starting dosage may be 0.5, 1, 2, 3, 4, 5, 10, 15, 20, 25, or 50 mg per day. In another embodiment, the recommended starting dosage may be 0.5, 1, 2, 3, 4, or 5 mg per day. The dose may be escalated to 10, 15, 20, 25, 30, 35, 40, 45, or 50 mg per day. In a specific embodiment, the compound can be administered in an amount of about 25 mg per day to patients with leukemia, including AML. In a particular embodiment, the compound can be administered in an amount of about 10 mg per day to patients with leukemia, including AML.

In certain embodiments, the therapeutically or prophylactically effective amount is from about 0.001 to about 100 mg/kg/day, from about 0.01 to about 50 mg/kg/day, from about 0.01 to about 25 mg/kg/day, from about 0.01 to about 10 mg/kg/day, from about 0.01 to about 9 mg/kg/day, 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, or from about 0.01 to about 1 mg/kg/day.

The administered dose can also be expressed in units other than mg/kg/day. For example, doses for parenteral administration can be expressed as $mg/m^2$/day. One of ordinary skill in the art would readily know how to convert doses from mg/kg/day to $mg/m^2$/day to given either the height or weight of a subject or both (see, www.fda.gov/cder/cancer/animalframe.htm). For example, a dose of 1 mg/kg/day for a 65 kg human is approximately equal to 38 $mg/m^2$/day.

In certain embodiments, the amount of the compound administered is sufficient to provide a plasma concentration of the compound at steady state, ranging from about 0.001 to about 500 μM, about 0.002 to about 200 μM, about 0.005 to about 100 μM, about 0.01 to about 50 μM, from about 1 to about 50 μM, about 0.02 to about 25 μM, from about 0.05 to about 20 μM, from about 0.1 to about 20 μM, from about 0.5 to about 20 μM, or from about 1 to about 20 μM.

In other embodiments, the amount of the compound administered is sufficient to provide a plasma concentration of the compound at steady state, ranging from about 5 to about 100 nM, about 5 to about 50 nM, about 10 to about 100 nM, about 10 to about 50 nM, or from about 50 to about 100 nM.

As used herein, the term "plasma concentration at steady state" is the concentration reached after a period of administration of a compound provided herein, e.g., the compound of Formula I, or a stereoisomer or a mixture of stereoisomers, tautomer, pharmaceutically acceptable salt, solvate, isotopologue, prodrug, hydrate, co-crystal, clathrate, or a polymorph thereof. Once steady state is reached, there are minor peaks and troughs on the time-dependent curve of the plasma concentration of the compound.

In certain embodiments, the amount of the compound administered is sufficient to provide a maximum plasma concentration (peak concentration) of the compound, ranging from about 0.001 to about 500 μM, about 0.002 to about 200 μM, about 0.005 to about 100 PM, about 0.01 to about 50 μM, from about 1 to about 50 μM, about 0.02 to about 25 μM, from about 0.05 to about 20 μM, from about 0.1 to about 20 μM, from about 0.5 to about 20 μM, or from about 1 to about 20 μM.

In certain embodiments, the amount of the compound administered is sufficient to provide a minimum plasma concentration (trough concentration) of the compound, ranging from about 0.001 to about 500 μM, about 0.002 to about 200 μM, about 0.005 to about 100 PM, about 0.01 to about 50 μM, from about 1 to about 50 μM, about 0.01 to about 25 μM, from about 0.01 to about 20 μM, from about 0.02 to about 20 μM, from about 0.02 to about 20 μM, or from about 0.01 to about 20 μM.

In certain embodiments, the amount of the compound administered is sufficient to provide an area under the curve (AUC) of the compound, ranging from about 100 to about 100,000 ng*hr/mL, from about 1,000 to about 50,000 ng*hr/mL, from about 5,000 to about 25,000 ng*hr/mL, or from about 5,000 to about 10,000 ng*hr/mL.

In certain embodiments, the patient to be treated with one of the methods provided herein has not been treated with anticancer therapy prior to the administration of the compound of Formula I, or a stereoisomer or a mixture of stereoisomers, tautomer, pharmaceutically acceptable salt, solvate, isotopologue, prodrug, hydrate, co-crystal, clathrate, or a polymorph thereof. In certain embodiments, the patient to be treated with one of the methods provided herein has been treated with anticancer therapy prior to the administration of the compound of Formula I, or a stereoisomer or a mixture of stereoisomers, tautomer, pharmaceutically acceptable salt, solvate, isotopologue, prodrug, hydrate, co-crystal, clathrate, or a polymorph thereof. In certain embodiments, the patient to be treated with one of the methods provided herein has developed drug resistance to the anticancer therapy. In certain embodiments, the compound of Formula I is Compound D or Compound E. In one embodiment, the compound of Formula I is Compound D. In another embodiment, the compound of Formula I is Compound E.

Depending on the disease to be treated and the subject's condition, the compound of Formula I, or a stereoisomer or a mixture of stereoisomers, tautomer, pharmaceutically acceptable salt, solvate, isotopologue, prodrug, hydrate, co-crystal, clathrate, or a polymorph thereof, may be administered by parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. The compound of Formula I, or a stereoisomer or a mixture of stereoisomers, tautomer, pharmaceutically acceptable salt, solvate, isotopologue, prodrug, hydrate, co-crystal, clathrate, or a polymorph thereof, may be formulated, alone or together, in suitable dosage unit with pharmaceutically acceptable excipients, carriers, adjuvants, and vehicles, appropriate for each route of administration. In certain embodiments, the compound of Formula I is Compound D or Compound E. In one embodiment, the compound of Formula I is Compound D. In another embodiment, the compound of Formula I is Compound E.

In one embodiment, the compound of Formula I, or a stereoisomer or a mixture of stereoisomers, tautomer, pharmaceutically acceptable salt, solvate, isotopologue, prodrug, hydrate, co-crystal, clathrate, or a polymorph thereof, is administered parenterally. In another embodiment, the compound of Formula I, or a stereoisomer or a mixture of stereoisomers, tautomer, pharmaceutically acceptable salt, solvate, isotopologue, prodrug, hydrate, co-crystal, clathrate, or a polymorph thereof, is administered intravenously. In certain embodiments, the compound of Formula I is Compound D or Compound E. In one embodiment, the compound of Formula I is Compound D. In another embodiment, the compound of Formula I is Compound E.

The compound of Formula I, or a stereoisomer or a mixture of stereoisomers, tautomer, pharmaceutically acceptable salt, solvate, isotopologue, prodrug, hydrate, co-crystal, clathrate, or a polymorph thereof, can be delivered as a single dose (e.g., a single bolus injection), or over time (e.g., continuous infusion over time or divided bolus doses over time). The compound can be administered repeatedly if necessary, for example, until the patient experiences stable disease or regression, or until the patient experiences disease progression or unacceptable toxicity. For example, stable disease for solid cancers generally means that the perpendicular diameter of measurable lesions has not increased by 25% or more from the last measurement. Therasse et al., *J. Natl. Cancer Inst.* 2000, 92(3):205-216. Stable disease or lack thereof is determined by methods known in the art such as evaluation of patient symptoms, physical examination, and visualization of the tumor that has been imaged using X-ray, CAT, PET, MRI scan, or other commonly accepted evaluation modalities. In certain embodiments, the compound of Formula I is Compound D or Compound E. In one embodiment, the compound of Formula I is Compound D. In another embodiment, the compound of Formula I is Compound E.

The compound of Formula I, or a stereoisomer or a mixture of stereoisomers, tautomer, pharmaceutically acceptable salt, solvate, isotopologue, prodrug, hydrate, co-crystal, clathrate, or a polymorph thereof, can be administered once daily (QD) or divided into multiple daily doses such as twice daily (BID), three times daily (TID), and four times daily (QID). In addition, the administration can be continuous (i.e., daily for consecutive days or every day) or intermittent, e.g., in cycles (i.e., including days, weeks, or months of rest without drug). As used herein, the term "daily" is intended to mean that a therapeutic compound, such as the compound of Formula I, or a stereoisomer or a mixture of stereoisomers, tautomer, pharmaceutically acceptable salt, solvate, isotopologue, prodrug, hydrate, co-crystal, clathrate, or a polymorph thereof, is administered once or more than once each day, for example, for a period of time. The term "continuous" is intended to mean that a therapeutic compound, such as the compound of Formula I, or a stereoisomer or a mixture of stereoisomers, tautomer, pharmaceutically acceptable salt, solvate, isotopologue, prodrug, hydrate, co-crystal, clathrate, or a polymorph thereof, is administered daily for an uninterrupted period of at least 10 days to 52 weeks. The term "intermittent" or "intermittently" as used herein is intended to mean stopping and starting at either regular or irregular intervals. For example, intermittent administration of the compound of Formula I, or a stereoisomer or a mixture of stereoisomers, tautomer, pharmaceutically acceptable salt, solvate, isotopologue, prodrug, hydrate, co-crystal, clathrate, or a polymorph thereof, is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as the compound of Formula I, or a stereoisomer or a mixture of stereoisomers, tautomer, pharmaceutically acceptable salt, solvate, isotopologue, prodrug, hydrate, co-crystal, clathrate, or a polymorph thereof, is administered daily or continuously but with a rest period. In certain embodiments, the rest period is the same length as the treatment period. In other embodiments, the rest period has different length from the treatment period. In some embodiments, the length of cycling is 1, 2, 3, 4, 5, 6, 7, 8, 9, or 10 weeks. In some embodiments of cycling, a therapeutic compound, such as the compound of Formula I, or a stereoisomer or a mixture of stereoisomers, tautomer, pharmaceutically acceptable salt, solvate, isotopologue, prodrug, hydrate, co-crystal, clathrate, or a polymorph thereof, is administered daily for a period of 1, 2, 3, 4, 5, 6, 7, 8, 9, 10, 15, 20, 25, or 30 days, followed by a rest period. In a particular embodiment, the therapeutic compound is administered daily for a period of 5 days of a 4 week cycle. In another particular embodiment, the therapeutic compound is administered daily for a period of 10 days of a 4 week cycle. In certain embodiments, the compound of Formula I is Compound D or Compound E. In one embodiment, the compound of Formula I is Compound D. In another embodiment, the compound of Formula I is Compound E.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, the compound of Formula I, or a stereoisomer or a mixture of stereoisomers, tautomer, pharmaceutically acceptable salt, solvate, isotopologue, prodrug, hydrate, co-crystal, clathrate, or a polymorph thereof, is administered once a day. In another embodiment, the compound of Formula I, or a stereoisomer or a mixture of stereoisomers, tautomer, pharmaceutically acceptable salt, solvate, isotopologue, prodrug, hydrate, co-crystal, clathrate, or a polymorph thereof, is administered twice a day. In yet another embodiment, the compound of Formula I, or a stereoisomer or a mixture of stereoisomers, tautomer, pharmaceutically acceptable salt, solvate, isotopologue, prodrug, hydrate, co-crystal, clathrate, or a polymorph thereof, is administered three times a day. In still another embodiment, the compound of Formula I, or a stereoisomer or a mixture of stereoisomers, tautomer, pharmaceutically acceptable salt, solvate, isotopologue, prodrug, hydrate, co-crystal, clathrate, or a polymorph thereof, is administered four times a day. In certain embodiments, the compound of Formula I is Compound D or Compound E. In one embodiment, the compound of Formula I is Compound D. In another embodiment, the compound of Formula I is Compound E.

In certain embodiments, the compound of Formula I, or a stereoisomer or a mixture of stereoisomers, tautomer, pharmaceutically acceptable salt, solvate, isotopologue, prodrug, hydrate, co-crystal, clathrate, or a polymorph thereof, is administered once per day from one day to six months, from one week to three months, from one week to four weeks, from one week to three weeks, or from one week to two weeks. In certain embodiments, the compound of Formula I, or a stereoisomer or a mixture of stereoisomers, tautomer, pharmaceutically acceptable salt, solvate, isotopologue, prodrug, hydrate, co-crystal, clathrate, or a polymorph thereof, is administered once per day for one week, two weeks, three weeks, or four weeks. In one embodiment, the compound of Formula I, or a stereoisomer or a mixture of stereoisomers, tautomer, pharmaceutically acceptable salt, solvate, isotopologue, prodrug, hydrate, co-crystal, clathrate, or a polymorph thereof, is administered once per day for one week. In another embodiment, the compound of Formula I, or a stereoisomer or a mixture of stereoisomers, tautomer, pharmaceutically acceptable salt, solvate, isotopologue, prodrug, hydrate, co-crystal, clathrate, or a polymorph thereof, is administered once per day for two weeks. In yet another embodiment, the compound of Formula I, or a stereoisomer or a mixture of stereoisomers, tautomer, pharmaceutically acceptable salt, solvate, isotopologue, prodrug, hydrate, co-crystal, clathrate, or a polymorph thereof, is administered once per day for three weeks. In still another embodiment, the compound of Formula I, or a stereoisomer or a mixture of stereoisomers, tautomer, pharmaceutically acceptable salt, solvate, isotopologue, prodrug, hydrate, co-crystal, clathrate, or a polymorph thereof, is administered once per day for four weeks. In certain embodiments, the compound of Formula I is Compound D or Compound E. In one embodiment, the compound of Formula I is Compound D. In another embodiment, the compound of Formula I is Compound E.

Also provided herein are methods for predicting or monitoring the responsiveness of a patient to a treatment compound, or efficacy of a treatment compound, using a biomarker (e.g., GSPT1, GSPT2, IKZF1, ATF4, ATF3, DDIT3, cleaved PARP, SRSF3 NMD transcript, or SFSR6 NMD transcript). In certain embodiments, provided herein are methods for predicting the responsiveness of a subject having or suspected of having cancer (e.g., multiple myeloma, lymphoma, MDS, or leukemia), to a treatment compound, using a predictive or prognostic factor, such as GSPT1, GSPT2, IKZF1, ATF4, ATF3, DDIT3, cleaved PARP, SRSF3 NMD transcript, or SFSR6 NMD transcript level. In some embodiments, provided herein are methods for monitoring the efficacy of a treatment of cancer (e.g., multiple myeloma, lymphoma, MDS, or leukemia) in a subject with a treatment compound using a biomarker (e.g., GSPT1, GSPT2, IKZF1, ATF4, ATF3, DDIT3, cleaved PARP, SRSF3 NMD transcript, or SFSR6 NMD transcript) level as a predictive or prognostic factor. In certain embodiments, the compound of Formula I is Compound D or Compound E. In one embodiment, the compound of Formula I is Compound D. In another embodiment, the compound of Formula I is Compound E.

Thus, in yet another aspect, provided herein is a method of predicting the responsiveness of a subject having or suspected of having cancer to a treatment compound, comprising:

(a) administering the treatment compound to the subject;

(b) obtaining a sample from the subject;

(c) determining the level of a biomarker in the sample;

(d) diagnosing the subject as being likely to be responsive to a treatment of the cancer with the treatment compound if the level of the biomarker in the sample is different from the level of the biomarker obtained from a reference sample;

wherein the treatment compound is a compound of Formula I:

I

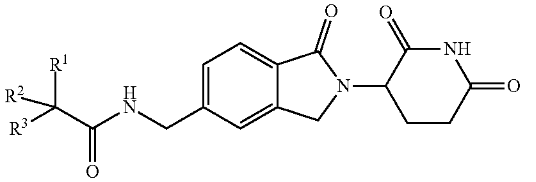

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, $—R^4OR^5$, $—R^4SR^5$, $—R^4N(R^6)(R^7)$, $—R^4OR^4N(R^6)(R^7)$, or $—R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In yet another aspect, provided herein is a method of predicting the responsiveness of a subject having or suspected of having cancer to a treatment compound, comprising:

(a) obtaining a sample from the subject;

(b) administering the treatment compound to the sample;

(c) determining the level of a biomarker in the sample;

(d) diagnosing the subject as being likely to be responsive to a treatment of the cancer with the treatment compound if the level of the biomarker in the sample is different from the level of the biomarker obtained from a reference sample;

wherein the treatment compound is a compound of Formula I:

I

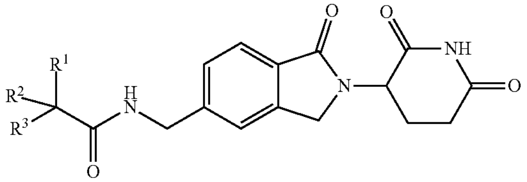

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, $—R^4OR^5$, $—R^4SR^5$, $—R^4N(R^6)(R^7)$, $—R^4OR^4N(R^6)(R^7)$, or $—R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In certain embodiments of the methods provided herein, the compound of Formula I is Compound D or Compound E. In one embodiment, the compound of Formula I is Compound D. In another embodiment, the compound of Formula I is Compound E.

In some embodiments of the methods provided herein, administering the treatment compound to the sample from the subject having cancer is performed in vitro. In other embodiments, administering the treatment compound to the sample from the subject having cancer is performed in vivo. In some embodiments, the sample is cells. In one embodiment, the cells are contacted with the compound for a period of time, e.g., 5, 10, 15, 20, 25, 30, 35, 40, 45, 50, or 55 minutes, or 1, 2, 3, 4, 5, 6, 7, 8, 9, 10, 11, 12, 13, 14, 15, 16, 17, 18, 19, 20, 21, 22, 23, or 24 hours, or 2, 3, or more days. In other embodiments, the cells are obtained from a subject having (or suspected of having) cancer.

In some embodiments of the various methods provided herein, the level of the biomarker in the sample is higher than the level of the biomarker obtained from the reference sample. In other embodiments of the various methods provided herein, the level of the biomarker in the sample is lower than the level of the biomarker obtained from the reference sample.

In yet another aspect, provided herein is a method of monitoring the efficacy of a treatment of cancer in a subject with a treatment compound, comprising:

(a) administering the treatment compound to the subject;

(b) obtaining a sample from the subject;

(c) determining the level of a biomarker in the sample;

(d) comparing the level of the biomarker in the sample with the level of the biomarker obtained from a reference sample, wherein a change in the level as compared to the reference is indicative of the efficacy of the treatment compound in treating the cancer in the subject;

wherein the treatment compound is a compound of Formula I:

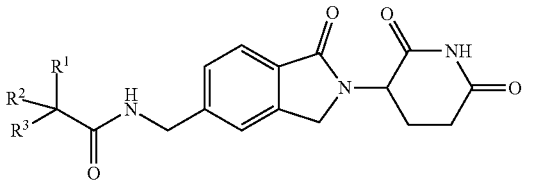

I or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, $—R^4OR^5$, $—R^4SR^5$, $—R^4N(R^6)(R^7)$, $—R^4OR^4N(R^6)(R^7)$, or $—R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In certain embodiments of the methods provided herein, the compound of Formula I is Compound D or Compound E. In one embodiment, the compound of Formula I is Compound D. In another embodiment, the compound of Formula I is Compound E.

In some embodiments, an increased level as compared to the reference is indicative of the efficacy of the treatment compound in treating the cancer in the subject. In other embodiments, a decreased level as compared to the reference is indicative of the efficacy of the treatment compound in treating the cancer in the subject.

In some embodiments of the various methods provided herein, the method further comprises administering a therapeutically effective amount of a second active agent or a support care therapy. The second active agents can be large molecules (e.g., proteins) or small molecules (e.g., synthetic inorganic, organometallic, or organic molecules). In some embodiments, the second active agent is a hematopoietic growth factor, cytokine, anti-cancer agent (e.g., a checkpoint inhibitor), antibiotic, cox-2 inhibitor, immunomodulatory agent, immunosuppressive agent, corticosteroid, therapeutic antibody that specifically binds to a cancer antigen or a pharmacologically active mutant, or derivative thereof. In certain embodiments, the anti-cancer agent is a checkpoint inhibitor.

In some embodiments, the second active agents are small molecules that can alleviate adverse effects associated with the administration of a compound provided herein, or a stereoisomer or a mixture of stereoisomers, tautomer, pharmaceutically acceptable salt, solvate, isotopologue, prodrug, hydrate, co-crystal, clathrate, or a polymorph thereof. Many small molecule second active agents are believed to be capable of providing a synergistic effect when administered with (e.g., before, after, or simultaneously) a compound provided herein, or a stereoisomer or a mixture of stereoisomers, tautomer, pharmaceutically acceptable salt, solvate, isotopologue, prodrug, hydrate, co-crystal, clathrate, or a polymorph thereof. Examples of small molecule second active agents include, but are not limited to, anti-cancer agents, antibiotics, immunosuppressive agents, and steroids.

In some embodiments of the various methods provided herein, the reference is prepared by using a control sample obtained from the subject prior to administering the treatment compound to the subject, and the control sample is from the same source as the sample. In other embodiments of the various methods provided herein, the reference is prepared by using a control sample obtained from a healthy subject not having cancer, and the control sample is from the same source as the sample.

In some embodiments of the various methods provided herein, the cancer is solid cancer or blood borne cancer. In some embodiments, the cancer is solid cancer. In some embodiments, the solid cancer is metastatic. In some embodiments, the solid cancer is hepatocellular carcinoma, melanoma, prostate cancer, ovarian cancer, or glioblastoma. In some embodiments, the cancer is blood borne tumor. In certain embodiments, the blood borne tumor is metastatic. In some embodiments of the various methods provided herein, the cancer is MM. In certain embodiments, the cancer is leukemia. The cancers provided herein include various types of leukemia such as CLL, CML, ALL, or AML. In a specific embodiment, the leukemia is AML. In a specific embodiment, the leukemia is relapsed, refractory, or resistant to conventional therapies. In certain embodiments, the cancer provided here is lymphoma, including but not limited to NHL. In some embodiments, the cancer provided herein is NHL, including but not limited to DLBCL. In some embodiments, the cancer provided herein is MDS.

In some embodiments, methods provided herein encompass treating, preventing, or managing various types of cancers. In one embodiment, methods provided herein encompass treating, preventing, or managing various types of leukemia such as CLL, CML, ALL, or AML by administering a therapeutically effective amount of a compound of Formula I, or a stereoisomer or a mixture of stereoisomers, tautomer, pharmaceutically acceptable salt, solvate, isotopologue, prodrug, hydrate, co-crystal, clathrate, or a polymorph thereof. In certain embodiments, the compound of Formula I is Compound D or Compound E. In one embodiment, the compound of Formula I is Compound D. In another embodiment, the compound of Formula I is Compound E.

In some embodiments, the methods provided herein encompass treating, preventing, or managing acute leukemia in a subject. In some embodiments, the acute leukemia is AML, which includes, but is not limited to, undifferentiated AML (M0), myeloblastic leukemia (M1), myeloblastic leukemia (M2), promyelocytic leukemia (M3 or M3 variant [M3V]), myelomonocytic leukemia (M4 or M4 variant with eosinophilia [M4E]), monocytic leukemia (M5), erythroleukemia (M6), and megakaryoblastic leukemia (M7). In one embodiment, the acute myeloid leukemia is undifferentiated AML (M0). In one embodiment, the acute myeloid leukemia is myeloblastic leukemia (M1). In one embodiment, the acute myeloid leukemia is myeloblastic leukemia (M2). In one embodiment, the acute myeloid leukemia is promyelocytic leukemia (M3 or M3 variant [M3V]). In one embodiment, the acute myeloid leukemia is myelomonocytic leukemia (M4 or M4 variant with eosinophilia [M4E]). In one embodiment, the acute myeloid leukemia is monocytic leukemia (M5). In one embodiment, the acute myeloid leukemia is erythroleukemia (M6). In one embodiment, the acute myeloid leukemia is megakaryoblastic leukemia (M7). Thus, the methods of treating, preventing, or managing AML in a subject comprise the step of administering to the subject an amount of a compound provided herein, or a stereoisomer or a mixture of stereoisomers, tautomer, pharmaceutically acceptable salt, solvate, isotopologue, prodrug, hydrate, co-crystal, clathrate, or a polymorph thereof, effective to treat, prevent, or manage acute myeloid leukemia alone or in combination with a second active agent. In some embodiments, the methods comprise the step of administering to the subject a compound provided herein, or a stereoisomer or a mixture of stereoisomers, tautomer, pharmaceutically acceptable salt, solvate, isotopologue, prodrug, hydrate, co-crystal, clathrate, or a polymorph thereof, in combination with a second active agent in amounts effective to treat, prevent, or manage AML.

In some embodiments, the methods provided herein encompass treating, preventing, and/or managing a myelodysplastic syndrome (MDS) in a subject. In some embodiments, the MDS is relapsed, resistant or refractory MDS. In some embodiments, MDS is selected from refractory anemia (RA); RA with ringed sideroblasts (RARS); RA with excess of blasts (RAEB); refractory cytopenia with multilineage dysplasia (RCMD), refractory cytopenia with unilineage dysplasia (RCUD); unclassifiable myelodysplastic syndrome (MDS-U), myelodysplastic syndrome associated with an isolated del(5q) chromosome abnormality, therapy-related myeloid neoplasms and chronic myelomonocytic leukemia (CMML). Thus, the methods of treating, preventing, or managing MDS in a subject comprise the step of administering to the subject an amount of a compound provided herein, or a stereoisomer or a mixture of stereoisomers, tautomer, pharmaceutically acceptable salt, solvate, isotopologue, prodrug, hydrate, co-crystal, clathrate, or a polymorph thereof, effective to treat, prevent, or manage MDS alone or in combination with a second active agent. In some embodiments, the methods comprise the step of administering to the subject a compound provided herein, or a stereoisomer or a mixture of stereoisomers, tautomer, pharmaceutically acceptable salt, solvate, isotopologue, prodrug, hydrate, co-crystal, clathrate, or a polymorph thereof, in combination with a second active agent in amounts effective to treat, prevent, or manage MDS.

In some embodiments, the methods provided herein encompass treating, preventing, or managing ALL in a subject. In some embodiments, ALL includes leukemia that originates in the blast cells of the bone marrow (B-cells), thymus (T-cells), and lymph nodes. The acute lymphocytic leukemia can be categorized according to the French-American-British (FAB) Morphological Classification Scheme as L1—Mature-appearing lymphoblasts (T-cells or pre-B-cells), L2—Immature and pleomorphic (variously shaped) lymphoblasts (T-cells or pre-B-cells), and L3—Lymphoblasts (B-cells or Burkitt's cells). In one embodiment, the ALL originates in the blast cells of the bone marrow (B-cells). In one embodiment, the ALL originates in the thymus (T-cells). In one embodiment, the ALL originates in the lymph nodes. In one embodiment, the ALL is L1 type characterized by mature-appearing lymphoblasts (T-cells or pre-B-cells). In one embodiment, the ALL is L2 type characterized by immature and pleomorphic (variously shaped) lymphoblasts (T-cells or pre-B-cells). In one embodiment, the ALL is L3 type characterized by lymphoblasts (B-cells or Burkitt's cells). In certain embodiments, the ALL is T-cell leukemia. In one embodiment, the T-cell leukemia is peripheral T-cell leukemia. In another embodiment, the T-cell leukemia is T-cell lymphoblastic leukemia. In another embodiment, the T-cell leukemia is cutaneous T-cell leukemia. In another embodiment, the T-cell leukemia is adult T-cell leukemia. Thus, the methods of treating, preventing, or managing ALL in a subject comprise the step of administering to the subject an amount of a compound provided herein, or a stereoisomer or a mixture of stereoisomers, tautomer, pharmaceutically acceptable salt, solvate, isotopologue, prodrug, hydrate, co-crystal, clathrate, or a polymorph thereof, effective to treat, prevent, or manage ALL alone or in combination with a second active agent. In some embodiments, the methods comprise the step of administering to the subject a compound provided herein, or a stereoisomer or a mixture of stereoisomers, tautomer, pharmaceutically acceptable salt, solvate, isotopologue, prodrug, hydrate, co-crystal, clathrate, or a polymorph thereof, in combination with a second active agent in amounts effective to treat, prevent, or manage ALL.

In some embodiments, the methods provided herein encompass treating, preventing, or managing CML in a subject. The methods comprise the step of administering to the subject an amount of a compound provided herein, or a stereoisomer or a mixture of stereoisomers, tautomer, pharmaceutically acceptable salt, solvate, isotopologue, prodrug, hydrate, co-crystal, clathrate, or a polymorph thereof, effective to treat, prevent, or manage chronic myelogenous leukemia alone or in combination with a second active agent. In some embodiments, the methods comprise the step of administering to the subject a compound provided herein, or a stereoisomer or a mixture of stereoisomers, tautomer, pharmaceutically acceptable salt, solvate, isotopologue, prodrug, hydrate, co-crystal, clathrate, or a polymorph thereof, in combination with a second active agent in amounts effective to treat, prevent, or manage CML.

In some embodiments, the methods provided herein encompass treating, preventing, or managing CLL in a subject. The methods comprise the step of administering to the subject an amount of a compound provided herein, or a stereoisomer or a mixture of stereoisomers, tautomer, pharmaceutically acceptable salt, solvate, isotopologue, prodrug, hydrate, co-crystal, clathrate, or a polymorph thereof, effective to treat, prevent, or manage chronic lymphocytic leukemia alone or in combination with a second active agent. In some embodiments, the methods comprise the step of administering to the subject a compound provided herein, or a stereoisomer or a mixture of stereoisomers, tautomer, pharmaceutically acceptable salt, solvate, isotopologue, prodrug, hydrate, co-crystal, clathrate, or a polymorph thereof, in combination with a second active agent in amounts effective to treat, prevent, or manage CLL.

In certain embodiments, provided herein are methods of treating, preventing, or managing lymphoma, including NHL, comprising administering a therapeutically effective amount of the compound of Formula I, or a stereoisomer or a mixture of stereoisomers, tautomer, pharmaceutically acceptable salt, solvate, isotopologue, prodrug, hydrate, co-crystal, clathrate, or a polymorph thereof, to a patient having lymphoma alone or in combination with a second active agent. In some embodiments, the methods comprise the step of administering to the subject a compound provided herein, or a stereoisomer or a mixture of stereoisomers, tautomer, pharmaceutically acceptable salt, solvate, isotopologue, prodrug, hydrate, co-crystal, clathrate, or a polymorph thereof, in combination with a second active agent in amounts effective to treat, prevent, or manage lymphoma. In some embodiments, provided herein are methods for the treatment or management of NHL, including but not limited to DLBCL. In certain embodiments, the compound of Formula I is Compound D or Compound E. In one embodiment, the compound of Formula I is Compound D. In another embodiment, the compound of Formula I is Compound E.

In certain embodiments, provided herein are methods of treating, preventing, or managing disease in patients with impaired renal function. In certain embodiments, provided herein are method of treating, preventing, or managing cancer in patients with impaired renal function. In certain embodiments, provided herein are methods of providing appropriate dose adjustments for patients with impaired renal function due to, but not limited to, disease, aging, or other patient factors.

In certain embodiments, provided herein are methods of treating, preventing, or managing MM, including relapsed/refractory MM in patients with impaired renal function or a symptom thereof, comprising administering a therapeutically effective amount of the compound of Formula I, or a stereoisomer or a mixture of stereoisomers, tautomer, pharmaceutically acceptable salt, solvate, isotopologue, prodrug, hydrate, co-crystal, clathrate, or a polymorph thereof, to a patient having relapsed/refractory MM with impaired renal function alone or in combination with a second active agent. In some embodiments, the methods comprise the step of administering to the subject a compound provided herein, or a stereoisomer or a mixture of stereoisomers, tautomer, pharmaceutically acceptable salt, solvate, isotopologue, prodrug, hydrate, co-crystal, clathrate, or a polymorph thereof, in combination with a second active agent in amounts effective to treat, prevent, or manage relapsed/refractory MM in patients with impaired renal function. In certain embodiments, the compound of Formula I is Compound D or Compound E. In one embodiment, the compound of Formula I is Compound D. In another embodiment, the compound of Formula I is Compound E.

In some embodiments of the various methods provided herein, the biomarker provided herein is selected from the group consisting of ATF3, ATF4, ATF6, BID, BIP, Caspase 3, Caspase 7, Caspase 8, Caspase 9, DDIT3, DNAJB9, EDEM1, eIF2α, eRF1, FAS, GADD45A, GCN2, IKZF1, IRE1, Mcl-1, PARP, PPP1R15A, GSPT1, GSPT2, SEC24D, SRSF3, SRSF6, TNFRSF10B, and XBP1. In some embodiments of the various methods provided herein, the biomarker is selected from the group consisting of GSPT1, GSPT2, IKZF1, ATF4, ATF3, and DDIT3. In other embodiments of the various methods provided herein, the biomarker is selected from the group consisting of cleaved PARP, SRSF3 NMD transcript, and SRSF6 NMD transcript.

In one embodiment, the biomarker is GSPT1. In another embodiment, the biomarker is GSPT2. In yet another embodiment, the biomarker is IKZF1. In still another embodiment, the biomarker is eRF1. In one embodiment, the biomarker is BIP. In a specific embodiment, the biomarker is unmodified BIP. In another specific embodiment, the biomarker is C-terminal modified BIP. In yet another specific embodiment, the biomarker is C-terminal modified BIP that cannot be recognized by KDEL antibody. In still another specific embodiment, the biomarker is C-terminal modified BIP that cannot be recognized by BIP antibody that recognizes unmodified C-terminus of BIP. In a specific embodiment, the biomarker is C-terminal modified BIP that cannot be recognized by both KDEL antibody and BIP antibody that recognizes unmodified C-terminus of BIP. In one embodiment, the biomarker is GCN2. In a specific embodiment, the biomarker is unphosphorylated GCN2. In another specific embodiment, the biomarker is phosphorylated GCN2. In one embodiment, the biomarker is eIF2α. In a specific embodiment, the biomarker is unphosphorylatd eIF2α. In another specific embodiment, the biomarker is phosphorylatd eIF2α. In one embodiment, the biomarker is ATF4. In another embodiment, the biomarker is ATF3. In yet another embodiment, the biomarker is the splicing variant of ATF3. In still another embodiment, the biomarker is DDIT3. In one embodiment, the biomarker is PPP1R15A. In another embodiment, the biomarker is TNFRSF10B. In yet another embodiment, the biomarker is GADD45A. In still another embodiment, the biomarker is FAS. In one embodiment, the biomarker is IRE1. In a specific embodiment, the biomarker is unphosphorylated IRE1. In another specific embodiment, the biomarker is phosphorylated IRE1. In one embodiment, the biomarker is XBP1. In another embodiment, the biomarker is SEC24D. In yet another embodiment, the biomarker is DNAJB9. In still another embodiment, the biomarker is EDEM1. In one embodiment, the biomarker is ATF6. In another embodiment, the biomarker is Caspase 8. In a specific embodiment, the biomarker is cleaved Caspase 8. In yet another embodiment, the biomarker is BID. In still another embodiment, the biomarker is Caspase 9. In a specific embodiment, the biomarker is cleaved Caspase 9. In one embodiment, the biomarker is Caspase 3. In a specific embodiment, the biomarker is cleaved Caspase 3. In another embodiment, the biomarker is PARP. In a specific embodiment, the biomarker is cleaved PARP. In yet another embodiment, the biomarker is Caspase 7. In a specific embodiment, the biomarker is cleaved Caspase 7. In still embodiment, the biomarker is Mcl-1. In a specific embodiment, the biomarker is SRSF3. In another embodiment, the biomarker is a splicing variant of SRSF3 containing premature stop codons (e.g., an NMD transcript for SRSF3). In yet another embodiment, the biomarker is SRSF6. In still another embodiment, the biomarker is a splicing variant of SRSF6 containing premature stop codons (e.g., an NMD transcript for SRSF6).

In some embodiments, the level of the biomarker decreases in response to the compound treatment. In some embodiments, the biomarker is selected from the group consisting of GSPT1, GSPT2, IKZF1, eRF1, BIP, and Mcl-1, and the level of the biomarker decreases as compared to a reference in response to a treatment compound.

In other embodiments the level of the biomarker increases in response to the compound treatment. In some embodiments, the biomarker is selected from the group consisting of ATF4, ATF3, and DDIT3, and the level of the biomarker increases as compared to a reference in response to a treatment compound. In other embodiments, the biomarker is selected from the group consisting of SEC24D, DNAJB9, XBP1, EDEM1, eIF2α, PPP1R15A, GADD45A, TNFRSF10B, cleaved form of Caspase 8, BID, cleaved form of Caspase 9, cleaved form of Caspase 3, cleaved form of Caspase 7, cleaved PARP, FAS, an NMD transcript for SRSF3, an NMD transcript for SRSF6, and the level of the biomarker increases in response to the compound treatment.

In certain embodiments of the various methods provided herein, the biomarker is a protein that is directly or indirectly affected by CRBN, for example through protein-protein interactions (e.g., certain CRBN substrates or downstream effectors thereof), or through various cellular pathways (e.g., signal transduction pathways). In specific embodiments, the biomarker is a CRBN-associated protein (CAP). In some embodiments, the biomarker is mRNA of a protein that is directly or indirectly affected by CRBN. In other embodiments, the biomarker is cDNA of a protein that is directly or indirectly affected by CRBN.

Thus, in some embodiments, provided herein is a method of identifying a subject having cancer who is likely to be responsive to a treatment compound, comprising:

(a) administering the treatment compound to the subject;

(b) obtaining a sample from the subject;

(c) determining the level of a biomarker in the sample, wherein the biomarker is a CAP; and (d) diagnosing the subject as being likely to be responsive to the treatment compound if the level of the biomarker in the sample is different from a reference level of the biomarker;

wherein the treatment compound is a compound of Formula I:

I

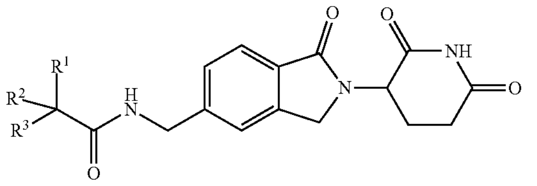

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, $—R^4OR^5$, $—R^4SR^5$, $—R^4N(R^6)(R^7)$, $—R^4OR^4N(R^6)(R^7)$, or $—R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In some embodiments, provided herein is a method of identifying a subject having cancer who is likely to be responsive to a treatment compound, comprising:

(a) obtaining a sample from the subject;

(b) administering the treatment compound to the sample;

(c) determining the level of a biomarker in the sample, wherein the biomarker is a CAP; and (d) diagnosing the subject as being likely to be responsive to the treatment compound if the level of the biomarker in the sample is different from a reference level of the biomarker;

wherein the treatment compound is a compound of Formula I:

I

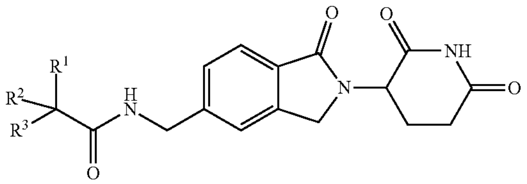

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, $—R^4OR^5$, $—R^4SR^5$, $—R^4N(R^6)(R^7)$, $—R^4OR^4N(R^6)(R^7)$, or $—R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In some embodiments, provided herein is a method of treating cancer, comprising:

(a) obtaining a sample from a subject having the cancer;

(b) determining the level of a biomarker in the sample, wherein the biomarker is a CAP;

(c) diagnosing the subject as being likely to be responsive to a treatment compound if the level of the biomarker in the sample is different from a reference level of the biomarker; and (d) administering a therapeutically effective amount of the treatment compound to the subject;

wherein the treatment compound is a compound of Formula I:

I

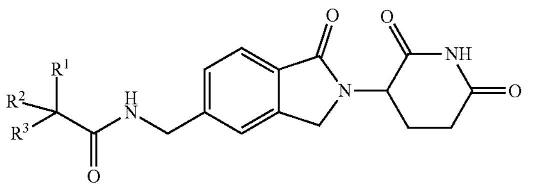

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, $—R^4OR^5$, $—R^4SR^5$, $—R^4N(R^6)(R^7)$, $—R^4OR^4N(R^6)(R^7)$, or $—R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In some embodiments, provided herein is a method of predicting the responsiveness of a subject having or suspected of having cancer to a treatment compound, comprising:

(a) administering the treatment compound to the subject;
(b) obtaining a sample from the subject;
(c) determining the level of a biomarker in the sample, wherein the biomarker is a CAP;
(d) diagnosing the subject as being likely to be responsive to a treatment of the cancer with the treatment compound if the level of the biomarker in the sample is different from the level of the biomarker obtained from a reference sample;

wherein the treatment compound is a compound of Formula I:

I

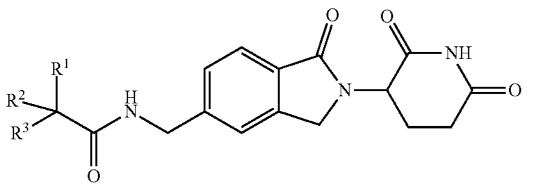

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, $—R^4OR^5$, $—R^4SR^5$, $—R^4N(R^6)(R')$, $—R^4OR^4N(R^6)(R^7)$, or $—R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In some embodiments, provided herein is a method of predicting the responsiveness of a subject having or suspected of having cancer to a treatment compound, comprising:

(a) obtaining a sample from the subject;
(b) administering the treatment compound to the sample;
(c) determining the level of a biomarker in the sample, wherein the biomarker is a CAP;
(d) diagnosing the subject as being likely to be responsive to a treatment of the cancer with the treatment compound if the level of the biomarker in the sample is different from the level of the biomarker obtained from a reference sample;

wherein the treatment compound is a compound of Formula I:

I

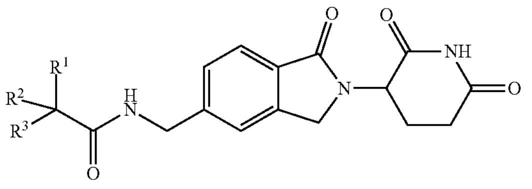

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, $—R^4OR^5$, $—R^4SR^5$, $—R^4N(R^6)(R^7)$, $—R^4OR^4N(R^6)(R^7)$, or $—R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In some embodiments, provided herein is a method of monitoring the efficacy of a treatment of cancer in a subject with a treatment compound, comprising:

(a) administering the treatment compound to the subject;

(b) obtaining a sample from the subject;

(c) determining the level of a biomarker in the sample, wherein the biomarker is a CAP;

(d) comparing the level of the biomarker in the sample with the level of the biomarker obtained from a reference sample, wherein a change in the level as compared to the reference is indicative of the efficacy of the treatment compound in treating the cancer in the subject;

wherein the treatment compound is a compound of Formula I:

I

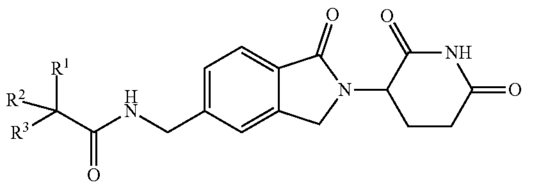

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, —$R^4OR^4N(R^6)(R^7)$, or —$R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In certain embodiments of the methods provided herein, the compound of Formula I is Compound D or Compound E. In one embodiment, the compound of Formula I is Compound D. In another embodiment, the compound of Formula I is Compound E.

In some embodiments, the biomarker is a CAP selected from the group consisting of GSPT1, GSPT2, and IKZF1. In some embodiments, the biomarker is an eRF3 family member, such as GSPT1 or GSPT2. In a specific embodiment, the biomarker is GSPT1. In another specific embodiment, the biomarker is GSPT2. In yet another specific embodiment, the biomarker is IKZF1. In other embodiments, the biomarker is a binding partner of, downstream effector of, or a factor in a cellular pathway impacted by GSPT1, GSPT2, or IKZF1. For example, in some embodiments, the biomarker is a binding partner of, downstream effector of, or a factor in a cellular pathway impacted by an eRF3 family member. In a specific embodiment, the biomarker is a binding partner of GSPT1, such as eRF1.

As shown in the Examples, the level of a biomarker, such as GSPT1, GSPT2, or IKZF1, decreases as compared to a reference in response to Compound D or E treatment. Accordingly, in some embodiments, the biomarker is selected from the group consisting of GSPT1, GSPT2, and IKZF1, and the level of the biomarker decreases in response to the Compound D or E treatment. Thus, in some embodiments of the various methods provided herein, the biomarker is GSPT1, GSPT2, or IKZF1, or a protein (or a factor) impacted thereby, and wherein the level of the biomarker is lower than a reference.

Thus, in some embodiments, provided herein is a method of identifying a subject having cancer who is likely to be responsive to a treatment compound, comprising:

(a) administering the treatment compound to the subject;

(b) obtaining a sample from the subject;

(c) determining the level of GSPT1, GSPT2, or IKZF1 in the sample, (d) diagnosing the subject as being likely to be responsive to the treatment compound if the level of GSPT1, GSPT2, or IKZF1 in the sample is lower than a reference level;

wherein the treatment compound is a compound of Formula I:

I

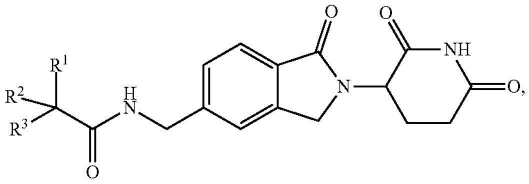

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, —$R^4OR^4N(R^6)(R^7)$, or —$R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In some embodiments, provided herein is a method of identifying a subject having cancer who is likely to be responsive to a treatment compound, comprising:

(a) obtaining a sample from the subject;

(b) administering the treatment compound to the sample;

(c) determining the level of GSPT1, GSPT2, or IKZF1 in the sample; and (d) diagnosing the subject as being likely to be responsive to the treatment compound if the level of GSPT1, GSPT2, or IKZF1 in the sample is lower than a reference level;

wherein the treatment compound is a compound of Formula I:

I

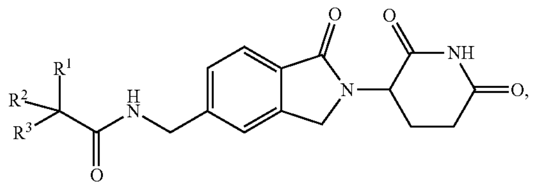

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, —$R^4OR^4N(R^6)(R^7)$, or —$R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In some embodiments, provided herein is a method of treating cancer, comprising:

(a) obtaining a sample from a subject having the caner;

(b) determining the level of GSPT1, GSPT2, or IKZF1 in the sample;

(c) diagnosing the subject as being likely to be responsive to the treatment compound if the level of GSPT1, GSPT2, or IKZF1 in the sample is lower than a reference level; and (d) administering a therapeutically effective amount of the treatment compound to the subject;

wherein the treatment compound is a compound of Formula I:

I

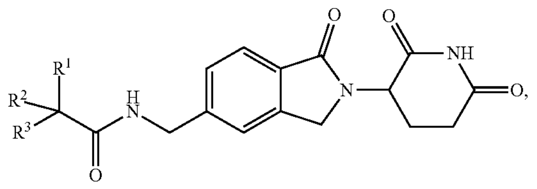

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, —$R^4OR^4N(R^6)(R^7)$, or —$R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In some embodiments, provided herein is a method of predicting the responsiveness of a subject having or suspected of having cancer to a treatment compound, comprising:

(a) administering the treatment compound to the subject;

(b) obtaining a sample from the subject;

(c) determining the level of GSPT1, GSPT2, or IKZF1 in the sample;

(d) diagnosing the subject as being likely to be responsive to a treatment of the cancer with the treatment compound if the level of GSPT1, GSPT2, or IKZF1 in the sample is lower than the level of GSPT1, GSPT2, or IKZF1 obtained from a reference sample;

wherein the treatment compound is a compound of Formula I:

I

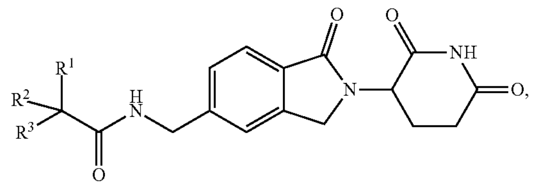

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, —$R^4OR^4N(R^6)(R^7)$, or —$R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In some embodiments, provided herein is a method of predicting the responsiveness of a subject having or suspected of having cancer to a treatment compound, comprising:

(a) obtaining a sample from the subject;

(b) administering the treatment compound to the sample;

(c) determining the level of GSPT1, GSPT2, or IKZF1 in the sample;

(d) diagnosing the subject as being likely to be responsive to a treatment of the cancer with the treatment compound if the level of GSPT1, GSPT2, or IKZF1 in the sample is lower than the level of GSPT1, GSPT2, or IKZF1 obtained from a reference sample;

wherein the treatment compound is a compound of Formula I:

I

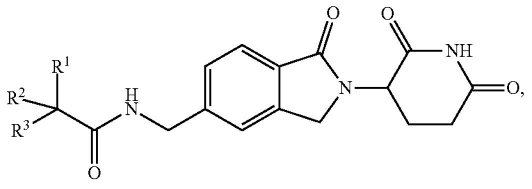

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, —$R^4OR^4N(R^6)(R^7)$, or —$R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In some embodiments, provided herein is a method of monitoring the efficacy of a treatment of cancer in a subject with a treatment compound, comprising:

(a) administering the treatment compound to the subject;

(b) obtaining a sample from the subject;

(c) determining the level of GSPT1, GSPT2, or IKZF1 in the sample;

(d) comparing the level of GSPT1, GSPT2, or IKZF1 in the sample with the level of GSPT1, GSPT2, or IKZF1 obtained from a reference sample, wherein a decreased level as compared to the reference is indicative of the efficacy of the treatment compound in treating the cancer in the subject;

wherein the treatment compound is a compound of Formula I:

I

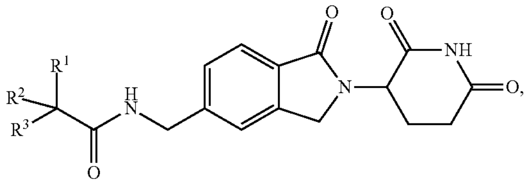

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R')$, —$R^4OR^4N(R^6)(R^7)$, or —$R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In certain embodiments of the methods provided herein, the compound of Formula I is Compound D or Compound E. In one embodiment, the compound of Formula I is Compound D. In another embodiment, the compound of Formula I is Compound E.

In a specific embodiment, the biomarker is GSPT1, and the cancer is multiple myeloma (MM), lymphoma, or leukemia. In a specific embodiment, the cancer is lymphoma. In some embodiments, the cancer is leukemia. In another specific embodiment, the leukemia is chronic lymphocytic leukemia, chronic myelocytic leukemia, acute lymphoblastic leukemia, or acute myeloid leukemia. In one embodiment, the leukemia is an acute myeloid leukemia (AML). In a specific embodiment, the biomarker is GSPT1, and the treatment compound is Compound D or Compound E. In a specific embodiment, the treatment compound is Compound D. In another specific embodiment, the treatment compound is Compound E.

In another specific embodiment, the biomarker is GSPT2, and the cancer is multiple myeloma (MM), lymphoma, or leukemia. In a specific embodiment, the cancer is lymphoma. In some embodiments, the cancer is leukemia. In another specific embodiment, the leukemia is chronic lymphocytic leukemia, chronic myelocytic leukemia, acute lymphoblastic leukemia, or acute myeloid leukemia. In one embodiment, the leukemia is an acute myeloid leukemia (AML). In another specific embodiment, the biomarker is GSPT2, and the treatment compound is Compound D or Compound E. In a specific embodiment, the treatment compound is Compound D. In another specific embodiment, the treatment compound is Compound E.

In another specific embodiment, the biomarker is IKZF1, and the cancer is multiple myeloma (MM), lymphoma, or leukemia. In a specific embodiment, the cancer is lymphoma. In some embodiments, the cancer is leukemia. In another specific embodiment, the leukemia is chronic lymphocytic leukemia, chronic myelocytic leukemia, acute lymphoblastic leukemia, or acute myeloid leukemia. In one embodiment, the leukemia is an acute myeloid leukemia (AML). In another specific embodiment, the biomarker is IKZF1, and the treatment compound is Compound D or Compound E. In a specific embodiment, the treatment compound is Compound D. In another specific embodiment, the treatment compound is Compound E.

In some embodiments, the biomarker is a factor or a protein involved in UPR or a downstream pathway thereof. In certain embodiments, the biomarker provided herein has a function in ER stress pathway. In other embodiments, the biomarker provided herein has a function in NMD pathway. In yet other embodiments, the biomarker provided herein is an RNA substrate of NMD pathway.

In other embodiments, the biomarker provided herein has a function in ATF4-related signaling pathway. In some embodiments, a biomarker involved in ATF4-related signaling pathway is used for identifying a subject having cancer who is likely to be responsive to a treatment compound; predicting the responsiveness of a subject having or suspected of having cancer to a treatment compound; monitoring the efficacy of a treatment of cancer in a subject with a treatment compound; or treating cancer. In some embodiments, the biomarker is a factor or protein involved in ATF4-related signaling pathway selected from a group consisting of ATF4, ATF3, PPP1R15A, TNFRSF10B, DDIT3, GADD45A, TNFRSF1A, TNFRSF1B, FAS, and FADD. In a specific embodiment, the biomarker is ATF4. In another specific embodiment, the biomarker is ATF3. In yet another specific embodiment, the biomarker is PPP1R15A. In still another specific embodiment, the biomarker is TNFRSF10B. In one specific embodiment, the biomarker is DDIT3. In another specific embodiment, the biomarker is GADD45A. In yet another specific embodiment, the biomarker is TNFRSF1A. In one embodiment, the biomarker is TNFRSF1B. In a specific embodiment, the biomarker is FAS. In another embodiment, the biomarker is FADD. In some embodiments, the cancer is multiple myeloma (MM), lymphoma, or leukemia. In a specific embodiment, the cancer is lymphoma. In some embodiments, the cancer is leukemia. In another specific embodiment, the leukemia is chronic lymphocytic leukemia, chronic myelocytic leukemia, acute lymphoblastic leukemia, or acute myeloid leukemia. In one embodiment, the leukemia is an acute myeloid leukemia (AML). In another specific embodiment, the treatment compound is Compound D or Compound E. In a specific embodiment, the treatment compound is Compound D. In another specific embodiment, the treatment compound is Compound E.

In other embodiments, the biomarker provided herein has a function in GCN-2 related signaling pathway. In some embodiments, a biomarker involved in GCN2 related signaling pathway is used for identifying a subject having cancer who is likely to be responsive to a treatment compound; predicting the responsiveness of a subject having or suspected of having cancer to a treatment compound; monitoring the efficacy of a treatment of cancer in a subject with a treatment compound; or treating cancer. In some embodiments, the biomarker is a factor or protein involved in GCN-2 related signaling pathway selected from a group consisting of GCN2, eIF2α, ATF4, ATF3, DDIT3, PPP1R15A, TNFRSF10B, GADD45A, and FAS. In a specific embodiment, the biomarker is GCN2. In another specific embodiment, the biomarker is eIF2α. In yet another specific embodiment, the biomarker is ATF4. In still another specific embodiment, the biomarker is ATF3. In one specific embodiment, the biomarker is DDIT3. In another specific embodiment, the biomarker is PPP1R15A. In yet another specific embodiment, the biomarker is TNFRSF10B. In still another specific embodiment, the biomarker is GADD45A. In a specific embodiment, the biomarker is FAS. In some embodiments, the cancer is multiple myeloma (MM), lymphoma, or leukemia. In a specific embodiment, the cancer is lymphoma. In some embodiments, the cancer is leukemia. In another specific embodiment, the leukemia is chronic lymphocytic leukemia, chronic myelocytic leukemia, acute lymphoblastic leukemia, or acute myeloid leukemia. In one embodiment, the leukemia is an acute myeloid leukemia (AML). In another specific embodiment, the treatment compound is Compound D or Compound E. In a specific embodiment, the treatment compound is Compound D. In another specific embodiment, the treatment compound is Compound E.

In other embodiments, the biomarker provided herein has a function in IRE1 related signaling pathway. In some embodiments, a biomarker involved in IRE1 related signaling pathway is used for identifying a subject having cancer who is likely to be responsive to a treatment compound; predicting the responsiveness of a subject having or suspected of having cancer to a treatment compound; monitoring the efficacy of a treatment of cancer in a subject with a treatment compound; or treating cancer. In some embodiments, the biomarker is a factor or protein involved in IRE1 related signaling pathway selected from a group consisting of IRE1, XBP1, SEC24D, DNAJB9, and EDEM1. In a specific embodiment, the biomarker is IRE1. In another specific embodiment, the biomarker is XBP1. In yet another specific embodiment, the biomarker is SEC24D. In still another specific embodiment, the biomarker is DNAJB9. In a specific embodiment, the biomarker is EDEM1. In some embodiments, the cancer is multiple myeloma (MM), lymphoma, or leukemia. In a specific embodiment, the cancer is lymphoma. In some embodiments, the cancer is leukemia. In another specific embodiment, the leukemia is chronic lymphocytic leukemia, chronic myelocytic leukemia, acute lymphoblastic leukemia, or acute myeloid leukemia. In one embodiment, the leukemia is an acute myeloid leukemia (AML). In another specific embodiment, the treatment compound is Compound D or Compound E. In a specific embodiment, the treatment compound is Compound D. In another specific embodiment, the treatment compound is Compound E.

In yet other embodiments, the biomarker provided herein has a function in XBP1 related signaling pathway. In some embodiments, a biomarker involved in XBP1 related signaling pathway is used for identifying a subject having cancer who is likely to be responsive to a treatment compound; predicting the responsiveness of a subject having or suspected of having cancer to a treatment compound; monitoring the efficacy of a treatment of cancer in a subject with a treatment compound; or treating cancer. In some embodiments, the biomarker is a factor or protein involved in XBP1 related signaling pathway selected from a group consisting of XBP1, SEC24D, DNAJB9, DNAJC6, EDEM1, EDEM2, and HYOU1. In a specific embodiment, the biomarker is XBP1. In another specific embodiment, the biomarker is SEC24D. In still another specific embodiment, the biomarker is DNAJB9. In one embodiment, the biomarker is DNAJC6. In a specific embodiment, the biomarker is EDEM1. In another specific embodiment, the biomarker is EDEM2. In yet another embodiment, the biomarker is HYOU1. In some embodiments, the cancer is multiple myeloma (MM), lymphoma, or leukemia. In a specific embodiment, the cancer is lymphoma. In some embodiments, the cancer is leukemia. In another specific embodiment, the leukemia is chronic lymphocytic leukemia, chronic myelocytic leukemia, acute lymphoblastic leukemia, or acute myeloid leukemia. In one embodiment, the leukemia is an acute myeloid leukemia (AML). In another specific embodiment, the treatment compound is Compound D or Compound E. In a specific embodiment, the treatment compound is Compound D. In another specific embodiment, the treatment compound is Compound E.

In yet other embodiments, the biomarker provided herein has a function in ATF6 related signaling pathway. In some embodiments, a biomarker involved in ATF6 related signaling pathway is used for identifying a subject having cancer who is likely to be responsive to a treatment compound; predicting the responsiveness of a subject having or suspected of having cancer to a treatment compound; monitoring the efficacy of a treatment of cancer in a subject with a treatment compound; or treating cancer. In some embodiments, the biomarker is a factor or protein involved in ATF6 related signaling pathway selected from a group consisting of ATF6, XBP1, and EDEM1. In a specific embodiment, the biomarker is ATF6. In another specific embodiment, the biomarker is XBP1. In yet another specific embodiment, the biomarker is EDEM1. In some embodiments, the cancer is multiple myeloma (MM), lymphoma, or leukemia. In a specific embodiment, the cancer is lymphoma. In some embodiments, the cancer is leukemia. In another specific embodiment, the leukemia is chronic lymphocytic leukemia, chronic myelocytic leukemia, acute lymphoblastic leukemia, or acute myeloid leukemia. In one embodiment, the leukemia is an acute myeloid leukemia (AML). In another specific embodiment, the treatment compound is Compound D or Compound E. In a specific embodiment, the treatment compound is Compound D. In another specific embodiment, the treatment compound is Compound E.

In some embodiments, the biomarker provided herein has a function in FAS/FADD related signaling and apoptosis pathway. In some embodiments, a biomarker involved in FAS/FADD related signaling pathway and apoptosis pathway is used for identifying a subject having cancer who is likely to be responsive to a treatment compound; predicting the responsiveness of a subject having or suspected of having cancer to a treatment compound; monitoring the efficacy of a treatment of cancer in a subject with a treatment compound; or treating cancer. In some embodiments, the biomarker is a factor or protein involved in ATF6 related signaling and apoptosis pathway selected from a group consisting of Caspase 3, Caspase 7, Caspase 8, Caspase 9, PARP, and Mcl-1. In a specific embodiment, the biomarker is Caspase 3. In another specific embodiment, the biomarker is Caspase 7. In yet another specific embodiment, the biomarker is Caspase 8. In still another specific embodiment, the biomarker is Caspase 9. In one specific embodiment, the biomarker is PARP. In a particular embodiment, the biomarker is cleaved PARP. In another specific embodiment, the biomarker is Mcl-1. In some embodiments, the cancer is multiple myeloma (MM), lymphoma, or leukemia. In a specific embodiment, the cancer is lymphoma. In some embodiments, the cancer is leukemia. In another specific embodiment, the leukemia is chronic lymphocytic leukemia, chronic myelocytic leukemia, acute lymphoblastic leukemia, or acute myeloid leukemia. In one embodiment, the leukemia is an acute myeloid leukemia (AML). In another specific embodiment, the treatment compound is Compound D or Compound E. In a specific embodiment, the treatment compound is Compound D. In another specific embodiment, the treatment compound is Compound E.

In some embodiments, the biomarker provided herein is a component along or an RNA substrate of NMD related signaling pathway. In some embodiments, a biomarker involved in NMD related signaling pathway is used for identifying a subject having cancer who is likely to be responsive to a treatment compound; predicting the responsiveness of a subject having or suspected of having cancer to a treatment compound; monitoring the efficacy of a treatment of cancer in a subject with a treatment compound; or treating cancer. In some embodiments, the biomarker is an RNA substrate of NMD related signaling pathway (e.g., an NMD transcript for SRSF3 or SRSF6). In a specific embodiment, the biomarker is an NMD transcript for SRSF3. In another specific embodiment, the biomarker is an NMD transcript for SRSF6. In some embodiments, the cancer is multiple myeloma (MM), lymphoma, or leukemia. In a specific embodiment, the cancer is lymphoma. In some embodiments, the cancer is leukemia. In another specific embodiment, the leukemia is chronic lymphocytic leukemia, chronic myelocytic leukemia, acute lymphoblastic leukemia, or acute myeloid leukemia. In one embodiment, the leukemia is an acute myeloid leukemia (AML). In another specific embodiment, the treatment compound is Compound D or Compound E. In a specific embodiment, the treatment compound is Compound D. In another specific embodiment, the treatment compound is Compound E.

In some more specific embodiments, the biomarker involved in GCN2 related signaling pathway is selected from the group consisting of ATF4, ATF3, or DDIT3, and wherein the level of the biomarker increases as compared to a reference. In certain more specific embodiments, the biomarker involved in FAS/FADD related signaling and apoptosis pathway is cleaved PARP, and wherein the level of the biomarker increases as compared to a reference. In other more specific embodiments, the biomarker involved in NMD related signaling pathway is selected from the group consisting of SRSF3 NMD transcript and SRSF6 NMD transcript, and wherein the level of the biomarker increases as compared to a reference.

Thus, in some embodiments, provided herein is a method of identifying a subject having cancer who is likely to be responsive to a treatment compound, comprising:

(a) administering the treatment compound to the subject;

(b) obtaining a sample from the subject;

(c) determining the level of ATF4, ATF3, DDIT3, cleaved PARP, SRSF3 NMD transcript, or SRSF6 NMD transcript in the sample; and (d) diagnosing the subject as being likely to be responsive to the treatment compound if the level of ATF4, ATF3, DDIT3, cleaved PARP, SRSF3 NMD transcript, or SRSF6 NMD transcript in the sample is higher than a reference level;

wherein the treatment compound is a compound of Formula I:

I

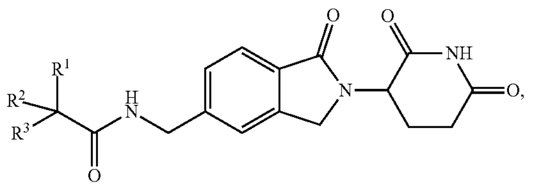

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, $—R^4OR^5$, $—R^4SR^5$, $—R^4N(R^6)(R^7)$, $—R^4OR^4N(R^6)(R^7)$, or $—R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In some embodiments, provided herein is a method of identifying a subject having cancer who is likely to be responsive to a treatment compound, comprising:

(a) obtaining a sample from the subject;

(b) administering the treatment compound to the sample;

(c) determining the level of ATF4, ATF3, DDIT3, cleaved PARP, SRSF3 NMD transcript, or SRSF6 NMD transcript in the sample; and (d) diagnosing the subject as being likely to be responsive to the treatment compound if the level of ATF4, ATF3, DDIT3, cleaved PARP, SRSF3 NMD transcript, or SRSF6 NMD transcript in the sample is higher than a reference level;

wherein the treatment compound is a compound of Formula I:

I

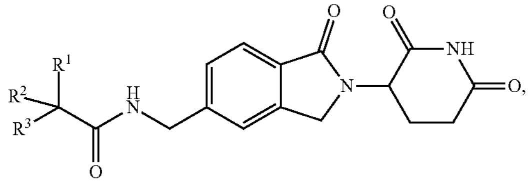

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, $—R^4OR^5$, $—R^4SR^5$, $—R^4N(R^6)(R^7)$, $—R^4OR^4N(R^6)(R^7)$, or $—R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In some embodiments, provided herein is a method of treating cancer, comprising:

(a) obtaining a sample from the subject;

(b) determining the level of ATF4, ATF3, DDIT3, cleaved PARP, SRSF3 NMD transcript, or SRSF6 NMD transcript in the sample;

(c) diagnosing the subject as being likely to be responsive to the treatment compound if the level of ATF4, ATF3, DDIT3, cleaved PARP, SRSF3 NMD transcript, or SRSF6 NMD transcript in the sample is higher than a reference level; and (d) administering a therapeutically effective amount of the treatment compound to the subject diagnosed to be likely to be responsive to the treatment compound;

wherein the treatment compound is a compound of Formula I:

I

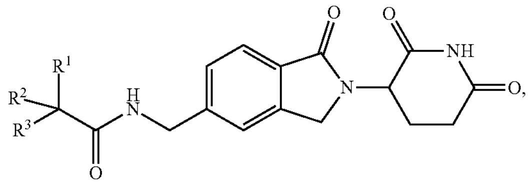

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, —$R^4OR^4N(R^6)(R^7)$, or —$R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In some embodiments, provided herein is a method of predicting the responsiveness of a subject having or suspected of having cancer to a treatment compound, comprising:

(a) administering the treatment compound to the subject;
(b) obtaining a sample from the subject;
(c) determining the level of ATF4, ATF3, DDIT3, cleaved PARP, SRSF3 NMD transcript, or SRSF6 NMD transcript in the sample;
(d) diagnosing the subject as being likely to be responsive to a treatment of the cancer with the treatment compound if the level of ATF4, ATF3, DDIT3, cleaved PARP, SRSF3 NMD transcript, or SRSF6 NMD transcript in the sample is higher than the level of ATF4, ATF3, DDIT3, cleaved PARP, SRSF3 NMD transcript, or SRSF6 NMD transcript obtained from a reference sample;

wherein the treatment compound is a compound of Formula I:

I

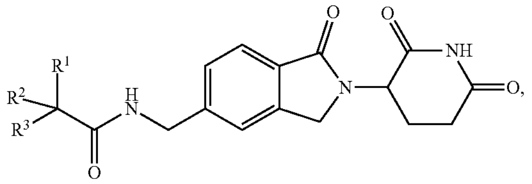

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, —$R^4OR^4N(R^6)(R^7)$, or —$R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In some embodiments, provided herein is a method of predicting the responsiveness of a subject having or suspected of having cancer to a treatment compound, comprising:

(a) obtaining a sample from the subject;
(b) administering the treatment compound to the sample;
(c) determining the level of ATF4, ATF3, DDIT3, cleaved PARP, SRSF3 NMD transcript, or SRSF6 NMD transcript in the sample; and
(d) diagnosing the subject as being likely to be responsive to a treatment of the cancer with the treatment compound if the level of ATF4, ATF3, DDIT3, cleaved PARP, SRSF3 NMD transcript, or SRSF6 NMD transcript in the sample is higher than the level of ATF4, ATF3, DDIT3, cleaved PARP, SRSF3 NMD transcript, or SRSF6 NMD transcript btained from a reference sample;

wherein the treatment compound is a compound of Formula I:

I

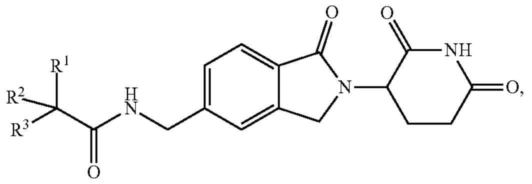

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, —$R^4OR^4N(R^6)(R^7)$, or —$R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In some embodiments, provided herein is a method of monitoring the efficacy of a treatment of cancer in a subject with a treatment compound, comprising:

(a) administering the treatment compound to the subject;

(b) obtaining a sample from the subject;

(c) determining the level of ATF4, ATF3, DDIT3, cleaved PARP, SRSF3 NMD transcript, or SRSF6 NMD transcript in the sample; and (d) comparing the level of ATF4, ATF3, DDIT3, cleaved PARP, SRSF3 NMD transcript, or SRSF6 NMD transcript in the sample with the level of ATF4, ATF3, DDIT3, cleaved PARP, SRSF3 NMD transcript, or SRSF6 NMD transcript obtained from a reference sample, wherein an increased level as compared to the reference is indicative of the efficacy of the treatment compound in treating the cancer in the subject;

wherein the treatment compound is a compound of Formula I:

I

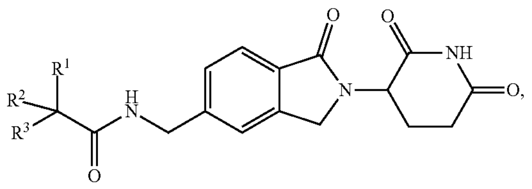

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, $—R^4OR^5$, $—R^4SR^5$, $—R^4N(R^6)(R^7)$, $—R^4OR^4N(R^6)(R^7)$, or $—R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In certain embodiments of the methods provided herein, the compound of Formula I is Compound D or Compound E. In one embodiment, the compound of Formula I is Compound D. In another embodiment, the compound of Formula I is Compound E.

In one specific embodiment, the biomarker is ATF4, and the cancer is MM, lymphoma, or leukemia. In one embodiment, the cancer is MM. In a specific embodiment, the cancer is lymphoma. In some embodiments, the cancer is leukemia. In another specific embodiment, the leukemia is CLL, CML, ALL, or AML. In one embodiment, the leukemia is AML. In a specific embodiment, the biomarker is ATF4, and the treatment compound is Compound D. In another specific embodiment, the biomarker is ATF4, and the treatment compound is Compound E.

In a specific embodiment, the biomarker is ATF3, and the cancer is MM, lymphoma, or leukemia. In one embodiment, the cancer is MM. In a specific embodiment, the cancer is lymphoma. In some embodiments, the cancer is leukemia. In another specific embodiment, the leukemia is CLL, CML, ALL, or AML. In one embodiment, the leukemia is AML. In a specific embodiment, the biomarker is ATF3, and the treatment compound is Compound D. In another specific embodiment, the biomarker is ATF3, and the treatment compound is Compound E.

In another specific embodiment, the biomarker is DDIT3, and the cancer is MM, lymphoma, or leukemia. In one embodiment, the cancer is MM. In a specific embodiment, the cancer is lymphoma. In some embodiments, the cancer is leukemia. In another specific embodiment, the leukemia is CLL, CML, ALL, or AML. In one embodiment, the leukemia is AML. In a specific embodiment, the biomarker is DDIT3, and the treatment compound is Compound D. In another specific embodiment, the biomarker is DDIT3, and the treatment compound is Compound E.

In one specific embodiment, the biomarker is cleaved PARP, and the cancer is MM, lymphoma, or leukemia. In one embodiment, the cancer is MM. In a specific embodiment, the cancer is lymphoma. In some embodiments, the cancer is leukemia. In another specific embodiment, the leukemia is CLL, CML, ALL, or AML. In one embodiment, the leukemia is AML. In a specific embodiment, the biomarker is cleaved PARP, and the treatment compound is Compound D. In another specific embodiment, the biomarker is cleaved PARP, and the treatment compound is Compound E.

In another specific embodiment, the biomarker is SRSF3 NMD transcript, and the cancer is MM, lymphoma, or leukemia. In one embodiment, the cancer is MM. In a specific embodiment, the cancer is lymphoma. In some embodiments, the cancer is leukemia. In another specific embodiment, the leukemia is CLL, CML, ALL, or AML. In one embodiment, the leukemia is AML. In a specific embodiment, the biomarker is SRSF3 NMD transcript, and the treatment compound is Compound D. In another specific embodiment, the biomarker is SRSF3 NMD transcript, and the treatment compound is Compound E.

In another specific embodiment, the biomarker is SRSF6 NMD transcript, and the cancer is MM, lymphoma, or leukemia. In one embodiment, the cancer is MM. In a specific embodiment, the cancer is lymphoma. In some embodiments, the cancer is leukemia. In another specific embodiment, the leukemia is CLL, CML, ALL, or AML. In one embodiment, the leukemia is AML. In a specific embodiment, the biomarker is SRSF6 NMD transcript, and the treatment compound is Compound D. In another specific embodiment, the biomarker is SRSF6 NMD transcript, and the treatment compound is Compound E.

In some embodiments of the various methods provided herein, the level of the biomarkers is measured by determining the protein level of the biomarker.

In other embodiments of the various methods provided herein, the level of the biomarkers is measured by determining the mRNA level of the biomarker.

In yet other embodiments of the various methods provided herein, the level of the biomarkers is measured by determining the cDNA level of the biomarker.

In some embodiments of the various methods provided herein, the treatment compound is a compound described in Section 5.7 below.

In some embodiments of the various methods provided herein, the treatment compound is a compound of Formula I:

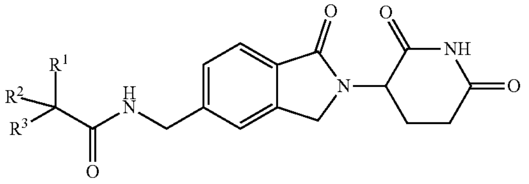
I or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, —$R^4OR^4N(R^6)(R^7)$, or —$R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In some embodiments of the various methods provided herein, the treatment compound is a compound of Formula I:

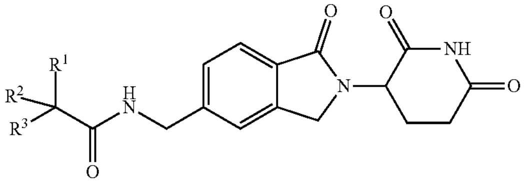
I or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is a halo-substituted aryl; and $R^2$ and $R^3$ are each halo.

In a specific embodiment, the treatment compound is 2-(4-chlorophenyl)-N-((2-(2,6-dioxopiperidin-3-yl)-1-oxoisoindolin-5-yl)methyl)-2,2-difluoroacetamide ("Compound D"), or a stereoisomer or a mixture of stereoisomers, tautomer, a pharmaceutically acceptable salt, solvate, isotopologue, prodrug, hydrate, co-crystal, clathrate, or a polymorph thereof.

In another specific embodiment, the treatment compound is the treatment compound is 2-(4-flurophenyl)-N-((2-(2,6-dioxopiperidin-3-yl)-1-oxoisoindolin-5-yl)methyl)-2,2-difluoroacetamide ("Compound E"), or a stereoisomer or a mixture of stereoisomers, tautomer, a pharmaceutically acceptable salt, solvate, isotopologue, prodrug, hydrate, co-crystal, clathrate, or a polymorph thereof.

In some embodiments, the treatment compound is Compound D, and the cancer is MM, lymphoma, or leukemia. In one embodiment, the cancer is MM. In a specific embodiment, the cancer is lymphoma. In some embodiments, the cancer is leukemia. In another specific embodiment, the leukemia is CLL, CML, ALL, or AML. In one embodiment, the leukemia is AML.

In some embodiments, the treatment compound is Compound E, and the cancer is MM, lymphoma, or leukemia. In one embodiment, the cancer is MM. In a specific embodiment, the cancer is lymphoma. In some embodiments, the cancer is leukemia. In another specific embodiment, the leukemia is CLL, CML, ALL, or AML. In one embodiment, the leukemia is AML.

In some embodiments, the responsiveness of a patient or a subject, or the efficacy of a treatment is determined by the overall survival (OS), complete remission rate (CRR), objective response rate (ORR), time to progression, relapse free survival (RFS), progression-free survival (PFS) event-free survival, duration of remission, duration of response, and/or time to remission/response of a patient having a cancer. In one embodiment, the cancer is a hematological cancer. In certain embodiments, the ORR includes all responses of complete remission (CR) (i.e., morphologic leukemia-free state, morphologic CR, cytogenetic CR, molecular CR, and morphologic CR with incomplete blood recovery), and partial remission.

In other embodiments, the various methods provided herein are for increasing the overall survival (OS), complete remission rate (CRR), objective response rate (ORR), time to progression, relapse free survival (RFS), progression-free survival (PFS) event-free survival, duration of remission, duration of response, and/or time to remission/response of a patient having a cancer, for example, a hematological cancer.

As used herein, Overall survival (OS) means the time from randomization in a clinical trial until death from any cause. Progression-free survival (PFS) means the time from randomization in a clinical trial until progression or death. Event-free survival (EFS) means the time from study entry until any treatment failure, including disease progression, treatment discontinuation for any reason, or death. Overall response rate (ORR) means the sum of the percentage of patients who achieve complete and partial responsess. Duration of response (DoR) is the time from achieving a response until relapse or disease progression.

5.3. Methods of Detecting and Quantifying Biomarkers

In certain embodiments, provided herein are methods of detecting and quantifying the protein level of biomarker, such as CRBN or a protein that is directly or indirectly affected by CRBN, from a biological sample, comprising contacting proteins within the sample with a first antibody that immunospecifically binds to the biomarker protein. In some embodiments, the methods provided herein further comprise (i) contacting the biomarker protein bound to the first antibody with a second antibody with a detectable label, wherein the second antibody immunospecifically binds to the biomarker protein, and wherein the second antibody immunospecifically binds to a different epitope on the biomarker protein than the first antibody; (ii) detecting the presence of the second antibody bound to the biomarker protein; and (iii) determining the amount of the biomarker protein based on the amount of detectable label in the second antibody. In other embodiments, the methods provided herein further comprise (i) contacting the biomarker protein bound to the first antibody with a second antibody with a detectable label, wherein the second antibody immunospecifically binds to the first antibody; (ii) detecting the presence of the second antibody bound to the first antibody; and (iii) determining the amount of the biomarker protein based on the amount of detectable label in the second antibody.

In some embodiments of the various methods provided herein, the method comprises using dual staining immunohistochemistry to determine the level of a biomarker, such as CRBN or a protein that is directly or indirectly affected by CRBN. In a dual staining immunohistochemistry assay, a biomarker provided herein and another cancer biomarker are simultaneously detected using a first labeled antibody targeting a biomarker provided herein and a second labeled antibody targeting a cancer biomarker. Such assay can improve the specificity, accuracy, and sensitivity for detecting and measuring a biomarker provided herein. In some embodiments, the cancer biomarker is a lymphoma biomarker. In other embodiments, the cancer biomarker is an NHL biomarker. In certain embodiments, the cancer biomarker is a DLBCL biomarker. In some embodiments, the cancer biomarker is an MM biomarker. In other embodiments, the cancer biomarker is a leukemia biomarker. In yet other embodiments, the cancer biomarker is an AML biomarker.

Thus, in some embodiments, the method provided herein comprises (i) contacting proteins within a sample with a first antibody that immunospecifically binds to a biomarker provided herein, the first antibody being coupled with a first detectable label; (ii) contacting the proteins within the sample with a second antibody that immunospecifically binds to a cancer biomarker, the second antibody being coupled with a second detectable label; (iii) detecting the presence of the first antibody and the second antibody bound to the proteins; and (iv) determining the level of the biomarker provided herein based on the amount of detectable label in the first antibody, and determining the level of the cancer biomarker based on the amount of detectable label in the second antibody. In some embodiments, the cancer biomarker is a lymphoma biomarker. In other embodiments, the cancer biomarker is an NHL biomarker. In certain embodiments, the cancer biomarker is a DLBCL biomarker. In some embodiments, the cancer biomarker is an MM biomarker. In other embodiments, the cancer biomarker is a leukemia biomarker. In yet other embodiments, the cancer biomarker is an AML biomarker.

In certain embodiments, provided herein are methods of detecting and quantifying the RNA (e.g., mRNA) level of a biomarker, such as CRBN or a biomarker provided herein, from a biological sample, comprising: (a) obtaining RNA from the sample; (b) contacting the RNA with a primer that specifically binds to a sequence in the RNA to generate a first DNA molecule having a sequence complementary to said RNA; (c) amplifying the DNA corresponding to a segment of a gene encoding the biomarker; and (d) determining the RNA level of the biomarker based on the amount of the amplified DNA.

In some embodiments, the biomarker(s) are evaluated in combination with other biomarker(s) provided herein, such as CRBN, GSPT1, GSPT2, IKZF1, ATF4, ATF3, and DDIT3.

In certain embodiments of the various methods provided herein, the two or more of the steps are performed sequentially. In other embodiments of the methods provided herein, two or more of steps are performed in parallel (e.g., at the same time).

Exemplary assays provided herein for the methods of detecting and quantifying the protein level of a biomarker, such as GSPT1, GSPT2, IKZF1, eRF1, BIP, GCN2, eIF2α, ATF4, ATF3, DDIT3, PPP1R15A, TNFRSF10B, GADD45A, FAS, IRE1, XBP1, SEC24D, DNAJB9, EDEM1, ATF6, Caspase 3, Caspase 7, Caspase 8, Caspase 9, BID, PARP, Mcl-1, SRSF3, SRSF6, or a combination thereof, are immunoassays, such as western blot analysis and enzyme-linked immunosorbent assay (ELISA) (e.g., a sandwich ELISA). An exemplary assay provided herein for the methods of detecting and quantifying the RNA level of a biomarker, such as GSPT1, GSPT2, IKZF1, eRF1, BIP, GCN2, eIF2α, ATF4, ATF3, DDIT3, PPP1R15A, TNFRSF10B, GADD45A, FAS, IRE1, XBP1, SEC24D, DNAJB9, EDEM1, ATF6, Caspase 3, Caspase 7, Caspase 8, Caspase 9, BID, PARP, Mcl-1, SRSF3, SRSF6, or a combination thereof, is reverse transcription polymerase chain reaction (RT-PCR), e.g., quantitative RT-PCR (qRT-PCR).

Exemplary assays provided herein for the methods of detecting and quantifying the protein level of a biomarker, such as CRBN or a protein that is directly or indirectly affected by CRBN (e.g., GSPT1, GSPT2, IKZF1, ATF4, ATF3, and DDIT3), or a combination thereof, are immunoassays, such as western blot analysis and enzyme-linked immunosorbent assay (ELISA) (e.g., a sandwich ELISA). An exemplary assay provided herein for the methods of detecting and quantifying the RNA level of a biomarker, such as CRBN or a protein that is directly or indirectly affected by CRBN (e.g., GSPT1, GSPT2, IKZF1, ATF4, ATF3, and DDIT3), or a combination thereof, is reverse transcription polymerase chain reaction (RT-PCR), e.g., quantitative RT-PCR (qRT-PCR).

5.4. Subjects, Samples, and Types of Cells

In certain embodiments, the various methods provided herein use samples (e.g., biological samples) from subjects or individuals (e.g., patients). The subject can be a patient, such as, a patient with a cancer (e.g., lymphoma, MM, or leukemia). The subject can be a mammal, for example, a human. The subject can be male or female, and can be an adult, a child, or an infant. Samples can be analyzed at a time during an active phase of a cancer (e.g., lymphoma, MM, or leukemia), or when the cancer (e.g., lymphoma, MM, or leukemia) is inactive. In certain embodiments, more than one sample from a subject can be obtained.

In certain embodiments, the sample used in the methods provided herein comprises body fluids from a subject. Non-limiting examples of body fluids include blood (e.g., whole blood), blood plasma, amniotic fluid, aqueous humor, bile, cerumen, cowper's fluid, pre-ejaculatory fluid, chyle, chyme, female ejaculate, interstitial fluid, lymph, menses, breast milk, mucus, pleural fluid, pus, saliva, sebum, semen, serum, sweat, tears, urine, vaginal lubrication, vomit, water, feces, internal body fluids (including cerebrospinal fluid surrounding the brain and the spinal cord), synovial fluid, intracellular fluid (the fluid inside cells), and vitreous humour (the fluid in the eyeball). In some embodiments, the sample is a blood sample. The blood sample can be obtained using conventional techniques as described in, e.g., Innis et al, eds., PCR Protocols (Academic Press, 1990). White blood cells can be separated from blood samples using conventional techniques or commercially available kits, e.g., RosetteSep kit (Stein Cell Technologies, Vancouver, Canada). Sub-populations of white blood cells, e.g., mononuclear cells, B cells, T cells, monocytes, granulocytes, or lymphocytes, can be further isolated using conventional techniques, e.g., magnetically activated cell sorting (MACS) (Miltenyi Biotec, Auburn, California) or fluorescently activated cell sorting (FACS) (Becton Dickinson, San Jose, California).

In one embodiment, the blood sample is from about 0.1 mL to about 10.0 mL, from about 0.2 mL to about 7 mL, from about 0.3 mL to about 5 mL, from about 0.4 mL to about 3.5 mL, or from about 0.5 mL to about 3 mL. In another embodiment, the blood sample is about 0.3, about 0.4, about 0.5, about 0.6, about 0.7, about 0.8, about 0.9, about 1.0, about 1.5, about 2.0, about 2.5, about 3.0, about 3.5, about 4.0, about 4.5, about 5.0, about 6.0, about 7.0, about 8.0, about 9.0, or about 10.0 mL.

In some embodiments, the sample used in the present methods comprises a biopsy (e.g., a tumor biopsy). The biopsy can be from any organ or tissue, for example, skin, liver, lung, heart, colon, kidney, bone marrow, teeth, lymph node, hair, spleen, brain, breast, or other organs. Any biopsy technique known by those skilled in the art can be used for isolating a sample from a subject, for instance, open biopsy, close biopsy, core biopsy, incisional biopsy, excisional biopsy, or fine needle aspiration biopsy.

In one embodiment, the sample used in the methods provided herein is obtained from the subject prior to the subject receiving a treatment for the disease or disorder. In another embodiment, the sample is obtained from the subject during the subject receiving a treatment for the disease or disorder. In another embodiment, the sample is obtained from the subject after the subject receiving a treatment for the disease or disorder. In various embodiments, the treatment comprises administering a compound (e.g., a compound provided in Section 5.7 below) to the subject.

In certain embodiments, the sample used in the methods provided herein comprises a plurality of cells, such as cancer (e.g., lymphoma, MM, or leukemia) cells. Such cells can include any type of cells, e.g., stem cells, blood cells (e.g., peripheral blood mononuclear cells (PBMC)), lymphocytes, B cells, T cells, monocytes, granulocytes, immune cells, or cancer cells.

B cells (B lymphocytes) include, for example, plasma B cells, memory B cells, B1 cells, B2 cells, marginal-zone B cells, and follicular B cells. B cells can express immunoglobulins (antibodies) and B cell receptor.

Specific cell populations can be obtained using a combination of commercially available antibodies (e.g., antibodies from Quest Diagnostic (San Juan Capistrano, California) or Dako (Denmark)).

In certain embodiments, the cells in the methods provided herein are PBMC. In certain embodiments, the sample used in the methods provided herein is from a disease tissue, e.g., from an individual having cancer (e.g., lymphoma, MM, or leukemia).

In certain embodiments, cell lines are used as disease models for evaluating effects of compounds, studying mechanisms of action, or establishing reference levels of biomarkers, etc. In some embodiments, the cells used in the methods provided herein are from a cancer (e.g., AML) cell line. In one embodiment, the AML cell line is KG-1 cell line. In another embodiment, the AIL cell line is KG-1a cell line. In yet another embodiment, the AML cell line is KASUMI-1 cell line. In still another embodiment, the AML cell line is NB4 cell line. In one embodiment, the AML cell line is MV-4-11 cell line. In another embodiment, the AML cell line is MOLM-13 cell line. In yet another embodiment, the AML cell line is HL-60 cell line. In still another embodiment, the AML cell line is U-937 cell line. In one embodiment, the AML cell line is OCI-AML2 cell line. In another embodiment, the AML cell line is OCI-AML3 cell line. In yet another embodiment, the AML cell line is HNT-34 cell line. In still another embodiment, the AML cell line is ML-2 cell line. In one embodiment, the AML cell line is AML-193 cell line. In another embodiment, the AML cell line is F36-P cell line.

In certain embodiments, the methods provided herein are useful for detecting gene rearrangement in cells from a healthy individual. In certain embodiments, the number of cells used in the methods provided herein can range from a single cell to about $10^9$ cells. In some embodiments, the number of cells used in the methods provided herein is about $1\times10^4$, about $5\times10^4$, about $1\times10^5$, about $5\times10^5$, about $1\times10^6$, about $5\times10^6$, about $1\times10^7$, about $5\times10^7$, about $1\times10^8$, about $5\times10^8$, or about $1\times10^9$.

The number and type of cells collected from a subject can be monitored, for example, by measuring changes in cell surface markers using standard cell detection techniques such as flow cytometry, cell sorting, immunocytochemistry (e.g., staining with tissue specific or cell-marker specific antibodies), fluorescence activated cell sorting (FACS), magnetic activated cell sorting (MACS), by examining the morphology of cells using light or confocal microscopy, and/or by measuring changes in gene expression using techniques well known in the art, such as PCR and gene expression profiling. These techniques can be used, too, to identify cells that are positive for one or more particular markers.

In certain embodiments, subsets of cells are used in the methods provided herein. Methods of sorting and isolating specific populations of cells are well-known in the art and can be based on cell size, morphology, or intracellular or extracellular markers. Such methods include, but are not limited to, flow cytometry, flow sorting, FACS, bead based separation such as magnetic cell sorting, size-based separation (e.g., a sieve, an array of obstacles, or a filter), sorting in a microfluidics device, antibody-based separation, sedimentation, affinity adsorption, affinity extraction, density gradient centrifugation, laser capture microdissection, etc. Fluorescence activated cell sorting (FACS) is a well-known method for separating particles, including cells, based on the fluorescent properties of the particles (Kamarch, Methods Enzymol. 1987, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used.

FACS sorted particles may be directly deposited into individual wells of 96-well or 384-well plates to facilitate separation and cloning.

In one embodiment, RNA (e.g., mRNA) or protein is purified from a tumor, and the presence or absence of a biomarker is measured by gene or protein expression analysis. In certain embodiments, the presence or absence of a biomarker is measured by quantitative real-time PCR (qRT-PCR), microarray, flow cytometry, or immunofluorescence. In other embodiments, the presence or absence of a biomarker is measured by ELISA or other similar methods known in the art.

5.5 Methods of Detecting mRNA Levels in a Sample

Several methods of detecting or quantitating mRNA levels are known in the art. Exemplary methods include, but are not limited to, northern blots, ribonuclease protection assays, PCR-based methods, and the like. The mRNA sequence of a biomarker (e.g., the mRNA of CRBN or a protein that is directly or indirectly affected by CRBN, or a fragment thereof) can be used to prepare a probe that is at least partially complementary to the mRNA sequence. The probe can then be used to detect the mRNA in a sample, using any suitable assay, such as PCR-based methods, northern blotting, a dipstick assay, and the like.

In other embodiments, a nucleic acid assay for testing for compound activity in a biological sample can be prepared. An assay typically contains a solid support and at least one nucleic acid contacting the support, where the nucleic acid corresponds to at least a portion of an mRNA that has altered expression during a compound treatment in a patient, such as the mRNA of a biomarker (e.g., CRBN or a protein that is directly or indirectly affected by CRBN). The assay can also have a means for detecting the altered expression of the mRNA in the sample.

The assay method can be varied depending on the type of mRNA information desired. Exemplary methods include but are not limited to Northern blots and PCR-based methods (e.g., qRT-PCR). Methods such as qRT-PCR can also accurately quantitate the amount of the mRNA in a sample.

Any suitable assay platform can be used to determine the presence of mRNA in a sample. For example, an assay may be in the form of a dipstick, a membrane, a chip, a disk, a test strip, a filter, a microsphere, a slide, a multi-well plate, or an optical fiber. An assay system may have a solid support on which a nucleic acid corresponding to the mRNA is attached. The solid support may comprise, for example, a plastic, silicon, a metal, a resin, glass, a membrane, a particle, a precipitate, a gel, a polymer, a sheet, a sphere, a polysaccharide, a capillary, a film, a plate, or a slide. The assay components can be prepared and packaged together as a kit for detecting an mRNA.

The nucleic acid can be labeled, if desired, to make a population of labeled mRNAs. In general, a sample can be labeled using methods that are well known in the art (e.g., using DNA ligase, terminal transferase, or by labeling the RNA backbone, etc.). See, e.g., Ausubel et al., *Short Protocols in Molecular Biology* (Wiley & Sons, 3rd ed. 1995); Sambrook et al., *Molecular Cloning: A Laboratory Manual* (Cold Spring Harbor, N.Y., 3rd ed. 2001). In some embodiments, the sample is labeled with fluorescent label. Exemplary fluorescent dyes include, but are not limited to, xanthene dyes, fluorescein dyes (e.g., fluorescein isothiocyanate (FITC), 6-carboxyfluorescein (FAM), 6 carboxy-2',4',7',4,7-hexachlorofluorescein (HEX), 6-carboxy-4',5'-dichloro-2',7'-dimethoxyfluorescein (JOE)), rhodamine dyes (e.g., rhodamine 110 (R110), N,N,N',N'-tetramethyl-6-carboxyrhodamine (TAMRA), 6-carboxy-X-rhodamine (ROX), 5-carboxyrhodamine 6G (R6G5 or G5), 6-carboxyrhodamine 6G (R6G6 or G6)), cyanine dyes (e.g., Cy3, Cy5 and Cy7), Alexa dyes (e.g., Alexa-fluor-555), coumarin, Diethylaminocoumarin, umbelliferone, benzimide dyes (e.g., Hoechst 33258), phenanthridine dyes (e.g., Texas Red), ethidium dyes, acridine dyes, carbazole dyes, phenoxazine dyes, porphyrin dyes, polymethine dyes, BODIPY dyes, quinoline dyes, Pyrene, Fluorescein Chlorotriazinyl, eosin dyes, Tetramethylrhodamine, Lissamine, Napthofluorescein, and the like.

In some embodiments, the mRNA sequences comprise at least one mRNA of a biomarker provided herein. In some embodiments, the biomarker is selected from the group consisting of mRNA of GSPT1, GSPT2, IKZF1, eRF1, BIP, GCN2, eIF2α, ATF4, ATF3, DDIT3, PPP1R15A, TNFRSF10B, GADD45A, FAS, IRE1, XBP1, SEC24D, DNAJB9, EDEM1, ATF6, Caspase 3, Caspase 7, Caspase 8, Caspase 9, BID, PARP, Mcl-1, SRSF3, SRSF6, or a fragment thereof.

In one embodiment, the biomarker is selected from the group consisting of the mRNA of GSPT1, GSPT2, IKZF1, ATF4, ATF3, and DDIT3, or a fragment thereof. In one embodiment, the mRNA is GSPT1 mRNA. In another embodiment, the mRNA is GSPT2 mRNA. In yet another embodiment, the mRNA is IKZF1 mRNA. In another embodiment, the mRNA is ATF4 mRNA. In still another embodiment, the mRNA is ATF3 mRNA. In other embodiments, the mRNA is DDIT3 mRNA. The nucleic acids may be present in specific, addressable locations on a solid support, each corresponding to at least a portion of mRNA sequences that are differentially expressed upon treatment of a compound in a cell or a patient.

A typical mRNA assay method can contain the steps of 1) obtaining surface-bound subject probes; 2) hybridizing a population of mRNAs to the surface-bound probes under conditions sufficient to provide for specific binding; (3) post-hybridization washing to remove nucleic acids not specifically bound to the surface-bound probes; and (4) detecting the hybridized mRNAs. The reagents used in each of these steps and their conditions for use may vary depending on the particular application.

Hybridization can be carried out under suitable hybridization conditions, which may vary in stringency as desired. Typical conditions are sufficient to produce probe/target complexes on a solid surface between complementary binding members, i.e., between surface-bound subject probes and complementary mRNAs in a sample. In certain embodiments, stringent hybridization conditions may be employed.

Hybridization is typically performed under stringent hybridization conditions. Standard hybridization techniques (e.g., under conditions sufficient to provide for specific binding of target mRNAs in the sample to the probes) are described in Kallioniemi et al., *Science* 1992, 258:818-821 and International Patent Application Publication No. WO 93/18186. Several guides to general techniques are available, e.g., Tijssen, *Hybridization with Nucleic Acid Probes*, Parts I and II (Elsevier, Amsterdam 1993). For descriptions of techniques suitable for in situ hybridizations, see Gall et al., *Meth. Enzymol.* 1981, 21:470-480; Angerer et al., *Genetic Engineering: Principles and Methods*, Vol 7, pgs 43-65 (Plenum Press, New York, Setlow and Hollaender, eds. 1985). Selection of appropriate conditions, including temperature, salt concentration, polynucleotide concentration, hybridization time, stringency of washing conditions, and the like will depend on experimental design, including source of sample, identity of capture agents, degree of complementarity expected, etc., and may be determined as a matter of routine experimentation for those of ordinary skill in the art.

Those of ordinary skill will readily recognize that alternative but comparable hybridization and wash conditions can be utilized to provide conditions of similar stringency.

After the mRNA hybridization procedure, the surface bound polynucleotides are typically washed to remove unbound nucleic acids. Washing may be performed using any convenient washing protocol, where the washing conditions are typically stringent, as described above. The hybridization of the target mRNAs to the probes is then detected using standard techniques.

Other methods, such as PCR-based methods, can also be used to detect the expression of CRBN or a protein that is directly or indirectly affected by CRBN. Examples of PCR methods can be found in U.S. Pat. No. 6,927,024, which is incorporated by reference herein in its entirety. Examples of RT-PCR methods can be found in U.S. Pat. No. 7,122,799, which is incorporated by reference herein in its entirety. A method of fluorescent in situ PCR is described in U.S. Pat. No. 7,186,507, which is incorporated by reference herein in its entirety.

In some embodiments, quantitative Reverse Transcription-PCR (qRT-PCR) can be used for both the detection and quantification of RNA targets (Bustin et al., Clin. Sci. 2005, 109:365-379). Quantitative results obtained by qRT-PCR are generally more informative than qualitative data. Thus, in some embodiments, qRT-PCR-based assays can be useful to measure mRNA levels during cell-based assays. The qRT-PCR method is also useful to monitor patient therapy. Examples of qRT-PCR-based methods can be found, for example, in U.S. Pat. No. 7,101,663, which is incorporated by reference herein in its entirety.

In contrast to regular reverse transcriptase-PCR and analysis by agarose gels, qRT-PCR gives quantitative results. An additional advantage of qRT-PCR is the relative ease and convenience of use. Instruments for qRT-PCR, such as the Applied Biosystems 7500, are available commercially, so are the reagents, such as TaqMan® Sequence Detection Chemistry. For example, TaqMan® Gene Expression Assays can be used, following the manufacturer's instructions. These kits are pre-formulated gene expression assays for rapid, reliable detection and quantification of human, mouse, and rat mRNA transcripts. An exemplary qRT-PCR program, for example, is 50° C. for 2 minutes, 95° C. for 10 minutes, 40 cycles of 95° C. for 15 seconds, then 60° C. for 1 minute.

To determine the cycle number at which the fluorescence signal associated with a particular amplicon accumulation crosses the threshold (referred to as the $C_T$), the data can be analyzed, for example, using 7500 Real-Time PCR System Sequence Detection software vs. using the comparative $C_T$ relative quantification calculation method. Using this method, the output is expressed as a fold-change of expression levels. In some embodiments, the threshold level can be selected to be automatically determined by the software. In some embodiments, the threshold level is set to be above the baseline but sufficiently low to be within the exponential growth region of an amplification curve.

5.6 Methods of Detecting Polypeptide or Protein Levels in a Sample

Several protein detection and quantization methods can be used to measure the level of a biomarker, such as CRBN or a protein that is directly or indirectly affected by CRBN. Any suitable protein quantization method can be used. In some embodiments, antibody-based methods are used. Exemplary methods that can be used include, but are not limited to, immunoblotting (Western blot), ELISA, immunohistochemistry, flow cytometry, cytometry bead array, mass spectroscopy, and the like. Several types of ELISA are commonly used, including direct ELISA, indirect ELISA, and sandwich ELISA.

In some embodiments, the biomarker is selected from the group consisting of the proteins of GSPT1, GSPT2, IKZF1, eRF1, BIP, GCN2, eIF2α, ATF4, ATF3, DDIT3, PPP1R15A, TNFRSF10B, GADD45A, FAS, IRE1, XBP1, SEC24D, DNAJB9, EDEM1, ATF6, Caspase 3, Caspase 7, Caspase 8, Caspase 9, BID, PARP, Mcl-1, SRSF3, and SRSF6. In certain embodiments, the biomarker is a protein that is directly or indirectly affected by CRBN. In one embodiment, the biomarker is selected from a group consisting of GSPT1, GSPT2, IKZF1, ATF4, ATF3, and DDIT3. In some embodiments, the biomarker is selected from a group consisting of GSPT1, GSPT2, and IKZF1. In other embodiments, the biomarker is selected from a group consisting of ATF4, ATF3, and DDIT3. In a specific embodiment, the biomarker is GSPT1. In another specific embodiment, the biomarker is GSPT2. In yet another specific embodiment, the biomarker is IKZF1. In another embodiment, the biomarker is ATF4. In still another specific embodiment, the biomarker is ATF3. In yet another specific embodiment, the biomarker is DDIT3.

5.7 Compounds

In certain embodiments, provided herein are compounds of Formula I:

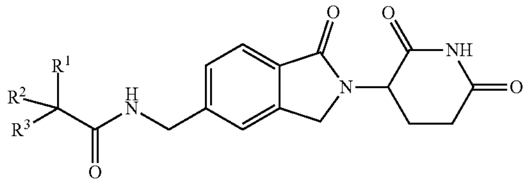

I or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, $—R^4OR^5$, $—R^4SR^5$, $—R^4N(R^6)(R^7)$, $—R^4OR^4N(R^6)(R^7)$, or $—R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In one embodiment, provided herein are compounds of Formula II:

II

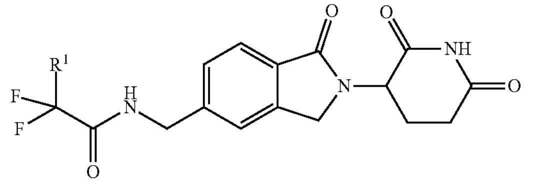

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, —$R^4OR^4N(R^6)(R^7)$, or —$R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In one embodiment, the compounds have Formula I or of Formula II, wherein $R^1$ is optionally substituted aryl;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, —$R^4OR^4N(R^6)(R^7)$, or —$R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In one embodiment, the compounds are of Formula I or of Formula II, wherein $R^1$ is optionally substituted aryl, optionally substituted cycloalkyl, optionally substituted heterocyclyl, or optionally substituted heteroaryl, where the substituents on $R^1$, when present are one to three groups Q, where each Q is independently halo, alkyl, optionally substituted cycloalkyl, optionally substituted aryl, —$R^4OR^5$, or —$R^4N(R^6)(R^7)$; each $R^4$ is independently a direct bond or alkylene; each $R^5$ is independently hydrogen, halo, alkyl, alkoxy, haloalkoxy, or haloalkyl; and i) $R^6$ and $R^7$ are each independently hydrogen or alkyl, or ii) $R^6$ and $R^7$ together with the nitrogen atom on which they are substituted form a 5 or 6-membered heterocyclyl or heteroaryl ring, optionally substituted with one or two halo, alkyl, or haloalkyl.

In one embodiment, the compounds have Formula I or Formula II, wherein $R^1$ is optionally substituted phenyl, optionally substituted cyclohexyl, optionally substituted piperidinyl, or optionally substituted pyridyl, where the substituents on $R^1$, when present are one to three groups Q, where each Q is independently halo, alkyl, —$R^4OR^5$, or —$R^4N(R^6)(R^7)$; each $R^4$ is independently a direct bond or alkylene; each $R^5$ is independently hydrogen, halo, alkyl, alkoxy, haloalkoxy, or haloalkyl; and i) $R^6$ and $R^7$ are each independently hydrogen or alkyl; or ii) $R^6$ and $R^7$ together with the nitrogen atom on which they are substituted form a 5 or 6-membered heterocyclyl ring.

In one embodiment, the compounds are of Formula I or of Formula II, wherein $R^1$ is optionally substituted phenyl, optionally substituted cyclohexyl, optionally substituted piperidinyl, or optionally substituted pyridyl, where the substituents on $R^1$, when present are one to three groups Q, where each Q is independently bromo, fluoro, chloro, methyl, isopropyl, tert butyl trifluromethyl, methoxy, ethoxy, isopropyloxy, methoxyethoxy, isopropyloxyethoxy, trifluoromethoxy, methylamino, dimethylamino, or piperidinyl.

In one embodiment, the compounds have Formula I or Formula II, wherein $R^1$ is optionally substituted aryl, where the substituents on $R^1$, when present are one to three groups Q, where each Q is independently halo, alkyl, —$R^4OR^5$, —$R^4SR^5$, or —$R^4OR^4C(O)N(R^6)(R^7)$; each $R^4$ is independently a direct bond or alkylene; each $R^5$ is independently hydrogen, halo, alkyl, or haloalkyl; and $R^6$ and $R^7$ are each independently hydrogen or alkyl.

In one embodiment, the compounds have Formula I or Formula II, wherein $R^1$ is optionally substituted aryl, where the substituents on $R^1$, when present are one to three groups Q, where each Q is independently fluoro, chloro, methyl, —$R^4OR^5$, —$R^4N(R^6)(R^7)$, —$R^4SR^5$, or —$R^4OR^4C(O)N(R^6)(R^7)$; each $R^4$ is independently a direct bond or methylene; each $R^5$ is independently hydrogen, methyl, ethyl, or trifluoromethyl; and $R^6$ and $R^7$ are each independently hydrogen or methyl.

In one embodiment, the compounds have Formula I or Formula II, wherein $R^1$ is optionally substituted phenyl, where the substituents on $R^1$, when present are one to three groups Q, where each Q is independently fluoro, chloro, methyl, tert butyl, —$R^4OR^5$, —$R^4N(R^6)(R^7)$, —$R^4SR^5$, or —$R^4OR^4C(O)N(R^6)(R^7)$; each $R^4$ is independently a direct bond or methylene; each $R^5$ is independently hydrogen, methyl, ethyl, or trifluoromethyl; and $R^6$ and $R^7$ are each independently hydrogen or methyl.

In one embodiment, provided herein are compounds of Formula III:

III

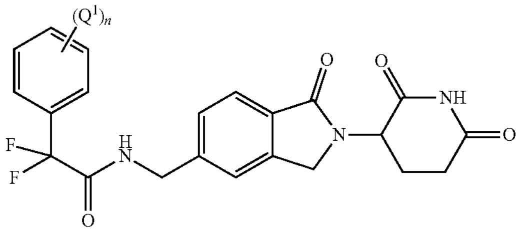

or a stereoisomer or a mixture of stereoisomers, tautomer, pharmaceutically acceptable salt, solvate, isotopologue, prodrug, hydrate, co-crystal, clathrate, or a polymorph thereof, wherein:

each $Q^1$ is independently alkyl, halo, haloalkyl, alkoxyalkyl, hydroxyl, alkoxy, optionally substituted cycloalkyl, optionally substituted cycloalkylalkyl, optionally substituted aryl, $—R^4OR^5$, $—R^4SR^5$, $—R^4N(R^6)(R^7)$, $—R^4OR^4N(R^6)(R^7)$, or $—R^4OR^4C(J)N(R^6)(R^7)$; each $R^4$ is independently alkylene, alkenylene, or a direct bond;

each $R^5$ is independently hydrogen, alkyl, haloalkyl, or hydroxyalkyl;

J is O or S;

$R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl; and n is 0-3.

In one embodiment, provided herein are compounds of Formula III or a stereoisomer or a mixture of stereoisomers, or a pharmaceutically acceptable salt, solvate, hydrate, co-crystal, clathrate, or polymorph thereof, wherein:

$Q^1$ is alkyl, halo, haloalkyl, hydroxyl, alkoxy, optionally substituted cycloalkyl, optionally substituted cycloalkylalkyl, optionally substituted aryl, $—R^4OR^5$, $—R^4SR^5$, $—R^4N(R^6)(R^7)$;

each $R^4$ is independently alkylene, alkenylene, or a direct bond;

each $R^5$ is independently hydrogen, alkyl, haloalkyl, or hydroxyalkyl;

$R^6$ and $R^7$ are selected as follows:

i) $R^6$ and $R^7$ are each independently hydrogen or alkyl; or ii) $R^6$ and $R^7$ together with the nitrogen atom on which they are substituted form a 5 or 6-membered heterocyclyl; and n is 0-3.

In one embodiment, the compounds herein are of Formula III, where $Q^1$ is hydrogen, Br, Cl, F, methyl, isopropyl, t-butyl, isopropyl, cyclopropyl, $—CF_3$, $—OH$, $—SCH_3$, $—SCF_3$, $—C(CH_3)_2F$, $—OCH_3$, $—OCF_3$, $—OCH_2CH_3$, $—OCH(CH_3)_2$, $—OCH_2CF_3$, $—O(CH_2)_2OCH_3$, $—O(CH_2)_2$ $OCH(CH_3)_2$, $—O(CH_2)_2O(CH_2)_2OCH_3$, $—NHCH_3$, $—N(CH_3)_2$, $—O(CH_2)_2$-morpholinyl, piperidyl, morpholinyl, $—CH_2$-morpholinyl, $—O(CH_2)_2$-4,4-difluoro-1-piperidyl, or p-fluorophenyl.

In one embodiment, provided herein are compounds of Formula IV:

IV

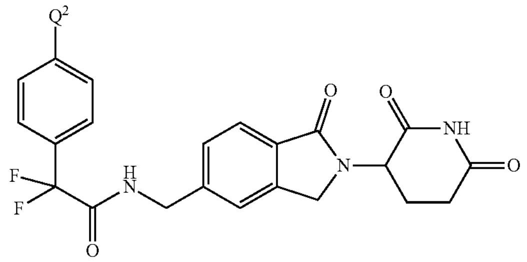

or a stereoisomer or a mixture of stereoisomers, tautomer, pharmaceutically acceptable salt, solvate, isotopologue, prodrug, hydrate, co-crystal, clathrate, or a polymorph thereof, wherein:

$Q^2$ is hydrogen, alkyl, halo, haloalkyl, hydroxyl, alkoxy, optionally substituted cycloalkyl, optionally substituted cycloalkylalkyl, optionally substituted aryl, $—R^4OR^5$, $—R^4SR^5$, $—R^4N(R^6)(R^7)$, $—R^4OR^4N(R^6)(R^7)$, or $—R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl.

In one embodiment, the compounds herein are of Formula IV, where $Q^2$ is hydrogen, halo, alkyl, optionally substituted aryl, $—R^4OR^5$, or $—R^4N(R^6)(R^7)$; $R^4$ is independently a direct bond or alkylene; $R^5$ is hydrogen, alkyl, or haloalkyl; and $R^6$ and $R^7$ are each independently hydrogen or alkyl. In some embodiments, $Q^2$ is hydrogen, Br, Cl, F, methyl, isopropyl, t-butyl, isopropyl, $—OCH_3$, $—SCH_3$, $—C(CH_3)_2$ F, $—OCH(CH_3)_2$, $—O(CH_2)_2OCH_3$, or p-fluorophenyl.

In one embodiment, provided herein are compounds of Formula V:

V

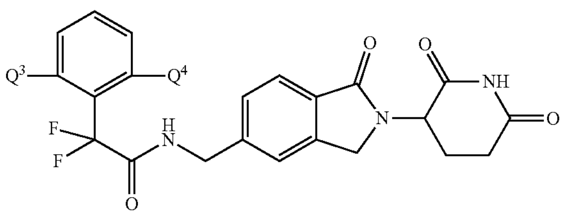

or a stereoisomer or a mixture of stereoisomers, tautomer, pharmaceutically acceptable salt, solvate, isotopologue, prodrug, hydrate, co-crystal, clathrate, or a polymorph thereof, wherein:

$Q^3$ and $Q^4$ are each independently hydrogen, alkyl, halo, haloalkyl, hydroxyl, alkoxy, optionally substituted cycloalkyl, optionally substituted cycloalkylalkyl, $—R^4OR^5$, $—R^4SR^5$, $—R^4N(R^6)(R^7)$, $—R^4OR^4N(R^6)(R^7)$, or $—R^4OR^4C(J)N(R^6)(R^7)$;

each $R^4$ is independently alkylene, alkenylene, or a direct bond;

each $R^5$ is independently hydrogen, alkyl, haloalkyl, hydroxyalkyl, or alkoxyalkyl;

J is O or S; and $R^6$ and $R^7$ are each independently hydrogen or alkyl.

In one embodiment, the compounds herein are of Formula V, where $Q^4$ and $Q^3$ are each independently hydrogen, halo, alkyl, alkoxyalkyl, —$R^4OR^5$, or —$R^4N(R^6)(R^7)$; $R^4$ is a direct bond or alkylene; and $R^5$ is hydrogen, alkyl, or haloalkyl; and $R^6$ and $R^7$ are each independently hydrogen or alkyl. In some such embodiments, $Q^4$ and $Q^3$ are each independently hydrogen, F, methyl, —$CF_3$, —OH, —$OCF_3$, —$OCH_2CH_3$, $OCH(CH_3)_2$, —$OCH_2CF_3$, or —$NHCH_3$.

In one embodiment, the compounds herein are of Formula V, where $Q^4$ is hydrogen, $Q^3$ is hydrogen, halo, alkyl, alkoxyalkyl, —$R^4N(R^6)(R^7)$, or —$R^4OR^5$; $R^4$ is a direct bond or alkylene; $R^5$ is hydrogen, alkyl, or haloalkyl; and $R^6$ and $R^7$ are each independently hydrogen or alkyl.

In one embodiment, provided herein are compounds of Formula VI:

VI

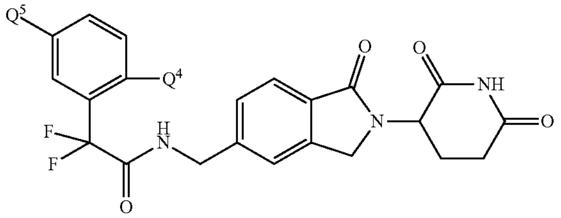

or a stereoisomer or a mixture of stereoisomers, tautomer, pharmaceutically acceptable salt, solvate, isotopologue, prodrug, hydrate, co-crystal, clathrate, or a polymorph thereof, wherein:

$Q^4$ and $Q^5$ are each independently hydrogen, alkyl, halo, haloalkyl, hydroxyl, alkoxy, optionally substituted cycloalkyl, optionally substituted cycloalkylalkyl, —$R^4OR^5$, —$R^4SR^5$, —$R^4N(R^6)(R^7)$, —$R^4OR^4N(R^6)(R^7)$, or —$R^4OR^4C(J)N(R^6)(R^7)$;

each $R^4$ is independently alkylene, alkenylene, or a direct bond;

each $R^5$ is independently hydrogen, alkyl, haloalkyl, alkoxyalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In one embodiment, the compounds herein are of Formula VI, where $Q^4$ and $Q^5$ are each independently hydrogen, halo, alkyl, alkoxyalkyl, —$R^4N(R^6)(R^7)$, or —$R^4OR^5$; $R^4$ is a direct bond or alkylene; $R^5$ is hydrogen, alkyl, or haloalkyl; and $R^6$ and $R^7$ together with the nitrogen atom on which they are substituted form a 6-membered heterocyclyl. In some such embodiments, $Q^4$ and $Q^5$ are each independently hydrogen, F, Cl, —OH, methyl, —$CF_3$, —$NHCH_3$, —$N(CH_3)_2$, —$OCF_3$, —$OCH_2CH_3$, —$OCH_2CF_3$, —$OCH(CH_3)_2$, —$O(CH_2)_2OCH_3$, —$O(CH_2)_2OCH(CH_3)_2$, —$O(CH_2)_2O(CH_2)_2OCH_3$, $O(CH_2)_2$-morpholinyl, piperidyl, morpholinyl, —$CH_2$-morpholinyl, or —$O(CH_2)_2$-4,4-difluoro-1-piperidyl.

In one embodiment, provided herein are compounds of Formula VII:

VII

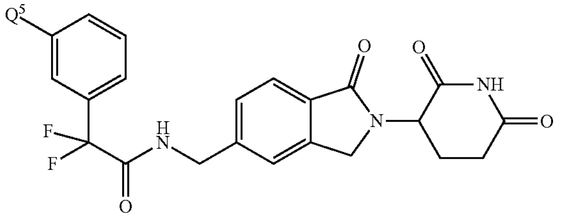

or a stereoisomer or a mixture of stereoisomers, tautomer, pharmaceutically acceptable salt, solvate, isotopologue, prodrug, hydrate, co-crystal, clathrate, or a polymorph thereof, wherein:

$Q^5$ is hydrogen, alkyl, halo, haloalkyl, hydroxyl, alkoxy, optionally substituted cycloalkyl, optionally substituted cycloalkylalkyl, —$R^4OR^5$, —$R^4SR^5$, —$R^4N(R^6)(R^7)$, —$R^4OR^4N(R^6)(R^7)$, or —$R^4OR^4C(J)N(R^6)(R^7)$;

each $R^4$ is independently alkylene, alkenylene, or a direct bond;

each $R^5$ is independently hydrogen, alkyl, haloalkyl, alkoxyalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In one embodiment, the compounds herein are of Formula VII, where $Q^5$ is hydrogen, halo, alkyl, alkoxyalkyl, —$R^4N(R^6)(R^7)$, or —$R^4OR^5$; $R^4$ is a direct bond or alkylene; $R^5$ is hydrogen, alkyl, or haloalkyl; and $R^6$ and $R^7$ together with the nitrogen atom on which they are substituted form a 6-membered heterocyclyl. In some such embodiments, $Q^5$ is hydrogen, F, Cl, methyl, piperidyl, morpholinyl, —$CH_2$-morpholinyl, —$N(CH_3)_2$, —$O(CH_2)_2OCH_3$, —$O(CH_2)_2OCH(CH_3)_2$, —$O(CH_2)_2O(CH_2)_2OCH_3$, or —$O(CH_2)_2$-4,4-difluoro-1-piperidyl.

In one embodiment, provided herein are compounds of Formula VIII:

VIII

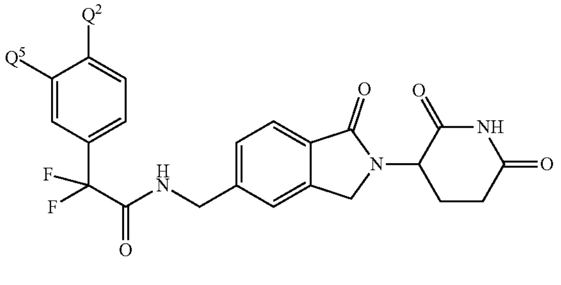

or a stereoisomer or a mixture of stereoisomers, tautomer, pharmaceutically acceptable salt, solvate, isotopologue, prodrug, hydrate, co-crystal, clathrate, or a polymorph thereof, wherein:

$Q^2$ and $Q^5$ are each independently hydrogen, alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, —$R^4OR^4N(R^6)(R^7)$, or —$R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 6-membered heterocyclyl.

In one embodiment, the compounds herein are of Formula VIII, where $Q^2$ and $Q^5$ are each independently hydrogen, halo, alkyl, alkoxyalkyl, optionally substituted aryl, or —$R^4OR^5$; $R^4$ is a direct bond or alkylene; and $R^5$ is hydrogen, alkyl, or haloalkyl. In some such embodiments, $Q^2$ and $Q^5$ are each independently hydrogen, F, Br, Cl, methyl, isopropyl, t-butyl, —$C(CH_3)_2F$, p-fluorophenyl, cyclopropyl, —$N(CH_3)_2$, —$OCH_3$, —$OCH(CH_3)_2$, —$O(CH_2)_2OCH_3$, —$O(CH_2)_2OCH(CH_3)_2$, —$O(CH_2)_2OCH_3$, —$O(CH_2)_2O(CH_2)_2OCH_3$, —$OCF_3$, —$O(CH_2)_2$-4,4-difluoro-1-piperidyl, —$SCF_3$, morpholinyl, piperidyl, or $CH_2$-morpholinyl.

In one embodiment, the compound provided herein is selected from the group consisting of:

2-(3-chloro-4-methylphenyl)-N-((2-(2,6-dioxopiperidin-3-yl)-1-oxoisoindolin-5-yl)methyl)-2,2-difluoroacetamide;

2-(4-chlorophenyl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl)methyl)-2,2-difluoro-2-(4-methoxyphenyl)acetamide;

2-(3-chlorophenyl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl)methyl)-2,2-difluoro-2-(4-fluorophenyl)acetamide;

N-((2-(2,6-dioxopiperidin-3-yl)-1-oxoisoindolin-5-yl)methyl)-2,2-difluoro-2-p-tolylacetamide;

2-(3,4-dichlorophenyl)-N-((2-(2,6-dioxopiperidin-3-yl)-1-oxoisoindolin-5-yl)methyl)-2,2-difluoroacetamide;

2-(2-chlorophenyl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl)methyl)-2,2-difluoro-2-(2-(trifluoromethyl)phenyl)acetamide;

2-(4-tert-butylphenyl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl)methyl)-2,2-difluoro-2-phenylacetamide;

2-(3-chloro-4-fluorophenyl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl)methyl)-2,2-difluoro-2-(4-(trifluoromethylthio)phenyl)acetamide;

2-(2,6-difluorophenyl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl)methyl)-2,2-difluoro-2-o-tolylacetamide;

N-((2-(2,6-dioxopiperidin-3-yl)-1-oxoisoindolin-5-yl)methyl)-2,2-difluoro-2-(2-fluorophenyl)acetamide;

N-((2-(2,6-dioxopiperidin-3-yl)-1-oxoisoindolin-5-yl)methyl)-2-(2-ethoxyphenyl)-2,2-difluoroacetamide;

N-((2-(2,6-dioxopiperidin-3-yl)-1-oxoisoindolin-5-yl)methyl)-2,2-difluoro-2-(2-(trifluoromethoxy)phenyl)acetamide;

2-(3-bromo-4-(trifluoromethoxy)phenyl)-N-((2-(2,6-dioxopiperidin-3-yl)-1-oxoisoindolin-5-yl)methyl)-2,2-difluoroacetamide;

2-(3-chloro-4-methoxyphenyl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl)methyl)-2,2-difluoro-2-m-tolylacetamide;

N-((2-(2,6-dioxopiperidin-3-yl)-1-oxoisoindolin-5-yl)methyl)-2,2-difluoro-2-(4-isopropoxyphenyl)acetamide;

2-(3,4-difluorophenyl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl)methyl)-2,2-difluoro-2-(3-fluorophenyl)acetamide;

N-((2-(2,6-dioxopiperidin-3-yl)-1-oxoisoindolin-5-yl)methyl)-2,2-difluoro-2-(3-(trifluoromethyl)pyridin-2-yl)acetamide;

N-((2-(2,6-dioxopiperidin-3-yl)-1-oxoisoindolin-5-yl)methyl)-2,2-difluoro-2-(4-isopropylphenyl)acetamide;

2-(2,4-dichlorophenyl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl)methyl)-2,2-difluoro-2-(2-methoxyphenyl)acetamide;

2-(4-cyclopropylphenyl)-N-((2-(2,6-dioxopiperidin-3-yl)-1-oxoisoindolin-5-yl)methyl)-2,2-difluoroacetamide;

2-(4-chloro-2-fluorophenyl)-N-((2-(2,6-dioxopiperidin-3-yl)-1-oxoisoindolin-5-yl)methyl)-2,2-difluoroacetamide;

2-(4-chloro-3-fluorophenyl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl)methyl)-2,2-difluoro-2-(3-fluoro-2-methylphenyl)acetamide;

2-(3-chloro-2-methylphenyl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl)methyl)-2,2-difluoro-2-(4-fluoro-2-(trifluoromethyl)phenyl)acetamide;

2-(4-chloro-2-methylphenyl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl)methyl)-2,2-difluoro-2-(4-fluoro-2-methylphenyl)acetamide;

2-(4-chloro-2-(trifluoromethyl)phenyl)-N-((2-(2,6-dioxopiperidin-3-yl)-1-oxoisoindolin-5-yl)methyl)-2,2-difluoroacetamide;

2-cyclohexyl-N-((2-(2,6-dioxopiperidin-3-yl)-1-oxoisoindolin-5-yl)methyl)-2,2-difluoroacetamide;

2-(4-chloro-2-(trifluoromethoxy)phenyl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl)methyl)-2,2-difluoro-2-(3-(2-methoxyethoxy)phenyl)acetamide;

N-((2-(2,6-dioxopiperidin-3-yl)-1-oxoisoindolin-5-yl)methyl)-2,2-difluoro-2-(3-(2-hydroxyethoxy)phenyl)acetamide;

N-((2-(2,6-dioxopiperidin-3-yl)-1-oxoisoindolin-5-yl)methyl)-2,2-difluoro-2-(4-(2-methoxyethoxy)phenyl)acetamide;

N-((2-(2,6-dioxopiperidin-3-yl)-1-oxoisoindolin-5-yl)methyl)-2,2-difluoro-2-(3-(2-hydroxyethyl)phenyl)acetamide;

2-(3-(dimethylamino)phenyl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl)methyl)-2,2-difluoro-2-(3-(piperidin-1-yl)phenyl)acetamide;

N-((2-(2,6-dioxopiperidin-3-yl)-1-oxoisoindolin-5-yl)methyl)-2,2-difluoro-2-(3-morpholinophenyl)acetamide;

N-((2-(2,6-dioxopiperidin-3-yl)-1-oxoisoindolin-5-yl) methyl)-2,2-difluoro-2-(4-fluoro-2-isopropoxyphenyl)acetamide;

N-((2-(2,6-dioxopiperidin-3-yl)-1-oxoisoindolin-5-yl) methyl)-2,2-difluoro-2-(2-(2,2,2-trifluoroethoxy)phenyl) acetamide;

N-((2-(2,6-dioxopiperidin-3-yl)-1-oxoisoindolin-5-yl) methyl)-2-(2-ethoxy-4-fluorophenyl)-2,2-difluoroacetamide;

N-((2-(2,6-dioxopiperidin-3-yl)-1-oxoisoindolin-5-yl) methyl)-2,2-difluoro-2-(2-isopropoxyphenyl)acetamide;

N-((2-(2,6-dioxopiperidin-3-yl)-1-oxoisoindolin-5-yl) methyl)-2,2-difluoro-2-(2-fluoro-4-isopropoxyphenyl)acetamide;

N-((2-(2,6-dioxopiperidin-3-yl)-1-oxoisoindolin-5-yl) methyl)-2,2-difluoro-2-(3-(morpholinomethyl)phenyl)acetamide;

N-((2-(2,6-dioxopiperidin-3-yl)-1-oxoisoindolin-5-yl) methyl)-2,2-difluoro-2-(4-fluoro-2-(2,2,2-trifluoroethoxy)phenyl)acetamide;

N-((2-(2,6-dioxopiperidin-3-yl)-1-oxoisoindolin-5-yl) methyl)-2,2-difluoro-2-(4-isopropoxy-2-methylphenyl) acetamide;

N-((2-(2,6-dioxopiperidin-3-yl)-1-oxoisoindolin-5-yl) methyl)-2,2-difluoro-2-(4-isopropoxy-3-methylphenyl) acetamide;

N-((2-(2,6-dioxopiperidin-3-yl)-1-oxoisoindolin-5-yl) methyl)-2,2-difluoro-2-(3-fluoro-4-isopropoxyphenyl)acetamide;

2-(3-chloro-4-isopropoxyphenyl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl) methyl)-2,2-difluoro-2-(2-methyl-4-(trifluoromethoxy) phenyl)acetamide;

N-((2-(2,6-dioxopiperidin-3-yl)-1-oxoisoindolin-5-yl) methyl)-2,2-difluoro-2-(2-fluoro-4-(trifluoromethoxy) phenyl)acetamide;

2-(5-chloropyridin-2-yl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl) methyl)-2,2-difluoro-2-(5-fluoropyridin-2-yl)acetamide;

2-(2,4-difluorophenyl)-N-((2-(2,6-dioxopiperidin-3-yl)-1-oxoisoindolin-5-yl)methyl)-2,2-difluoroacetamide;

2-(4-bromophenyl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl) methyl)-2,2-difluoro-2-(2-(2-methoxyethoxy)phenyl)acetamide;

N-((2-(2,6-dioxopiperidin-3-yl)-1-oxoisoindolin-5-yl) methyl)-2,2-difluoro-2-(1-hydroxycyclohexyl)acetamide;

N-((2-(2,6-dioxopiperidin-3-yl)-1-oxoisoindolin-5-yl) methyl)-2,2-difluoro-2-(1-hydroxycyclopentyl)acetamide;

N-((2-(2,6-dioxopiperidin-3-yl)-1-oxoisoindolin-5-yl) methyl)-2,2-difluoro-2-(3-methyl-4-(trifluoromethoxy) phenyl)acetamide;

N-((2-(2,6-dioxopiperidin-3-yl)-1-oxoisoindolin-5-yl) methyl)-2-(3-ethoxypyridin-2-yl)-2,2-difluoroacetamide;

N-((2-(2,6-dioxopiperidin-3-yl)-1-oxoisoindolin-5-yl) methyl)-2,2-difluoro-2-(3-methylpyridin-2-yl)acetamide;

N-((2-(2,6-dioxopiperidin-3-yl)-1-oxoisoindolin-5-yl) methyl)-2,2-difluoro-2-(5-methylpyridin-2-yl)acetamide;

N-((2-(2,6-dioxopiperidin-3-yl)-1-oxoisoindolin-5-yl) methyl)-2-(2-ethoxy-6-fluorophenyl)-2,2-difluoroacetamide;

N-((2-(2,6-dioxopiperidin-3-yl)-1-oxoisoindolin-5-yl) methyl)-2,2-difluoro-2-(4'-fluorobiphenyl-4-yl)acetamide;

N-((2-(2,6-dioxopiperidin-3-yl)-1-oxoisoindolin-5-yl) methyl)-2-(2-ethoxy-5-fluorophenyl)-2,2-difluoroacetamide;

2-cyclopentyl-N-((2-(2,6-dioxopiperidin-3-yl)-1-oxoisoindolin-5-yl)methyl)-2,2-difluoroacetamide;

2-(3-chloro-4-(trifluoromethoxy)phenyl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl) methyl)-2,2-difluoro-2-(4-methoxy-2-(trifluoromethyl) phenyl)acetamide;

N-((2-(2,6-dioxopiperidin-3-yl)-1-oxoisoindolin-5-yl) methyl)-2,2-difluoro-2-(2-(2-hydroxyethoxy)phenyl)acetamide;

2-(4-chloro-2-ethoxyphenyl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl) methyl)-2,2-difluoro-2-(2-hydroxyphenyl)acetamide;

N-((2-(2,6-dioxopiperidin-3-yl)-1-oxoisoindolin-5-yl) methyl)-2,2-difluoro-2-(2-(methylamino)phenyl)acetamide;

N-((2-(2,6-dioxopiperidin-3-yl)-1-oxoisoindolin-5-yl) methyl)-2,2-difluoro-2-(4-isopropoxy-2-(trifluoromethyl)phenyl)acetamide;

N-((2-(2,6-dioxopiperidin-3-yl)-1-oxoisoindolin-5-yl) methyl)-2,2-difluoro-2-(4-methylcyclohexyl)acetamide;

N-((2-(2,6-dioxopiperidin-3-yl)-1-oxoisoindolin-5-yl) methyl)-2,2-difluoro-2-(3-(2-isopropoxyethoxy)phenyl) acetamide;

N-((2-(2,6-dioxopiperidin-3-yl)-1-oxoisoindolin-5-yl) methyl)-2,2-difluoro-2-(3-hydroxyphenyl)acetamide;

N-((2-(2,6-dioxopiperidin-3-yl)-1-oxoisoindolin-5-yl) methyl)-2,2-difluoro-2-(3-((4-methylpiperazin-1-yl) methyl)phenyl)acetamide;

N-((2-(2,6-dioxopiperidin-3-yl)-1-oxoisoindolin-5-yl) methyl)-2,2-difluoro-2-(4-methyl-2-(trifluoromethyl) phenyl)acetamide;

N-((2-(2,6-dioxopiperidin-3-yl)-1-oxoisoindolin-5-yl) methyl)-2,2-difluoro-2-(3-(2-(2-methoxyethoxy)ethoxy) phenyl)acetamide;

2-(3-(2-(dimethylamino)ethoxy)phenyl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl) methyl)-2,2-difluoro-2-(5-isopropylpyridin-2-yl)acetamide;

N-((2-(2,6-dioxopiperidin-3-yl)-1-oxoisoindolin-5-yl) methyl)-2,2-difluoro-2-(3-(2-(methylsulfonyl)ethoxy) phenyl)acetamide;

N-((2-(2,6-dioxopiperidin-3-yl)-1-oxoisoindolin-5-yl) methyl)-2,2-difluoro-2-(3-(3-(methylsulfonyl)propyl) phenyl)acetamide;

N-((2-(2,6-dioxopiperidin-3-yl)-1-oxoisoindolin-5-yl) methyl)-2,2-difluoro-2-(4-(2-fluoropropan-2-yl)phenyl) acetamide;

2-(1-benzyl-6-oxo-1,6-dihydropyridin-3-yl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl) methyl)-2,2-difluoro-2-(5-methoxypyridin-2-yl)acetamide;

N-((2-(2,6-dioxopiperidin-3-yl)-1-oxoisoindolin-5-yl) methyl)-2,2-difluoro-2-(1-methyl-6-oxo-1,6-dihydropyridin-3-yl)acetamide;

2-(5-tert-butylpyridin-2-yl)-N-((2-(2,6-dioxopiperidin-3-yl)-1-oxoisoindolin-5-yl)methyl)-2,2-difluoroacetamide;
2-(5-cyclopropylpyridin-2-yl)-N-((2-(2,6-dioxopiperidin-3-yl)-1-oxoisoindolin-5-yl)methyl)-2,2-difluoroacetamide;
N-((2-(2,6-dioxopiperidin-3-yl)-1-oxoisoindolin-5-yl)methyl)-2,2-difluoro-2-(5-isopropoxypyridin-2-yl)acetamide;
2-(5-bromopyridin-2-yl)-N-((2-(2,6-dioxopiperidin-3-yl)-1-oxoisoindolin-5-yl)methyl)-2,2-difluoroacetamide;
N-((2-(2,6-dioxopiperidin-3-yl)-1-oxoisoindolin-5-yl)methyl)-2,2-difluoro-2-(4-fluoro-2-(trifluoromethoxy)phenyl)acetamide;
N-((2-(2,6-dioxopiperidin-3-yl)-1-oxoisoindolin-5-yl)methyl)-2,2-difluoro-2-(4-fluorocyclohexyl)acetamide;
N-((2-(2,6-dioxopiperidin-3-yl)-1-oxoisoindolin-5-yl)methyl)-2,2-difluoro-2-(4-(methylsulfonyl)phenyl)acetamide;
N-((2-(2,6-dioxopiperidin-3-yl)-1-oxoisoindolin-5-yl)methyl)-2,2-difluoro-2-(3-(methylsulfonyl)phenyl)acetamide;
2-(2-aminopyrimidin-5-yl)-N-((2-(2,6-dioxopiperidin-3-yl)-1-oxoisoindolin-5-yl)methyl)-2,2-difluoroacetamide;
N-((2-(2,6-dioxopiperidin-3-yl)-1-oxoisoindolin-5-yl)methyl)-2,2-difluoro-2-(5-(trifluoromethylthio)pyridin-2-yl)acetamide;
N-((2-(2,6-dioxopiperidin-3-yl)-1-oxoisoindolin-5-yl)methyl)-2,2-difluoro-2-(3-(2-(methylamino)ethoxy)phenyl)acetamide;
N-((2-(2,6-dioxopiperidin-3-yl)-1-oxoisoindolin-5-yl)methyl)-2,2-difluoro-2-(1-methyl-6-oxo-1,6-dihydropyridazin-3-yl)acetamide;
2-(2-aminopyrimidin-4-yl)-N-((2-(2,6-dioxopiperidin-3-yl)-1-oxoisoindolin-5-yl)methyl)-2,2-difluoroacetamide;
N-((2-(2,6-dioxopiperidin-3-yl)-1-oxoisoindolin-5-yl)methyl)-2,2-difluoro-2-(pyrimidin-4-yl)acetamide;
N-((2-(2,6-dioxopiperidin-3-yl)-1-oxoisoindolin-5-yl)methyl)-2,2-difluoro-2-(3-(2-(piperidin-1-yl)ethoxy)phenyl)acetamide;
N-((2-(2,6-dioxopiperidin-3-yl)-1-oxoisoindolin-5-yl)methyl)-2,2-difluoro-2-(3-(2-morpholinoethoxy)phenyl)acetamide;
2-(3-(2-(4,4-difluoropiperidin-1-yl)ethoxy)phenyl)-N-((2-(2,6-dioxopiperidin-3-yl)-1-oxoisoindolin-5-yl)methyl)-2,2-difluoroacetamide;
N-((2-(2,6-dioxopiperidin-3-yl)-1-oxoisoindolin-5-yl)methyl)-2,2-difluoro-2-(1-methyl-6-oxo-1,6-dihydropyridazin-4-yl)acetamide; and
N-((2-(2,6-dioxopiperidin-3-yl)-1-oxoisoindolin-5-yl)methyl)-2,2-difluoro-2-(3-(4-methylpiperazin-1-yl)phenyl)acetamide.

In a specific embodiment, the treatment compound is 2-(4-chlorophenyl)-N-((2-(2,6-dioxopiperidin-3-yl)-1-oxoisoindolin-5-yl)methyl)-2,2-difluoroacetamide (Compound D), or a stereoisomer or a mixture of stereoisomers, tautomer, pharmaceutically acceptable salt, solvate, isotopologue, prodrug, hydrate, co-crystal, clathrate, or a polymorph thereof.

In another specific embodiment, the treatment compound is 2-(4-flurophenyl)-N-((2-(2,6-dioxopiperidin-3-yl)-1-oxoisoindolin-5-yl)methyl)-2,2-difluoroacetamide (Compound E), or a stereoisomer or a mixture of stereoisomers, tautomer, pharmaceutically acceptable salt, solvate, isotopologue, prodrug, hydrate, co-crystal, clathrate, or a polymorph thereof.

The various compounds provided herein contain one or more chiral centers, and can exist as mixtures of enantiomers (e.g., racemic mixtures) or mixtures of diastereomers. The methods provided herein encompass the use of stereomerically pure forms of such compounds as well as mixtures of those forms. For example, mixtures comprising equal or unequal amounts of the enantiomers of a particular compound may be used in methods provided herein. These isomers may be asymmetrically synthesized or resolved using standard techniques, such as chiral columns or chiral resolving agents. See, Jacques et al., *Enantiomers, Racemates and Resolutions* (Wiley-Interscience, New York, 1981); Wilen et al., *Tetrahedron* 1977, 33:2725-2736; Eliel, *Stereochemistry of Carbon Compounds* (McGraw-Hill, N Y, 1962); Wilen, *Tables of Resolving Agents and Optical Resolutions*, p. 268 (Eliel, ed., Univ. of Notre Dame Press, Notre Dame, IN, 1972).

Also provided herein are isotopically enriched analogs of the compounds provided herein. Isotopic enrichment (for example, deuteration) of pharmaceuticals to improve pharmacokinetics ("PK"), pharmacodynamics ("PD"), and toxicity profiles, has been demonstrated previously with some classes of drugs. See, for example, Lijinsky et. al., *Food Cosmet. Toxicol.,* 20: 393 (1982); Lijinsky et. al., *J. Nat. Cancer Inst.,* 69: 1127 (1982); Mangold et. al., *Mutation Res.* 308: 33 (1994); Gordon et. al., *Drug Metab. Dispos.,* 15: 589 (1987); Zello et. al., *Metabolism,* 43: 487 (1994); Gately et. al., *J. Nucl. Med.,* 27: 388 (1986); Wade D, *Chem. Biol. Interact.* 117: 191 (1999).

Without being limited by any particular theory, isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrease the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g., Foster et al., Adv. Drug Res., vol. 14, pp. 1-36 (1985); Kushner et al., Can. J. Physiol. Pharmacol., vol. 77, pp. 79-88 (1999)).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. Without being limited by a particular theory, high DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects.

Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, will provide a similar kinetic isotope effects.

The animal body expresses a variety of enzymes for the purpose of eliminating foreign substances, such as therapeutic agents, from its circulation system. Examples of such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. As a result, these drugs often require the administration of multiple or high daily doses.

Isotopic enrichment at certain positions of a compound provided herein may produce a detectable KIE that affects the pharmacokinetic, pharmacologic, and/or toxicological profiles of a compound provided herein in comparison with a similar compound having a natural isotopic composition. In one embodiment, the deuterium enrichment is performed on the site of C—H bond cleavage during metabolism.

Standard physiological, pharmacological and biochemical procedures are available for testing the compounds to identify those that possess the desired anti-proliferative activity.

Such assays include, for example, biochemical assays such as binding assays, radioactivity incorporation assays, as well as a variety of cell based assays. The compounds provided herein can be prepared by methods known to one of skill in the art and following procedures similar to those described in the Examples section herein and routine modifications thereof.

An exemplary reaction scheme for the preparation of compounds is illustrated below:

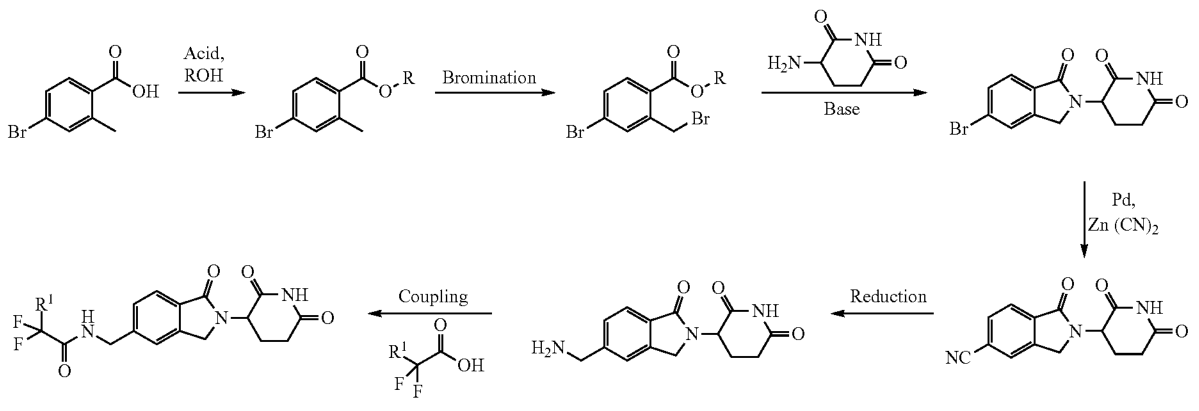

It is understood that the foregoing detailed description and accompanying examples are merely illustrative, and are not to be taken as limitations upon the scope of the subject matter. Various changes and modifications to the disclosed embodiments will be apparent to those skilled in the art. Such changes and modifications, including without limitation those relating to the chemical structures, substituents, derivatives, intermediates, syntheses, formulations and/or methods of use provided herein, may be made without departing from the spirit and scope thereof. U.S. patents and publications referenced herein are incorporated by reference.

5.8 Pharmaceutical Compositions

In certain embodiments, provided herein are pharmaceutical compositions comprising a compound of Formula I, or a stereoisomer or a mixture of stereoisomers, tautomer, pharmaceutically acceptable salt, solvate, isotopologue, prodrug, hydrate, co-crystal, clathrate, or a polymorph thereof. In some embodiments, the pharmaceutical compositions provided herein contain therapeutically effective amounts of one or more of the compounds provided herein and a pharmaceutically acceptable carrier, diluents, or excipient. In some embodiments, the compounds may be formulated as the sole pharmaceutically active ingredient in the composition or may be combined with other active ingredients. In certain embodiments, the compound of Formula I is Compound D or Compound E. In one embodiment, the compound of Formula I is Compound D. In another embodiment, the compound of Formula I is Compound E.

The compounds can be formulated into suitable pharmaceutical compositions for different routes of administration, such as injection, sublingual and buccal, rectal, vaginal, ocular, otic, nasal, inhalation, nebulization, cutaneous, or transdermal. Typically the compounds described above are formulated into pharmaceutical compositions using techniques and procedures well known in the art (see, e.g., Ansel, *Introduction to Pharmaceutical Dosage Forms*, (7th ed. 1999)).

In the compositions, effective concentrations of one or more compounds or pharmaceutically acceptable salts are mixed with a suitable pharmaceutical carrier or vehicle. In certain embodiments, the concentrations of the compounds in the compositions are effective for delivery of an amount, upon administration, that treats, prevents, or ameliorates one or more of the symptoms and/or progression of cancer, including solid cancer and blood borne cancer.

The active compound is in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans. The concentration of active compound in the pharmaceutical composition will depend on absorption, tissue distribution, inactivation, and excretion rates of the active compound, the physicochemical characteristics of the compound, the dosage schedule, and amount administered as well as other factors known to those of skill in the art.

The pharmaceutically therapeutically active compounds and salts thereof are formulated and administered in unit dosage forms or multiple dosage forms. Unit dose forms as used herein refer to physically discrete units suitable for human and animal subjects and packaged individually as is known in the art. Each unit dose contains a predetermined quantity of the therapeutically active compound sufficient to produce the desired therapeutic effect, in association with the required pharmaceutical carriers, vehicles, or diluents. Examples of unit dose forms include ampoules and syringes and individually packaged tablets or capsules. Unit dose forms may be administered in fractions or multiples thereof. A multiple dose form is a plurality of identical unit dosage forms packaged in a single container to be administered in segregated unit dose form. Examples of multiple dose forms include vials, bottles of tablets or capsules, or bottles of pints or gallons. Hence, multiple dose form is a multiple of unit doses which are not segregated in packaging.

It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Solutions or suspensions used for parenteral, intradermal, subcutaneous, or topical application can include any of the following components: a sterile diluents (such as water, saline solution, fixed oil, polyethylene glycol, glycerine, propylene glycol, dimethyl acetamide, or other synthetic solvent), antimicrobial agents (such as benzyl alcohol and methyl parabens), antioxidants (such as ascorbic acid and sodium bisulfate), chelating agents (such as ethylenediaminetetraacetic acid (EDTA)), buffers (such as acetates, citrates, and phosphates), and agents for the adjustment of tonicity (such as sodium chloride or dextrose). Parenteral preparations can be enclosed in ampoules, pens, disposable syringes, or single or multiple dose vials made of glass, plastic, or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolving the compound in aqueous sodium hydroxide, sodium bicarbonate, or hydrochloric acid.

Sustained-release preparations can also be prepared. Suitable examples of sustained-release preparations include semipermeable matrices of solid hydrophobic polymers containing the compound provided herein, which matrices are in the form of shaped articles, e.g., films or microcapsule. Examples of sustained-release matrices include iontophoresis patches, polyesters, hydrogels (for example, poly(2-hydroxyethyl-methacrylate) or poly(vinylalcohol)), polylactides, copolymers of L-glutamic acid and ethyl-L-glutamate, non-degradable ethylene-vinyl acetate, degradable lactic acid-glycolic acid copolymers such as LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated compound remain in the body for a long time, they may denature or aggregate as a result of exposure to moisture at 37° C., resulting in a loss of biological activity and possible changes in their structure. Rational strategies can be devised for stabilization depending on the mechanism of action involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Lactose-free compositions provided herein can contain excipients that are well known in the art and are listed, for example, in *The U.S. Pharmacopeia* (USP). In general, lactose-free compositions contain an active ingredient, a binder/filler, and a lubricant in pharmaceutically compatible and pharmaceutically acceptable amounts. Exemplary lactose-free dosage forms contain an active ingredient, microcrystalline cellulose, pre-gelatinized starch, and magnesium stearate.

Further encompassed are anhydrous pharmaceutical compositions and dosage forms containing a compound provided herein. Anhydrous pharmaceutical compositions and dosage forms provided herein can be prepared using anhydrous or low moisture containing ingredients and low moisture or low humidity conditions, as known by those skilled in the art. An anhydrous pharmaceutical composition should be prepared and stored such that its anhydrous nature is maintained. Accordingly, anhydrous compositions are packaged using materials known to prevent exposure to water such that they can be included in suitable formulatory kits. Examples of suitable packaging include, but are not limited to, hermetically sealed foils, plastics, unit dose containers (e.g., vials), blister packs, and strip packs.

Dosage forms or compositions containing active ingredient in the range of 0.001% to 100% with the balance made up from non-toxic carrier may be prepared. In some embodiments, the contemplated compositions contain from about 0.005% to about 95% active ingredient. In other embodiments, the contemplated compositions contain from about 0.01% to about 90% active ingredient. In certain embodiments, the contemplated compositions contain from about 0.1% to about 85% active ingredient. In other embodiments, the contemplated compositions contain from about 0.1% to about 75-95% active ingredient.

The compositions may include other active compounds to obtain desired combinations of properties. The compounds provided herein, or pharmaceutically acceptable salts thereof as described herein, may also be advantageously administered for therapeutic or prophylactic purposes together with another pharmacological agent known in the general art to be of value in treating one or more of the diseases or medical conditions referred to herein above, such as solid cancer or blood born cancer. It is to be understood that such combination therapy constitutes a further aspect of the compositions and methods of treatment provided herein.

5.8.1 Injectables, Solutions, and Emulsions

Parenteral administration of the compositions includes intravenous, subcutaneous, and intramuscular administrations. Compositions for parenteral administration include sterile solutions ready for injection, sterile dry soluble products, such as lyophilized powders, ready to be combined with a solvent just prior to use, sterile suspensions ready for injection, and sterile emulsions. The solutions may be either aqueous or nonaqueous. The unit dose parenteral preparations are packaged in an ampoule, a vial or a syringe with a needle. All preparations for parenteral administration must be sterile, as is known and practiced in the art.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents, and other pharmaceutically acceptable substances.

Examples of aqueous vehicles include sodium chloride injection, Ringer's injection, isotonic dextrose injection, sterile water injection, dextrose and lactated Ringer's injection. Nonaqueous parenteral vehicles include fixed oils of vegetable origin, such as cottonseed oil, corn oil, sesame oil, and peanut oil. Antimicrobial agents in bacteriostatic or fungistatic concentrations must be added to parenteral preparations packaged in multiple dose containers, which include phenols or cresols, mercurials, benzyl alcohol, chlorobutanol, methyl and propyl-p-hydroxybenzoic acid esters, thimerosal, benzalkonium chloride, and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles, and sodium hydroxide, hydrochloric acid, citric acid, or lactic acid for pH adjustment.

Injectables are designed for local and systemic administration. Typically a therapeutically effective dosage is formulated to contain a concentration of at least about 0.1% w/w up to about 90% w/w or more, such as more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

5.8.2 Lyophilized Powders

Of interest herein are also lyophilized powders, which can be reconstituted for administration as solutions, emulsions, and other mixtures. They may also be reconstituted and formulated as solids or gels.

The sterile, lyophilized powder is prepared by dissolving a compound provided herein, or a pharmaceutically acceptable salt thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose, or other suitable agent. The solvent may also contain a buffer, such as citrate, phosphate, or other buffers known to those of skill in the art. Subsequent sterile filtration of the solution followed by lyophilization under standard conditions known to those of skill in the art provides the desired formulation. Generally, the resulting solution will be apportioned into vials for lyophilization. Each vial will contain a single dosage or multiple dosages of the compound. The lyophilized powder can be stored under appropriate conditions, such as at about 4° C. to room temperature.

In one aspect, the lyophilized formulations are suitable for reconstitution with a suitable diluent to the appropriate concentration prior to administration. In one embodiment, the lyophilized formulation is stable at room temperature. In one embodiment, the lyophilized formulation is stable at room temperature for up to about 24 months. In one embodiment, the lyophilized formulation is stable at room temperature for up to about 24 months, up to about 18 months, up to about 12 months, up to about 6 months, up to about 3 months or up to about 1 month. In one embodiment, the lyophilized formulation is stable upon storage under accelerated condition of 40° C./75% RH for up to about 12 months, up to about 6 months or up to about 3 months.

In some embodiments, the lyophilized formulation is suitable for reconstitution with an aqueous solution for intravenous administrations. In certain embodiments, the lyophilized formulation provided herein is suitable for reconstitution with water. In one embodiment, the reconstituted aqueous solution is stable at room temperature for up to about 24 hours upon reconsititution. In one embodiment, the reconstituted aqueous solution is stable at room temperature from about 1-24, 2-20, 2-15, 2-10 hours upon reconsititution. In one embodiment, the reconstituted aqueous solution is stable at room temperature for up to about 20, 15, 12, 10, 8, 6, 4 or 2 hours upon reconsititution. In certain embodiments, the lyophilized formulations upon reconstitution have a pH of about 4 to 5.

In certain embodiment, the lyophilized formulations comprise a compound of Formula I, or a stereoisomer or a mixture of stereoisomers, tautomer, pharmaceutically acceptable salt, solvate, isotopologue, prodrug, hydrate, co-crystal, clathrate, or a polymorph thereof, a buffer and a bulking agent.

In one embodiment, the lyophilized formulation comprises about 0.1-2% comprise a compound of Formula I, or a stereoisomer or a mixture of stereoisomers, tautomer, pharmaceutically acceptable salt, solvate, isotopologue, prodrug, hydrate, co-crystal, clathrate, or a polymorph thereof, about 1-15% buffer and about 70-95% bulking agent based on the total weight of the lyophilized formulation.

In certain embodiments, a lyophilized formulation comprises a compound of Formula I, or a stereoisomer or a mixture of stereoisomers, tautomer, pharmaceutically acceptable salt, solvate, isotopologue, prodrug, hydrate, co-crystal, clathrate, or a polymorph thereof, in about 0.1 to about 2% based on the total weight of the lyophilized formulation. In some embodiments, a lyophilized formulation comprises a compound of Formula I, or a stereoisomer or a mixture of stereoisomers, tautomer, pharmaceutically acceptable salt, solvate, isotopologue, prodrug, hydrate, co-crystal, clathrate, or a polymorph thereof, in an amount of about 0.1 mg to about 5 mg in a vial, for example, a 20 ml vial.

In certain embodiments, a lyophilized formulation comprises a citrate buffer in an amount from about 5% to about 25% based on total weight of the lyophilized formulation. In one embodiment, the citrate buffer comprises anhydrous citric acid and anhydrous sodium citrate.

In some embodiments, the bulking agent in the lyophilized formulations comprises Captisol®, mannitol or Kleptose®, for example, O-cyclodextrin, hydroxypropyl O-cyclodextrin and methylated β-cyclodextrin.

The lyophilized formulation can be reconstituted for parenteral administration to a patient using any pharmaceutically acceptable diluent. Such diluents include, but are not limited to Sterile Water for Injection (SWFI), Dextrose 5% in Water (D5W), or a cosolvent system. Any quantity of diluent may be used to reconstitute the lyophilized formulation such that a suitable solution for injection is prepared. Accordingly, the quantity of the diluent must be sufficient to dissolve the lyophilized formulation. In one embodiment, 1-5 mL or 1-3 mL of a diluent are used to reconstitute the lyophilized formulation to yield a final concentration of about 0.1-5 mg/mL, about 0.1-1 mg/mL, or about 0.5-1 mg/mL of a compound of Formula I, or a stereoisomer or a mixture of stereoisomers, tautomer, pharmaceutically acceptable salt, solvate, isotopologue, prodrug, hydrate, co-crystal, clathrate, or a polymorph thereof. In certain embodiments, the final concentration of a compound of Formula I, or a stereoisomer or a mixture of stereoisomers, tautomer, pharmaceutically acceptable salt, solvate, isotopologue, prodrug, hydrate, co-crystal, clathrate, or a polymorph thereof, in the reconstituted solution is about 0.5 mg/mL. In certain embodiment, the volume of the reconstitution diluent varies between 2 ml and 20 ml to yield a final concentration of 0.05-0.5 mg/mL. In certain embodiment, depending on the required dose, multiple vials may be used for reconstitution.

5.8.3 Topical Administration

Topical mixtures are prepared as described for the local and systemic administration. The resulting mixture may be a solution, suspension, emulsion, or the like and are formulated as creams, gels, ointments, emulsions, solutions, elixirs, lotions, suspensions, tinctures, pastes, foams, aerosols, irrigations, sprays, suppositories, bandages, dermal patches, or any other formulations suitable for topical administration.

The compounds or pharmaceutically acceptable salts thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will have diameters of less than 50 microns or less than 10 microns.

These solutions, particularly those intended for ophthalmic use, may be formulated as 0.01%-10% isotonic solutions, pH about 5-7, with appropriate salts.

5.8.4 Compositions for Other Routes of Administration

Other routes of administration such as transdermal patches and rectal administration are also contemplated herein.

For example, pharmaceutical dosage forms for rectal administration are rectal suppositories, capsules, and tablets for systemic effect. Rectal suppositories as used herein mean solid bodies for insertion into the rectum, which melt or soften at body temperature releasing one or more pharmacologically or therapeutically active ingredients. Pharmaceutically acceptable substances utilized in rectal suppositories include bases (or vehicles) and agents that raise the melting point. Examples of bases include, for example, cocoa butter (theobroma oil), glycerin gelatin, carbowax (polyoxyethylene glycol), and appropriate mixtures of mono, di and triglycerides of fatty acids. Combinations of the various bases may be used. Agents to raise the melting point of suppositories include, for example, spermaceti and wax. Rectal suppositories may be prepared either by the compressed method or by molding. An exemplary weight of a rectal suppository is about 2 to 3 grams.

5.8.5 Sustained Release Compositions

Active ingredients provided herein can be administered by controlled release means or by delivery devices that are well known to those of ordinary skill in the art. Examples include, but are not limited to, those described in U.S. Pat. Nos. 3,845,770, 3,916,899, 3,536,809, 3,598,123, 4,008,719, 5,674,533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461, 6,419,961, 6,589,548, 6,613,358, 6,699,500, and 6,740,634, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof, to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over their non-controlled counterparts. In one embodiment, the use of an optimally designed controlled-release preparation in medical treatment is characterized by a minimum of drug substance being employed to cure or control the condition in a minimum amount of time. In certain embodiments, advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side effects (e.g., adverse effects).

Most controlled-release formulations are designed to initially release an amount of drug (active ingredient) that promptly produces the desired therapeutic effect, then to gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, other physiological conditions, or compounds.

In certain embodiments, the agent may be administered using intravenous infusion, an implantable osmotic pump, a transdermal patch, liposomes, or other modes of administration. In one embodiment, a pump may be used. See, Sefton, *CRC Crit. Ref Biomed. Eng.* 1987, 14:201-240; Buchwald et al., *Surgery* 1980, 88:507-516; Saudek et al., *N. Engl. J. Med.* 1989, 321:574-579. In another embodiment, polymeric materials can be used. In yet another embodiment, a controlled release system can be placed in proximity of the therapeutic target, thus requiring only a fraction of the systemic dose. See, e.g., Goodson, *Medical Applications of Controlled Release*, vol. 2, pp. 115-138 (1984).

In some embodiments, a controlled release device is introduced into a subject in proximity of the site of inappropriate immune activation or a tumor. Other controlled release systems are discussed in the review by Langer (Science 1990, 249:1527-1533). The active ingredient can be dispersed in a solid inner matrix (e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate). In some embodiments, the inner matrix is surrounded by an outer polymeric membrane (e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene, propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer). In certain embodiments, the outer polymeric membrane is insoluble in body fluids. The active ingredient then diffuses through the outer polymeric membrane in a release rate controlling step. The percentage of active ingredient contained in such parenteral compositions depends on the specific nature thereof, as well as the needs of the subject.

5.8.6 Targeted Formulations

The compounds provided herein, or pharmaceutically acceptable salts thereof, may also be formulated to target a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542, and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLVs) may be formed by drying down egg phosphatidyl choline and brain phosphatidyl serine (7:3 molar ratio) on the inside of a flask. A solution of a compound provided herein in phosphate buffered saline (PBS) lacking divalent cations is added, and the flask is shaken until the lipid film is dispersed. The resulting vesicles are washed to remove unencapsulated compound, pelleted by centrifugation, and then resuspended in PBS.

5.8.7 Articles of Manufacture

The compounds or pharmaceutically acceptable salts can be packaged as articles of manufacture containing packaging material, a compound or pharmaceutically acceptable salt thereof provided herein, which is used for treatment, prevention, or amelioration of one or more symptoms or progression of cancer, including solid cancers and blood borne tumors, and a label indicating that the compound or pharmaceutically acceptable salt thereof is used for treatment, prevention, or amelioration of one or more symptoms or progression of cancer, including solid cancers and blood borne tumors.

The articles of manufacture provided herein contain packaging materials. Packaging materials for use in packaging pharmaceutical products are well known to those of skill in the art. See, e.g., U.S. Pat. Nos. 5,323,907, 5,052,558, and 5,033,252. Examples of pharmaceutical packaging materials include, but are not limited to, blister packs, bottles, tubes, inhalers, pumps, bags, vials, containers, syringes, pens, bottles, and any packaging material suitable for a selected formulation and intended mode of administration and treatment. A wide array of formulations of the compounds and compositions provided herein are contemplated.

5.9 Kits

In one aspect, provided herein is a kit for identifying a subject having cancer who is likely to be responsive to a treatment compound, comprising a means for detecting the level of a biomarker in a sample that has been treated with the treatment compound, wherein the treatment compound is a compound of Formula I:

I

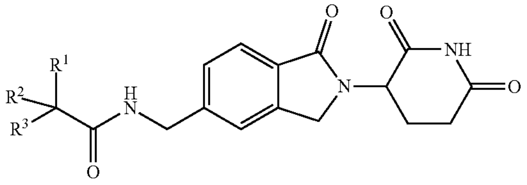

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, —$R^4OR^4N(R^6)(R^7)$, or —$R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In another aspect, provided herein is a kit for treating cancer, comprising a means for detecting the level of a biomarker in a sample that has been treated with a treatment compound, wherein the treatment compound is a compound of Formula I:

I

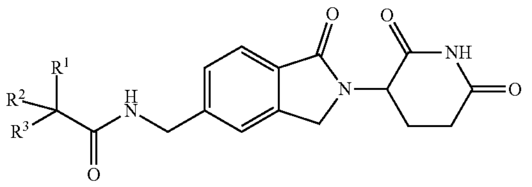

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, —$R^4OR^4N(R^6)(R^7)$, or —$R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In yet another aspect, provided herein is a kit for predicting the responsiveness of a subject having or suspected of having cancer to a treatment compound, comprising a means for detecting the level of a biomarker in a sample that has been treated with the treatment compound, wherein the treatment compound is a compound of Formula I:

I

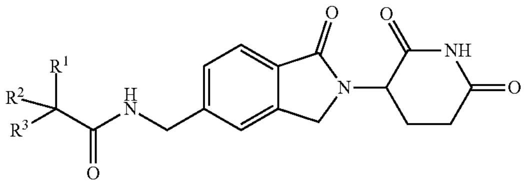

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, —$R^4OR^4N(R^6)(R^7)$, or —$R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In yet another aspect, provided herein is a kit for monitoring the efficacy of a treatment compound in treating cancer in a subject, comprising a means for detecting the level of a biomarker in a sample that has been treated with the treatment compound, wherein the treatment compound is a compound of Formula I:

I

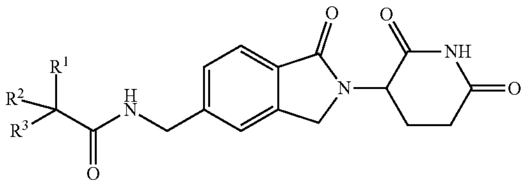

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, —$R^4OR^4N(R^6)(R^7)$, or —$R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

In certain embodiments of various kits provided herein, the treatment compound is Compound D. In other embodiments, the treatment compound is Compound E.

In certain embodiments, the biomarker detected by various kits provided herein is a CAP. In some embodiments, the biomarker comprises one CAP. In other embodiments, the biomarker comprises two CAPs. In yet other embodiments, the biomarker comprises three CAPs. In still other embodiments, the biomarker comprises four CAPs. In some embodiments, the biomarker comprises five CAPs. In certain embodiments, the biomarker comprises six CAPs. In other embodiments, the biomarker comprises seven CAPs. In yet other embodiments, the biomarker comprises eight CAPs. In still other embodiments, the biomarker comprises nine CAPs. In some embodiments, the biomarker comprises ten or more CAPs.

In certain embodiments, the biomarker detected by various kits provided herein is a CAP selected from the group consisting of GSPT1, GSPT2, IKZF1, eRF1, BIP, GCN2, eIF2α, ATF4, ATF3, DDIT3, PPP1R15A, TNFRSF10B, GADD45A, FAS, IRE1, XBP1, SEC24D, DNAJB9, EDEM1, ATF6, Caspase 3, Caspase 7, Caspase 8, Caspase 9, BID, PARP, Mcl-1, SRSF3, and SRSF6. In some embodiments, the biomarker is selected from the group consisting of GSPT1, GSPT2, IKZF1, ATF4, ATF3, and DDIT3. In some embodiments, the biomarker is GSPT1. In certain embodiments, the biomarker is GSPT2. In other embodiments, the biomarker is IKZF1. In yet other embodiments, the biomarker is ATF4. In still other embodiments, the biomarker is ATF3. In some embodiments, the biomarker is DDIT3.

In certain embodiments, the biomarker detected by various kits provided herein has a function in UPR. In some embodiments, the biomarker has a function in GCN2 related signaling pathway. In other embodiments, the biomarker has a function in ATF4 related signaling pathway. In yet other embodiments, the biomarker has a function in IRE1 related signaling pathway. In still other embodiments, the biomarker has a function in XBP1 related signaling pathway. In certain embodiments, the biomarker has a function in ATF6 related signaling pathway. In other embodiments, the biomarker has a function in apoptosis pathway. In yet other embodiments, the biomarker has a function in NMD pathway. In still other embodiments, the biomarker is an RNA substrate of NMD pathway.

In certain embodiments of various kits provided herein, the sample is obtained from a tumor biopsy, a node biopsy, or a biopsy from the bone marrow, spleen, liver, brain, or breast.

In some embodiments of various kits provided herein, the cancer is blood cancer. In certain embodiments, the blood cancer is selected from the group consisting of multiple myeloma, leukemia, and lymphoma. In one embodiment, the leukemia is chronic lymphocytic leukemia, chronic myelocytic leukemia, acute lymphoblastic leukemia, or acute myeloid leukemia (AML). In a specific embodiment, the leukemia is AML. In certain embodiments, the leukemia is relapsed, refractory or resistant to conventional therapy.

In certain embodiments, provided herein is a kit for detecting the mRNA level of one or more biomarkers. In certain embodiments, the kit comprises one or more probes that bind specifically to the mRNAs of the one or more biomarkers. In certain embodiments, the kit further comprises a washing solution. In certain embodiments, the kit further comprises reagents for performing a hybridization assay, mRNA isolation or purification means, detection means, as well as positive and negative controls. In certain embodiments, the kit further comprises an instruction for using the kit. The kit can be tailored for in-home use, clinical use, or research use.

In certain embodiments, provided herein is a kit for detecting the protein level of one or more biomarkers. In certain embodiments, the kits comprises a dipstick coated with an antibody that recognizes the protein biomarker, washing solutions, reagents for performing the assay, protein isolation or purification means, detection means, as well as positive and negative controls. In certain embodiments, the kit further comprises an instruction for using the kit. The kit can be tailored for in-home use, clinical use, or research use.

Such a kit can employ, for example, a dipstick, a membrane, a chip, a disk, a test strip, a filter, a microsphere, a slide, a multi-well plate, or an optical fiber. The solid support of the kit can be, for example, a plastic, silicon, a metal, a resin, glass, a membrane, a particle, a precipitate, a gel, a polymer, a sheet, a sphere, a polysaccharide, a capillary, a film, a plate, or a slide. The biological sample can be, for example, a cell culture, a cell line, a tissue, an organ, an organelle, a biological fluid, a blood sample, a urine sample, or a skin sample.

In another embodiment, the kit comprises a solid support, nucleic acids attached to the support, where the nucleic acids are complementary to at least 20, 50, 100, 200, 350, or more bases of mRNA, and a means for detecting the expression of the mRNA in a biological sample.

In a specific embodiment, the pharmaceutical or assay kit comprises, in a container, a compound or a pharmaceutical composition thereof, and further comprises, in one or more containers, components for isolating RNA. In another specific embodiment, the pharmaceutical or assay kit comprises, in a container, a compound or a pharmaceutical composition, and further comprises, in one or more containers, components for conducting RT-PCR, qRT-PCR, deep sequencing, or microarray In certain embodiments, the kits provided herein employ means for detecting the expression of a biomarker by quantitative real-time PCR (qRT-PCR), microarray, flow cytometry, or immunofluorescence. In other embodiments, the expression of the biomarker is measured by ELISA-based methodologies or other similar methods known in the art.

In another specific embodiment, the pharmaceutical or assay kit comprises, in a container, a compound or a pharmaceutical composition thereof, and further comprises, in one or more containers, components for isolating protein. In another specific embodiment, the pharmaceutical or assay kit comprises, in a container, a compound or a pharmaceutical composition, and further comprises, in one or more containers, components for conducting flow cytometry or ELISA.

In another aspect, provided herein are kits for measuring biomarkers that supply the materials necessary to measure the abundance of one or more gene products of the biomarkers or a subset of the biomarkers (e.g., one, two, three, four, five, or more biomarkers) provided herein. Such kits may comprise materials and reagents required for measuring RNA or protein. In some embodiments, such kits include microarrays, wherein the microarray is comprised of oligonucleotides and/or DNA and/or RNA fragments which hybridize to one or more gene products of the biomarkers or a subset of the biomarkers provided herein, or any combination thereof. In some embodiments, such kits may include primers for PCR of either the RNA product or the cDNA copy of the RNA product of the biomarkers or a subset of the biomarkers, or both. In some embodiments, such kits may include primers for PCR as well as probes for qPCR. In some embodiments, such kits may include multiple primers and multiple probes, wherein some of the probes have different fluorophores so as to permit simultaneously measuring multiple gene products of the biomarkers or a subset of the biomarkers provided herein. In some embodiments, such kits may further include materials and reagents for creating cDNA from RNA. In some embodiments, such kits may include antibodies specific for the protein products of the biomarkers or a subset of the biomarkers provided herein. Such kits may additionally comprise materials and reagents for isolating RNA and/or proteins from a biological sample. In addition, such kits may include materials and reagents for synthesizing cDNA from RNA isolated from a biological sample. In some embodiments, such kits may include a computer program product embedded on computer readable media for predicting whether a patient is clinically sensitive to a compound. In some embodiments, the kits may include a computer program product embedded on a computer readable media along with instructions.

In some embodiments, such kits measure the expression of one or more nucleic acid products of the biomarkers or a subset of the biomarkers provided herein. In accordance with this embodiment, the kits may comprise materials and reagents that are necessary for measuring the expression of particular nucleic acid products of the biomarkers or a subset of the biomarkers provided herein. For example, a microarray or RT-PCR kit may be produced for a specific condition and contain only those reagents and materials necessary for measuring the levels of specific RNA transcript products of the biomarkers or a subset of the biomarkers provided herein, to predict whether a hematological cancer in a patient is clinically sensitive to a compound. Alternatively, in some embodiments, the kits can comprise materials and reagents necessary for measuring the expression of particular nucleic acid products of genes other than the biomarkers provided herein. For example, in certain embodiments, the kits comprise materials and reagents necessary for measuring the expression levels of 1, 2, 3, 4, 5, 6, 7, 8, 9, 10, 15, 20, 25, 30, 35, 40, 45, 50, or more of the genes of the biomarkers provided herein, in addition to reagents and materials necessary for measuring the expression levels of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, or more genes other than the biomarkers provided herein. In other embodiments, the kits contain reagents and materials necessary for measuring the expression levels of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, or more of the biomarkers provided herein, and 1, 2, 3, 4, 5, 10, 15, 20, 25, 30, 35, 40, 45, 50, 55, 60, 65, 70, 75, 80, 85, 90, 95, 100, 125, 150, 175, 200, 225, 250, 300, 350, 400, 450, or more genes that are not the biomarkers provided herein. In certain embodiments, the kits contain reagents and materials necessary for measuring the expression levels of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, or more of the genes of the biomarkers provided herein, and 1-10, 1-100, 1-150, 1-200, 1-300, 1-400, 1-500, 1-1000, 25-100, 25-200, 25-300, 25-400, 25-500, 25-1000, 100-150, 100-200, 100-300, 100-400, 100-500, 100-1000 or 500-1000 genes that are not the biomarkers provided herein.

For nucleic acid microarray kits, the kits generally comprise probes attached to a solid support surface. In one such embodiment, probes can be either oligonucleotides or longer probes including probes ranging from 150 nucleotides to 800 nucleotides in length. The probes may be labeled with a detectable label. In a specific embodiment, the probes are specific for one or more of the gene products of the biomarkers provided herein. The microarray kits may comprise instructions for performing the assay and methods for interpreting and analyzing the data resulting from performing the assay. In a specific embodiment, the kits comprise instructions for predicting whether a hematological cancer in a patient is clinically sensitive to a compound. The kits may also comprise hybridization reagents and/or reagents necessary for detecting a signal produced when a probe hybridizes to a target nucleic acid sequence. Generally, the materials and reagents for the microarray kits are in one or more containers. Each component of the kit is generally in its own suitable container.

In certain embodiments, a nucleic acid microarray kit comprises materials and reagents necessary for measuring the expression levels of 1, 2, 3, 4, 5, 6, 7, 8, 9, 10, 15, 20, 25, 30, 35, 40, 45, 50, or more of the genes of the biomarkers provided herein, or a combination thereof, in addition to reagents and materials necessary for measuring the expression levels of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, or more genes other than those of the biomarkers provided herein. In other embodiments, a nucleic acid microarray kit contains reagents and materials necessary for measuring the expression levels of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, or more of the genes of the biomarkers provided herein, or any combination thereof, and 1, 2, 3, 4, 5, 10, 15, 20, 25, 30, 35, 40, 45, 50, 55, 60, 65, 70, 75, 80, 85, 90, 95, 100, 125, 150, 175, 200, 225, 250, 300, 350, 400, 450, or more genes that are not of the biomarkers provided herein. In another embodiment, a nucleic acid microarray kit contains reagents and materials necessary for measuring the expression levels of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, or more of the genes of the biomarkers provided herein, or any combination thereof, and 1-10, 1-100, 1-150, 1-200, 1-300, 1-400, 1-500, 1-1000, 25-100, 25-200, 25-300, 25-400, 25-500, 25-1000, 100-150, 100-200, 100-300, 100-400, 100-500, 100-1000, or 500-1000 genes that are not of the biomarkers provided herein.

For quantitative PCR, the kits generally comprise preselected primers specific for particular nucleic acid sequences. The quantitative PCR kits may also comprise enzymes suitable for amplifying nucleic acids (e.g., polymerases such as Taq polymerase), deoxynucleotides, and buffers needed for amplification reaction. The quantitative PCR kits may also comprise probes specific for the nucleic acid sequences associated with or indicative of a condition. The probes may or may not be labeled with a fluorophore. The probes may or may not be labeled with a quencher molecule. In some embodiments, the quantitative PCR kits also comprise components suitable for reverse-transcribing RNA, including enzymes (e.g., reverse transcriptases such as AMV, MMLV, and the like) and primers for reverse transcription along with deoxynucleotides and buffers needed for reverse transcription reaction. Each component of the quantitative PCR kit is generally in its own suitable container. Thus, these kits generally comprise distinct containers suitable for each individual reagent, enzyme, primer and probe. Further, the quantitative PCR kits may comprise instructions for performing the reaction and methods for interpreting and analyzing the data resulting from performing the reaction. In a specific embodiment, the kits contain instructions for predicting whether a hematological cancer in a patient is clinically sensitive to a compound.

For antibody-based kits, the kit can comprise, for example: (1) a first antibody (which may or may not be attached to a solid support) that binds to a peptide, polypeptide or protein of interest; and, optionally, (2) a second, different antibody that binds to either the first antibody or the peptide, polypeptide, or protein, and is conjugated to a detectable label (e.g., a fluorescent label, radioactive isotope, or enzyme). In a specific embodiment, the peptide, polypeptide, or protein of interest is associated with or indicative of a condition (e.g., a disease). The antibody-based kits may also comprise beads for conducting immunoprecipitation. Each component of the antibody-based kits is generally in its own suitable container. Thus, these kits generally comprise distinct containers suitable for each antibody and reagent. Further, the antibody-based kits may comprise instructions for performing the assay and methods for interpreting and analyzing the data resulting from performing the assay. In a specific embodiment, the kits contain instructions for predicting whether a hematological cancer in a patient is clinically sensitive to a compound.

In one embodiment, a kit provided herein comprises a compound provided herein, or a pharmaceutically acceptable salt, solvate, stereoisomer, isotopologue, prodrug, hydrate, co-crystal, clathrate, or a polymorph thereof. Kits may further comprise additional active agents, including but not limited to those disclosed herein.

Kits provided herein may further comprise devices that are used to administer the active ingredients. Examples of such devices include, but are not limited to, syringes, drip bags, patches, and inhalers.

Kits may further comprise cells or blood for transplantation, as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to, water for injection USP; aqueous vehicles (such as, but not limited to, sodium chloride injection, Ringer's injection, dextrose injection, dextrose and sodium chloride injection, and lactated Ringer's injection); water-miscible vehicles (such as, but not limited to, ethyl alcohol, polyethylene glycol, and polypropylene glycol); and non-aqueous vehicles (such as, but not limited to, corn oil, cottonseed oil, peanut oil, sesame oil, ethyl oleate, isopropyl myristate, and benzyl benzoate).

In certain embodiments of the methods and kits provided herein, solid phase supports are used for purifying proteins, labeling samples, or carrying out the solid phase assays. Examples of solid phases suitable for carrying out the methods disclosed herein include beads, particles, colloids, single surfaces, tubes, multi-well plates, microtiter plates, slides, membranes, gels, and electrodes. When the solid phase is a particulate material (e.g., a bead), it is, in one embodiment, distributed in the wells of multi-well plates to allow for parallel processing of the solid phase supports.

It is noted that any combination of the above-listed embodiments, for example, with respect to one or more reagents, such as, without limitation, nucleic acid primers, solid support, and the like, are also contemplated in relation to any of the various methods and/or kits provided herein.

Certain embodiments of the invention are illustrated by the following non-limiting examples.

6. EXAMPLES

The examples below are carried out using standard techniques, which are well known and routine to those of skill in the art, except where otherwise described in detail. The examples are intended to be merely illustrative.

6.1 Preparation of 2-(4-chlorophenyl)-N-((2-(2,6-dioxopiperidin-3-yl)-1-oxoisoindolin-5-yl)methyl)-2,2-difluoroacetamide (Compound D A. Methyl 4-bromo-2-methylbenzoate: 4-Bromo-2-methylbenzoic acid (100 g, 465.02 mmol), concentrated sulfuric acid (52 mL) in methanol (1 L) were combined and heated to 65° C. for 18 h. The reaction was concentrated and the residue diluted with ethyl acetate (500 mL), washed with saturated sodium bicarbonate solution (150 mL), water (200 mL), brine (250 mL) and dried over sodium sulfate. The organic phase was concentrated under reduced pressure and further dried under high vacuum to give methyl 4-bromo-2-methylbenzoate (102 g, 445.27 mmol, 95% yield) as a red liquid. 1H NMR (400 MHz, Chloroform-di) S 7.78 (d, J=8.3 Hz, 1H), 7.45-7.30 (m, 2H), 3.88 (s, 3H), 2.57 (s, 3H).

B. Methyl-4-bromo-2-(bromomethyl) benzoate: Methyl 4-bromo-2-methylbenzoate (102 g, 445.27 mmol), NBS (79.2 g, 445.27 mmol), Azo-isobutyronitrile (2.58 g, 16 mmol) in acetonitrile (600 mL) were combined and refluxed at 85° C. for 18 h. The mixture was concentrated, and to the residue was added dichloromethane (150 mL). The resultant solid was removed by filtration. The filtrate was concentrated and purified by flash column chromatography (04% EtOAc in Hexanes). Fractions containing product was concentrated under reduced pressure and further dried under high vacuum to give Methyl-4-bromo-2-(bromomethyl) benzoate (100 g, 324.70 mmol, 72.9% yield) as an off-white solid. 1H NMR (300 MHz, Dimethylsulfoxide-$d_6$) δ 7.88 (d, J=2.2 Hz, 1H), 7.82 (dd, J=8.4, 2.1 Hz, 1H), 7.72-7.64 (m, 1H), 5.00 (s, 2H), 3.88 (s, 3H).

C. 3-(5-Bromo-1-oxoisoindolin-2-yl)piperidine-2,6-dione: Methyl-4-bromo-2-(bromomethyl) benzoate (100 g, 324.70 mmol), 3-Aminopiperidine-2,6-dione.hydrochloride (53.2 g, 324.70 mmol), triethylamine (113.29 mL, 811.75 mmol), and dry dimethylformamide (400 mL) were combined and stirred at room temperature under inert atmosphere for 18 h. The reaction was cooled to 5° C. and diluted with water (400 mL), acetic acid (115 mL), diethylether (300 mL) with continued stirring at room temperature for 2 hrs. The resultant solid was filtered, washed with ether (100 mL) and further dried under high vacuum to give 3-(5-Bromo-1-oxoisoindolin-2-yl)piperidine-2,6-dione (46 g, 142.35 mmol, 43.8% yield) as a light blue solid. MS (ESI) m/z 325.0 $[M+1]^+$.

D. 2-(2,6-dioxopiperidin-3-yl)-1-oxoisoindoline-5-carbonitrile: 3-(5-Bromo-1-oxoisoindolin-2-yl)piperidine-2,6-dione (46 g, 142.35 mmol), 1,1'-Bis(diphenylphosphino)ferrocene (788 mg, 1.423 mmol), zinc cyanide (25 g, 213.52 mmol), zinc acetate (7.83 g, 42.7 mmol) and dry dimethylformamide (360 mL) were combined and degassed before addition of tris(dibenzylideneacetone)dipalladium(0) (0.364 g, 0.398 mmol). The mixtures was evacuated and replaced with argon 3 times, then stirred at 120° C. for 20 h. The mixture was cooled to room temperature, filtered and purified by silica column chromatography (0-5% methanol in dichloromethane). Fractions containing product were combined and solvent removed under reduced pressure and then further dried under high vacuum to give 2-(2,6-dioxopiperidin-3-yl)-1-oxoisoindoline-5-carbonitrile (22 g, 81.78 mmol, 57.2% yield) as a brown solid. MS (ESI) m/z 268.0 $[M-H]^+$.

E. 3-(5-(aminomethyl)-1-oxoisoindolin-2-yl)piperidine-2,6-dione: 2-(2,6-Dioxopiperidin-3-yl)-1-oxoisoindoline-5-carbonitrile (10 g, 37.13 mmol), methanesulfonic acid (2.6 mL, 40.85 mmol), 10% dry Palladium on carbon (4 g) and dimethylacetamide (320 mL) were combined and shaken in a hydrogenation vessel and kept under 50 Psi at 40° C. for 20 h. The hydrogen atmosphere was evacuated and the mixture was filtered through a celite pad, washed with water (100 mL), and concentrated. To the resulting residue was added 1% methanol-dichloromethane which upon filtration and drying under high vacuum gave 3-(5-(aminomethyl)-1-oxoisoindolin-2-yl)piperidine-2,6-dione (5.6 g, 15.17 mmol, 40% yield) as an off-white solid. MS (ESI) m/z 272.0 [M−1].

F. 2-(4-chlorophenyl)-N-((2-(2,6-dioxopiperidin-3-yl)-1-oxoisoindolin-5-yl)methyl)-2,2-difluoroacetamide. To 3-(5-(aminomethyl)-1-oxoisoindolin-2-yl)piperidine-2,6-dione methanesulfonate (0.200 g, 0.541 mmol) in DMF (3 mL) was added HATU (0.226 g, 0.596 mmol), 2-(4-chlorophenyl)-2,2-difluoroacetic acid (0.112 g, 0.541 mmol) followed by N-ethyl-N-isopropylpropan-2-amine (0.262 ml, 1.624 mmol). Let stir at 25° C. for 16 h. Added 30 mL of water and filtered. Rinsed with EtOAc, dried under vacuum to afford 2-(4-chlorophenyl)-N-((2-(2,6-dioxopiperidin-3-yl)-1-oxoisoindolin-5-yl)methyl)-2,2-difluoroacetamide (0.080 g, 0.173 mmol, 32.0% yield) as a white solid. $^1$H NMR (500 MHz, DMSO-$d_6$) δ ppm 10.98 (s, 1H) 9.68 (t, J=6.15 Hz, 1H) 7.69 (d, J=7.88 Hz, 1H) 7.58-7.66 (m, 4H) 7.33-7.44 (m, 2H) 5.11 (dd, J=13.24, 5.04 Hz, 1H) 4.39-4.50 (m, 3H) 4.24-4.35 (m, 1H) 2.85-2.98 (m, 1H) 2.61 (dd, J=15.29, 2.05 Hz, 1H) 2.39 (dd, J=12.93, 4.73 Hz, 1H) 1.95-2.07 (m, 1H). MS (ESI) m z 462.0 $[M+1]^+$.

6.2 Preparation of N-((2-(2,6-dioxopiperidin-3-yl)-1-oxoisoindolin-5-yl)methyl)-2,2-difluoro-2-(4-fluorophenyl)acetamide (Compound E 3-(5-(aminomethyl)-1-oxoisoindolin-2-yl)piperidine-2,6-dione can be prepared using a method provided in Example 5.1. To 3-(5-(aminomethyl)-1-oxoisoindolin-2-yl)piperidine-2,6-dione methanesulfonate (0.200 g, 0.541 mmol) in DMF (3 mL) was added HATU (0.226 g, 0.596 mmol), 2,2-difluoro-2-(4-fluorophenyl)acetic acid (0.103 g, 0.541 mmol) followed by N-ethyl-N-isopropylpropan-2-amine (0.262 ml, 1.624 mmol). Let stir at 25° C. for 16 h. Added 30 mL of water and filtered. Rinsed with EtOAc, dried under vacuum to afford N-((2-(2,6-dioxopiperidin-3-yl)-1-oxoisoindolin-5-yl)methyl)-2,2-difluoro-2-(4-fluorophenyl)acetamide (0.100 g, 0.225 mmol, 41.5% yield) as a white solid. $^1$H NMR (500 MHz, DMSO-$d_6$) δ ppm 10.98 (br. s., 1H) 9.66 (t, J=5.99 Hz, 1H) 7.58-7.73 (m, 3H) 7.29-7.47 (m, 4H) 5.11 (dd, J=13.40, 5.20 Hz, 1H) 4.38-4.53 (m, 3H) 4.24-4.36 (m, 1H) 2.81-3.00 (m, 1H) 2.56-2.67 (m, 1H) 2.40 (qd, J=13.19, 4.57 Hz, 1H) 1.91-2.07 (m, 1H).

6.3 Compound D has a Broad Anti-Proliferation Effect Across AML Cell Lines

A plethora of AML cell lines were treated with serial dilutions of Compound D. $IC_{50}$ value of the anti-proliferation effect of Compound D (as determined in 72-hour CTG assays) in each cell line is summarized in Table 1.

TABLE 1

$IC_{50}$ Values of the Anti-proliferative Effect of Compound D in AML Cell Lines

| AML Cell Lines | HNT-34 | KG-1 | KG-1a | KASUMI-1 | NB-4 | MV-4-11 | MOLM-13 | HL-60 | U-937 | OCI-AML2 | OCI-AML3 |
|---|---|---|---|---|---|---|---|---|---|---|---|
| Cmp D ($IC_{50}$/ μM) | 0.003 ± 0.001 | 0.015 ± 0.006 | 0.021 ± 0.010 | 0.021 ± 0.013 | 0.017 ± 0.005 | 0.029 ± 0.010 | 0.075 ± 0.033 | 0.020 ± 0.010 | 0.074 ± 0.025 | 0.057 ± 0.021 | 3.397 ± 3.326 |

In contrast, Compound D exhibited an $IC_{50}$ value of approximately 10 μM in a nontumorigenic human hepatocellular cell line THLE-2 and an $IC_{50}$ value of greater than 10 μM in healthy donor PBMCs (data not shown).

Figure 1A:
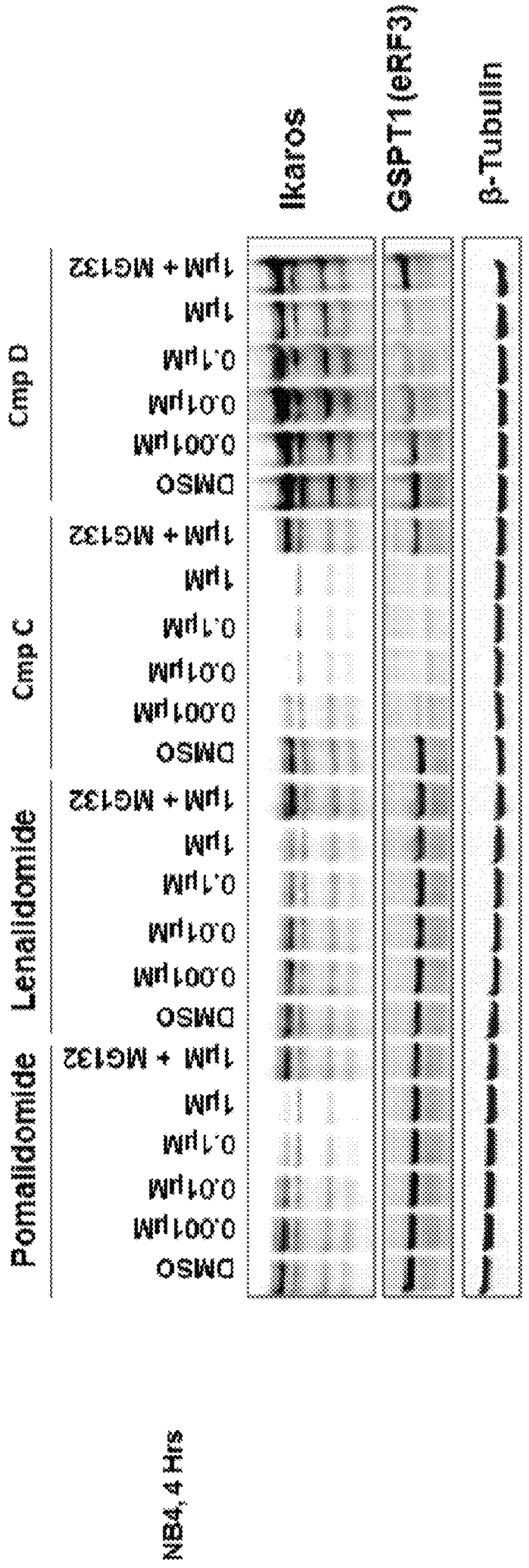

FIG. 1A shows representatively that, in NB4 cell line, Compound D induced degradation of GSPT1 and IKZF1, which can be blocked by MG132, a proteasome inhibitor. In contrast, pomalidomide and lenalidomide had no significant effect on GSPT1 level, although they induced degradation of IKZF1 at much lower concentrations than Compound D did. This suggests that Compound D has a different mechanism of action in inhibiting cell proliferation than pomalidomide and lenalidomide.

Figure 1B:
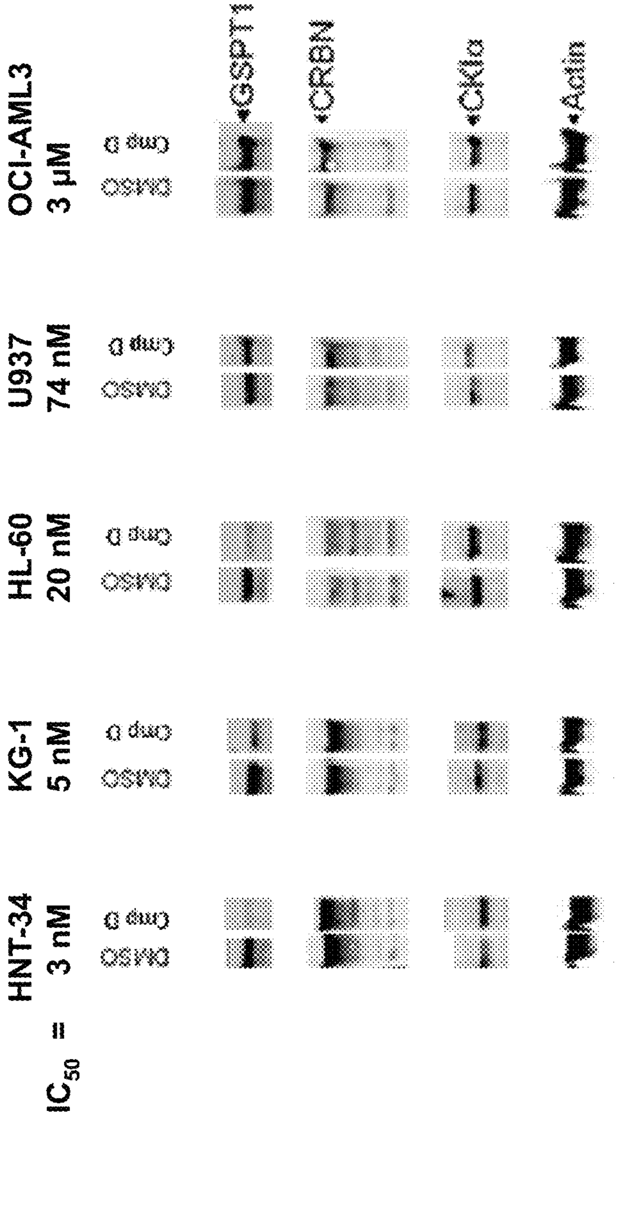

FIG. 1B shows that the extent of GSPT1 protein reduction in a 4-hour exposure to Compound D correlated with the anti-proliferative potency of Compound D, indicated as $IC_{50}$ values in Table 1. Among the five AML cell lines tested, Compound D demonstrated the most potent anti-proliferative activity ($IC_{50}$ of 3 nM) and induced the greatest loss of GSPT1 protein in HNT-34 cell line. On the other hand, GSPT1 protein level barely changed in OCI-AML3 cell line, which is relatively insensitive to the anti-proliferative effect of Compound D. The lack of an effect of Compound D on GSPT1 reduction in OCI-AML3 cells indicates that loss of GSPT1 protein is necessary for Compound D-induced inhibition of cell growth.

Figure 2B:
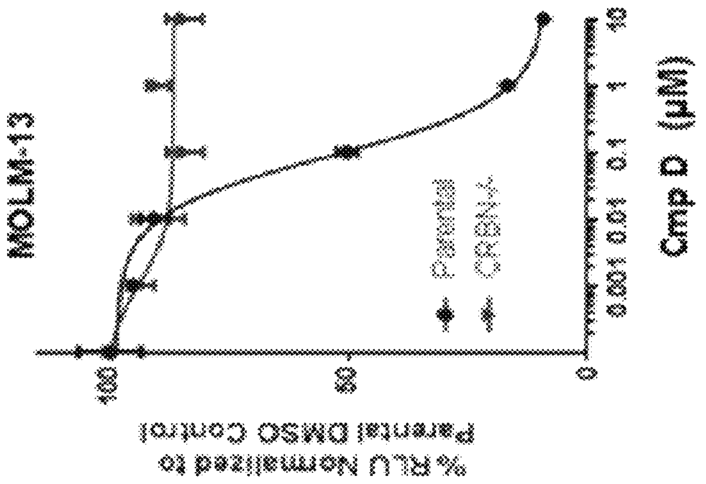
Figure 2A:
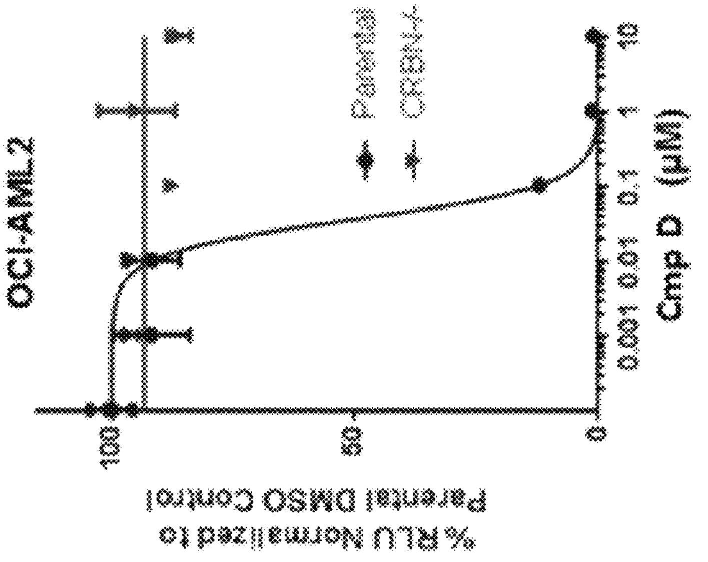
Figure 2D:
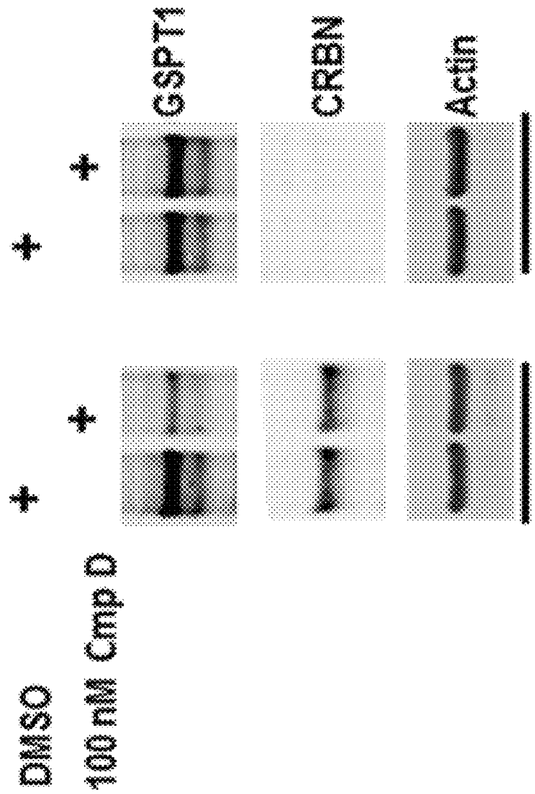
Figure 2C:
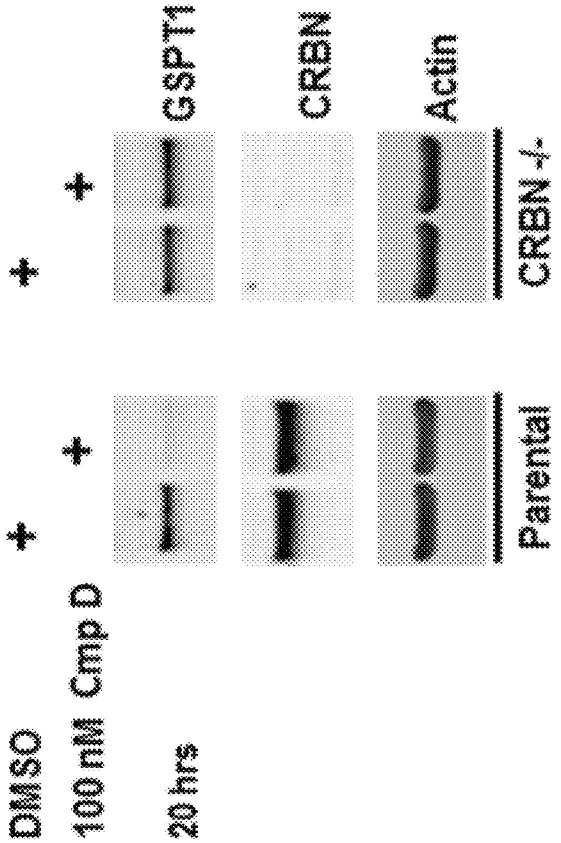

6.4 the Anti-Proliferative Effect of Compound D and Compound D-Induced Degradation of GSPT1 are CRBN-Dependent Two different AML cell lines, OCI-AML2 and MOLM-13, and their CRBN −/− counterparts were treated with serial dilutions of Compound D. As shown in FIGS. 2A and 2B, Compound D exhibited dose-dependent anti-proliferative effect in parental OCI-AML2 cells (FIG. 2A) and MOLM-13 cells (FIG. 2B). Depletion of CRBN completely abrogated this effect, suggesting that the anti-proliferative effect of Compound D in these cells is CRBN-dependent. Western blot demonstrates that in parental cells, 100 nM of Compound D induced degradation of GSPT1 (FIGS. 2C and 2D, left panels), and that the same concentration of Compound D could not induce degradation of GSPT1 in CRBN −/− OCI-AML2 cells (FIG. 2C, right panel) and CRBN −/− MOLM-13 cells (FIG. 2D, right panel). Thus, Compound D-induced GSPT1 degradation is also CRBN-dependent.

A different CRBN-binding compound, Compound F, that demonstrated anti-proliferative activity in non-AML hematological cancer cell lines (such as multiple myeloma) did not inhibit cell growth in any of the 11 AML cell lines tested, including the ten cell lines that were sensitive to the growth inhibitory activity of Compound D (data not shown). However, when excess Compound F was added to KG-1 AML cell cultures in the presence of Compound D, the anti-proliferative activity of Compound D was reduced, presumably due to competition for binding of Compound D to CRBN. The relative impact of Compound F on the anti-proliferative effect of Compound D progressively increased with increasing concentrations of Compound F (Table 2). In the presence of 100 μM Compound F, the potency of Compound D in inhibiting cell growth reduced by approximately 60-fold, evidenced by a change of $IC_{50}$ from 0.01 μM (without Compound F) to 6.8 μM (with Compound F), and the potency of Compound D in inducing apoptosis reduced by approximately 40-fold, evidenced by a change of $EC_{50}$ from 0.02 μM (without Compound F) to 8 μM (with Compound F) (Table 2). These results established that the interaction of Compound D with CRBN is a key factor in the anti-proliferative activity of Compound D.

TABLE 2

Competition with Compound F Reduced Potency of Compound D in Inhibiting Cell Growth and Inducing Apoptosis

| Concentration of Compound F (μM) | Inhibition of Cell Proliferation by Compound D (CTG assay) $IC_{50}$ (μM) | Induction of Apoptosis by Compound D (Annexin V assay) $EC_{50}$ (μM) |
|---|---|---|
| 0 | 0.01 | 0.02 |
| 0.1 | 0.013 | 0.03 |
| 1.0 | 0.05 | 0.1 |
| 10 | 0.5 | 1 |
| 30 | 1.5 | ND |
| 100 | 6.8 | 8 |

Figure 3A:
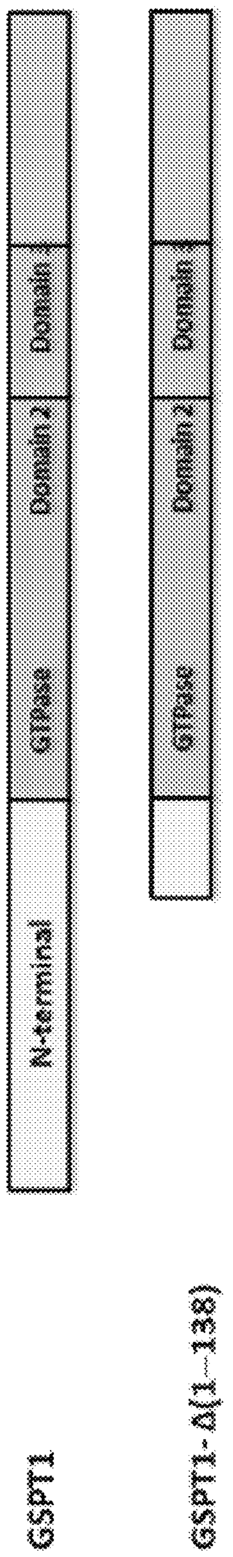
Figure 3B:
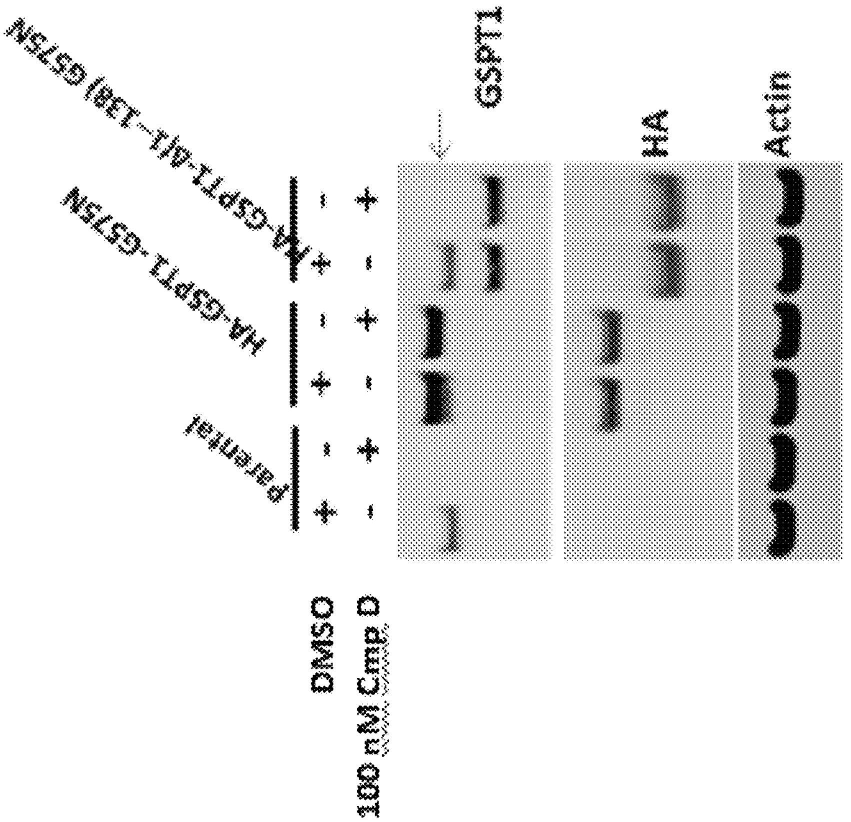
Figure 3C:
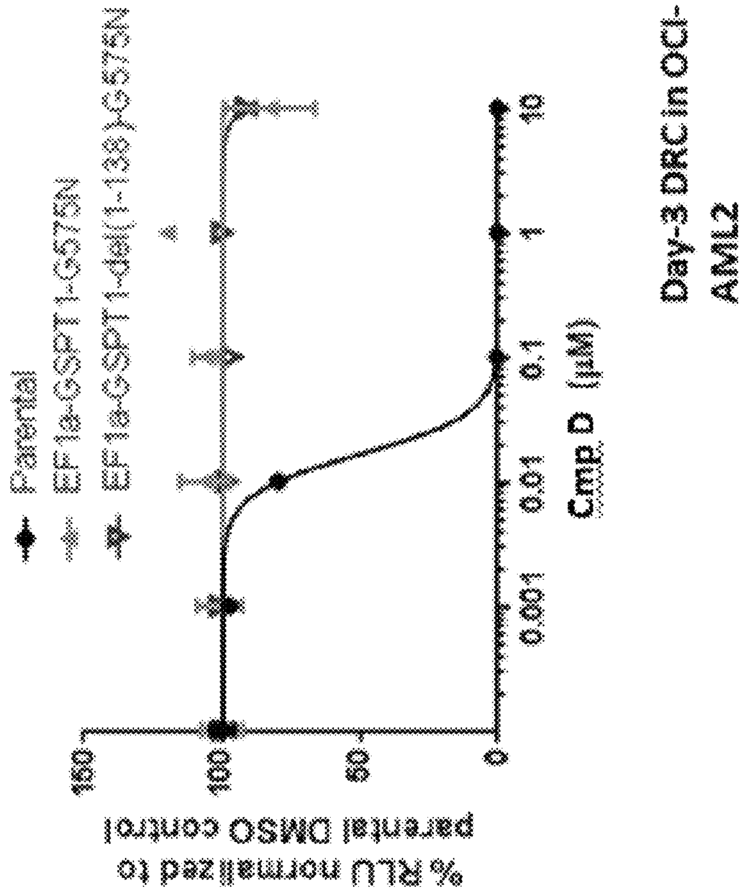

6.5 Stabilization of GSPT1 Abrogated the Anti-Proliferative Effect of Compound D To further investigate whether stabilization of GSPT1 confers resistance to the anti-proliferative effect of Compound D, HA-tagged GSPT1 with a G575N mutation (HA-GSPT1-G575N) and HA-tagged GSPT1 with a deletion of amino acids 1-138 and a G575N mutation (HA-GSPT1-Δ(1-138)-G575N) were overexpressed in OCI-AML2 cells. The G575N mutation in GSPT1 makes GSPT1 resistant to the degradation by CRBN ubiquitin E3-ligase complex. FIG. 3A illustrates the full-length GSPT1 and GSPT1 with a deletion of amino acids 1-138. FIG. 3B shows that, wild type GSPT1 in parental OCI-AML2 cells were degraded upon Compound D treatment, whereas HA-GSPT1-G575N and HA-GSPT1-Δ(1-138)-G575N stayed intact in the presence of Compound D. The anti-proliferative effect of Compound D was investigated in parental OCI-AML2 cells and OCI-AML2 cells transfected with EF1a-GSPT1-G575N or EF1a-GSPT1-Δ(1-138)-G575N. FIG. 3C demonstrates that overexpression of GSPT1-G575N and GSPT1-Δ(1-138)-G575N abrogated the anti-proliferative effect of Compound D, suggesting that stabilization of GSPT1 confers resistance to the anti-proliferative effect of Compound D in OCI-AML2 cells.

6.6 Depletion of GSPT1 Inhibited Cell Proliferation

Figure 4A:
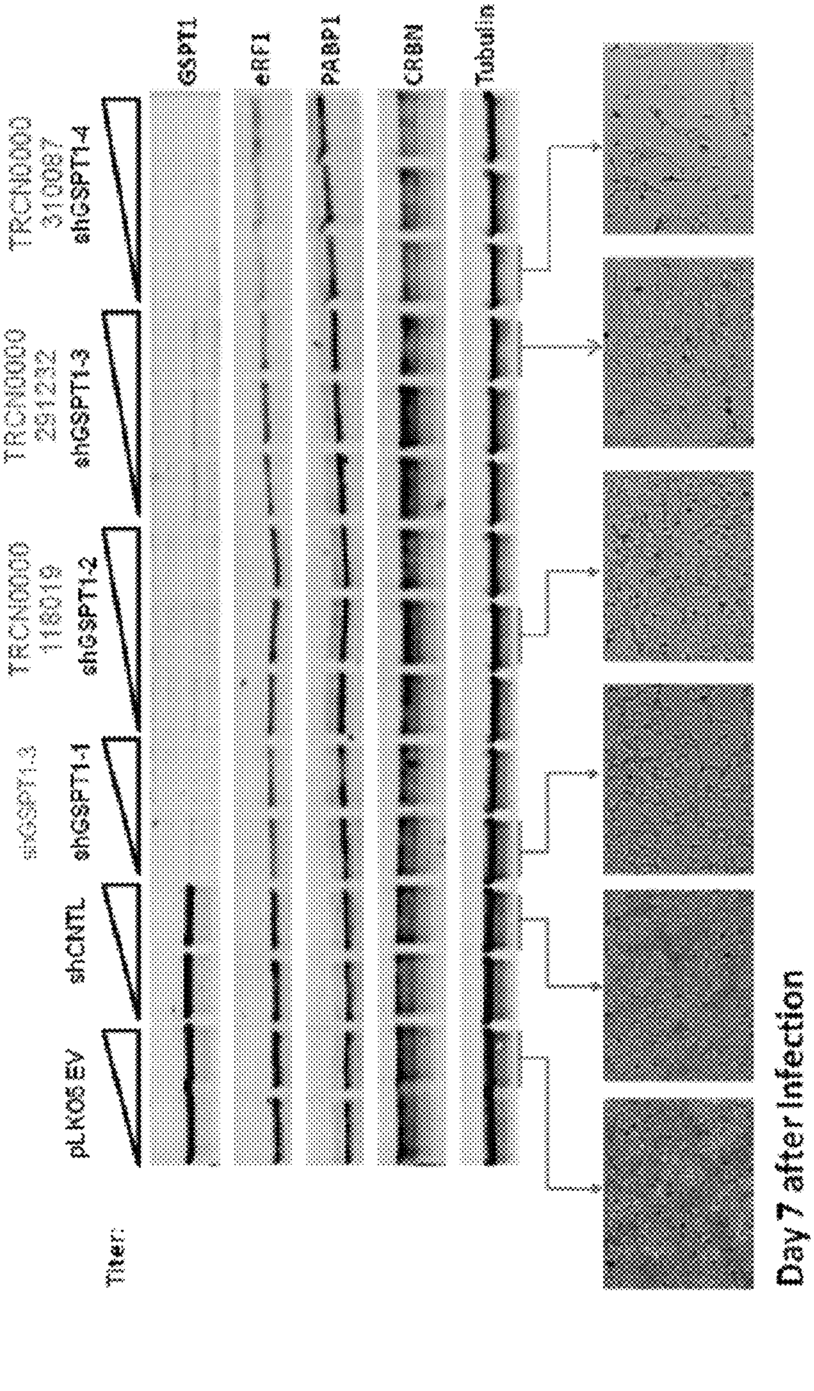
Figure 4B:
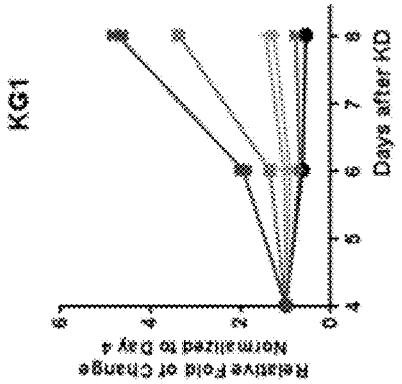
Figure 4C:
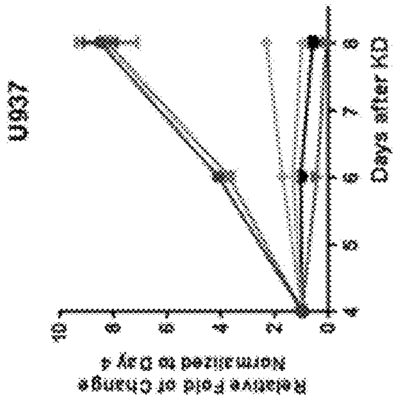
Figure 4D:
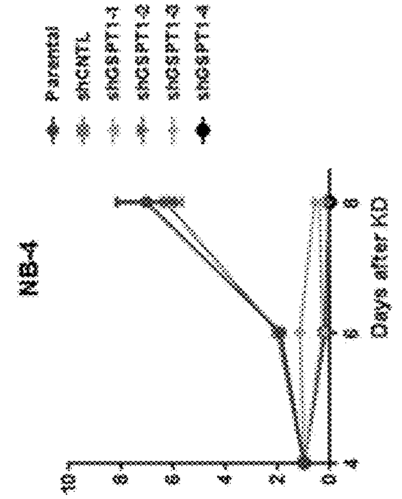
Figure 4E:
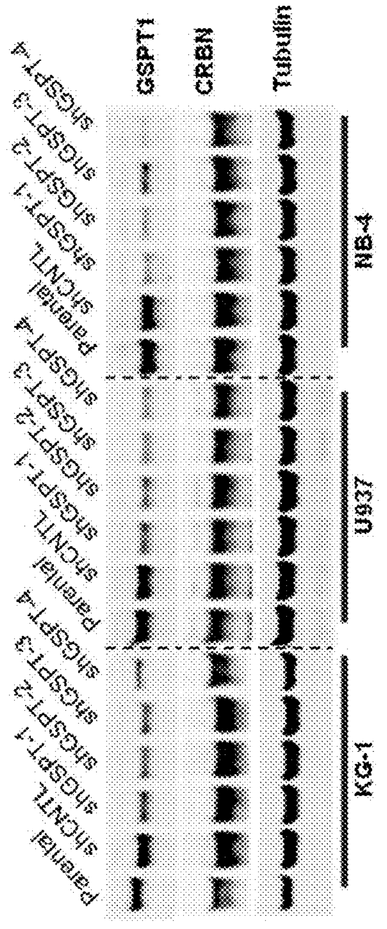
Figure 4F:
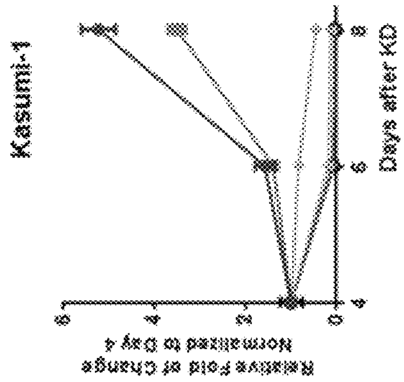
Figure 4G:
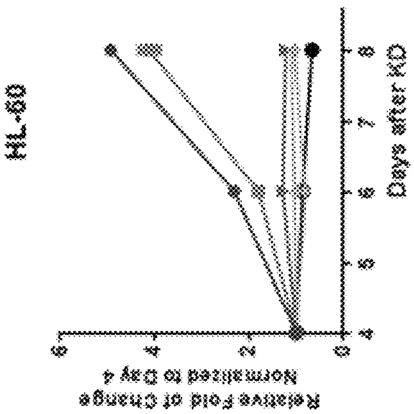
Figure 4H:
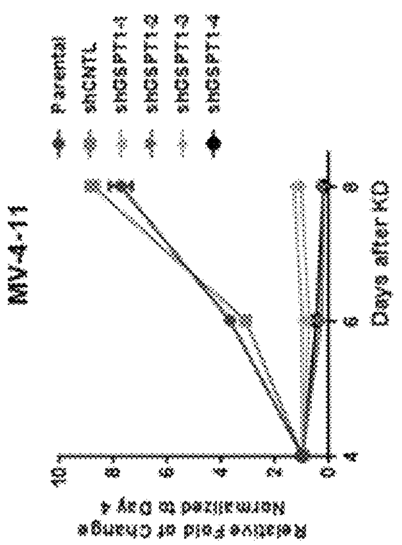
Figure 4I:
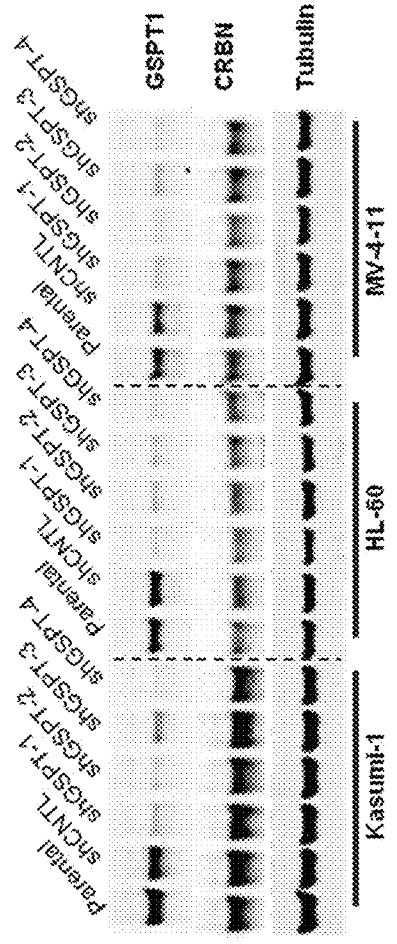

The effect of depletion of GSPT1 on cell proliferation was determined in 293FT human embryonic kidney cells expressing shRNAs specifically targeting various GSPT1 regions. As shown in FIG. 4A, at day 7 after infection, cells with the expression vector alone or control shRNA that is not GSPT1-specific showed normal cell proliferation, whereas cells expressing GSPT1-specific shRNAs (such as shGSPT1-1, shGSPT1-2, shGSPT1-3, and shGSPT1-4) showed various degrees of inhibition on cell proliferation.

The expression levels of various genes in infected cells were also measured in FIG. 4A. Compared to the expression vector alone or control shRNA, all four GSPT1-specific shRNAs blocked the expression of GSPT1. In particular, shGSPT1-4 reduced the expression of eRF1 and CRBN. Thus, depletion of GSPT1 inhibited cell proliferation possibly due to the inactivation of the eRF1/GSPT1 (GSPT1) complex.

Figure 4K:
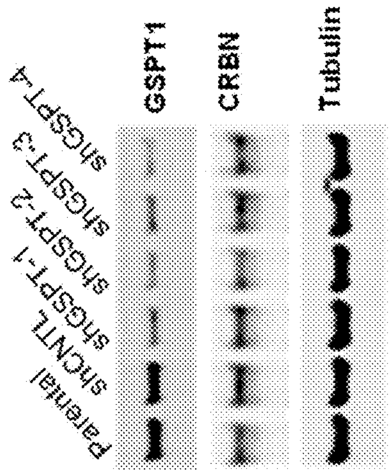
Figure 4J:
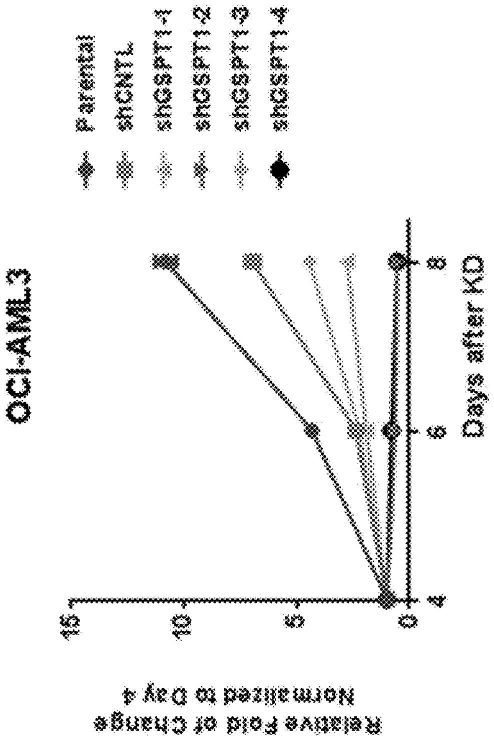

The direct relationship between GSPT1 depletion and anti-proliferative activity was studied in seven AML cell lines (KG1, U937, NB-4, Kasumi-1, HL-60, MV-4-11, and OCI-AML3). In all seven cell lines, GSPT1 knockdown decreased cell proliferation and viability with each of four different shRNAs, essentially phenocopying the effect of incubation with Compound D (FIGS. 4B-4K). Knockdown of GSPT1 was effective in inducing inhibition of cell growth in the absence of Compound D even in OCI-AML3, the AML cell line that is the least sensitive to the anti-proliferative activity of Compound D (FIGS. 4J-4K).

6.7 Overexpression of GSPT1 Antagonized the Anti-Proliferative Effect of Compound D and Compound E in U937, MOLM13, and OCI-AML2 Cells The effect of overexpression of GSPT1 on the anti-proliferative effect of Compound D and Compound E was determined in human histiocytic lymphoma cell line U937 and human leukemia cell line MOLM13. Treatment compounds (e.g., Compound D or Compound E) were titrated from 0.001 μM to 10 μM. Cell proliferation was measured by CellTiter-Glo cell viability assay at 48 hours after treatment. As shown in FIGS. 5A-5D, in parental cells, Compound D and Compound E inhibited cell proliferation. Yet in CRBN −/− cells, this anti-proliferative effect was completely abolished, which suggests that the anti-proliferative effect of these compounds is CRBN-dependent. However, when exogenous GSPT1 was overproduced via the EF1α promoter, as shown in FIGS. 5A-5D, the anti-proliferative effect of Compound D and Compound E reduced. This result suggests that overexpression of GSPT1 antagonized the anti-proliferative effect of Compound D and Compound E.

Figures 5A, 5B, 5C, 5D:
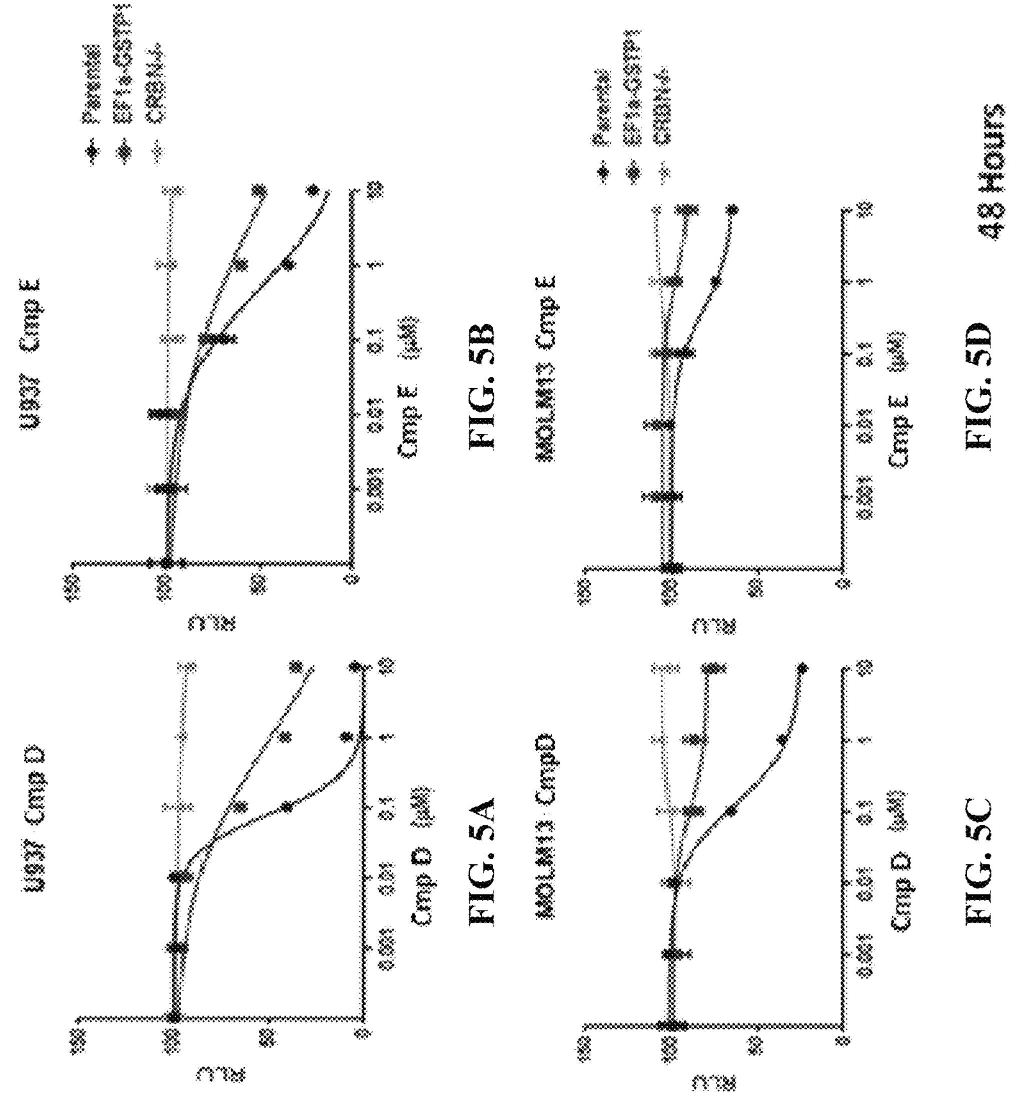
Figure 5F:
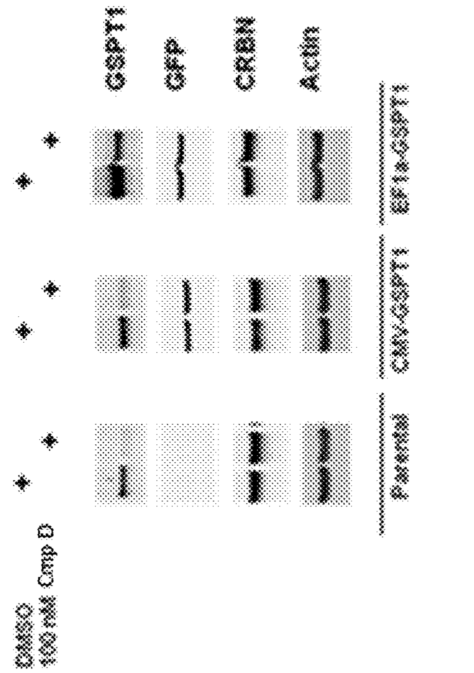
Figure 5E:
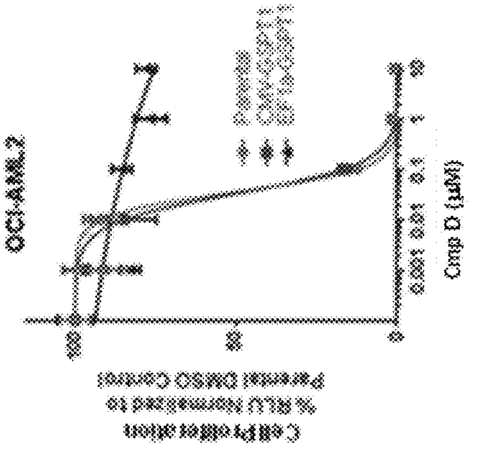
Figure 5H:
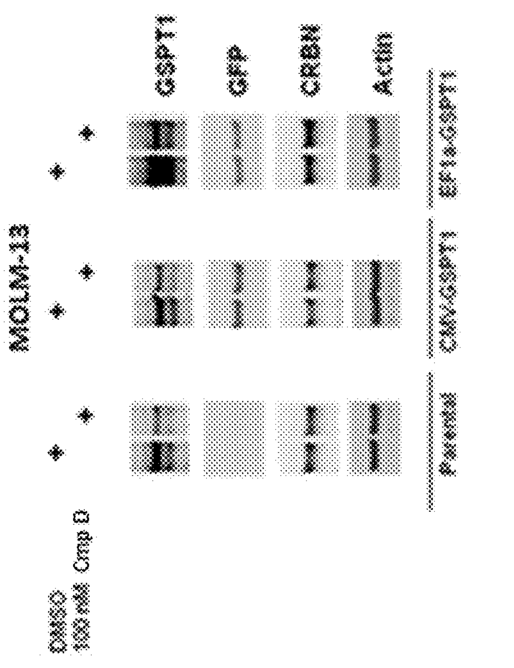
Figure 5G:
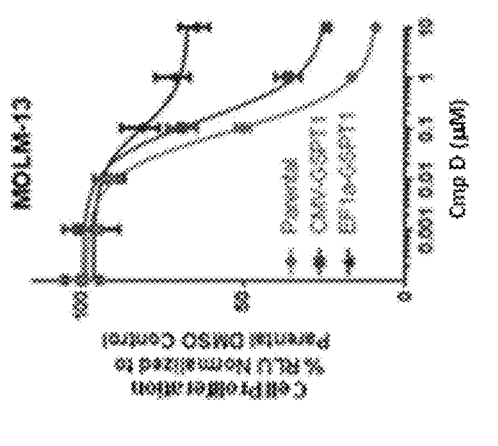

Two different promoters (EF1α or cytomegalovirus [CMV]) were used to drive the overproduction of exogenous GSPT1 in OCI-AML2 and MOLM-13 cells via lentiviral transduction (FIGS. 5F and 511, DMSO lanes for transduced cell extracts). Robust destruction of endogenous GSPT1 was triggered by incubation of OCI-AML2 parental cells (FIG. 5F, left panel) and MOLM-13 parental cells (FIG. 5H, left panel) with Compound D. In contrast, GSPT1 overexpression driven by the EF1α promoter in the transduced cells counteracted the Compound D-induced depletion of GSPT1 (FIG. 5F, right panel [OCI-AML2] and FIG. 5H, right panel [MOLM-13]). Assessment of cell proliferation in the transduced cells revealed that overexpression of GSPT1 driven by the EF1α promoter substantially reduced the anti-proliferative effect of Compound D in comparison with that seen in the corresponding parental cells (FIG. 5E [OCI-AML2] and FIG. 5G [MOLM-13]). No significant difference in the level of CRBN protein between parental and GSPT1-overexpressing cells was observed (FIGS. 5F and 511). These results demonstrate the relationship between Compound D-mediated effects on GSPT1 reduction and growth inhibition in AML cells.

Figures 6A, 6B, 6C, 6D:
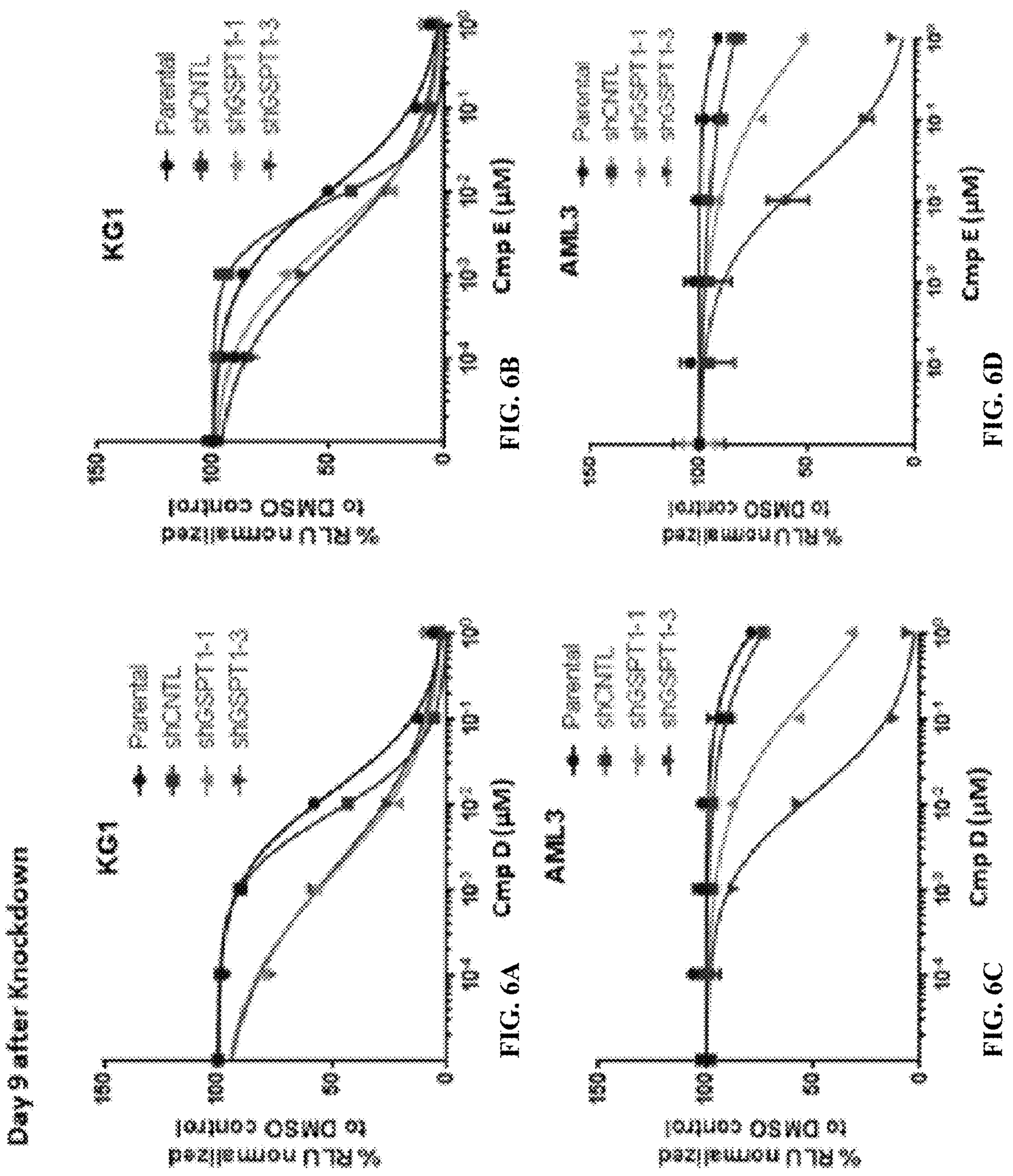
Figure 6E:
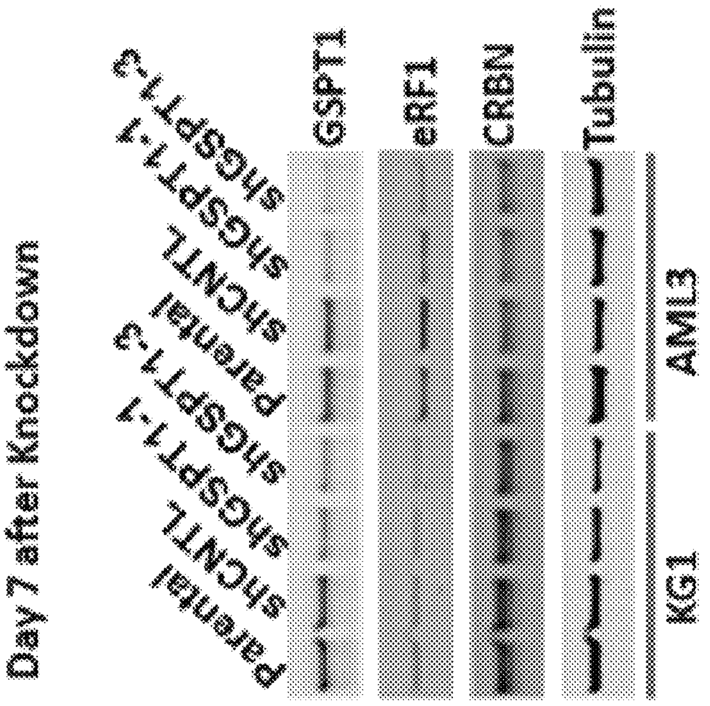

6.8 Depletion of GSPT1 Sensitized Acute Myelogenous Leukemia Cell Lines AML3 and KG1 to Compound D and Compound E The effect of depletion of GSPT1 on the anti-proliferative effect of compound Compound D and Compound E was also determined in human acute myelogenous leukemia cell lines AML and KG1. Cells were infected with lentiviral vectors expressing control shRNA, shGSPT1-1 or shGSPT1-3 for 7 days and then treated with DMSO, Compound D or Compound E in a titration from 0.0001 μM to 1 μM. Two days after treatment, cell proliferation was measured by CellTiter-Glo cell viability. As shown in FIGS. 6A-6D, in parental cells or cells infected with control shRNA that was not GSPT1-specific, Compound D and Compound E exhibited anti-proliferative effect, particularly at high concentration. Yet when the expression of GSPT1 was depleted by shGSPT1-1 or shGSPT1-3, this anti-proliferative effect dramatically increased. As shown in FIG. 6E, the expression level of GSPT1 was measured at day 7 after knockdown in KG1 and AML3 cells. Both shGSPT1-1 and shGSPT1-3 reduced the expression of GSPT1, eRF1, and slightly of CRBN.

6.9 Compound D-Induced Unfolded Protein Response (UPR) Preceded Apoptotic Cell Death in Human Acute Myeloblastic Leukemia Cell Line KG1

Figure 7B:
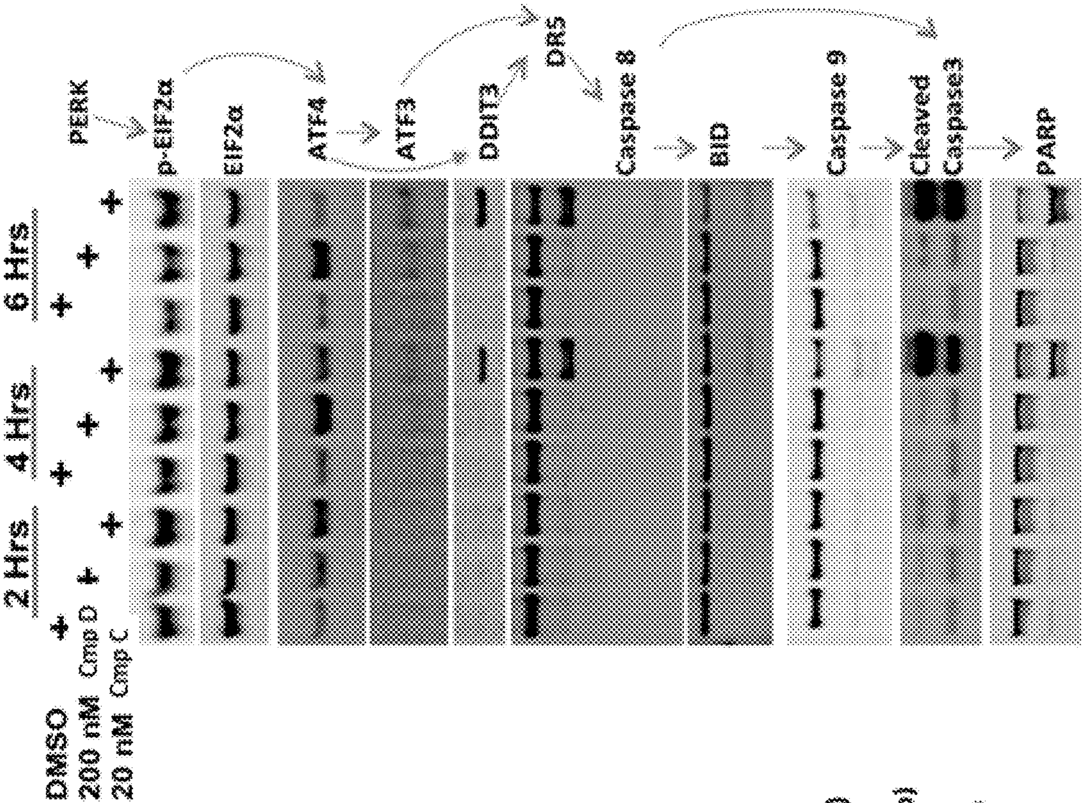
Figure 7A:
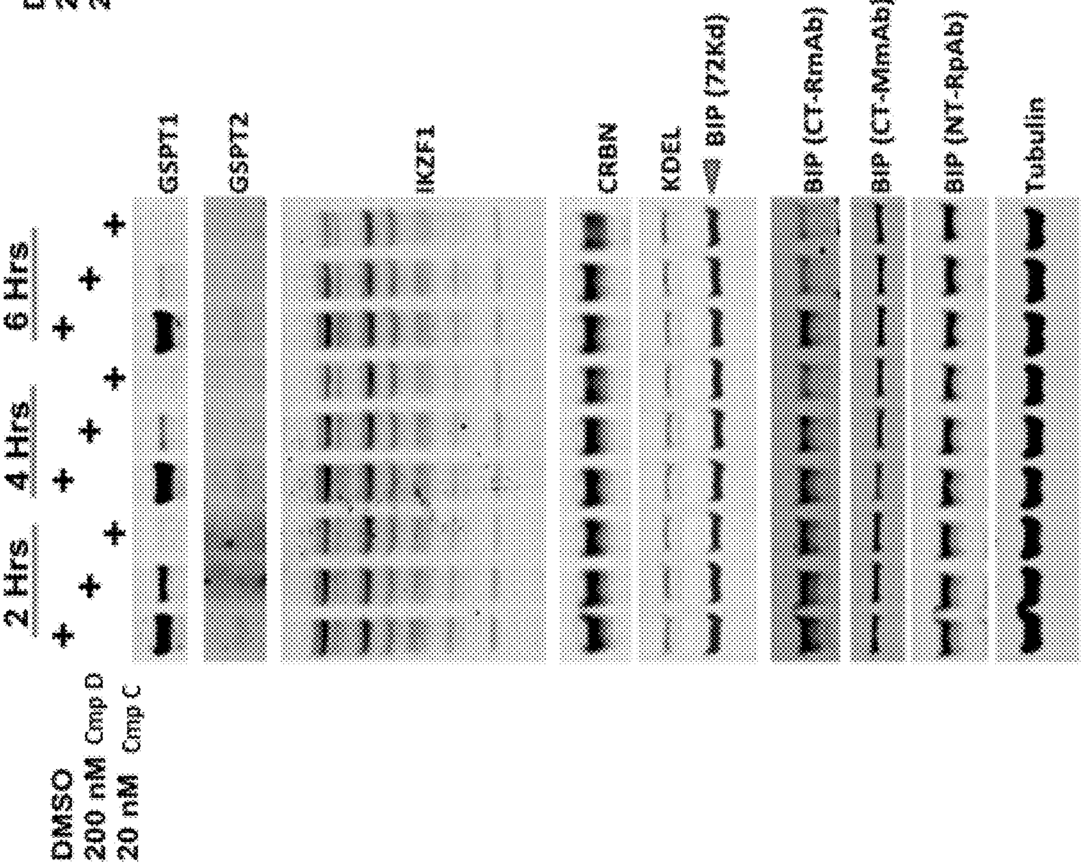

The cellular effect of Compound D-induced degradation of GSPT1 was further studied in KG1 cells. Cells were treated with DMSO alone or 200 nM Compound D. After 2, 4, or 6 hours, the expression levels of various cellular components along UPR or apoptosis pathways were measured. As shown in FIG. 7A, Compound D induced degradation of GSPT1, GSPT2, and BIP (detected by CT-RmAb). Reduction of BIP indicates UPR. Similarly, as shown in FIG. 7B, Compound D increased the expression of ATF-4 and its downstream target ATF-3. The level of p-eIF2α, DDIT3, cleaved Caspase-3, cleaved Caspase-8, cleaved Caspase-9, and cleaved PARP also increased, suggesting the onset of apoptosis.

6.10 Compound D and Compound E Induced Apoptosis in Human Acute Myeloblastic Leukemia Cell Line KG1

Figure 8B:
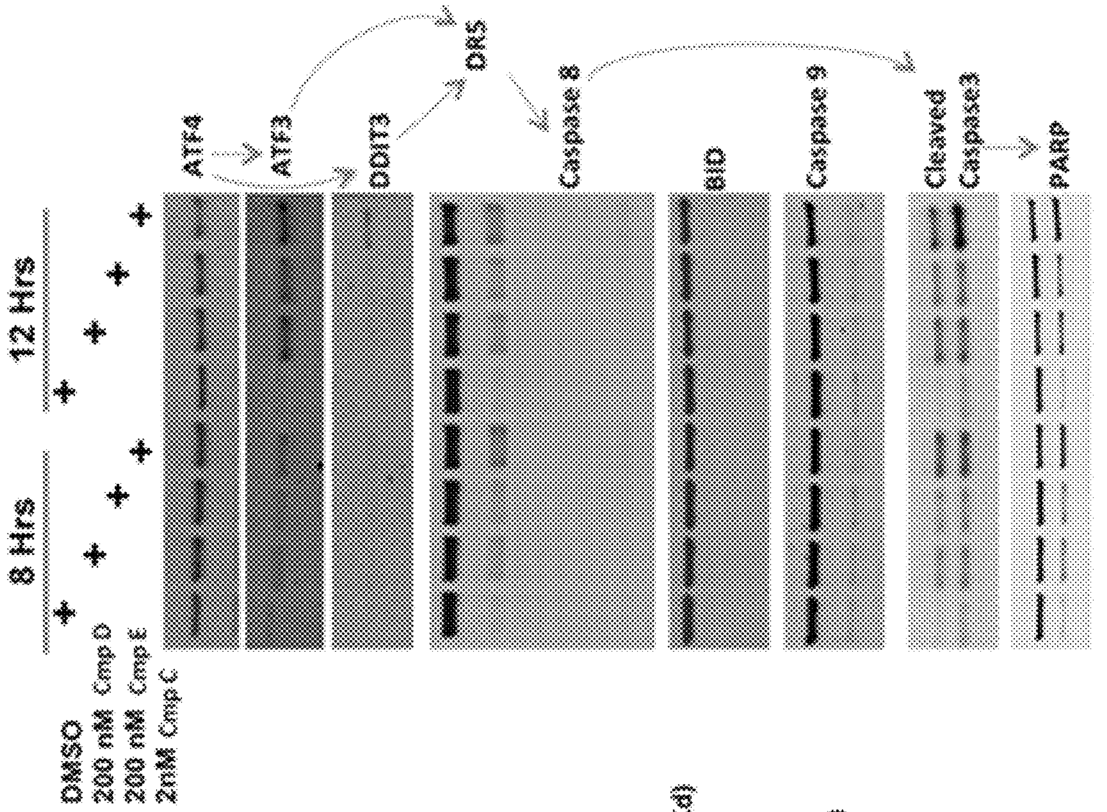
Figure 8A:
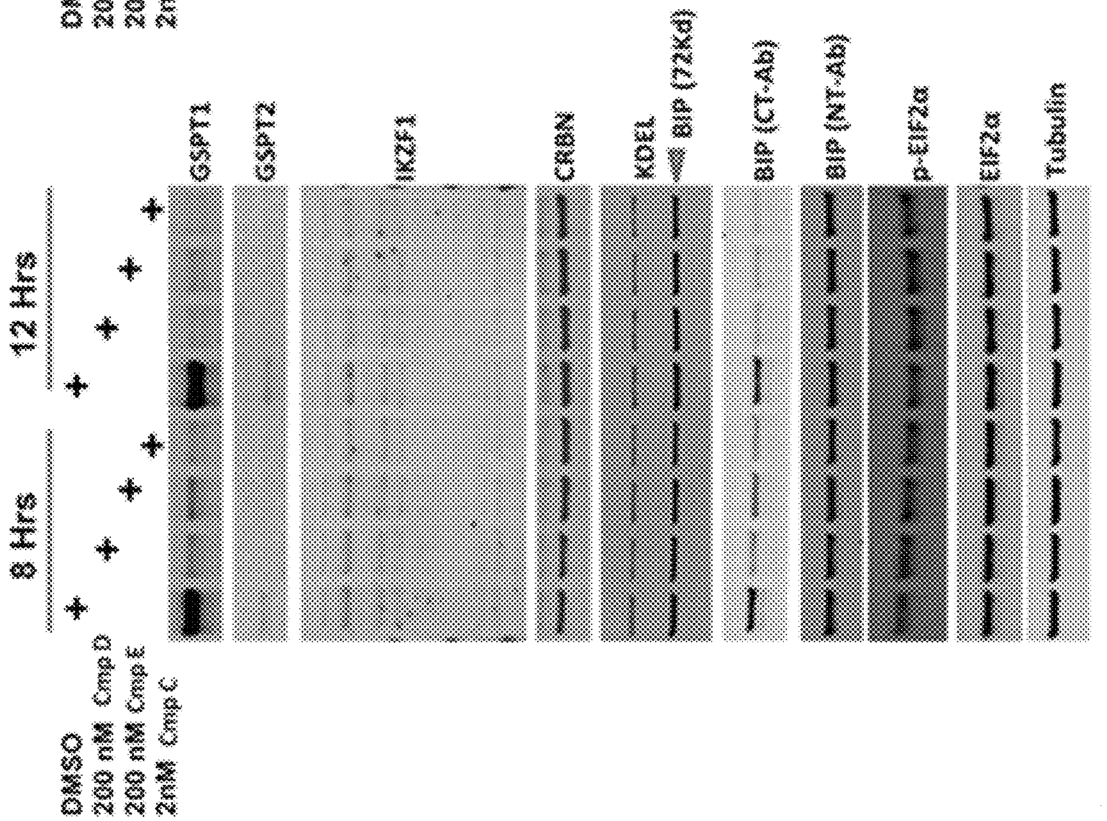

The cellular effects of Compound D- or Compound E-induced degradation of GSPT1 were further studied in KG1 cells. Cells were treated with DMSO alone, 200 nM Compound D, or 200 nM Compound E. After 8 or 12 hours, the expression levels of various cellular components along UPR or apoptosis pathways were measured. As shown in FIG. 8A, Compound D or Compound E induced degradation of GSPT1, GSPT2, and BIP (detected by CT-Ab). Reduction of BIP indicates UPR. Similarly, as shown in FIG. 8B, Compound D or Compound E increased the level of ATF3, DDIT3, cleaved Caspase-3, cleaved Caspase-8, and cleaved PARP, suggesting the onset of apoptosis.

Figure 9B:
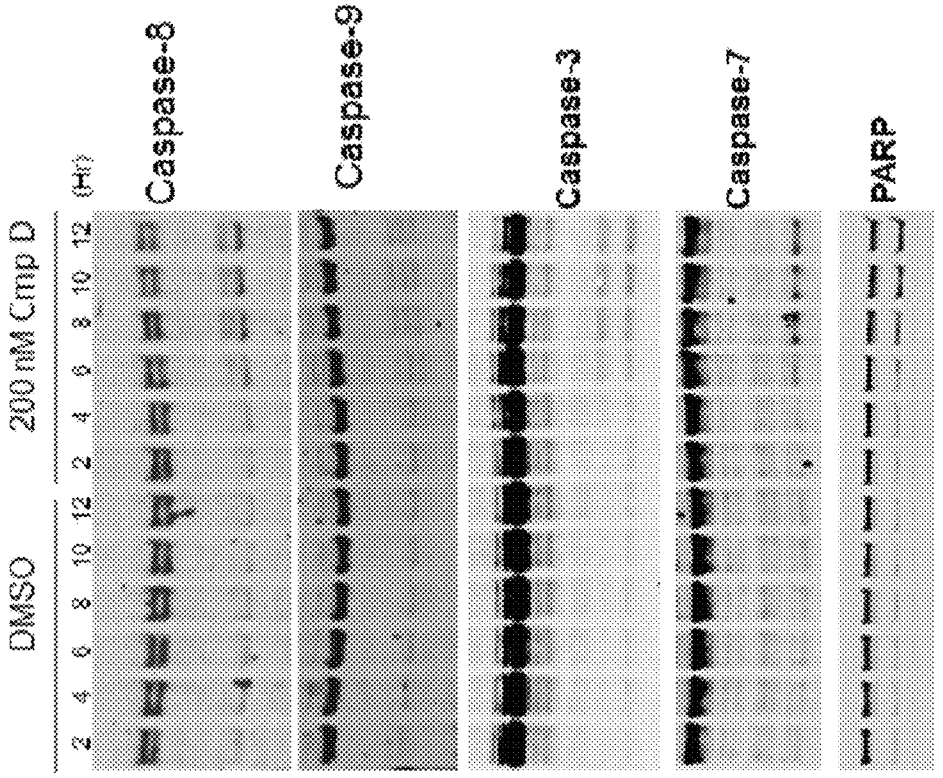
Figure 9A:
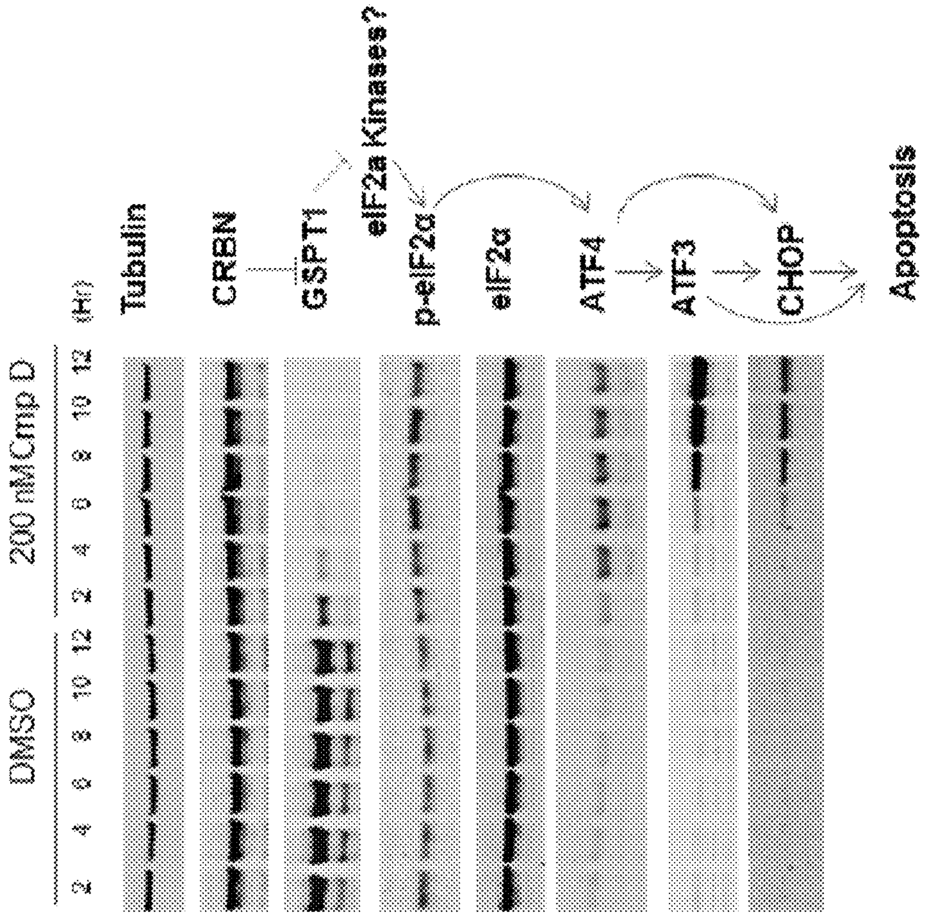

6.11 the Activation of the ATF4 Pathway Induced by Compound D Preceded the Appearance of Apoptotic Markers in KG-1 Cells To further investigate the timeline of cellular events upon Compound D treatment, KG1 cells were treated with DMSO alone or 200 nM Compound D. At 2, 4, 6, 8, 10, or 12 hours, the expression levels of various cellular components along ATF4 or apoptosis pathways were measured. As shown in FIG. 9A, Compound D induced degradation of GSPT1 as early as at 2 hrs and increased the level of p-eIF2α, ATF4, ATF3, and CHOP (i.e., DDIT3), the components along the ATF4 pathway. FIG. 9B shows that the levels of apoptotic markers, such as cleaved Caspase-8, cleaved Caspase-9, cleaved Caspase-3, cleaved Caspase-7, and cleaved PARP, increased starting at approximately 6 hrs. These data demonstrated that Compound D induced the activation of the ATF4 pathway, which then led to apoptosis.

Figure 10B:
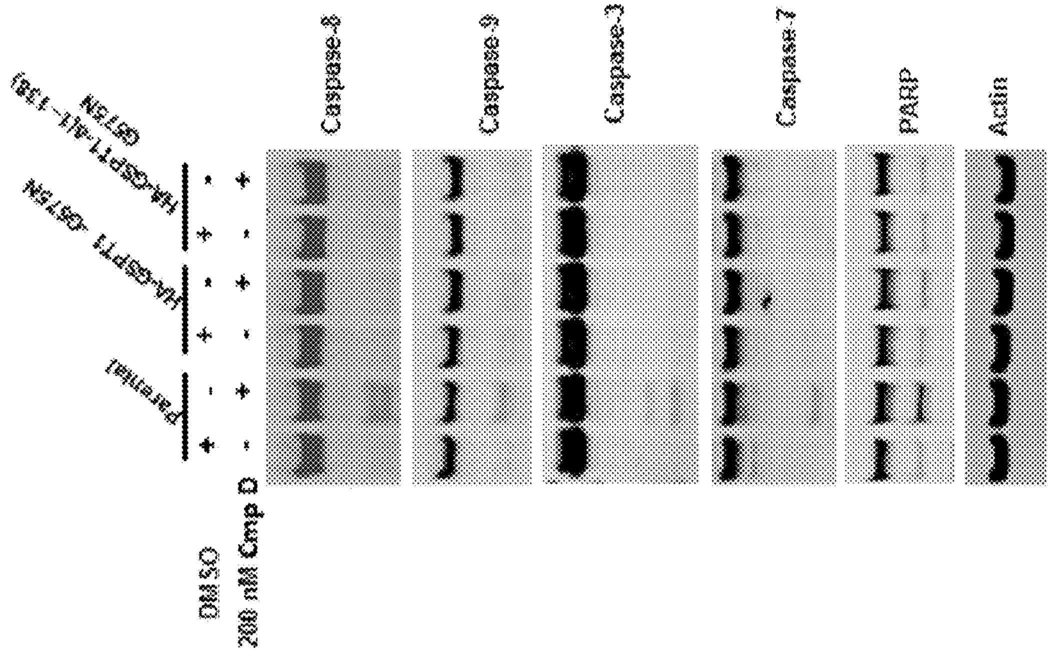
Figure 10A:
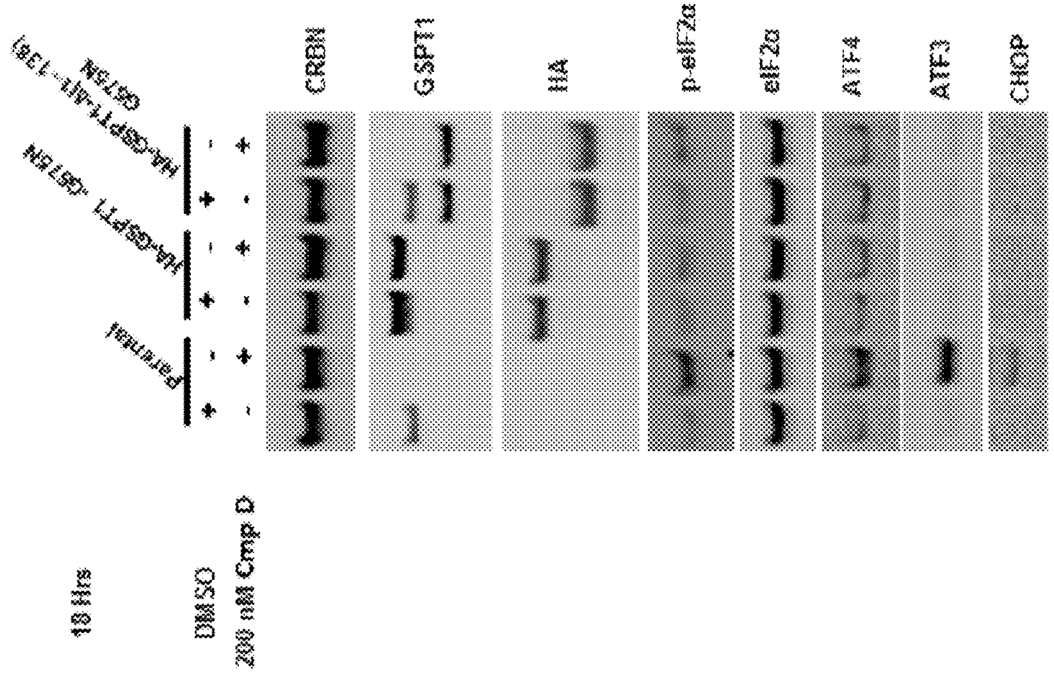

6.12 Stabilization of GSPT1 Abrogated the Activation of ATF4 Pathway by Compound D in OCI-AML2 Cells Parental OCI-AML2 cells, as well as OCI-AML2 cells expressing HA-GSPT1-G575N or HA-GSPT1-Δ(1-138)-G575N, were treated with DMSO alone or 200 nM Compound D. FIG. 10A shows that OCI-AML2 cells expressing HA-GSPT1-G575N or HA-GSPT1-Δ(1-138)-G575N did not respond the same way as parental OCI-AML2 cells to Compound D. For example, whereas Compound D induced the levels of p-eIF2α, ATF4, ATF3, CHOP/DDIT3, cleaved Caspase-8, cleaved Caspase-9, cleaved Caspase-3, cleaved Caspase-7, and cleaved PARP in parental cells, the levels of these cellular components remained unchanged in cells expressing HA-GSPT1-G575N or HA-GSPT1-Δ(1-138)-G575N (FIGS. 10A and 10B). The resistance of cells expressing HA-GSPT1-G575N or HA-GSPT1-Δ(1-138)-G575N to Compound D treatment might be due to stabilization of GSPT1, as shown in FIG. 10A.

6.13 Compound D Activated the ATF4 Pathway in KG-1 Cells

Figure 11:
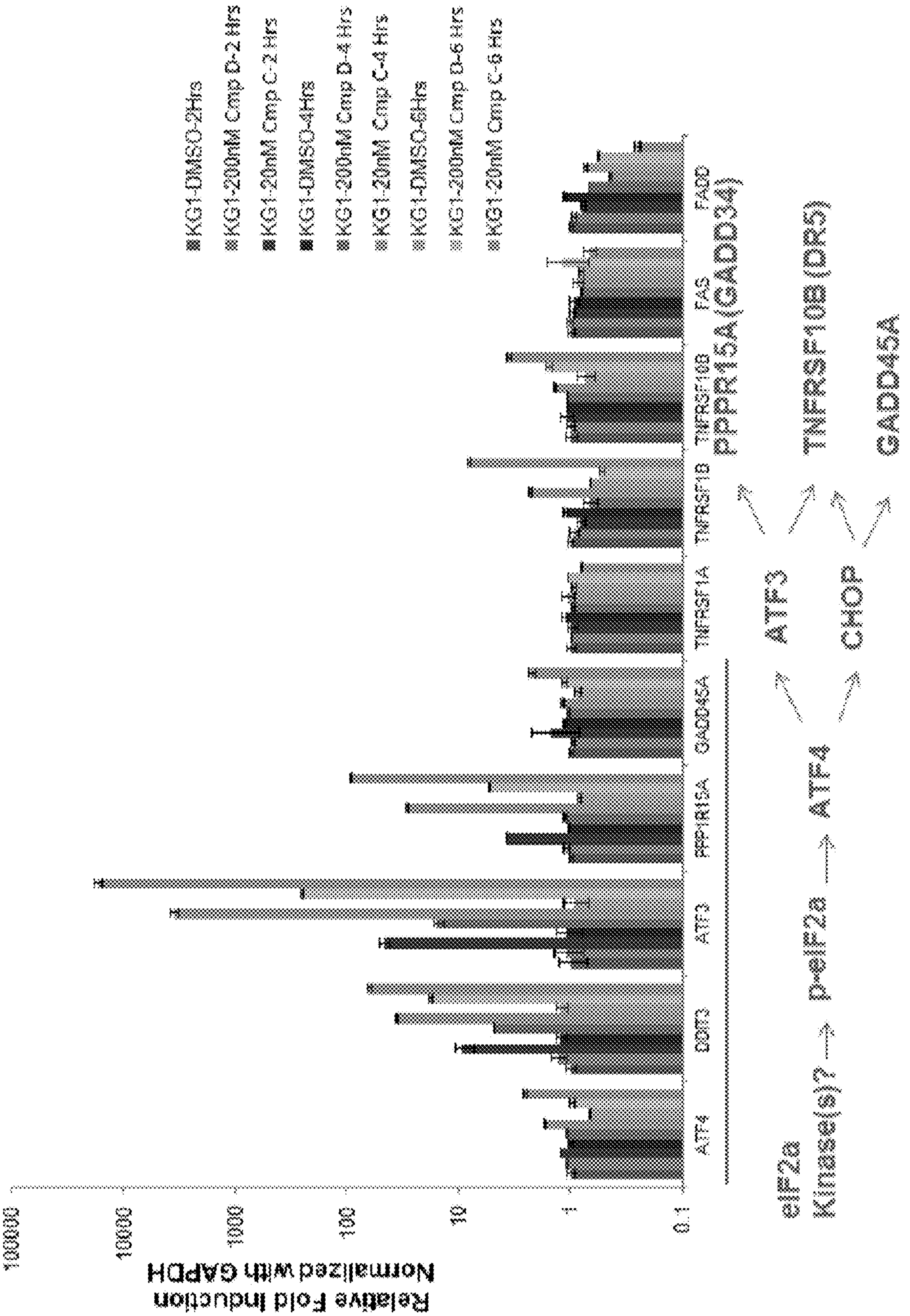

KG-1 cells were treated with DMSO alone or 200 nM Compound D. At 2, 4, or 6 hours of treatment, the mRNA expression levels of various cellular components along the ATF4 pathway were measured. FIG. 11 demonstrates Compound D-induced expression of ATF-4, ATF-3, DDIT3/CHOP, PPP1R15A, GADD45A, and TNFRSF10B, components along the eIF2α kinase(s)/p-eIF2α/ATF4 pathway in KG1 cells.

6.14 Compound D Activated the IRE1 and ATF6 Pathways in KG-1 Cells

Figure 12:
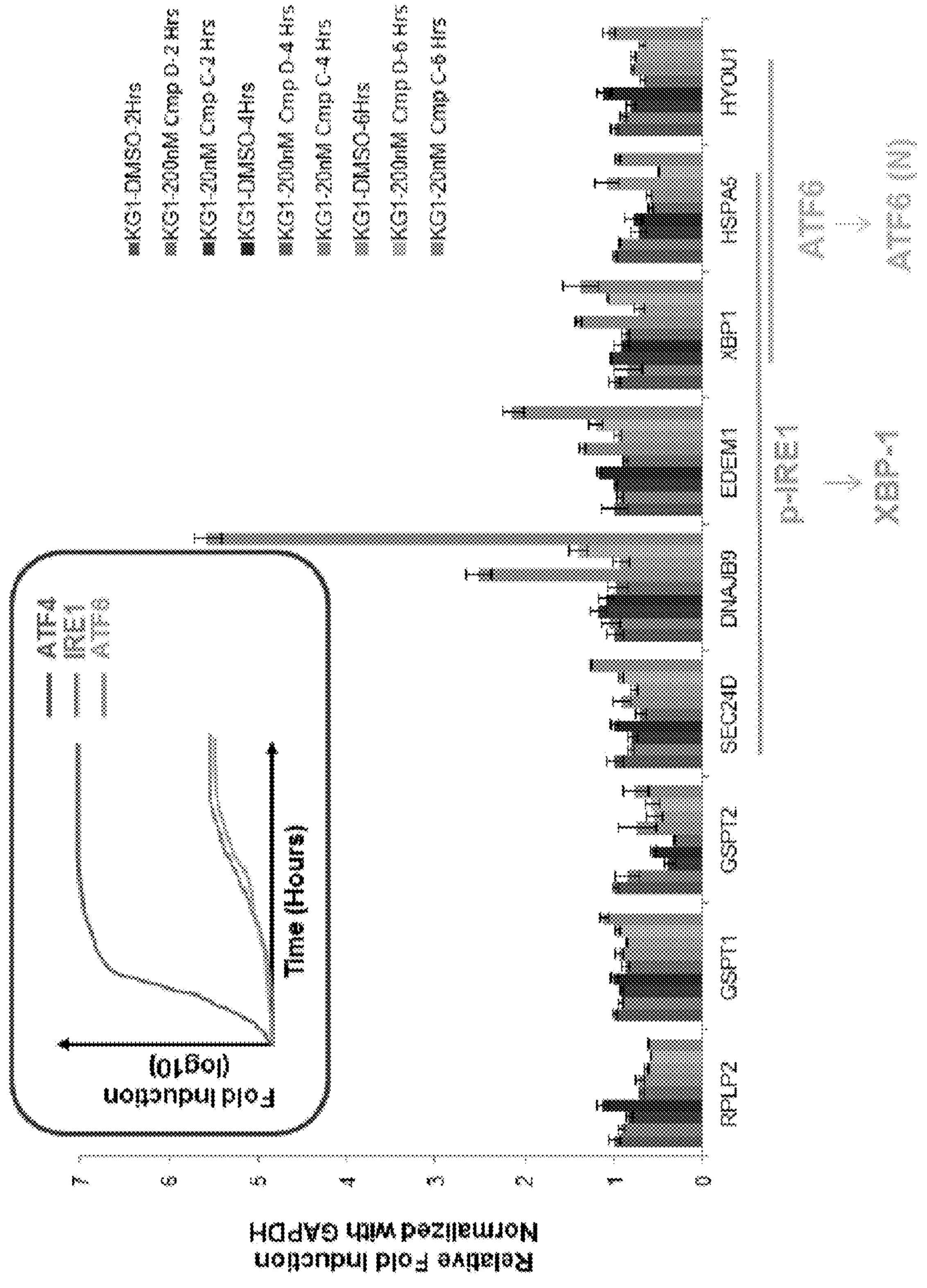

KG-1 cells were treated with DMSO alone or 200 nM Compound D. At 2, 4, or 6 hours of treatment, the mRNA expression levels of various cellular components along the IRE1 or ATF6 pathways were measured. FIG. 12 demonstrates Compound D-induced expression of SEC24D, DNAJB9, EDEM1, and XBP1, components along the IRE1 or ATF6 pathways in KG1 cells.

6.15 Loss of PERK Delayed TG-Induced UPR and Apoptosis

Figure 13:
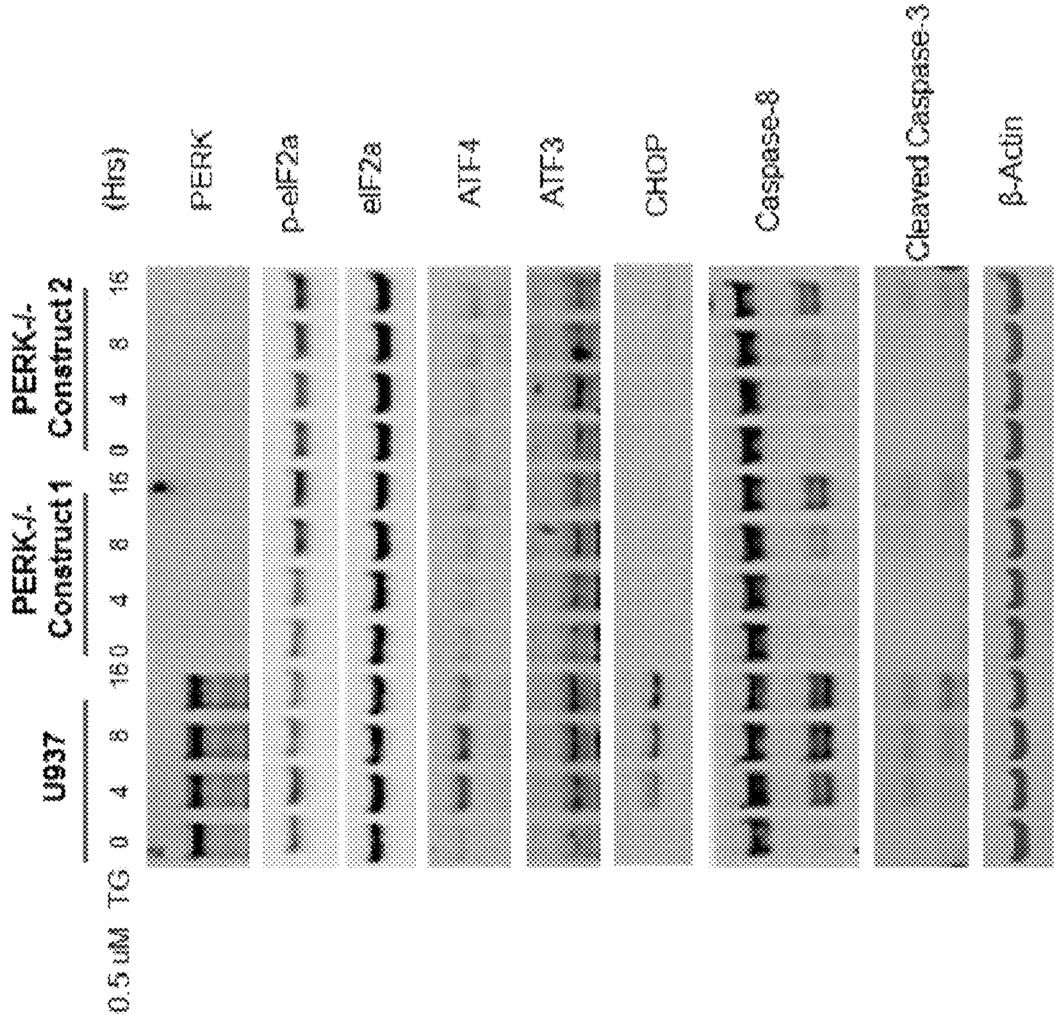
FIG. 13 shows that loss of PERK delayed TG-induced UPR and apoptosis in U937 cells.

PERK, one of the four eIF2α, kinases, was knocked out in U937 cells by CRISPR-mediated gene editing using PERK−/− Construct 1 or PERK−/− Construct 2. FIG. 13 shows that, 0.5 μM of TG induced UPR and apoptosis in wild type U937 cells, but the effect of TG was delayed in cells within which PERK was knocked out. For example, in wild type U937 cells, the levels of p-eIF2α, ATF4, ATF3, CHOP/DDIT3, cleaved Caspase-8, and cleaved Caspase-3 increased at 4 hrs after the treatment of TG; however, in PERK knockout cells, the levels of p-eIF2α, ATF4, ATF3, CHOP, cleaved Caspase-8, and cleaved Caspase-3 did not increase until 8 or 16 hrs after the treatment of TG.

6.16 Loss of PERK Did not Affect Compound D-Induced Apoptosis

Figure 14:
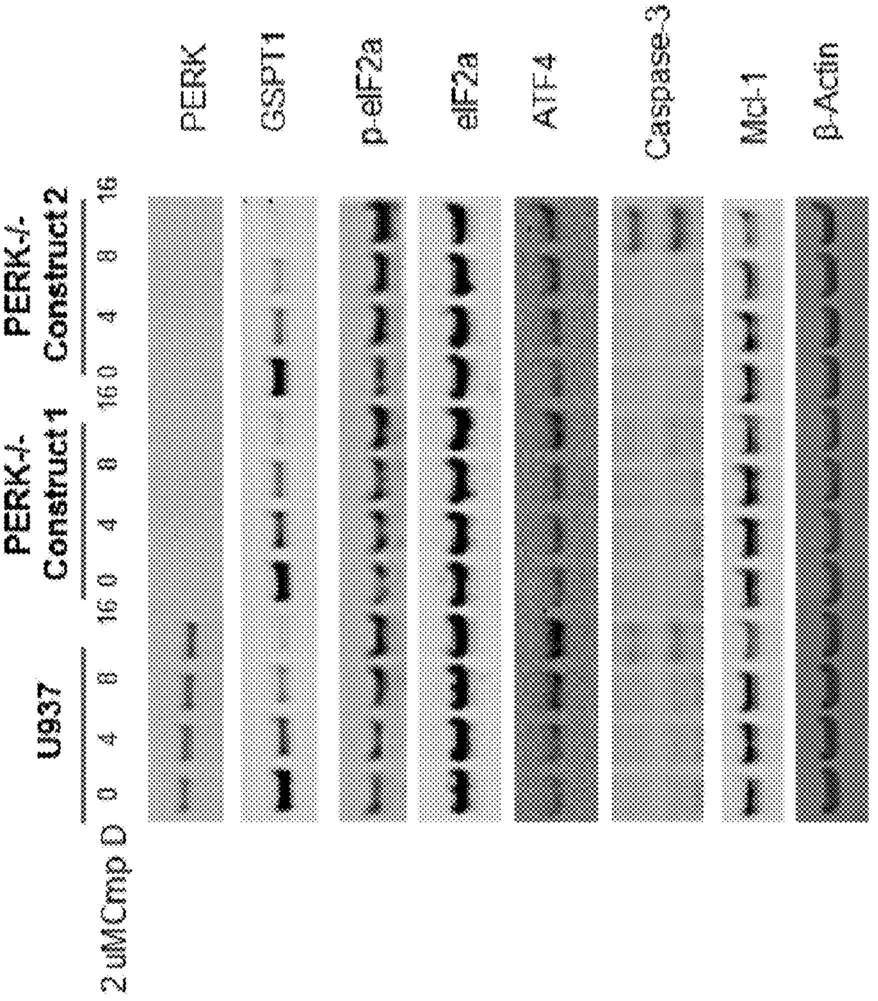
FIG. 14 shows that loss of PERK did not affect Compound D-induced UPR and apoptosis in U937 cells.

FIG. 14 shows that 2 μM of Compound D induced apoptosis in wild type U937 cells, as well as U937 cells within which PERK was knocked out. For example, in both wild type and PERK knockout U937 cells, the levels of GSPT1 and Mcl-1 decreased and the levels of p-eIF2α, ATF4, and cleaved Caspase-3 increased after the treatment of Compound D. This suggests that loss of PERK did not affect Compound D-induced apoptosis; thus, PERK is not the eIF2α, kinase that is activated by the treatment of Compound D.

Figure 15:
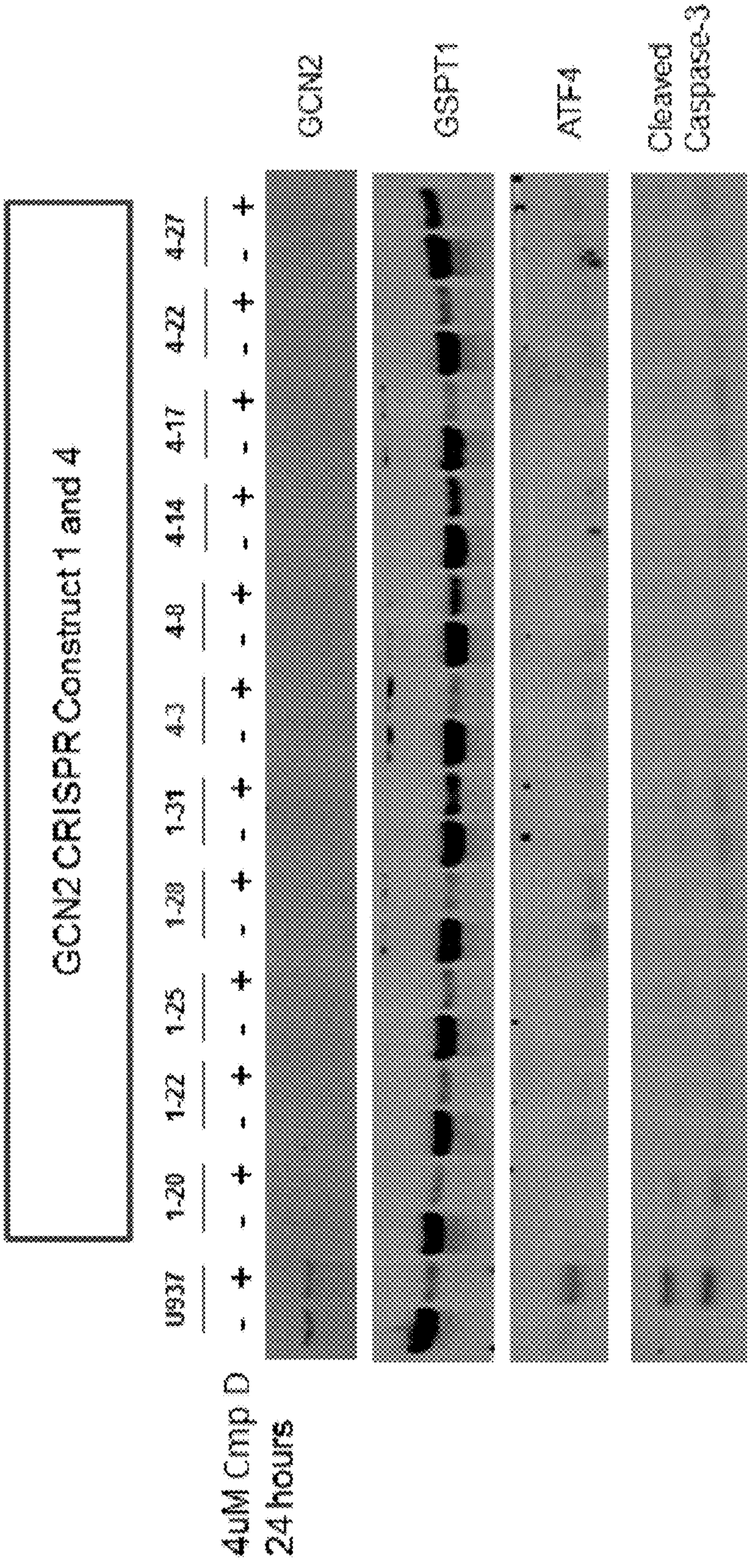
FIG. 15 shows that loss of GCN2 blocked Compound D-induced increase of ATF4 and cleaved Caspase-3 in U937 Cells.

6.17 Loss of GCN2 Blocked the Induction of Apoptosis by Compound D in U937 Cells GCN2, one of the four eIF2α, kinases, was knocked out in U937 cells by CRISPR-mediated gene editing using GCN2 CRISPR Construct 1 or GCN2 CRISPR Construct 4. FIG. 15 shows that, 4 μM of Compound D induced the ATF4 pathway and apoptosis in wild type U937 cells, but in U937 cells within which GCN2 was knocked out, these effects of Compound D was blocked. For example, in wild type U937 cells, the levels of GSPT1 decreased and the levels of ATF4 and cleaved Caspase-3 increased after the treatment of Compound D. In GCN2 knockout U937 cells, the induction of ATF4 and cleaved Caspase-3 were significantly blocked although the levels of GSPT1 decreased after the treatment of Compound D. This suggests that loss of GCN2 blocked Compound D-induced activation of the ATF4 pathway and apoptosis; thus, GCN2 is the eIF2α, kinase that is activated by the treatment of Compound D.

Figure 16:
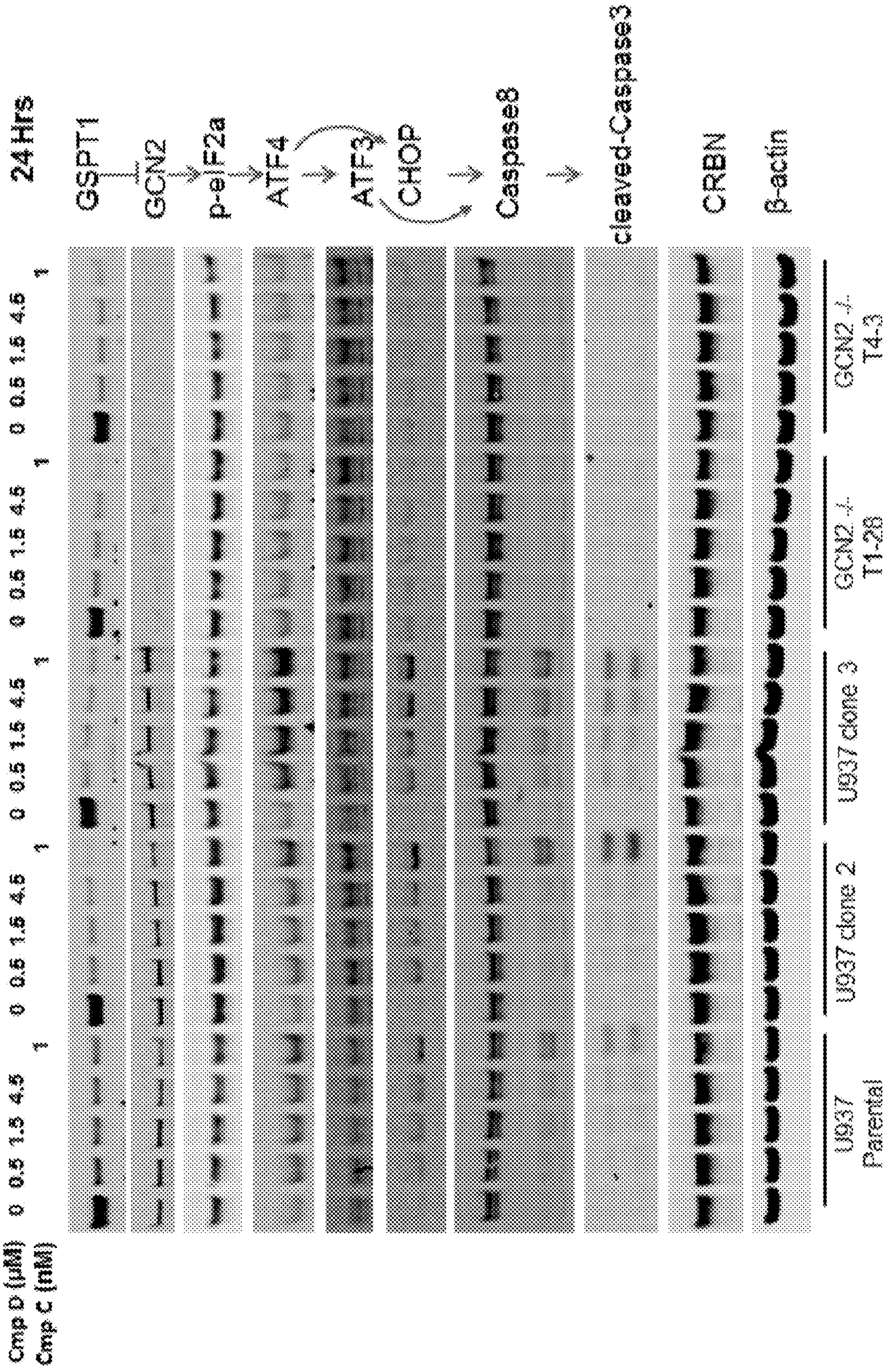
FIG. 16 shows that depletion of GCN2 abolished the dose-dependent induction of apoptosis by Compound D in U937 cells.

FIG. 16 shows that depletion of GCN2 abolished the dose-dependent induction of apoptosis by Compound D in U937 cells. In U937 parental, clone 2, and clone 3 cells, 0.5-4.5 μM of Compound D induced the ATF4 pathway and apoptosis, as indicated by the increased level of ATF4, ATF3, CHOP/DDIT3, cleaved Caspase-8, and cleaved Caspase-3. In contrast, in GCN2 −/− T1-28 and GCN2 −/− T4-3 cells, the levels of ATF4, ATF3, CHOP/DDIT3, cleaved Caspase-8, and cleaved Caspase-3 did not change upon the treatment of Compound D, although GSPT1 was degraded in response to Compound D. Thus, ablation of GCN2 blocked the dose-dependent activation of the ATF4 pathway and apoptosis by Compound D in U937 cells.

Figure 17:
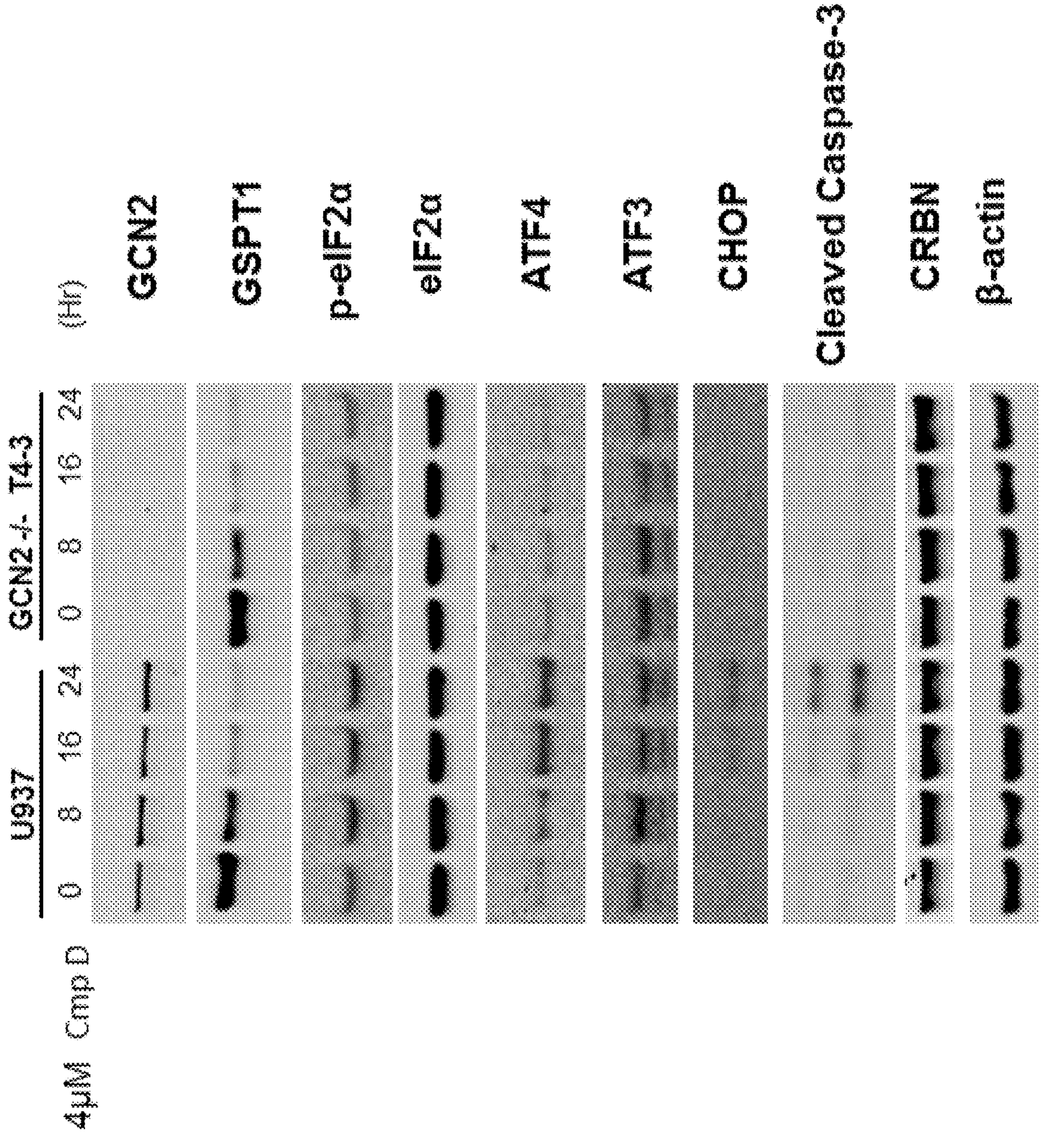
FIG. 17 shows that Compound D induced the activation of the ATF4 and apoptosis pathways in a time-dependent manner in U937 cells, and that depletion of GCN2 abolished these effects.

FIG. 17 shows that Compound D induced the activation of the ATF4 pathway and apoptosis in a time-dependent manner in U937 cells, and that depletion of GCN2 abolished these effects. For example, in wild type U937 cells, 4 μM of Compound D induced the degradation of GSPT1 and the activation of ATF4 pathway and apoptosis, as indicated by the increased level of p-eIF2α, ATF4, ATF3, CHOP/DDIT3, and cleaved Caspase-3. But in U937 cells within which GCN2 was knocked out, the levels of p-eIF2α, ATF4, ATF3, CHOP/DDIT3, and cleaved Caspase-3 remained unchanged upon the treatment of Compound D, even though Compound D induced the degradation of GSPT1. Thus, loss of GCN2 blocked Compound D-induced activation of the ATF4 pathway and apoptosis.

6.18 Loss of GCN2 Abrogated the Induction of ATF-4 Pathway and Apoptosis by Compound D in AML Cell Lines OCI-AML2 and MV-4-11

Figure 18A:
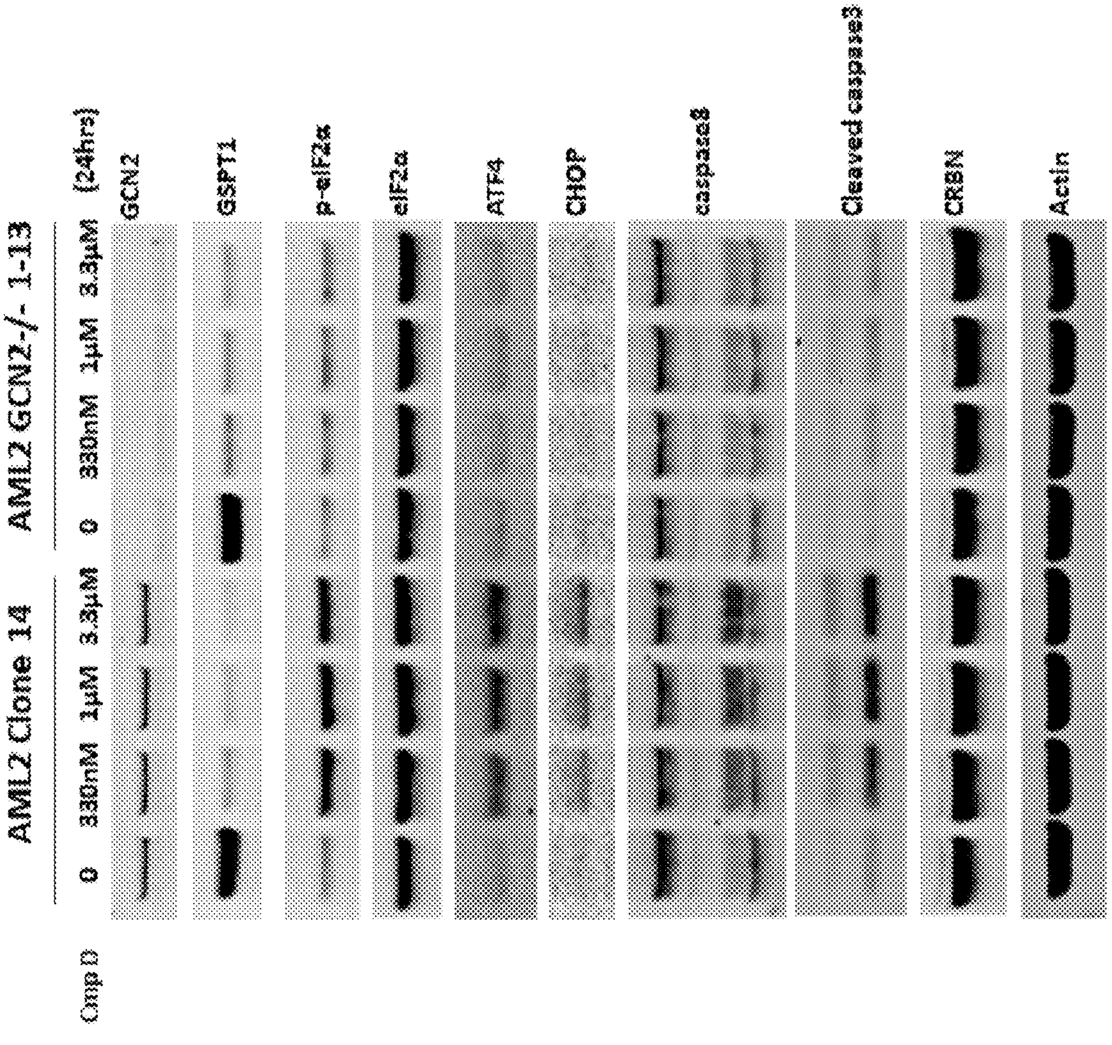
FIGS. 18A and 18B show that knockout of GCN2 abrogated the induction of ATF-4 pathway and apoptosis induced by Compound D in AML cell lines OCI-AML2 (FIG. 18A) and MV-4-11 (FIG. 18B).
Figure 18B:
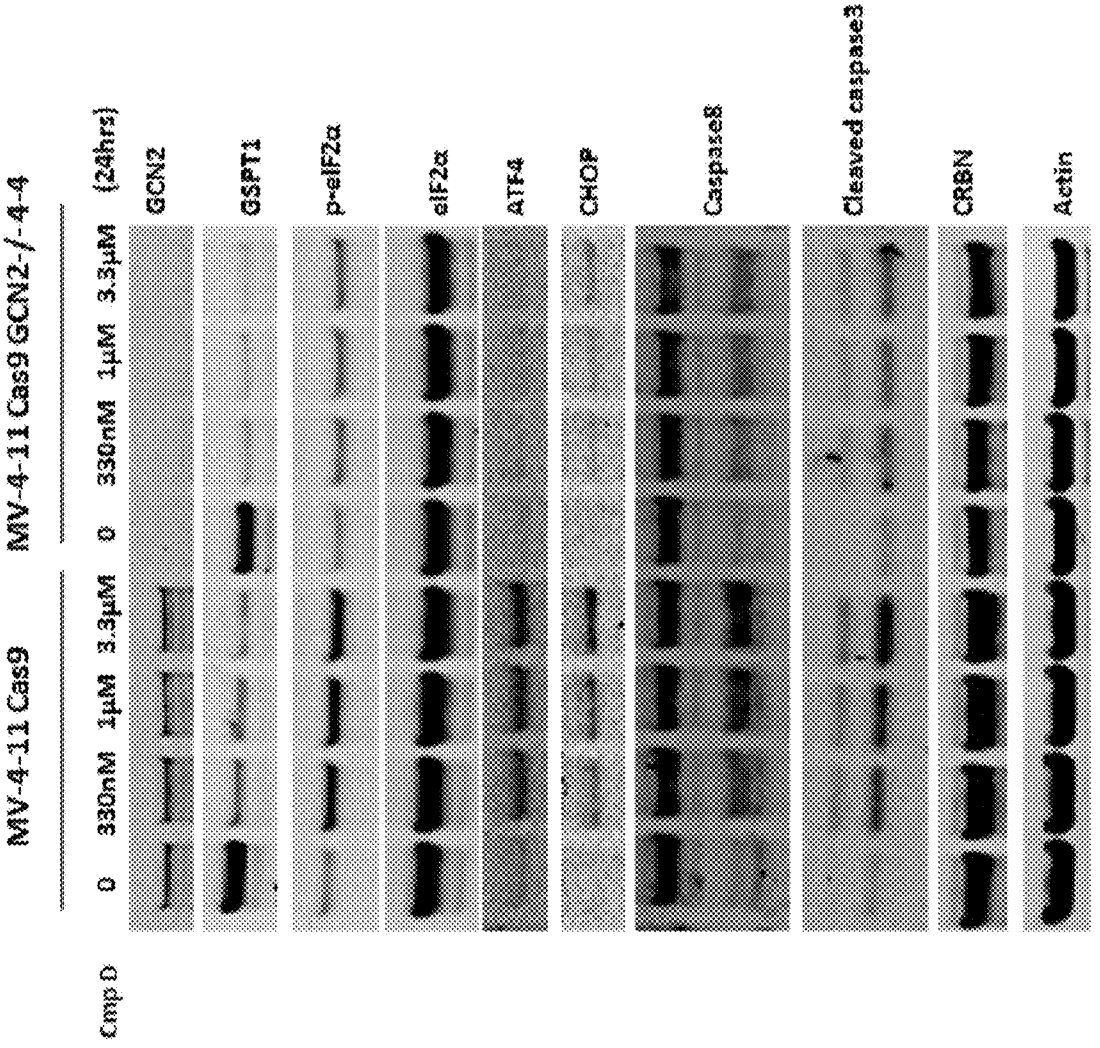

AML cell line OCI-AML2 clone 14 and OCI-AML2 with GCN2 knockout clone 1-13 were treated with a serial dilution of Compound D (0, 330 nM, 1 μM, 3.3 μM) for 24 hours. FIG. 18A shows that knockout of GCN2 did not affect Compound D-induced degradation of GSPT1 but abrogated Compound D-induced phosphorylation of eIF2α, subsequent activation of ATF-4 pathway (shown by increased levels of ATF-4 and CHOP) and apoptosis (shown by increased levels of cleaved Caspase-8 and cleaved Caspase-3). Similar effects were observed in another AML cell line MV-4-11 (shown in FIG. 18B).

6.19 HRI is Dispensable for the Induction of Apoptosis by Compound D

Figure 19:
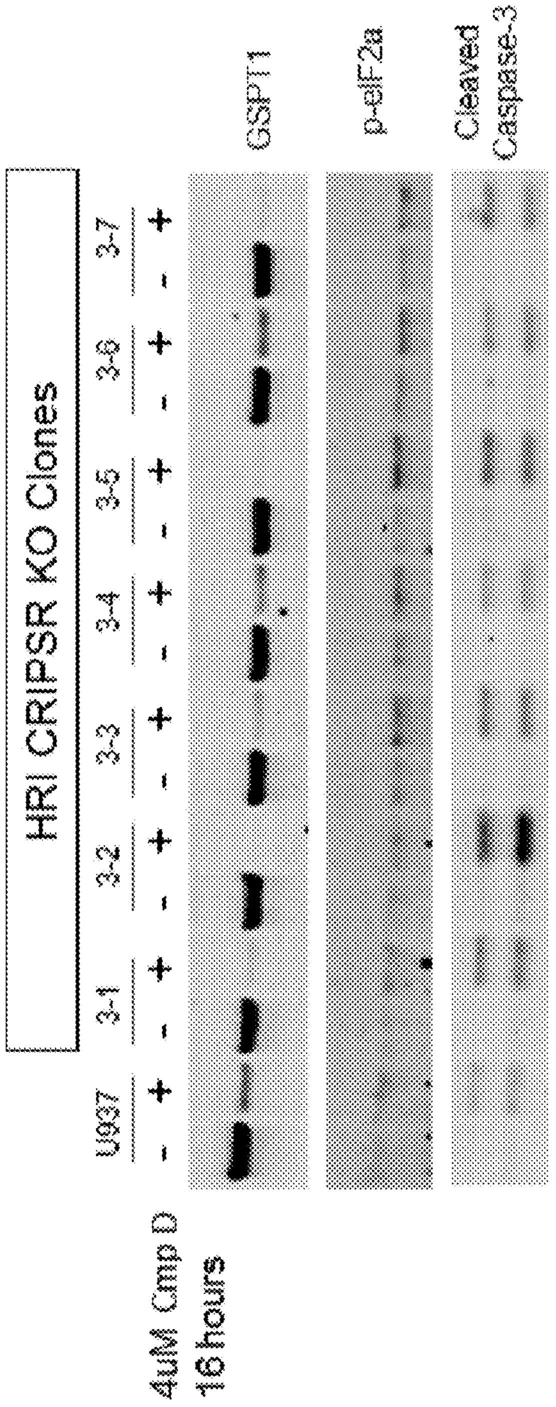
FIG. 19 shows that HRI is not required for Compound D-induced apoptosis in OCI-AML2 cells.

HRI, one of the four eIF2α, kinases, was knocked out in U937 cells by CRISPR-mediated gene editing using HRI CRISPR Construct 3. Wild type U937 cells or HRI CRISPR knockout U937 cells were treated with 4 μM Compound D for 16 hours. FIG. 19 shows that the knockout of HRI did not affect Compound D-induced increase in the levels of p-eIF2α, and cleaved Caspase-3, indicating that HRI may be dispensable for the activation of the ATF4 pathway and induction of apoptosis by Compound D.

6.20 PKR is Dispensable for the Induction of Apoptosis by Compound D

Figure 20:
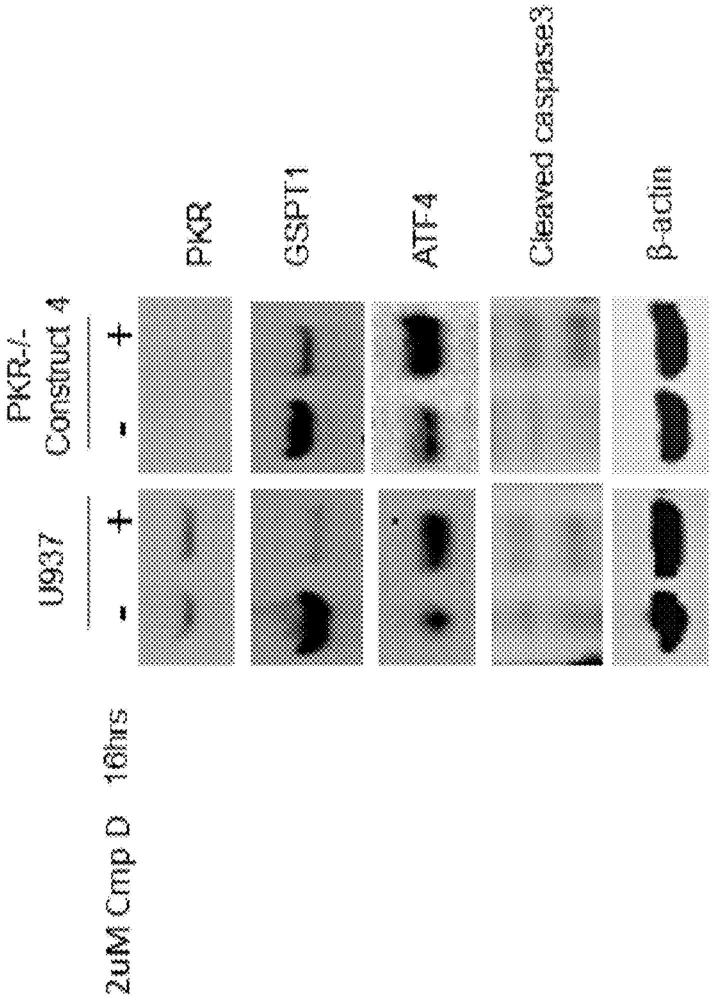
FIG. 20 shows that PKR is not required for Compound D-induced apoptosis in OCI-AML2 cells.

PKR, another kinase of the four eIF2α, kinases, was knocked out in U937 cells by CRISPR-mediated gene editing using PKR CRISPR Construct 4. Wild type U937 cells or PKR CRISPR knockout U937 cells were treated with 2 μM Compound D for 16 hours. FIG. 20 shows that the knockout of PKR did not affect Compound D-induced increase in the levels of ATF4 and cleaved Caspase-3, indicating that PKR may also not be required for the activation of the ATF4 pathway and induction of apoptosis by Compound D.

Figure 21:
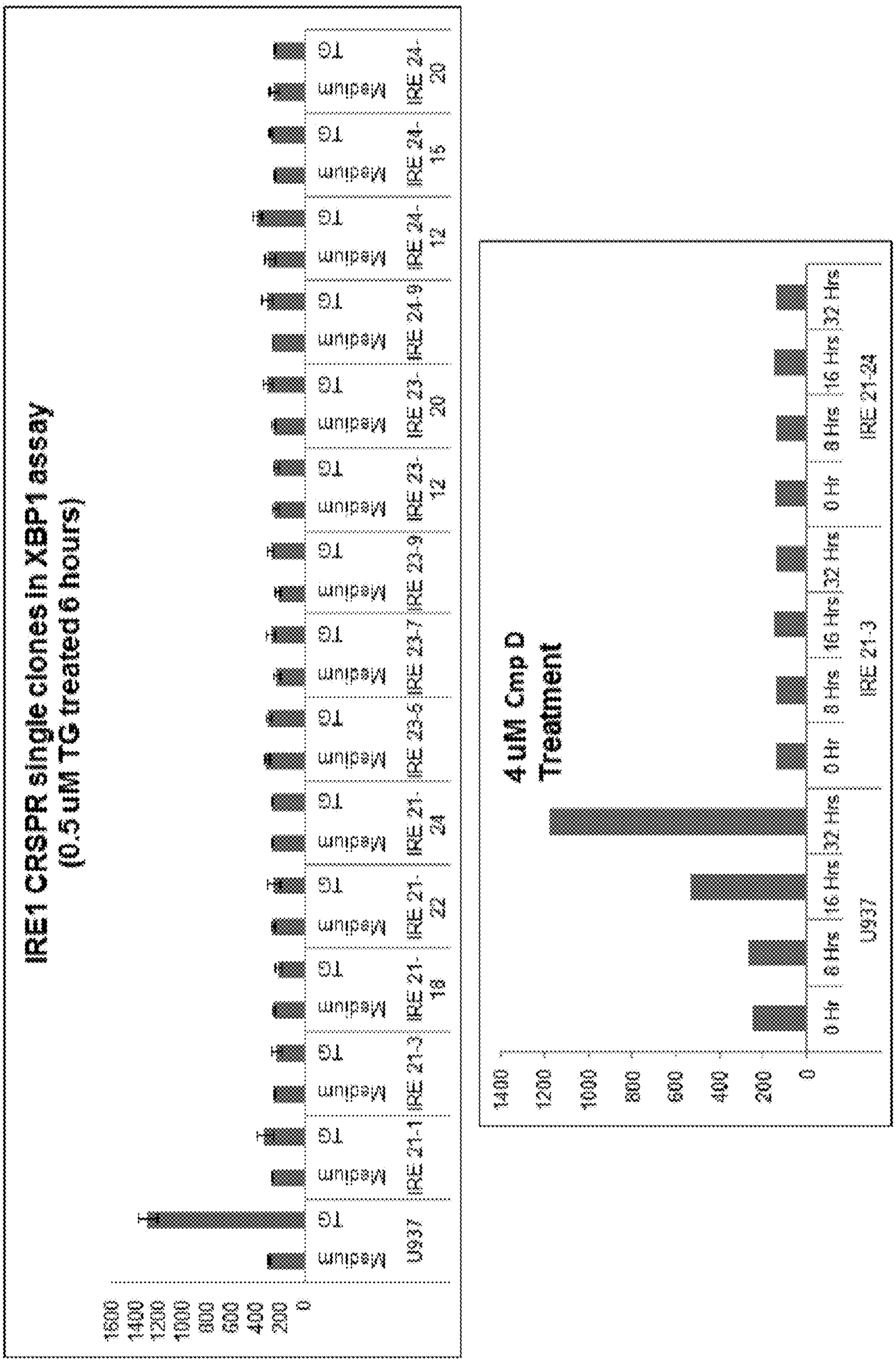
FIG. 21 shows that ablation of IRE1 prevented the accumulation of XBP1 induced by TG (top panel) or Compound D (bottom panel).

6.21 Ablation of IRE1 Prevented the Accumulation of XBP1 Induced by TG or Compound D IRE1, a kinase that activates the XBP1 pathway, was knocked out in U937 cells by CRISPR-mediated gene editing using IRE1 CRISPR constructs. Wild type U937 cells or IRE1 CRISPR knockout U937 cells were treated with 0.5 μM TG for 6 hours or 4 μM Compound D for 8, 16, or 32 hours, then subject to XBP1 assay. FIG. 21 shows that the knockout of RE1 effectively blocked TG-(top panel) or Compound D-(bottom panel) induced increase in the levels of XBP1, indicating that both TG and Compound D activated the XBP1 pathway through IRE1.

6.22 Loss of IRE1 Did not Affect the Induction of Apoptosis by Compound D

Figure 22:
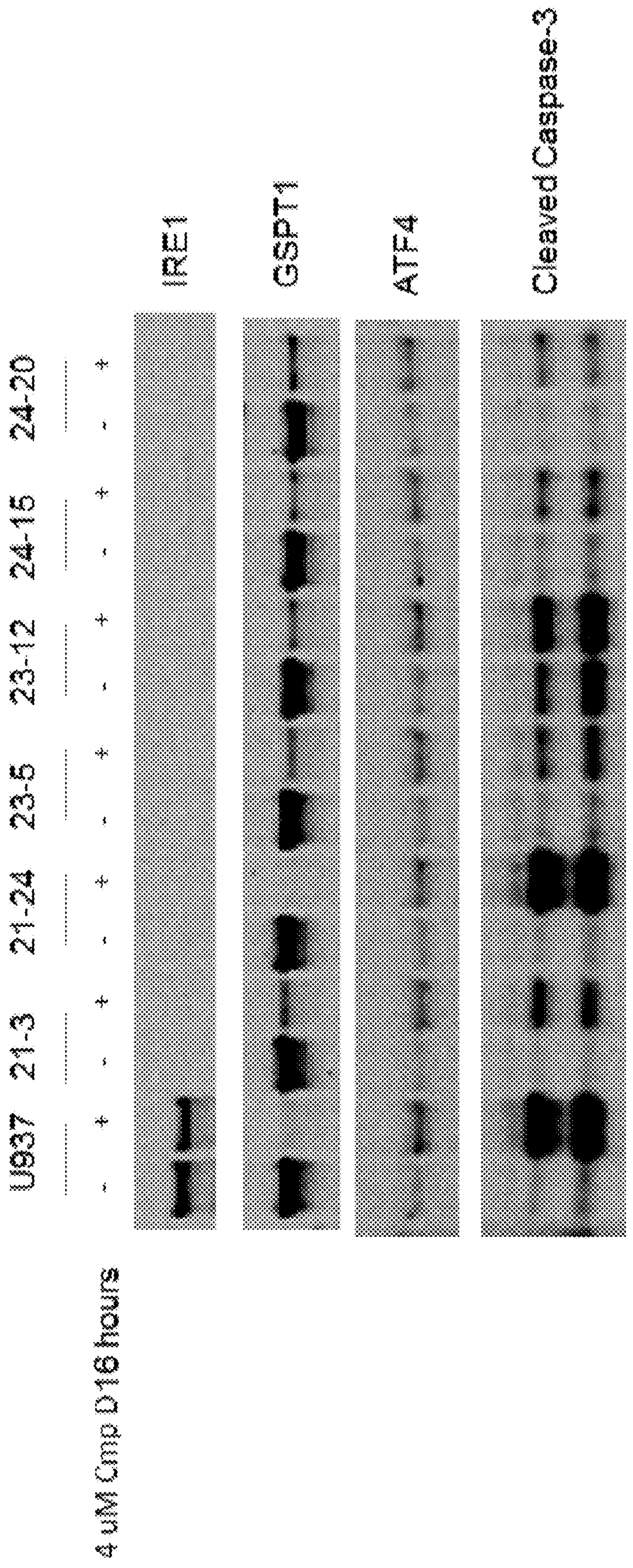
FIG. 22 shows that IRE1 is not required for the activation of the ATF4 pathway and induction of apoptosis by Compound D.

Wild type U937 cells or IRE1 CRISPR knockout U937 cells were treated with 4 μM Compound D for 16 hours. FIG. 22 shows that the knockout of IRE1 did not affect Compound D-induced increase in the levels of ATF4 and cleaved Caspase-3, indicating that IRE1 is not required for the activation of the ATF4 pathway and induction of apoptosis by Compound D.

Figure 23:
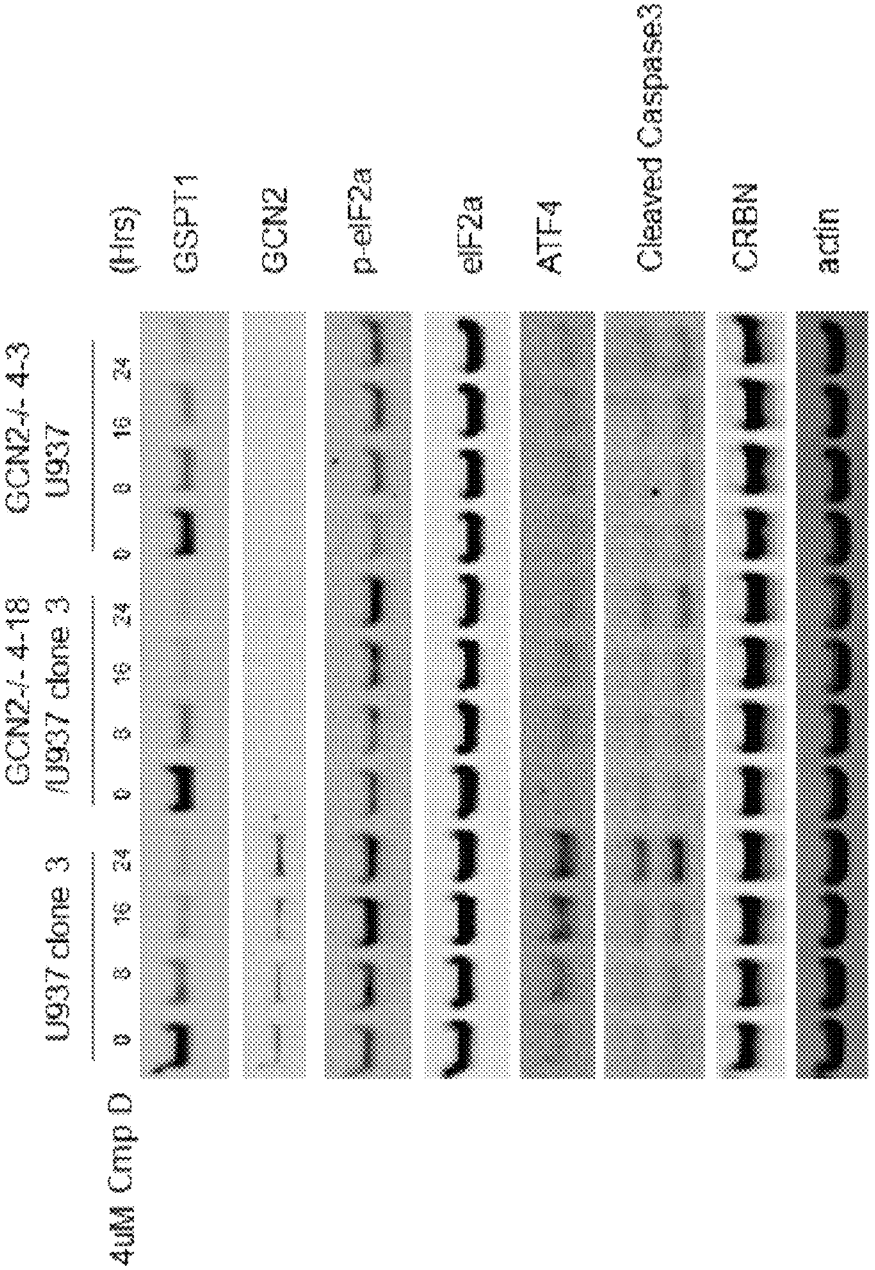
FIG. 23 shows that loss of GCN2 abolished the induction of apoptosis by Compound D in U937 Cells with the same genetic background.

6.23 Loss of GCN2 Abolished the Induction of Apoptosis by Compound D in U937 Cells with the Same Genetic Background U937 clone 3 cells, U937 clone 3 cells with GCN2 knockout by GCN2 −/− 4-18, and U937 cells with GCN2 knockout by GCN2 −/− 4-3 were treated with 4 μM Compound D for 8, 16, or 24 hours. FIG. 23 shows that the knockout of GCN2 abolished Compound D-induced apoptosis in both U937 clone 3 cells and U937 cells. For example, Compound D-induced increase in the levels of ATF4 and cleaved Caspase-3 was abolished by GCN2 knockout. However, phosphorylation of eIF2α, was not completely blocked but delayed compared to U937 clone 3, suggesting that another kinase (other than GCN2) might phosphorylate eIF2α, at a time later than when GCN2 normally phosphorylated eIF2α.

Figure 24:
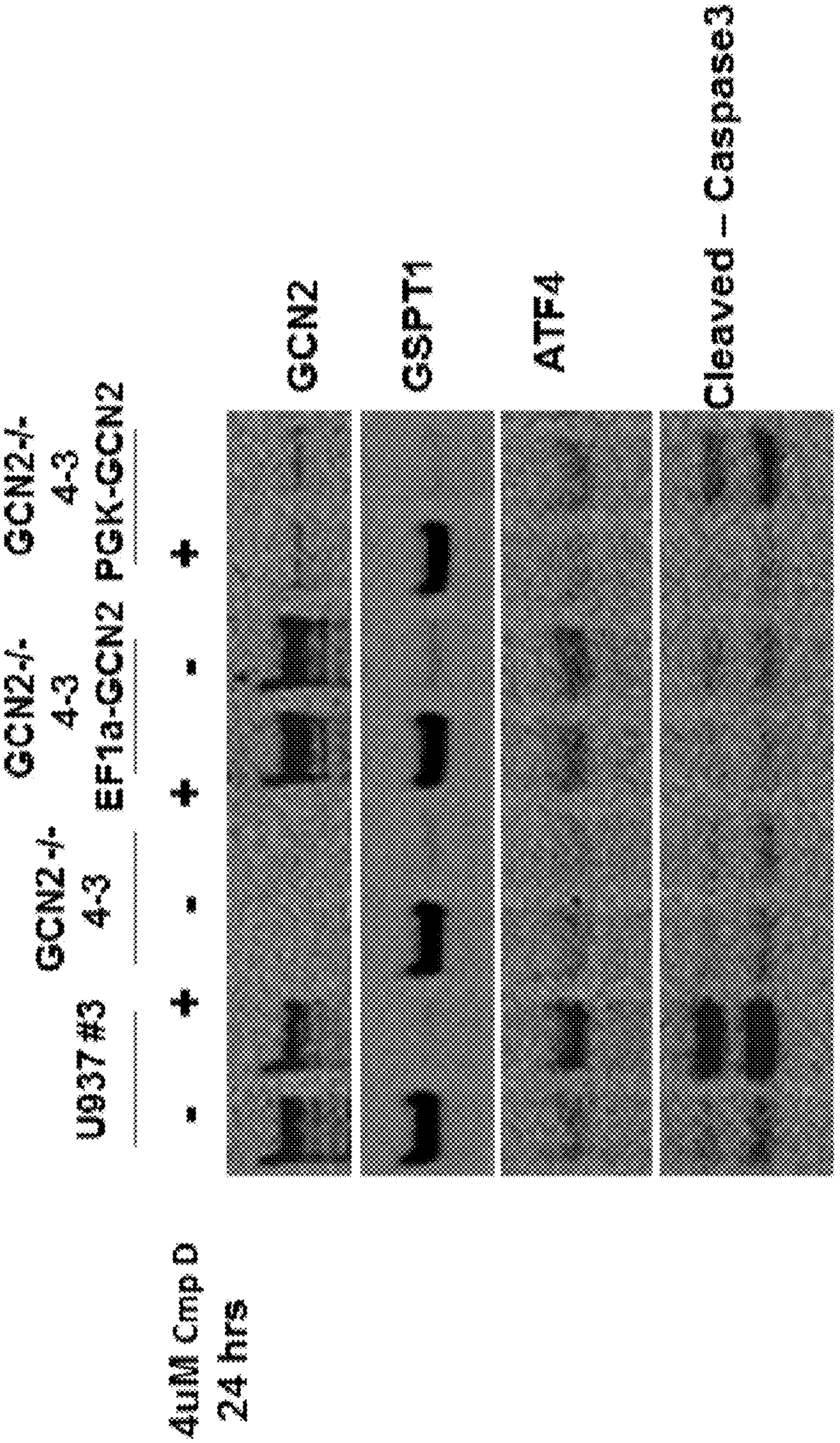
FIG. 24 shows that overexpression of GCN2 desensitized the cells to Compound D, which may be due to chronic activation of the ATF4 pathway at a low level.

6.24 Overexpression of GCN2 Desensitized the Cells to Compound D Presumably Due to Chronic Activation of the ATF4 Pathway at a Low Level U937 clone 3 cells, GCN2 knockout U937 cells by GCN2 −/− 4-3, GCN2 knockout U937 cells transfected with EF1a-GCN2, and GCN2 knockout U937 cells transfected with PGK-GCN2 were treated with 4 μM Compound D for 24 hours. Either EF1a or PGK promoter drove expression of exogenous GCN2 in transfected cells. FIG. 24 shows that overexpression of GCN2 driven by EF1a promoter desensitized the cells to Compound D, which may be due to chronic activation of the ATF4 pathway at a low level, indicated by a slightly increased level of ATF4 in cells not treated by Compound D. In comparison, in cells transfected with PGK-GCN2, the expression of GCN2 was at very low level; accordingly, the ATF4 level was lower in cells not treated by Compound D, and the cells were not as desensitized to Compound D-induced apoptosis (shown by an increased level of cleaved Caspase-3 upon Compound D treatment).

6.25 Reintroduction of Wild Type GCN2 but not Mutant GCN2 Restored the Induction of Apoptosis Induced by Compound D and Anti-Proliferative Effect of Compound D in U937 GCN2 Null Cells FIG. 25A shows Cell TiterGlo in a 48-well plate, seeded with U937 clone 3 cells, GCN2 knockout U937 cells by GCN2 −/− 4-3, GCN2 knockout U937 cells transfected with EF1a-GCN2, and GCN2 knockout U937 cells transfected with PGK-GCN2. The cells were treated with serial dilutions of Compound D (1 nM, 10 nM, 100 nM, 1 μM, and 10 μM). The Cell TiterGlo data indicate that GCN2 knockout conferred resistance to Compound D-induced apoptosis, and that reintroduction of exogenous GCN2 restored the anti-proliferative effect of Compound D. Consistent with the results in Example 6.24, overexpression of GCN2 by EF1a promoter desensitized the cells to Compound D-induced apoptosis, compared to cells expressing GCN2 from PGK promoter.

Various GCN2 mutants were generated, including T899A/T904A (blocking autophosphorylation of GCN2), K619R (abrogating kinase activity), and F1143L/R1144L (blocking tRNA binding). Wild type GCN2 or such mutants were reintroduced into U937 GCN2 null cells, and the cells were treated with 4 μM Compound D for 24 hours. FIG. 25B shows that reintroduction of wild type but not mutant GCN2 restored the activation of ATF-4 pathway and apoptosis induced by Compound D. In a proliferation assay, wild type GCN2 or such mutants were reintroduced into U937 GCN2 null cells, and the cells were treated with serial dilutions of Compound D (10 nM, 100 nM, 1 μM, and 10 μM). FIG. 25C shows that reintroduction of wild type but not mutant GCN2 restored the anti-proliferative effect of Compound D.

6.26 Translational Readthrough is not the Cause of Increased Levels of p-eIF2α

It is known that amino acid starvation causes GCN2 activation, which phosphorylates eIF2α. Because GSPT1 mediates normal translation termination, it is hypothesized that depletion of GSPT1 by Compound D may cause readthrough of stop codons. Whether the translational readthrough induced by Compound D contributes to the increased levels of p-eIF2α was investigated. OCI-AML2 cells stably expressing the Fluc/Nluc-G36A readthrough reporter were treated with 300 μg/ml G418 or 200 nM Compound D for 2, 4, 6, 8, 10, 12, or 16 hours. The levels of p-eIF2α were measured by immunoblot analysis. AML2 readthrough assay was conducted to measure the readthrough reporter. FIG. 26A shows that Compound D and G418 induced translational readthrough at a comparable level. FIG. 26B shows that Compound D increased the levels of p-eIF2α, whereas G418 had little effect on the levels of p-eIF2α. Thus, the results shown in FIG. 26A and FIG. 26B together indicates that translational readthrough may not be the cause of increased levels of p-eIF2α.

6.27 GSPT1, p-eIF2α, ATF4, ATF3, DDIT3, Cleaved Caspase-3, and Cleaved PARP Serve as Predictive Biomarkers for Compound D- and Compound E-Induced Apoptosis The expression levels of various genes along the ATF4 and apoptotic pathways were measured in cells treated with 1 μM Compound D or 1 μM Compound E. As shown in FIG. 27, the level of GSPT1 decreased in response to treatment with Compound D or Compound E. In cells where GSPT1 was knocked down by shRNA, both Compound D and Compound E increased the levels of p-eIF2α, ATF4, ATF3, and DDIT3, which consequently activated Caspase-3 by increasing cleaved Caspase-3. The cleaved Caspase-3 then inactivated PARP by cleaving PARP and induced apoptosis.

Thus, GSPT1, p-eIF2α, ATF4, ATF3, DDIT3, cleaved Caspase-3, and cleaved PARP can serve as biomarkers indicating Compound D- or Compound E-induced apoptosis.

6.28 Prediction of Compound Toxicity in Normal Peripheral Blood Mononuclear Cell (PBMC The toxicity of compounds was monitored by the levels of GSPT1, p-eIF2α, ATF3, DDIT3, and downstream apoptosis indicators in PBMC. PBMC were treated with 1 nM, 10 nM, 100 nM, or 1000 nM of Compound D or Compound E for 20 hours. As shown in FIG. 28A, both Compound D and Compound E decreased the expression of GSPT1, but increased the level of p-eIF2α, ATF3 (likely in a splicing variant) and DDIT3, which consequently activated Caspase-3 by increasing cleaved Caspase-3. The cleaved Caspase-3 then inactivated PARP by cleaving PARP and induced apoptosis. Thus, GSPT1, p-eIF2α, ATF3, DDIT3, cleaved Caspase-3, and cleaved PARP can serve as biomarkers predicting the toxicity of compounds.

Compound D-mediated reduction in GSPT1 protein level was evaluated in human normal PBMCs (ID no. 4328 and 4379) and AML patient PBMCs (ID no. 11SH and 09P6) by western analysis (FIG. 28B). Quantification of western blots showed a concentration- and time-dependent reduction of GSPT1 protein in both normal PBMC samples and in one AML patient PBMC sample (ID no. 11SH). Little to no basal GSPT1 expression was observed in AML patient PBMC sample ID no. 09P6. The concentration-dependent reduction of GSPT1 in the AML patient sample ID no. 11SH was similar to that observed in the sensitive AML cell lines, with 100 nM Compound D causing 86% reduction of GSPT1 at 8 hours (Table 3). In the two Normal PBMC samples there was less response of GSPT1 to 100 nM Compound D, with only 39% and 67% reduction of GSPT1 at 8 hours (Table 3). Thus, GSPT1 protein level can serve as a biomarker for compound toxicity in PBMCs.

TABLE 3

Reduction of GSPTI Levels by Compound D in PBMCs from Normal Donors and AML Patients

| PBMC Sample ID Number | Reduction in GSPT1 Protein Level (%) | | | |
|---|---|---|---|---|
| | 100 nM Compound D | | 300 nM Compound D | |
| | 8 hours | 22 hours | 8 hours | 22 hours |
| 4379 (normal) | 39 | 73 | 58 | 83 |
| 4328 (normal) | 67 | 92 | 80 | 98 |
| 11SH (AML) | 86 | 100 | 100 | 100 |
| 09P6 (AML) | NQ | NQ | NQ | NQ |

6.29 Compound D Induced UPR Pathway and Inhibited NMD Pathway in KG-1 and HL-60 Cells Compound D regulates UPR stress RNAs, ATF3 and CHOP, and nonsense-mediated decay (NMD) RNAs, SRSF3 and SRSF6, in KG-1 cells in both dose- and time-dependent manners. KG-1 cells were plated in 10 $cm^2$ dishes and incubated overnight. The following day, KG-1 cells were treated with a 6-point dose response (0, 3, 10, 30, 100, 300 nM) of Compound D and incubated for 2, 4, 8, and 20 hours. Cells were removed from dishes and cell pellets were prepared for RNA isolation (Qiagen RNA isolation kit). Total RNA was quantitated using NanoDrop spectrophotometer and cDNA was reversely transcribed using 1 μg total RNA. Quantitative PCR was performed in replicates for each sample using primer sets for ATF3, CHOP, and both NMD and normal transcripts of SRSF3 and SRSF6. Data was doubly normalized to the 18S housekeeping gene and 2 hour DMSO control. Normalized RNA expression (y-axis) versus drug concentration in nM (x-axis) for each time point was plotted. SRSF3-1 NMD and SRSF6-1 NMD depict amplification of NMD transcript for SRSF3 and SRSF6, respectively. SRSF3-3 Normal and SRSF6-3 Normal depict amplification of normal transcript for SRSF3 and SRSF6 genes, respectively. Both dose- and time-dependent increases in ATF3, CHOP, and NMD transcripts for SRSF3 and SRSF6, were observed with Compound D treatment of KG-1 cells.

FIGS. 29A-29F show effects of Compound D treatment on UPR and NMD pathways in KG-1 cells. FIGS. 29A and 29B show that 100 nM Compound D increased the mRNA levels of ATF3 (FIG. 29A) and DDIT3 (CHOP) (FIG. 29B) within 4 hrs of treatment. ATF3 and CHOP increases were observed with 30 nM Compound D or greater within 8 hrs of treatment. Additionally, 100 nM Compound D or greater induced the mRNA levels of ATF3 and DDIT3 (CHOP) approximately 100-fold and 10-fold, respectively. FIGS. 29C and 29D show that 100 nM Compound D increased the mRNA levels of SRSF3-1 (transcript subject to NMD) (FIG. 29C) but not those of SRSF3-3 (normal transcript) (FIG. 29D) within 8 hrs of treatment. FIGS. 29E and 29F show that Compound D increased the mRNA levels of SRSF6-1 (NMD transcript) (FIG. 29E) but not those of SRSF6-3 (normal transcript) (FIG. 29F) within 8 hrs of treatment. Thus, accumulation of NMD transcripts suggests that Compound D inhibited the NMD pathway in KG-1 cells. The inhibition of NMD pathway may be due to degradation of GSPT1.

Concentration- and time-dependent increases in ATF3, CHOP, and SRSF3 NMD transcript (SRSF3-1) and SRSF6 NMD transcript (SRSF6-1) induced by Compound D were similarly observed in another sensitive AML cell line, HL-60. Treatment of HL-60 cells with 100 nM or greater Compound D increased expression of ATF3, CHOP, and SRSF3 and SRSF6 NMD transcripts, but not non-NMD transcripts (SRSF3-3 and SRSF6-3), at the 8-hour time point (FIGS. 29G-29J). Increases in ATF3, CHOP, and NMD transcripts were observed at 30 nM Compound D concentration at the 20-hour time point; however, increased expression of ATF3 and CHOP plateaued at higher drug concentrations (FIGS. 29G-29J). No significant change in gene regulation was observed at 2- and 4-hour time-points in the Compound D concentration range studied.

6.30 Correlation of GSPT1 Reduction, UPR Pathway Activation, and NMD Pathway Inhibition with Apoptosis Induction in KG-1 and HL-60 Cell Lines In two sensitive AML cell lines, KG-1 and HL-60, both a concentration-dependent decrease in GSPT1 protein and an increase in RNA expression of ATF3, CHOP, and SRSF3 and SRSF6 NMD transcripts at the 8-hour time point were compared to caspase 3/7 activation (apoptosis) at the 24-hour (FIG. 30A [KG-1]; FIG. 30C [HL-60]) and 48-hour (FIG. 30B [KG-1]; FIG. 30D [HL-60]) time points.

A complete reduction of GSPT1 was observed with >30 nM Compound D at 8 hours in HL-60 cells, while ATF3, CHOP, and the SRSF3 and SRSF6 NMD transcripts increased with >100 nM Compound D (FIG. 30C). Apoptosis induction was observed at concentrations of Compound D between 41 and 123 nM at the 24 hour time-point, with an average percent increase of 9% and 19%, respectively (FIG. 30C). A greater induction in apoptosis was observed at the 48-hour time point (FIG. 30D).

Similar results were observed in Compound D-treated KG-1 cells, with a concentration of 100 nM or greater reducing GSPT1 protein levels >90%, while inducing RNA expression of ATF3, CHOP, and SRSF3 and SRSF6 NMD transcripts (FIG. 30A). Apoptosis induction was observed at the 24 hour time point, with an average percent increase in apoptosis of 11% at 41 nM and 16% at 123 nM Compound D (FIG. 30A). A greater induction in apoptosis was observed at the 48-hour time point (FIG. 30B).

6.31 Compound D Induced Apoptosis in the Most Sensitive AML Cell Line, HNT-34, within Eight to Sixteen Hours of Incubation Cells were incubated with 0.01, 0.1, or 1 μM Compound D for specified intervals of time (e.g., 1, 2, 4, 8, 16, 24, 48, or 72 hrs). At the end of treatment, cells were washed and reincubated in medium containing 1000-fold excess glutaramide without Compound D for the remainder of a 72-hour incubation. At the 72-hour time point, all cultures were assessed for apoptosis by Annexin V/7-aminoactinomycin D (7-AAD) flow cytometry. In the most sensitive AML cell line, HNT-34, cells were committed to apoptosis within 8 to 16 hours of treatment with 100 nM Compound D and maximal apoptosis occurred within 8 to 16 hours of incubation (FIG. 31B). The concentration of Compound D required for half-maximal apoptotic response in HNT-34 cells steadily decreased over the first 24 hours of the time course, at which time the potency was comparable to that seen in cultures exposed to Compound D for 72 hours (FIG. 31A).

6.32 Compound D Induced UPR and Subsequent Apoptosis in HNT-34 Cells but Exhibited Reduced Effects in PBMCs The time course of GSPT1 degradation was monitored by western blot analysis of HNT-34 AML cells and normal PBMCs (FIGS. 32A-32D) following incubation with Compound D (1, 10, and 100 nM). In HNT-34 cells, GSPT1 degradation was evident within 2 hours of incubation with 10 nM Compound D, with the induction of ATF4 protein occurring at 8 hours, ATF3 protein at 12 hours, and PARP cleavage at 24 hours (FIG. 32A [blot] and FIGS. 32B-32E [densitometry measurements]). Degradation of GSPT1 in healthy PBMCs incubated with 10 nM Compound D was evident at 4 hours (FIGS. 32F and 32G) but induction of proteins in the UPR pathway or cleavage of PARP did not occur.

Figure 33C:
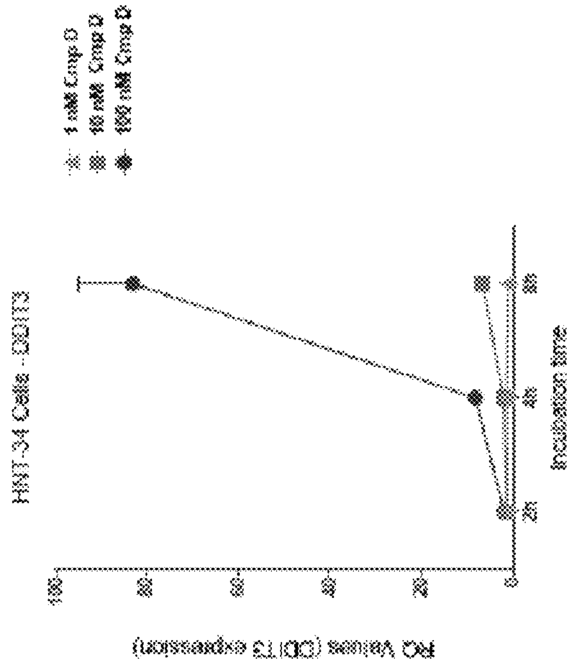

The kinetics of induction of mRNA for UPR factors ATF3 and DDIT3 in HNT-34 cells also strongly differed from that in PBMCs. Compound D induced ATF3 and DDIT3 mRNA within 8 hours in HNT-34 cells (FIGS. 33A and 33C). In contrast, no induction of ATF3 or DDIT3 mRNA was detected by 8 hours in healthy PBMCs incubated with Compound D (FIGS. 33B and 33D). Despite evidence of degradation of GSPT1 in normal PBMCs, apoptosis did not occur, lending further support to the potential of a therapeutic window for this compound. This is also consistent with the reduced cytotoxicity observed for Compound D in normal adult lymphocytes as compared with tumor cells (data not shown).

6.33 Correlation Between GSPT1 Reduction and Apoptosis Responses in a Panel of AML Cell Lines Treated with Compound D The effect of Compound D on GSPT1 protein levels was evaluated by western analysis in a panel of nine AML cell lines that exhibited different sensitivities to Compound D-mediated apoptosis. The apoptosis $EC_{50}$ values for Compound D are summarized in Table 4. The reduction in the level of GSPT1 protein was concentration-dependent over the range of 3 to 1000 nM in eight of the nine AML cell lines and over the range of 300 to 1000 nM in one relatively insensitive AML cell line. The time course of the reduction in GSPT1 by Compound D also was studied for up to 48 hours. The progressive degradation of GSPT1 over the course of 1 to 20 hours was evident in the presence of all concentrations of Compound D studied from 3 to 300 nM in HNT-34, HL-60, and ML-2 cells, with little GSPT1 remaining by 20 hours at 100 or 300 nM Compound D in HNT-34 or HL-60 cells (FIG. 34 and FIG. 35C). Time-dependent reduction in GSPT1 was also observed in KG-1 and OCI-AML2 cells at 3 to 1000 nM Compound D, with little GSPT1 remaining in KG-1 cells at 100 to 300 nM at 24 hours or in OCI-AML2 cells at 300 and 1000 nM at 24 hours (FIG. 35D). Loss of GSPT1 occurred more slowly in Kasumi-1, AML-193, and F36-P cells. Compound D did not demonstrate strong reduction in GSPT1 protein levels in OCI-AML3 cells. Only slight loss of GSPT1 was observed at 300 and 1000 nM at 24 and 48 hours in OCI-AML3 cells.

TABLE 4

Compound D-induced Apoptosis in AML Cell Lines

| AML Cell Line | Compound D-induced Apoptosis $EC_{50}$ (μM) 12 hr | 24 hr | 48 hr | 72 hr | 96 hr | Rank at 24 hr | Rank at 48 hr |
|---|---|---|---|---|---|---|---|
| HNT-34 | NF | 0.007 | 0.004 | NF | 0.002 | 1 | 1 |
| HL-60 | NF | 0.073 | 0.015 | 0.008 | NF | 3 | 2 |
| ML-2 | 0.179 | 0.062 | 0.031 | 0.021 | 0.025 | 2 | 3 |
| KG-1 | 0.053 | 0.108 | 0.039 | 0.026 | 0.025 | 4 | 4 |
| OCI-AML2 | NF | 0.436 | 0.081 | 0.041 | 0.038 | 6 | 5 |
| AML-193 | NF | 0.254 | 0.089 | 0.047 | 0.060 | 5 | 6 |

TABLE 4-continued

| Compound D-induced Apoptosis in AML Cell Lines | | | | | | | |
|---|---|---|---|---|---|---|---|
| AML | Compound D-induced Apoptosis $EC_{50}$ (μM) | | | | | | |
| Cell Line | 12 hr | 24 hr | 48 hr | 72 hr | 96 hr | Rank at 24 hr | Rank at 48 hr |
| Kasumi-1 | NF | NF | 0.124 | 0.254 | 0.055 | 7 | 7 |
| F36-P | NF | NF | 0.335 | 0.252 | 0.229 | 8 | 8 |
| OCI-AML3 | NF | NF | 0.896 | 0.971 | 0.418 | 9 | 9 |

Protein levels of GSPT1 were reduced by greater than 800 at 4 hours in the highly sensitive cell lines, HNT-34, HL-60 and KG-1 and at 8 hours in cell lines OC-AML2 and ML-2 with 100 nM Compound D (FIGS. 35A and 35B; Table 5). Greater than 90% reduction of GSPT1 was observed at 8 hours in HNT-34, HL-60, and KG-1 cells. The moderately sensitive cell lines, Kasumi-1 and AML-193, showed a range of GSPT1 reduction of 51% to 61%, respectively, while the insensitive cell lines, F36-P and OCI-AML3, showed a range of GSPT1 reduction of 18% to 37%, respectively, with 300 nM Compound D at 8 hours. All cell lines, with the exception of OCI-AML3, showed >800% GSPT1 reduction with 100 nM Compound D at 20 to 24 hours.

TABLE 5

| Compound D-mediated GSPT1 Reduction and Caspase 3/7 Activation in a Panel of AML Cell Lines | | | | |
|---|---|---|---|---|
| | Percent Reduction at 100 nM Compound D | Average Percent Increase in Apoptosis at 123 nM Compound D | | |
| AML Cell Line | GSPTI (8 hr) | Apoptosis (12 hr) | Apoptosis (24 hr) | Apoptosis (48 hr) |
| HNT-34 | 100 | 3 | 12 | 32 |
| HL-60 | 100 | 1 | 19 | 62 |
| KG-1 | 92 | 2 | 16 | 42 |
| OCI-AML2 | 89 | 0 | 3 | 33 |
| ML-2 | 82 | 2 | 17 | 51 |
| Kasumi-1 | 64 | 1 | 3 | 18 |
| AML-193 | 49 | 0 | 5 | 40 |
| F36-P | 39[a] | 0 | 2 | 6 |
| OCI-AML3 | ~30[b] | 0 | 1 | 2 |

[a]Change in GSPT1 for F36-P was not concentration-dependent at the 8-hour time point,
[b]Visual interpolation between 3 and 300 nM.

Compound D-mediated GSPT1 reduction at 8 hours was compared to induction of caspase 3/7 activation (apoptosis) at 12, 24, and 48 hour time points in these nine AML cell lines. As shown in Table 5, at 8 hours, the reduction in GSPT1 protein ranged from 32% (OCI-AML3) to 100% (HL-60 and HNT-34). Apoptosis was observed at 24 hours in 4 of 5 cell lines showing >80% GSPT1 reduction (HL-60, HNT-34, KG-1, ML-2) at 100 nM Compound D, with the OCI-AML2 cell line being the sole exception. A positive association ($r^2$=0.50; R=0.71; p value=4.86E-002) was observed between the level of GSPT1 reduction and apoptosis induction in the AML cell panel (FIG. 36), with >90% GSPT1 reduction correlating with induction of apoptosis.

From the foregoing, it will be appreciated that, although specific embodiments have been described herein for the purpose of illustration, various modifications may be made without deviating from the spirit and scope of what is provided herein. All of the references referred to above are incorporated herein by reference in their entireties.

What is claimed is:

1. A method of identifying a subject having cancer who is likely to be responsive to a treatment compound, comprising:

(a) administering the treatment compound to the subject;

(b) obtaining a sample from the subject;

(c) determining the level of a biomarker in the sample; and (d) diagnosing the subject as being likely to be responsive to the treatment compound if the level of the biomarker in the sample is different from a reference level of the biomarker;

wherein the biomarker is selected from the group consisting of IKZF1, eRF1, BIP, GCN2, eIF2α, PPP1R15A, TNFRSF10B, GADD45A, FAS, IRE1, XBP1, SEC24D, DNAJB9, EDEM1, ATF6, Caspase 3, Caspase 7, Caspase 8, Caspase 9, BID, and Mcl-1;

wherein the treatment compound is a compound of Formula I:

I

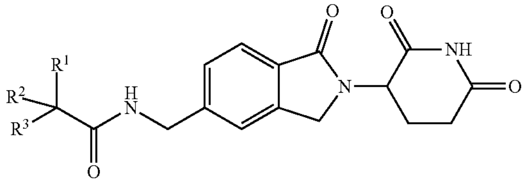

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, —$R^4OR^4N(R^6)(R^7)$, or —$R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

2. A method of identifying a subject having cancer who is likely to be responsive to a treatment compound, comprising:

(a) obtaining a sample from the subject;

(b) administering the treatment compound to the sample;

(c) determining the level of a biomarker in the sample; and (d) diagnosing the subject as being likely to be responsive to the treatment compound if the level of the biomarker in the sample is different from a reference level of the biomarker;

wherein the biomarker is selected from the group consisting of IKZF1, eRF1, BIP, GCN2, eIF2a, PPP1R15A, TNFRSF10B, GADD45A, FAS, IRE1, XBP1, SEC24D, DNAJB9, EDEM1, ATF6, Caspase 3, Caspase 7, Caspase 8, Caspase 9, BID, and Mcl-1;

wherein the treatment compound is a compound of Formula I:

I

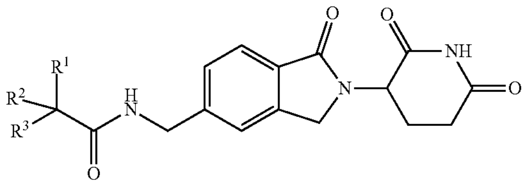

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, —$R^4OR^4N(R^6)(R^7)$, or —$R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

3. A method of treating cancer, comprising:

(a) obtaining a sample from a subject having the cancer;

(b) determining the level of a biomarker in the sample;

(c) diagnosing the subject as being likely to be responsive to a treatment compound if the level of the biomarker in the sample is different from a reference level of the biomarker; and (d) administering a therapeutically effective amount of the treatment compound to the subject;

wherein the biomarker is selected from the group consisting of IKZF1, eRF1, BIP, GCN2, eIF2α, PPP1R15A, TNFRSF10B, GADD45A, FAS, IRE1, XBP1, SEC24D, DNAJB9, EDEM1, ATF6, Caspase 3, Caspase 7, Caspase 8, Caspase 9, BID, and Mcl-1;

wherein the treatment compound is a compound of Formula I:

I

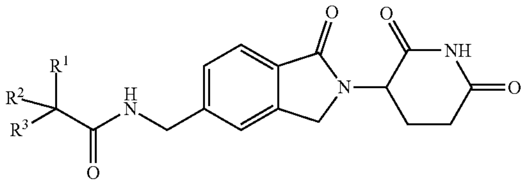

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, —$R^4OR^4N(R^6)(R^7)$, or —$R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

4. A method of predicting the responsiveness of a subject having or suspected of having cancer to a treatment compound, comprising:

(a) administering the treatment compound to the subject;

(b) obtaining a sample from the subject;

(c) determining the level of a biomarker in the sample;

(d) diagnosing the subject as being likely to be responsive to a treatment of the cancer with the treatment compound if the level of the biomarker in the sample is different from the level of the biomarker obtained from a reference sample;

wherein the biomarker is selected from the group consisting of IKZF1, eRF1, BIP, GCN2, eIF2α, PPP1R15A, TNFRSF10B, GADD45A, FAS, IRE1, XBP1, SEC24D, DNAJB9, EDEM1, ATF6, Caspase 3, Caspase 7, Caspase 8, Caspase 9, BID, and Mcl-1;

wherein the treatment compound is a compound of Formula I:

I

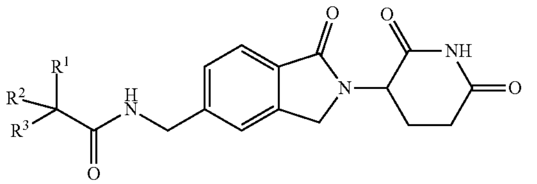

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, $—R^4OR^5$, $—R^4SR^5$, $—R^4N(R^6)(R^7)$, $—R^4OR^4N(R^6)(R^7)$, or $—R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

5. A method of predicting the responsiveness of a subject having or suspected of having cancer to a treatment compound, comprising:

(a) obtaining a sample from the subject;

(b) administering the treatment compound to the sample;

(c) determining the level of a biomarker in the sample;

(d) diagnosing the subject as being likely to be responsive to a treatment of the cancer with the treatment compound if the level of the biomarker in the sample is different from the level of the biomarker obtained from a reference sample;

wherein the biomarker is selected from the group consisting of IKZF1, eRF1, BIP, GCN2, eIF2α, PPP1R15A, TNFRSF10B, GADD45A, FAS, IRE1, XBP1, SEC24D, DNAJB9, EDEM1, ATF6, Caspase 3, Caspase 7, Caspase 8, Caspase 9, BID, and Mcl-1;

wherein the treatment compound is a compound of Formula I:

I

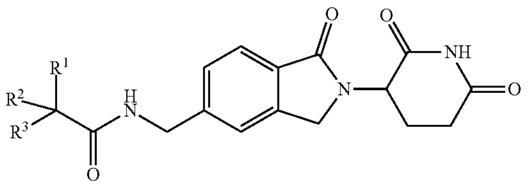

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, $—R^4OR^5$, $—R^4SR^5$, $—R^4N(R^6)(R^7)$, $—R^4OR^4N(R^6)(R^7)$, or $—R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

6. A method of monitoring the efficacy of a treatment compound in treating cancer in a subject, comprising:

(a) administering the treatment compound to the subject;

(b) obtaining a sample from the subject;

(c) determining the level of a biomarker in the sample;

(d) comparing the level of the biomarker in the sample with the level of the biomarker obtained from a reference sample, wherein a change in the level as compared to the reference is indicative of the efficacy of the treatment compound in treating the cancer in the subject;

wherein the biomarker is selected from the group consisting of IKZF1, eRF1, BIP, GCN2, eIF2α, PPP1R15A, TNFRSF10B, GADD45A, FAS, IRE1, XBP1, SEC24D, DNAJB9, EDEM1, ATF6, Caspase 3, Caspase 7, Caspase 8, Caspase 9, BID, and Mcl-1;

wherein the treatment compound is a compound of Formula I:

I

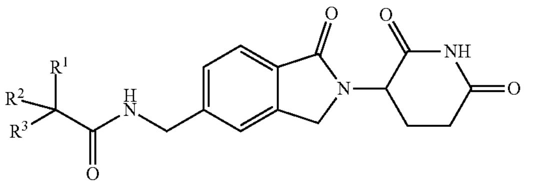

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is H, optionally substituted cycloalkyl, optionally substituted aryl, optionally substituted heteroaryl, or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, $—R^4OR^5$, $—R^4SR^5$, $—R^4N(R^6)(R^7)$, $—R^4OR^4N(R^6)(R^7)$, or $—R^4OR^4C(J)N(R^6)(R^7)$;

each $R^4$ is independently alkylene, alkenylene, or a direct bond;

each $R^5$ is independently hydrogen, alkyl, haloalkyl, or hydroxyalkyl;

J is O or S; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl, or haloalkyl.

7. The method of claim 3, further comprising administering a therapeutically effective amount of a second active agent or a support care therapy.

8. The method of claim 7, wherein the second active agent is a hematopoietic growth factor, cytokine, anti-cancer agent, antibiotic, cox-2 inhibitor, immunomodulatory agent, immunosuppressive agent, corticosteroid, therapeutic antibody that specifically binds to a cancer antigen or a pharmacologically active mutant, or derivative thereof.

9. The method of claim 3, wherein the reference level of the biomarker is determined in a control sample obtained from the subject prior to administering the treatment compound to the subject, and wherein the control sample is from the same source as the sample.

10. The method of claim 3, wherein the reference level of the biomarker is determined in a control sample obtained from a healthy subject not having the cancer, and wherein the control sample is from the same source as the sample.

11. The method of claim 3, wherein the cancer is multiple myeloma (MM), lymphoma, or leukemia.

12. The method of claim 3, wherein the cancer is lymphoma.

13. The method of claim 3, wherein the cancer is leukemia.

14. The method of claim 13, wherein the leukemia is chronic lymphocytic leukemia, chronic myelocytic leukemia, acute lymphoblastic leukemia, acute myeloid leukemia, or myelodysplastic syndrome (MDS).

15. The method of claim 13, wherein the leukemia is acute myeloid leukemia (AML).

16. The method of claim 13, wherein the leukemia is relapsed, refractory or resistant to conventional therapy.

17. The method of claim 3, wherein the level of the biomarker in the sample is higher than the reference level of the biomarker.

18. The method of claim 3, wherein the level of the biomarker in the sample is lower than the reference level of the biomarker.

19. The method of claim 3, wherein the biomarker is IKZF1.

20. The method of claim 3, wherein the level of the biomarker is measured by determining the protein level of the biomarker.

21. The method of claim 3, wherein the level of the biomarker is measured by determining the mRNA level of the biomarker.

22. The method of claim 3, wherein the level of the biomarker is measured by determining the cDNA level of the biomarker.

23. The method of claim 3, wherein the treatment compound is a compound of Formula I:

I

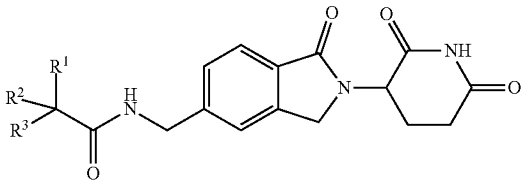

or a stereoisomer or a mixture of stereoisomers, tautomer, pharmaceutically acceptable salt, solvate, isotopologue, prodrug, hydrate, co-crystal, clathrate, or a polymorph thereof, wherein:

$R^1$ is a halo-substituted aryl; and $R^2$ and $R^3$ are each halo.

24. The method of claim 3, wherein the treatment compound is 2-(4-chlorophenyl)-N-((2-(2,6-dioxopiperidin-3-yl)-1-oxoisoindolin-5-yl) methyl)-2,2-difluoroacetamide (Compound D), or a stereoisomer or a mixture of stereoisomers, tautomer, pharmaceutically acceptable salt, solvate, isotopologue, prodrug, hydrate, co-crystal, clathrate, or a polymorph thereof.

25. The method of claim 3, wherein the treatment compound is 2-(4-fluorophenyl)-N-((2-(2,6-dioxopiperidin-3-yl)-1-oxoisoindolin-5-yl) methyl)-2,2-difluoroacetamide (Compound E), or a stereoisomer or a mixture of stereoisomers, tautomer, pharmaceutically acceptable salt, solvate, isotopologue, prodrug, hydrate, co-crystal, clathrate, or a polymorph thereof.

* * * * *